(12) United States Patent
Chen et al.

(10) Patent No.: US 11,161,868 B2
(45) Date of Patent: Nov. 2, 2021

(54) N-ACETYLATED SIALIC ACIDS AND RELATED SIALOSIDES

(71) Applicant: The Regents of the University of California, Oakland, CA (US)

(72) Inventors: Xi Chen, Davis, CA (US); An Xiao, Davis, CA (US); Anoopjit Kooner, Davis, CA (US); Abhishek Santra, Davis, CA (US); Ajit Varki, San Diego, CA (US); Hai Yu, Davis, CA (US); Lee-Ping Wang, Davis, CA (US); Wanqing Li, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/418,758

(22) Filed: May 21, 2019

(65) Prior Publication Data

US 2019/0367548 A1 Dec. 5, 2019

Related U.S. Application Data

(63) Continuation of application No. PCT/US2017/063094, filed on Nov. 22, 2017.

(60) Provisional application No. 62/426,089, filed on Nov. 23, 2016.

(51) Int. Cl.

| C07H 15/04 | (2006.01) |
|---|---|
| C07H 15/12 | (2006.01) |
| C07H 15/14 | (2006.01) |
| C07H 15/203 | (2006.01) |
| C12P 19/28 | (2006.01) |
| C12P 19/44 | (2006.01) |
| C12P 19/64 | (2006.01) |

(52) U.S. Cl.
CPC .............. *C07H 15/04* (2013.01); *C07H 15/12* (2013.01); *C07H 15/14* (2013.01); *C07H 15/203* (2013.01); *C12P 19/28* (2013.01); *C12P 19/44* (2013.01); *C12P 19/64* (2013.01)

(58) Field of Classification Search
CPC .............. A61K 31/7016; A61K 31/702; C07H 15/00–26
See application file for complete search history.

(56) References Cited

U.S. PATENT DOCUMENTS

| 4,501,728 | A | | 2/1985 | Geho et al. | |
|---|---|---|---|---|---|
| 5,646,123 | A | * | 7/1997 | Ippolito | ................. C07H 19/10 514/25 |
| 5,674,988 | A | * | 10/1997 | Sabesan | ................. A61P 43/00 536/17.9 |
| 2005/0148541 | A1 | * | 7/2005 | Sharma | ................. A61L 2/0082 514/54 |
| 2010/0080773 | A1 | | 4/2010 | Geho et al. | |

OTHER PUBLICATIONS

Kiefel, M. et al "Recent advances in the synthesis of sialic acid derivatives . . . " Chem. Rev., vol. 102, pp. 471-490. (Year: 2002).*
Blixt, O. et al "Sialoside analogue arrays . . . " JACS, vol. 130, pp. 6680-6681. (Year: 2008).*
International Search Report and Written Opinion in PCT Application PCT/US2017/063094 dated Mar. 7, 2018; 14 pages.
Pubchem, Substance Record for SID 113527330; Available Date Mar. 16, 2011; retrieved on Jan. 3, 2018; https://pubchem.ncbi.nlm.nih.gov/substance/113527330#section=Top; 6 pages.
Varki, A. et al.; "Multifarious roles of sialic acids in immunity"; *Annals of the New York Academy of Sciences* ; vol. 1253; 2012; pp. 16-36.
Chen, X. et al.; "Advances in the Biology and Chemistry of Sialic Acids"; *ACS Chemical Biology*; vol. 5, No. 2; Dec. 18, 2009; pp. 163-176.
Angata, T. et al.; "Chemical Diversity in the Sialic Acids and Related alpha-Keto Acids: An Evolutionary Perspective"; *Chemical Reviews*; vol. 102, No. 2; 2002; pp. 439-469.
Schauer, R.; "Achievements and challenges of sialic acid research"; *Glycoconjugate Journal*; vol. 17; 2000; pp. 485-499.
Klein, A. et al.; "0-Acetylation of sialic acids"; *Biochimie*; vol. 80; 1998; pp. 49-57.
Varki, A. et al.; "The Release and Purification of Sialic Acids from Glycoconjugates: Methods to Minimize the Loss and Migration of 0-Acetyl Groups"; *Analytical Biochemistry*; vol. 137; 1984; pp. 236-247.
Kamerling, J.P. et al.; "Migration of 0-acetyl groups in N,0-acetylneuraminic acids"; *Eur. J. Biochem.*; vol. 162; 1987; pp. 601-607.
Klotz, F.W. et al.; "Binding of *Plasmodium* falciparum 175-kilodalton erythrocyte binding antigen and invation of murine erythrocytes requires N-acetylneuraminic acid but not its 0-acetylated form"; *Molecular and Biochemical Parasitology*; vol. 51; 1992; pp. 49-54.
Rogers, G.N. et al.; "Influenze C Virus Uses 9-0-Acetyl-N-acetylneuraminic Acid as a High Affinity Receptor Determinant for Attachment to Cells"; *The Journal of Biological Chemistry*; vol. 261, No. 13; May 5, 1986; pp. 5947-5951.
Varki, A. et al.; "An Autosomal Dominant Gene Regulates the Extent of 9-0-Acetylation of Murine Erythrocyte Sialic Acids"; *J. Exp. Med.*; vol. 152; Sep. 1980; pp. 532-544.
Khedri, A. et al.; "A Chemical Biology Solution to Problems with Studying Biologically Important but Unstable 9-0-Acetyl Sialic Acids"; *ACS Chemical Biology*; vol. 12; 2017; pp. 214-224.
Herrler, G. et al.; "A Synthetic Sialic Acid Analogue Is Recognized by Influenza C Virus as a Receptor Deteminrant but Is Resistant to the Receptor-destroying Enzyme"; *The Journal of Biological Chemistry*; vol. 267, No. 18; Jun. 25, 1992; pp. 12501-12505.
Bakkers, M.J.G. et al.; "Coronavirus receptor switch explained from the stereochemistry of protein-carbohydrate interactions and a single mutation"; *Proc. Natl. Acad. Sci.*; vol. 113; May 12, 2016; pp. E3111-E3119.
Yu, H. et al.; "One-pot three-enzyme chemoenzymatic approach to the synthesis of sialosides containing natural and non-natural functionalities"; *Nature Protocols*; vol. 1, No. 5; 2007; pp. 2485-2492.

(Continued)

*Primary Examiner* — Leigh C Maier
(74) *Attorney, Agent, or Firm* — Kilpatrick Townsend and Stockton LLP

(57) ABSTRACT

The present invention provides N-acetyl derivatives of sialic acids, including N-acetyl derivatives of Neu5Ac and Neu5Gc. Methods for preparing related precursors and a variety of sialosides are also disclosed.

3 Claims, 11 Drawing Sheets

(56) References Cited

OTHER PUBLICATIONS

Chokhawala H.A. et al.; "High-Throughput Substrate Specificity Studies of Sialidases by Using Chemoenzymatically Synthesized Sialoside Libraries"; *Chembiochem*; vol. 8; 2007; pp. 194-201.

Khedri, Z. et al.; "Probe sialidase substrate specificity using chemoenzymatically synthesized sialosides containing C9-modified sialic acid"; *Chem. Commun.*; vol. 48; 2012; pp. 3357-3359.

Yu, H. et al.; "Chemoenzymatic synthesis of C8-modified sialic acids and related alpha2-3-and alpha2-6-linked sialosides"; *Bioorganic and Medicinal Chemistry Letters*; vol. 21; 2011; pp. 5037-5040.

Li, Y. et al.; "High-throughput neuraminidase substrate specificity study of human and avian influenza A viruses"; *Virology*; vol. 415; 2011; pp. 12-19.

Li, Y. et al.; "*Pasteurella multocida* sialic acid aldolase: a promising biocatalyst"; *Appl. Microbiol. Biotechnol.*; vol. 79; 2008; pp. 963-970.

Yu, H. et al.; "Chemoenzymatic synthesis of CMP-sialic acid derivatives by a one-pot two-enzyme system: comparison of substrate flexibility of three microbial CMP-sialic acid synthetases"; *Bioorganic and Medicinal Chemistry*; vol. 12; 2004; pp. 6427-6435.

Sun, M. et al.; "N-terminal 112 amino acid residues are not required for the sialyltransferase activity of *Photobacterium damsel* alpha2,6-sialyltransferase", *Biotechnol. Lett.*; vol. 30; Apr. 2008; pp. 671-676.

Yu, H. et al.; "A Multifunctional *Pasteurella multocide* Sialyltransferase: A Powerful Tool for the Synthesis of Sialoside Libraries"; *J. Am. Chem. Soc.*; vol. 127; 2005; pp. 17618-17619.

Sugiarto, G. et al.; "A Sialyltransferase Mutant with Decreased Donor Hydrolysis and Reduced Sialidase Activities for Directly Sialylating Lewis"; *ACS Chemical Biology*; vol. 7; 2012; pp. 1232-1240.

Yu, H. et al.; "Highly Efficient Chemoenzymatic Synthesis of Naturally Occurring and Non-Natural alpha-2,6-Linked Sialosides: A *P. damsel* alpha-2,6-Sialyltransferase with Extremely Flexible Donor-Substrate Specificity"; *Angewandte Chemie Int. Ed. Engl.*; vol. 45; 2006; pp. 3938-3944.

Ding, L. et al.; "Efficient chemoenzymatic synthesis of sialyl Tn-antigens and derivatives"; *Chem. Commun.*; vol. 47; 2011; pp. 8691-8693.

Ding, L. et al.; "A *Photobacterium* sp. Alpha2-6-sialyltransferase (Psp2,6ST) mutant with an increased expression level and improved activities in sialylating Tn antigens"; *Carbohydrate Research*; vol. 408; 2015; pp. 127-133.

Ye, J. et al.; "Diversity-Oriented Enzymatic Modular Assembly of ABO Histo-blood Group Antigens"; *ACS Catalysis*; vol. 6; 2016; pp. 8140-8144.

Li, Y. et al.; "Identifying selective inhibitors against the human cytosolic sialidase NEU2 by substrate specificity studies." *Molecular BioSystems*; vol. 7, No. 4; Apr. 1, 2011; pp. 1060-1072.

Sela, D.A. et al.; "An Infant-associated Bacterial Commensal Utilizes Breast Milk Sialyloligosaccharides"; *The Journal of Biological Chemistry*; vol. 286, No. 14; Apr. 8, 2011; pp. 11909-11918.

Tasnima, N. et al.; "Chemoenzymatic synthesis of para-nitrophenol (pNP)-tagged alpha2-8-sialosides and high-throughput substrate specificity studies of alpha2-8-sialidases"; *Organic & Biomolecular Chemistry*; vol. 15; 2017; pp. 160-167.

Owen, C.D. et al.; "*Streptococcus pneumoniae* NanC"; *The Journal of Biological Chemistry*; vol. 290, No. 46; Nov. 13, 2015; pp. 27736-27748.

Xu, G. et al.; "Three *Streptococcus pneumoniae* Sialidases: Three Different Products"; *Journal of the American Chemical Society*; vol. 133; 2011; pp. 1718-1721.

\* cited by examiner

Potential (Cmpnd 3; NAc)

Δ(Potential) (Nac - OAc)

−30    +30
(kcal/mol)

Full ensemble of OAc

Only seen with OAc

N-ACETYLATED SIALIC ACIDS AND RELATED SIALOSIDES

CROSS-REFERENCES TO RELATED APPLICATIONS

The present application is a continuation of PCT Application PCT/US2017/063094 filed Nov. 22, 2017, which claims priority to U.S. Provisional Appl. No. 62/426,089, filed on Nov. 23, 2016, which applications are incorporated herein by reference in their entirety.

STATEMENT AS TO RIGHTS TO INVENTIONS MADE UNDER FEDERALLY SPONSORED RESEARCH AND DEVELOPMENT

This invention was made with Government support under Grant Nos. AI130684, GM032373, GM120419, and HD065122, awarded by the National Institutes of Health (NIH). The Government has certain rights in the invention.

BACKGROUND OF THE INVENTION

The first sialic acid discovered (crystallized by Gunner Blix from a hot mild acid extract of bovine submaxillary mucin in 1936) contained two acetyl groups, only one possibly attached to nitrogen. In retrospect, Blix likely isolated a 9-O-acetyl variant of the common sialic acid N-acetylneuraminic acid (Neu5Ac), 9-O-acetyl-N-acetylneuraminic acid (Neu5,9Ac$_2$) (1, FIG. 1). Neu5,9Ac$_2$ along with N-acetylneuraminic acid (Neu5Ac) and N-glycolylneuraminic acid (Neu5Gc) are the three most frequently occurring sialic acid forms in mammals. It has long been known that 9-O-acetylation of sialic acids masks the recognition by influenza A virus hemagglutinin and by other lectins such as Factor H, CD22/Siglec-2, and Sialoadhesin/Siglec-1, while being required for the binding of influenza C virus hemagglutinin. Despite such early recognition and understanding of their importance, studies of the biological significance of sialoglycans presenting this common O-acetylated form of sialic acid have lagged far behind those of the parent molecules. The reasons are many, and have been detailed elsewhere, including their lability to both acidic and basic conditions (often used in standard purification methods for glycans and glycoconjugates), their propensity to migrate from one position to another, and their relative or absolute effects in blocking sialidase action. However, when it has been further studied, such O-acetyl group modification turns out to be a key determinant modulating recognition by viruses, antibodies, and mammalian lectins, as well as modulating sialidase action and cellular apoptosis.

Overall, exploration of the functions of Neu5,9Ac$_2$ and its biological and pathological interactions has been greatly hampered by the chemical instability of the O-acetyl group and/or the esterase cleavage of such a group. Taken together with the fact that it is eliminated by basic conditions during conventional approaches to glycomic analysis such as beta-elimination and permethylation, it has come to the point where 9-O-acetylation tends to be simply ignored in many studies. Synthetic analogs of Neu5,9Ac$_2$ with chemical modifications of the 9-position of sialic acids generated included a 9-N-acetyl analog, 9-acetamido-9-deoxy-N-acetylneuraminic acid (Neu5Ac9NAc) (2, FIG. 1), which was shown to mimic Neu5,9Ac$_2$ in binding to influenza C virus without being destroyed by esterase activity of the hemagglutinin-esterase. This observation was not however further explored for chemical and biological studies of Neu5,9Ac$_2$. Herein, efficient chemoenzymatic methods for synthesizing new N-acetyl sialic acids and related sialosides are disclosed. Applications in glycan microarray and cell feeding studies are described, laying the foundation for a new approach to elucidate the important roles of O-acetylation of sialic acids.

BRIEF SUMMARY OF THE INVENTION

Described herein are compounds according to Formula I:

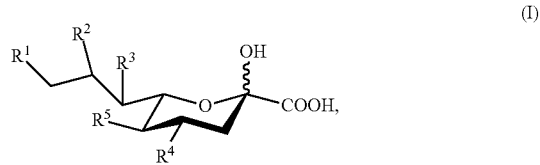

(I)

wherein:
$R^1$, $R^2$, $R^3$, and $R^4$ are independently selected from the group consisting of —NHAc, —N$_3$, —NH$_2$, —OAc, —OH, and hydrogen;
$R^5$ is selected from the group consisting of —NHR$^{5a}$, —N$_3$, —NH$_2$, —OAc, —OH, and hydrogen;
$R^{5a}$ is selected from the group consisting of Ac, Gc, GcAc, GcN$_3$, GcNH$_2$, GcNAc, and hydrogen;
Ac is —C(O)CH$_3$; Gc is —C(O)CH$_2$OH; GcAc is —C(O)CH$_2$OC(O)CH$_3$;
GcN$_3$ is —C(O)CH$_2$N$_3$; GcNH$_2$ is —C(O)CH$_2$NH$_2$; and
GcNAc is —C(O)CH$_2$NHC(O)CH$_3$;
provided that when $R^5$ is —OH or —OAc, at least one of $R^1$, $R^2$, $R^3$, and $R^4$ are independently —NHAc or —N$_3$;
provided that when $R^5$ is —NHR$^{5a}$, at least one of $R^1$, $R^2$, $R^3$, and $R^4$ is —NHAc or —N$_3$;
provided that when $R^5$ and $R^1$ are —NHAc, at least one of $R^2$, $R^3$, and $R^4$ is —NHAc; and
provided that when $R^5$ and $R^4$ are —NHAc, at least one of $R^1$, $R^2$, and $R^3$ is —NHAc.

Also described are compounds according to Formula IV:

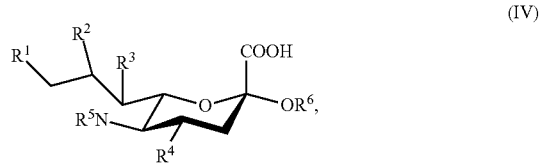

(IV)

wherein:
$R^1$, $R^2$, $R^3$, and $R^4$ are independently selected from the group consisting of —NHAc, —N$_3$, —NH$_2$, —OAc, —OH, and hydrogen;
$R^5$ is selected from the group consisting of —NHR$^{5a}$, —N$_3$, —NH$_2$, —OAc, —OH, and hydrogen;
$R^{5a}$ is selected from the group consisting of Ac, Gc, GcAc, GcN$_3$, GcNH$_2$, GcNAc, and hydrogen;
Ac is —C(O)CH$_3$; Gc is —C(O)CH$_2$OH; GcAc is —C(O)CH$_2$OC(O)CH$_3$;
GcN$_3$ is —C(O)CH$_2$N$_3$; GcNH$_2$ is —C(O)CH$_2$NH$_2$;
GcNAc is —C(O)CH$_2$NHC(O)CH$_3$; and
$R^6$ is selected from the group consisting of a galactoside, an N-acetylgalactosaminide, a glucoside, an N-acetylglucosaminide, and a sialoside.

Methods for making and using compounds according to Formula I and compounds according to Formula IV are also described herein.

DETAILED DESCRIPTION OF THE INVENTION

I. General

Figure 1:
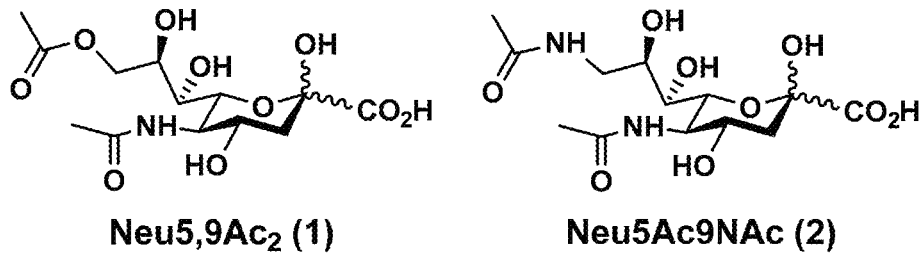
FIG. 1 shows the structures of 9-O-acetyl-N-acetyl-neuraminic acid (Neu5,9Ac$_2$) (1) and its N-acetyl analog Neu5Ac9NAc (2).

Described herein are new N-acyl sialic acid compounds and convenient chemoenzymatic methods for synthesizing the N-acyl sialic acid and sialosides containing them. Applications in glycan microarray and cell feeding studies are described, which provide a new approach for elucidating the important roles of O-acetylation of sialic acids.

In certain embodiments, one-pot three-enzyme (OP3E) sialylation systems are used for efficient, high-yield production of a library of Neu5Ac9NAc-containing α2-3- and α2-6-linked sialosides with diverse underlying glycans from chemically synthesized 6-acetamido-6-deoxy-N-acetylmannosamine (ManNAc6NAc). Among these, the use of para-nitrophenylated α2-3- and α2-6-linked sialyl galactosides is demonstrated in microtiter plate-based high-throughput substrate specificity studies of nine different sialidases including those from humans and bacteria.

II. Definitions

As used herein, the term "monosaccharide" refers to a sugar having a six-membered carbon backbone (i.e., a hexose). Examples of monosaccharides include, but are not limited to, glucose (Glc), galactose (Gal), mannose (Man), glucuronic acid (GlcA), and iduronic acid (IdoA). Monosaccharides also include hexoses substituted with hydroxy groups, oxo groups, amino groups, acetamido groups, and other functional groups. "Deoxy" monosaccharides refer to monosaccharides having carbon atoms one or more carbon atoms in the hexose backbone having only hydrogen substituents. Monosaccharides also include, but are not limited to, glucosamine (2-amino-2-deoxy-glucose; GlcN), N-acetylglucosamine (2-acetamido-2-deoxy-glucose; GlcNAc), galactosamine (2-amino-2-deoxy-galactose; GalN), N-acetylgalactosamine (2-acetamido-2-deoxy-galactose; GalNAc), mannosamine (2-amino-2-deoxy-mannose; ManN), and N-acetylmannosamine (2-acetamido-2-deoxy-mannose; ManNAc).

As used herein, the term "oligosaccharide" refers to a compound containing at least two sugars covalently linked together. Oligosaccharides include disaccharides, trisaccharides, tetrasaccharides, pentasaccharides, hexasaccharides, heptasaccharides, octasaccharides, and the like. Covalent linkages for linking sugars generally consist of glycosidic linkages (i.e., C—O—C bonds) formed from the hydroxyl groups of adjacent sugars. Linkages can occur between the 1-carbon (the anomeric carbon) and the 4-carbon of adjacent sugars (i.e., a 1-4 linkage), the 1-carbon (the anomeric carbon) and the 3-carbon of adjacent sugars (i.e., a 1-3 linkage), the 1-carbon (the anomeric carbon) and the 6-carbon of adjacent sugars (i.e., a 1-6 linkage), or the 1-carbon (the anomeric carbon) and the 2-carbon of adjacent sugars (i.e., a 1-2 linkage). A sugar can be linked within an oligosaccharide such that the anomeric carbon is in the α- or β-configuration. The oligosaccharides prepared according to the methods of the invention can also include linkages between carbon atoms other than the 1-, 2-, 3-, 4-, and 6-carbons.

As used herein, the term "isomer" refers to a compound having the same bond structure as a reference compound but having a different three-dimensional arrangement of the bonds. An isomer can be, for example, an enantiomer or a diastereomer.

As used herein, the term "glycoside" refers to a saccharide compound having a moiety "—OR" replacing a hydroxyl group of the parent compound, wherein R is another saccharide (e.g., a monosaccharide, oligosaccharide, or polysaccharide) or a non-saccharide moiety (e.g., a lipid, a protein, a peptide, a linker moiety, a label moiety, etc.). In some embodiments, the moiety —OR in the glycoside replaces the hydroxyl group of the anomeric carbon at the reducing end of the parent saccharide.

A "galactoside" refers to a galactopyranose moiety or a galactofuranose moiety wherein one of the hydroxyl groups of the parent compound is replaced with a moiety —OR as described above. Galactosides include, for example, lactosides (i.e., β-D-galactopyranosyl-(1→4)-D-glucopyranoses).

An "N-acetylgalactosaminide" refers to a galactopyranose moiety or a galactofuranose moiety wherein one of the hydroxyl groups of the parent compound is replaced with a moiety —OR as described above, and wherein at least one additional hydroxyl group of the parent compound is replaced with —NC(O)R', wherein R' is $C_{1-6}$ alkyl or $C_{1-6}$ hydroxyalkyl. N-Acetylgalactosaminides include, for example, N-acetylgalactosamine (GalNAc)-derived 2-acetamido-2-deoxy-D-galactopyranosides.

A "glucoside" refers to a glucopyranose moiety or a glucofuranose moiety wherein one of the hydroxyl groups of the parent compound is replaced with a moiety —OR as described above.

An "N-acetylglucosaminide" refers to a glucopyranose moiety or a glucofuranose moiety wherein one of the hydroxyl groups of the parent compound is replaced with a moiety —OR as described above, and wherein at least one additional hydroxyl group of the parent compound is replaced with —NC(O)R', wherein R' is $C_{1-6}$ alkyl or $C_{1-6}$ hydroxyalkyl. N-Acetylglucosaminides include, for example, N-acetylglucosamine (GlcNAc)-derived 2-acetamido-2-deoxy-D-glucopyranosides.

A "sialoside" refers to a sialic acid moiety wherein one of the hydroxyl groups of the parent compound is replaced with a moiety —OR as described above. Sialic acid is a general term for N- and O-substituted derivatives of neuraminic acid, and includes, but is not limited to, N-acetyl (Neu5Ac) or N-glycolyl (Neu5Gc) substitutions, as well as O-substitutions including acetyl, lactyl, methyl, sulfate and phosphate, among others.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. The term "alkylene" refers to a divalent alkyl radical, wherein the two points of attachment to the diradical are on the same carbon atom or different carbon atoms.

As used herein, the terms "halo" and "halogen" refer to a fluorine, chlorine, bromine, or iodine atom.

As used herein, the term "sialic acid aldolase" refers to an aldolase that catalyzes a reversible reaction that converts a suitable hexosamine, hexose, pentose, or derivative (such as N-acetyl mannosamine) to sialic acid via reaction with pyruvate.

As used herein, the term "CMP-sialic acid synthetase" refers to a polypeptide that catalyzes the synthesis of cytidine monophosphate sialic acid (CMP-sialic acid) from cytidine triphosphate (CTP) and sialic acid.

As used herein, the term "sialyltransferase" refers to an enzyme that catalyzes the transfer of a sialic acid to a monosaccharide, an oligosaccharide, or another glycosylated molecule.

As used herein, the term "sialidase" refers to an enzyme that catalyzes the cleavage of a terminal sialic acid from a sialylated target such as an oligosaccharide, a polysaccharide, or a glycosylated protein.

The term "variant," in the context of the enzymes in the present disclosure, means a polypeptide, typically recombinant, that comprises one or more amino acid substitutions relative to a corresponding, naturally-occurring or unmodified sialyltransferase.

The term "amino acid" refers to any monomeric unit that can be incorporated into a peptide, polypeptide, or protein. Amino acids include naturally-occurring α-amino acids and their stereoisomers, as well as unnatural (non-naturally occurring) amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid).

Naturally-occurring amino acids are those encoded by the genetic code, as well as those amino acids that are later modified, e.g., hydroxyproline, γ-carboxyglutamate and 0-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either the commonly known three letter symbols or by the one-letter symbols recommended by the IUPAC-IUB Biochemical Nomenclature Commission. Nucleotides, as described herein, may also be referred to by their commonly accepted single-letter codes.

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

The terms "amino acid modification" and "amino acid alteration" refer to a substitution, a deletion, or an insertion of one or more amino acids. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains exemplary amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Identical" and "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 75%, at least 80%, at least 85%, at least 90%, at least 95%, or at least 99% identical over a specified region), when compared and aligned for maximum correspondence over a comparison window, or designated region as measured using one of the following sequence comparison algorithms or by manual alignment and visual inspection. These definitions also refer to the complement of a nucleic acid test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

In certain embodiments, an enzyme variant will have at least about 80%, e.g., at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to any one of the amino acid sequences set forth herein.

In some embodiments, the polypeptide further comprises one or more heterologous amino acid sequences located at the N-terminus and/or the C-terminus of the polypeptide. The polypeptide can contain a number of heterologous sequences that are useful for expressing, purifying, and/or using the polypeptide. The polypeptide can contain, for example, a poly-histidine tag (e.g., a His$_6$ tag); a calmodulin-binding peptide (CBP) tag; a NorpA peptide tag; a Strep tag (e.g., Trp-Ser-His-Pro-Gln-Phe-Glu-Lys) for recognition by/binding to streptavidin or a variant thereof; a FLAG peptide (i.e., Asp-Tyr-Lys-Asp-Asp-Asp-Asp-Lys) for recognition by/binding to anti-FLAG antibodies (e.g., M1, M2, M5); a glutathione S-transferase (GST); or a maltose binding protein (MBP) polypeptide. In some embodiments, the invention provides an isolated polypeptide comprising the amino acid sequence set forth in SEQ ID NO: 2, SEQ ID NO: 4, SEQ ID NO: 6, or SEQ ID NO: 8 with a His$_6$ peptide fused to the C-terminal residue of the amino acid sequence. In some embodiments, the polypeptide comprises the amino acid sequence set forth in SEQ ID NO: 2 with a His$_6$ peptide fused to the C-terminal residue of the amino acid sequence.

As used herein, the term "forming a reaction mixture" refers to the process of bringing into contact at least two distinct species such that they mix together and can react, either modifying one of the initial reactants or forming a third distinct species, i.e., a product. It should be appreciated, however, the resulting reaction product can be produced directly from a reaction between the added reagents or from an intermediate from one or more of the added reagents which can be produced in the reaction mixture.

III. Sialic Acid Analog Compounds

The sialic acid compounds described herein can be to prepare a variety of useful sugars and glycoconjugates which can, in turn, be used for the study of biological and pathological processes in fields as diverse as immunology, oncology, virology, neuroscience. N-acetyl sialic acids, in particular, can be used as mimics of naturally occurring O-acetyl sialic acids without the instability associated with O-acetylation.

Accordingly, one aspect the invention provides compounds according to Formula I:

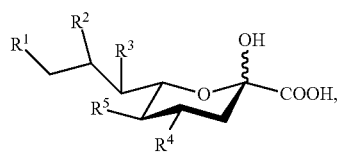

(I)

or a salt thereof, wherein:
$R^1$, $R^2$, $R^3$, and $R^4$ are independently selected from the group consisting of —NHAc, —N$_3$, —NH$_2$, —OAc, —OH, and hydrogen;
$R^5$ is selected from the group consisting of —NHR$^{5a}$, —N$_3$, —NH$_2$, —OAc, —OH, and hydrogen;
$R^{5a}$ is selected from the group consisting of Ac, Gc, GcAc, GcN$_3$, GcNH$_2$, GcNAc, and hydrogen;
Ac is —C(O)CH$_3$; Gc is —C(O)CH$_2$OH; GcAc is —C(O)CH$_2$OC(O)CH$_3$;
GcN$_3$ is —C(O)CH$_2$N$_3$; GcNH$_2$ is —C(O)CH$_2$NH$_2$; and
GcNAc is —C(O)CH$_2$NHC(O)CH$_3$;
provided that when $R^5$ is —OH or —OAc, at least one of $R^1$, $R^2$, $R^3$, and $R^4$ are independently —NHAc or —N$_3$;
provided that when $R^5$ is —NHR$^{5a}$, at least one of $R^1$, $R^2$, $R^3$, and $R^4$ is —NHAc or —N$_3$;
provided that when $R^5$ and $R^1$ are —NHAc, at least one of $R^2$, $R^3$, and $R^4$ is —NHAc; and provided that when $R^5$ and $R^4$ are —NHAc, at least one of $R^1$, $R^2$, and $R^3$ is —NHAc.

In some embodiments, compounds according to Formula I are provided as described above wherein:
$R^1$, $R^2$, $R^3$, and $R^4$ are independently selected from the group consisting of —NHAc, —N$_3$, —OAc, —OH, and hydrogen;
$R^5$ is selected from the group consisting of —NHR$^{5a}$, —N$_3$, —OAc, —OH, and hydrogen; and
$R^{5a}$ is selected from the group consisting of Ac and Gc.

In some embodiments, $R^1$, $R^2$, $R^3$, and $R^4$ are independently selected from the group consisting of —N$_3$, —NH$_2$, and —OH. In some embodiments, $R^1$, $R^2$, $R^3$, and $R^4$ are independently selected from the group consisting of —N$_3$ and —OH. In some such embodiments, $R^5$ is selected from the group consisting of —NHR$^{5a}$, —OH, and —OAc. In some embodiments, $R^1$, $R^2$, $R^3$, and $R^4$ are independently selected from the group consisting of —N$_3$ and —OH, and $R^5$ is —NHR$^{5a}$. In some embodiments, $R^1$, $R^2$, $R^3$, and $R^4$ are independently selected from the group consisting of —N$_3$ and —OH, and $R^5$ is —NHAc. In some embodiments, $R^1$, $R^2$, $R^3$, and $R^4$ are independently selected from the group consisting of —N$_3$ and —OH, and $R^5$ is —NHGc.

In some embodiments, $R^1$, $R^2$, $R^3$, and $R^4$ are —N$_3$. In some such embodiments, $R^5$ is selected from the group consisting of —NHR$^{5a}$, —OH, and —OAc. In some embodiments, $R^1$, $R^2$, $R^3$, and $R^4$ are —N$_3$ and $R^5$ is —NHR$^5$a. In some embodiments, $R^1$, $R^2$, $R^3$, and $R^4$ are —N$_3$ and $R^5$ is —NHAc. In some embodiments, $R^1$, $R^2$, $R^3$, and $R^4$ are —N$_3$ and $R^5$ is —NHGc.

In some embodiments, $R^1$, $R^2$, $R^3$, and $R^4$ are independently selected from the group consisting of —NHAc and —OH. In some such embodiments, $R^5$ is selected from the group consisting of —NHR$^{5a}$, —OH, and —OAc. In some embodiments, $R^1$, $R^2$, $R^3$, and $R^4$ are independently selected from the group consisting of —NHAc and —OH, and $R^5$ is —NHR$^{5a}$. In some embodiments, $R^1$, $R^2$, $R^3$, and $R^4$ are independently selected from the group consisting of —NHAc and —OH, and $R^5$ is —NHAc. In some embodiments, $R^1$, $R^2$, $R^3$, and $R^4$ are independently selected from the group consisting of —NHAc and —OH, and $R^5$ is —NHGc.

In some embodiments, $R^1$, $R^2$, $R^3$, and $R^4$ are —NHAc. In some such embodiments, $R^5$ is selected from the group consisting of —NHR$^{5a}$, —OH, and —OAc. In some embodiments, $R^1$, $R^2$, $R^3$, and $R^4$ are —NHAc and $R^5$ is —NHR$^5$a. In some embodiments, $R^1$, $R^2$, $R^3$, and $R^4$ are —NHAc and $R^5$ is —NHAc. In some embodiments, $R^1$, $R^2$, $R^3$, and $R^4$ are —NHAc and $R^5$ is —NHGc.

In some embodiments, $R^5$ is —NHR$^{5a}$ and at least one of $R^1$, $R^2$, $R^3$, and $R^4$ is independently —NHAc, —NH$_2$, or —N$_3$. In some embodiments, $R^5$ is —NHR$^{5a}$ and at least one of $R^1$, $R^2$, $R^3$, and $R^4$ is independently —NHAc or —N$_3$. In some embodiments, $R^5$ is —NHR$^5$a and at least two of $R^1$, $R^2$, $R^3$, and $R^4$ are independently —NHAc or —N$_3$. In some embodiments, $R^5$ is —NHR$^{5a}$ and at least three of $R^1$, $R^2$, $R^3$, and $R^4$ are independently —NHAc or —N$_3$. In some embodiments, $R^5$ is —NHR$^5$a and $R^1$, $R^2$, $R^3$, and $R^4$ are independently —NHAc or —N$_3$. In some embodiments, remaining $R^1$, $R^2$, $R^3$, and $R^4$ groups are independently selected from —OH and —OAc. In some such embodiments, the remaining $R^1$, $R^2$, $R^3$, and $R^4$ groups are —OH.

In some embodiments, $R^5$ is —NHR$^{5a}$ and at least one of $R^1$, $R^2$, $R^3$, and $R^4$ is —N$_3$ or —NH$_2$. In some embodiments, $R^5$ is —NHR$^5$a and at least one of $R^1$, $R^2$, $R^3$, and $R^4$ is —N$_3$. In some embodiments, $R^5$ is —NHR$^{5a}$ and at least two of $R^1$, $R^2$, $R^3$, and $R^4$ are —N$_3$. In some embodiments, $R^5$ is —NHR$^{5a}$ and at least three of R$^1$, R$^2$, R$^3$, and R$^4$ are —N$_3$. In some embodiments, R$^5$ is —NHR$^5$a and R$^1$, R$^2$, R$^3$, and R$^4$ are —N$_3$. In some embodiments, remaining R$^1$, R$^2$, R$^3$, and R$^4$ groups are independently selected from —OH and —OAc. In some such embodiments, the remaining R$^1$, R$^2$, R$^3$, and R$^4$ groups are —OH.

In some embodiments, R$^5$ is —NHR$^{5a}$ and at least one of R$^1$, R$^2$, R$^3$, and R$^4$ is —NHAc. In some embodiments, R$^5$ is —NHR$^{5a}$ and at least two of R$^1$, R$^2$, R$^3$, and R$^4$ are —NHAc. In some embodiments, R$^5$ is —NHR$^{5a}$ and at least three of R$^1$, R$^2$, R$^3$, and R$^4$ are —NHAc. In some embodiments, R$^5$ is —NHR$^5$a and R$^1$, R$^2$, R$^3$, and R$^4$ are —NHAc. In some embodiments, remaining R$^1$, R$^2$, R$^3$, and R$^4$ groups are independently selected from —OH and —OAc. In some such embodiments, the remaining R$^1$, R$^2$, R$^3$, and R$^4$ groups are —OH.

In some embodiments, R$^5$ is —NHAc and at least one of R$^1$, R$^2$, R$^3$, and R$^4$ is —N$_3$ or —NH$_2$. In some embodiments, R$^5$ is —NHAc and at least one of R$^1$, R$^2$, R$^3$, and R$^4$ is —N$_3$. In some embodiments, R$^5$ is —NHAc and at least two of R$^1$, R$^2$, R$^3$, and R$^4$ are —N$_3$. In some embodiments, R$^5$ is —NHAc and at least three of R$^1$, R$^2$, R$^3$, and R$^4$ are —N$_3$. In some embodiments, R$^5$ is —NHAc and R$^1$, R$^2$, R$^3$, and R$^4$ are —N$_3$. In some embodiments, remaining R$^1$, R$^2$, R$^3$, and R$^4$ groups are independently selected from —OH and —OAc. In some such embodiments, the remaining R$^1$, R$^2$, R$^3$, and R$^4$ groups are —OH.

In some embodiments, R$^5$ is —NHGc and at least one of R$^1$, R$^2$, R$^3$, and R$^4$ is —NHAc. In some embodiments, R$^5$ is —NHGc and at least two of R$^1$, R$^2$, R$^3$, and R$^4$ are —NHAc. In some embodiments, R$^5$ is —NHGc and at least three of R$^1$, R$^2$, R$^3$, and R$^4$ are —NHAc. In some embodiments, R$^5$ is —NHGc and R$^1$, R$^2$, R$^3$, and R$^4$ are —NHAc. In some embodiments, remaining R$^1$, R$^2$, R$^3$, and R$^4$ groups are independently selected from —OH and —OAc. In some such embodiments, the remaining R$^1$, R$^2$, R$^3$, and R$^4$ groups are —OH.

In some embodiments, R$^5$ is —NHR$^{5a}$, and at least one of R$^1$, R$^2$, R$^3$, and R$^4$ is —NHAc, —N$_3$, or —NH$_2$. In some embodiments, R$^5$ is —NHR$^5$a, and at least one of R$^1$, R$^2$, R$^3$, and R$^4$ is —NHAc or —N$_3$.

In some embodiments, R$^5$ and R$^1$ are —NHAc, and at least one of R$^2$, R$^3$, and R$^4$ is —NHAc.

In some embodiments, R$^5$ and R$^4$ are —NHAc, and at least one of R$^1$, R$^2$, and R$^3$ is —NHAc.

In some embodiments, compounds according to Formula Ia are provided:

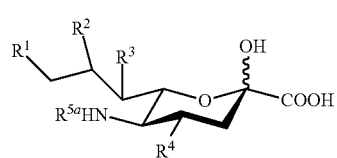

(Ia)

or a salt thereof, wherein:

R$^1$ is selected from the group consisting of hydrogen, —NHAc, and —OH; and

R$^2$, R$^3$, and R$^4$ are independently selected from the group consisting of —NHAc and —OH.

In some embodiments, the compound is selected from Group A consisting of:

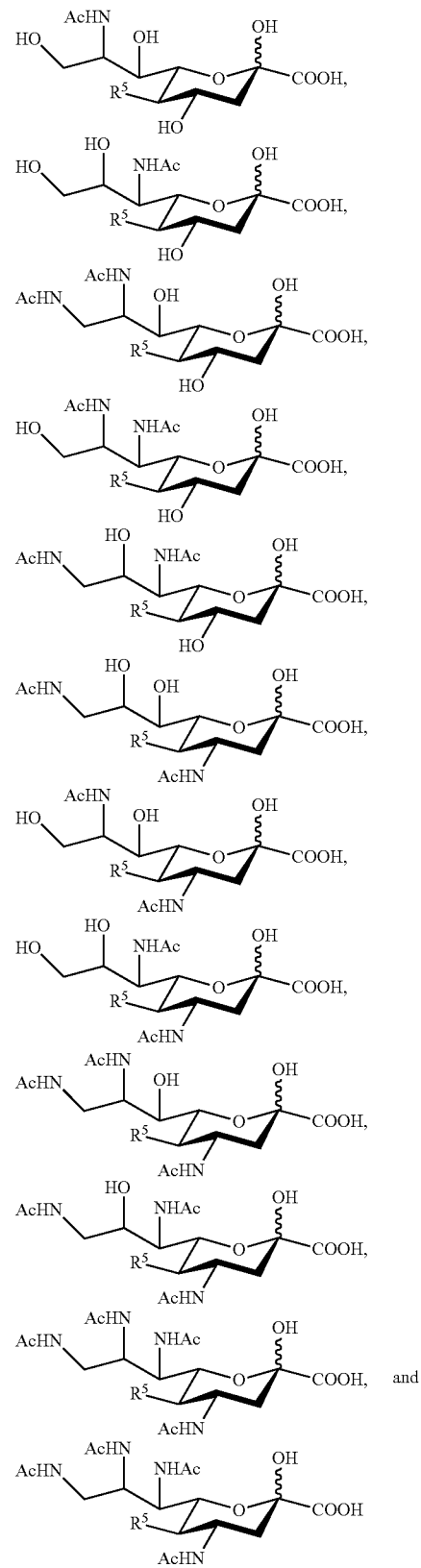

In some embodiments, R$^5$ is —OH in compounds of Group A. In some embodiments, R$^5$ is —OAc in compounds of Group A. In some embodiments, R$^5$ is —N$_3$ or —NH$_2$ in compounds of Group A. In some embodiments, $R^5$ is —$N_3$ in compounds of Group A. In some embodiments, $R^5$ is —NHAc in compounds of Group A. In some embodiments, $R^5$ is —NHGc in compounds of Group A.

In some embodiments, the compound is selected from Group B consisting of:

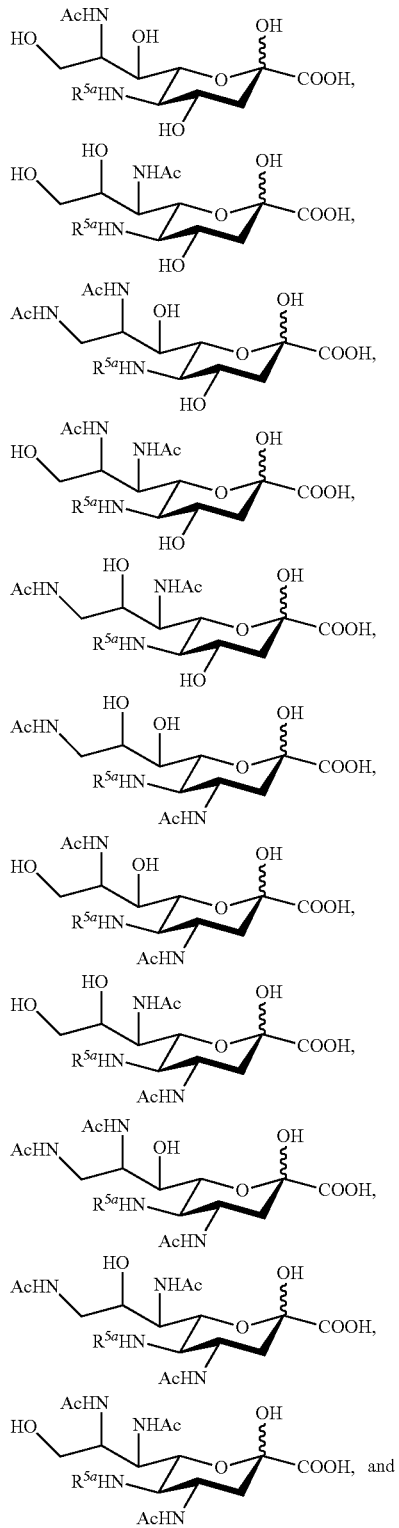

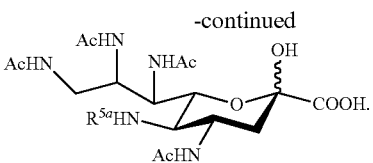

In some embodiments, $R^{5a}$ is Ac in compounds of Group B. In some embodiments, $R^{5a}$ is Gc in compounds of Group B.

In some embodiments, $R^1$ is H, and $R^2$, $R^3$, and $R^4$ are independently selected from the group consisting of —$N_3$, —$NH_2$, and —OH. In some embodiments, $R^1$ is H, and $R^2$, $R^3$, and $R^4$ are independently selected from the group consisting of —$N_3$ and —OH. In some such embodiments, $R^5$ is selected from the group consisting of —$NHR^{5a}$, —OH, and —OAc. In some embodiments, $R^1$ is H; $R^2$, $R^3$, and $R^4$ are independently selected from the group consisting of —$N_3$ and —OH; and $R^5$ is —$NHR^5$a. In some embodiments, $R^1$ is H; $R^2$, $R^3$, and $R^4$ are independently selected from the group consisting of —$N_3$ and —OH; and $R^5$ is —NHAc. In some embodiments, $R^1$ is H; $R^2$, $R^3$, and $R^4$ are independently selected from the group consisting of —$N_3$ and —OH; and $R^5$ is —NHGc.

In some embodiments, $R^1$ is H, and $R^2$, $R^3$, and $R^4$ are —$N_3$ or —$NH_2$. In some embodiments, $R^1$ is H, and $R^2$, $R^3$, and $R^4$ are —$N_3$. In some such embodiments, $R^5$ is selected from the group consisting of —$NHR^{5a}$, —OH, and —OAc. In some embodiments, $R^1$ is H; $R^2$, $R^3$, and $R^4$ are —$N_3$; and $R^5$ is —$NHR^5$a. In some embodiments, $R^1$ is H; $R^2$, $R^3$, and $R^4$ are —$N_3$; and $R^5$ is —NHAc. In some embodiments, $R^1$ is H; $R^2$, $R^3$, and $R^4$ are —$N_3$; and $R^5$ is —NHGc.

In some embodiments, $R^1$ is H, and $R^2$, $R^3$, and $R^4$ are independently selected from the group consisting of —NHAc and —OH. In some such embodiments, $R^5$ is selected from the group consisting of —$NHR^{5a}$, —OH, and —OAc. In some embodiments, $R^1$ is H; $R^2$, $R^3$, and $R^4$ are independently selected from the group consisting of —NHAc and —OH; and $R^5$ is —$NHR^{5a}$. In some embodiments, $R^1$ is H; $R^2$, $R^3$, and $R^4$ are independently selected from the group consisting of —NHAc and —OH; and $R^5$ is —NHAc. In some embodiments, $R^1$ is H; $R^2$, $R^3$, and $R^4$ are independently selected from the group consisting of —NHAc and —OH; and $R^5$ is —NHGc.

In some embodiments, $R^1$ is H, and $R^2$, $R^3$, and $R^4$ are —NHAc. In some such embodiments, $R^5$ is selected from the group consisting of —$NHR^{5a}$, —OH, and —OAc. In some embodiments, $R^1$ is H; $R^2$, $R^3$, and $R^4$ are —NHAc; and $R^5$ is —$NHR^5$a. In some embodiments, $R^1$ is H; $R^2$, $R^3$, and $R^4$ are —NHAc; and $R^5$ is —NHAc. In some embodiments, $R^1$ is H; $R^2$, $R^3$, and $R^4$ are —NHAc; and $R^5$ is —NHGc.

In some embodiments, $R^1$ is H; $R^5$ is —OH or —OAc; and at least one of $R^2$, $R^3$, and $R^4$ is independently —NHAc, —$N_3$, or —$NH_2$. In some embodiments, $R^1$ is H; $R^5$ is —OH or —OAc; and at least one of $R^2$, $R^3$, and $R^4$ is independently —NHAc or —$N_3$. In some embodiments, $R^1$ is H; $R^5$ is —OH or —OAc; and at least two of $R^2$, $R^3$, and $R^4$ are independently —NHAc or —$N_3$. In some embodiments, $R^1$ is H; $R^5$ is —OH or —OAc; and $R^2$, $R^3$, and $R^4$ are independently —NHAc or —$N_3$. In some embodiments, remaining $R^2$, $R^3$, and $R^4$ groups are independently selected from —OH and —OAc. In some such embodiments, the remaining $R^2$, $R^3$, and $R^4$ groups are —OH.

In some embodiments, $R^1$ is H; $R^5$ is —OH; and at least one of $R^2$, $R^3$, and $R^4$ is independently —NHAc, —$N_3$, or —NH$_2$. In some embodiments, R$^1$ is H; R$^5$ is —OH; and at least one of R$^2$, R$^3$, and R$^4$ is independently —NHAc or —N$_3$. In some embodiments, R$^1$ is H; R$^5$ is —OH; and at least two of R$^2$, R$^3$, and R$^4$ are independently —NHAc or —N$_3$. In some embodiments, R$^1$ is H; R$^5$ is —OH; and R$^2$, R$^3$, and R$^4$ are independently —NHAc or —N$_3$. In some embodiments, remaining R$^2$, R$^3$, and R$^4$ groups are independently selected from —OH and —OAc. In some such embodiments, the remaining R$^2$, R$^3$, and R$^4$ groups are —OH.

In some embodiments, R$^1$ is H; R$^5$ is —OAc; and at least one of R$^2$, R$^3$, and R$^4$ is independently —NHAc, —N$_3$, or —NH$_2$. In some embodiments, R$^1$ is H; R$^5$ is —OAc; and at least one of R$^2$, R$^3$, and R$^4$ is independently —NHAc or —N$_3$. In some embodiments, R$^1$ is H; R$^5$ is —OAc; and at least two of R$^2$, R$^3$, and R$^4$ are independently —NHAc or —N$_3$. In some embodiments, R$^1$ is H; R$^5$ is —OAc; and R$^2$, R$^3$, and R$^4$ are independently —NHAc or —N$_3$. In some embodiments, remaining R$^2$, R$^3$, and R$^4$ groups are independently selected from —OH and —OAc. In some such embodiments, the remaining R$^2$, R$^3$, and R$^4$ groups are —OH.

In some embodiments, R$^1$ is H; R$^5$ is —OH; and at least one of R$^2$, R$^3$, and R$^4$ is —N$_3$ or —NH$_2$. In some embodiments, R$^1$ is H; R$^5$ is —OH; and at least one of R$^2$, R$^3$, and R$^4$ is —N$_3$. In some embodiments, R$^1$ is H; R$^5$ is —OH; and at least two of R$^2$, R$^3$, and R$^4$ are —N$_3$. In some embodiments, R$^1$ is H; R$^5$ is —OH; and R$^2$, R$^3$, and R$^4$ are —N$_3$. In some embodiments, remaining R$^2$, R$^3$, and R$^4$ groups are independently selected from —OH and —OAc. In some such embodiments, the remaining R$^2$, R$^3$, and R$^4$ groups are —OH.

In some embodiments, R$^1$ is H; R$^5$ is —OAc; and at least one of R$^2$, R$^3$, and R$^4$ is —N$_3$ or —NH$_2$. In some embodiments, R$^1$ is H; R$^5$ is —OAc; and at least one of R$^2$, R$^3$, and R$^4$ is —N$_3$. In some embodiments, R$^1$ is H; R$^5$ is —OAc; and at least two of R$^2$, R$^3$, and R$^4$ are —N$_3$. In some embodiments, R$^1$ is H; R$^5$ is —OAc; and R$^2$, R$^3$, and R$^4$—N$_3$. In some embodiments, remaining R$^2$, R$^3$, and R$^4$ groups are independently selected from —OH and —OAc. In some such embodiments, the remaining R$^2$, R$^3$, and R$^4$ groups are —OH.

In some embodiments, R$^1$ is H; R$^5$ is —OH; and at least one of R$^2$, R$^3$, and R$^4$ is —NHAc. In some embodiments, R$^1$ is H; R$^5$ is —OH; and at least two of R$^2$, R$^3$, and R$^4$ are —NHAc. In some embodiments, R$^1$ is H; R$^5$ is —OH; and R$^2$, R$^3$, and R$^4$ are —NHAc. In some embodiments, remaining R$^2$, R$^3$, and R$^4$ groups are independently selected from —OH and —OAc. In some such embodiments, the remaining R$^2$, R$^3$, and R$^4$ groups are —OH.

In some embodiments, R$^1$ is H; R$^5$ is —OAc; and at least one of R$^2$, R$^3$, and R$^4$ is —NHAc. In some embodiments, R$^1$ is H; R$^5$ is —OAc; and at least two of R$^2$, R$^3$, and R$^4$ are —NHAc. In some embodiments, R$^1$ is H; R$^5$ is —OAc; and R$^2$, R$^3$, and R$^4$ are —NHAc. In some embodiments, remaining R$^2$, R$^3$, and R$^4$ groups are independently selected from —OH and —OAc. In some such embodiments, the remaining R$^2$, R$^3$, and R$^4$ groups are —OH.

In some embodiments, R$^1$ is H; R$^5$ is —NHR$^{5a}$; and at least one of R$^2$, R$^3$, and R$^4$ is independently —NHAc, —N$_3$, or —NH$_2$. In some embodiments, R$^1$ is H; R$^5$ is —NHR$^{5a}$; and at least one of R$^2$, R$^3$, and R$^4$ is independently —NHAc or —N$_3$. In some embodiments, R$^1$ is H; R$^5$ is —NHR$^{5a}$; and at least two of R$^2$, R$^3$, and R$^4$ are independently —NHAc or —N$_3$. In some embodiments, R$^1$ is H; R$^5$ is —NHR$^{5a}$; and R$^2$, R$^3$, and R$^4$ are independently —NHAc or —N$_3$. In some embodiments, remaining R$^2$, R$^3$, and R$^4$ groups are independently selected from —OH and —OAc. In some such embodiments, the remaining R$^2$, R$^3$, and R$^4$ groups are —OH.

In some embodiments, R$^1$ is H; R$^5$ is —NHR$^{5a}$; and at least one of R$^2$, R$^3$, and R$^4$ is —N$_3$ or —NH$_2$. In some embodiments, R$^1$ is H; R$^5$ is —NHR$^{5a}$; and at least one of R$^2$, R$^3$, and R$^4$ is —N$_3$. In some embodiments, R$^1$ is H; R$^5$ is —NHR$^{5a}$; and at least two of R$^2$, R$^3$, and R$^4$ are —N$_3$. In some embodiments, R$^1$ is H; R$^5$ is —NHR$^{5a}$; and R$^2$, R$^3$, and R$^4$ are —N$_3$. In some embodiments, remaining R$^2$, R$^3$, and R$^4$ groups are independently selected from —OH and —OAc. In some such embodiments, the remaining R$^2$, R$^3$, and R$^4$ groups are —OH.

In some embodiments, R$^1$ is H; R$^5$ is —NHR$^{5a}$; and at least one of R$^2$, R$^3$, and R$^4$ is —NHAc. In some embodiments, R$^1$ is H; R$^5$ is —NHR$^{5a}$; and at least two of R$^2$, R$^3$, and R$^4$ are —NHAc. In some embodiments, R$^1$ is H; R$^5$ is —NHR$^{5a}$; and R$^2$, R$^3$, and R$^4$ are —NHAc. In some embodiments, remaining R$^2$, R$^3$, and R$^4$ groups are independently selected from —OH and —OAc. In some such embodiments, the remaining R$^2$, R$^3$, and R$^4$ groups are —OH.

In some embodiments, R$^1$ is H; R$^5$ is —NHAc; and at least one of R$^2$, R$^3$, and R$^4$ is —N$_3$ or —NH$_2$. In some embodiments, R$^1$ is H; R$^5$ is —NHAc; and at least one of R$^2$, R$^3$, and R$^4$ is —N$_3$. In some embodiments, R$^1$ is H; R$^5$ is —NHAc; and at least two of R$^2$, R$^3$, and R$^4$ are —N$_3$. In some embodiments, R$^1$ is H; R$^5$ is —NHAc; and R$^2$, R$^3$, and R$^4$ are —N$_3$. In some embodiments, remaining R$^2$, R$^3$, and R$^4$ groups are independently selected from —OH and —OAc. In some such embodiments, the remaining R$^2$, R$^3$, and R$^4$ groups are —OH.

In some embodiments, R$^1$ is H; R$^5$ is —NHGc; and at least one of R$^2$, R$^3$, and R$^4$ is —NHAc. In some embodiments, R$^1$ is H; R$^5$ is —NHGc; and at least two of R$^2$, R$^3$, and R$^4$ are —NHAc. In some embodiments, R$^1$ is H; R$^5$ is —NHGc; and R$^2$, R$^3$, and R$^4$ are —NHAc. In some embodiments, remaining R$^2$, R$^3$, and R$^4$ groups are independently selected from —OH and —OAc. In some such embodiments, the remaining R$^2$, R$^3$, and R$^4$ groups are —OH.

In some embodiments, R$^1$ is H, and each of R$^2$, R$^3$, and R$^4$ is independently selected from the group consisting of H, —NHAc, and —OH.

In some embodiments, R$^1$ is H, and each of R$^2$, R$^3$, and R$^4$ is independently selected from the group consisting of H, —N$_3$, —NH$_2$, and —OH. In some embodiments, R$^1$ is H, and each of R$^2$, R$^3$, and R$^4$ is independently selected from the group consisting of H, —N$_3$, and —OH.

In some embodiments, the compound is selected from Group C consisting of:

-continued

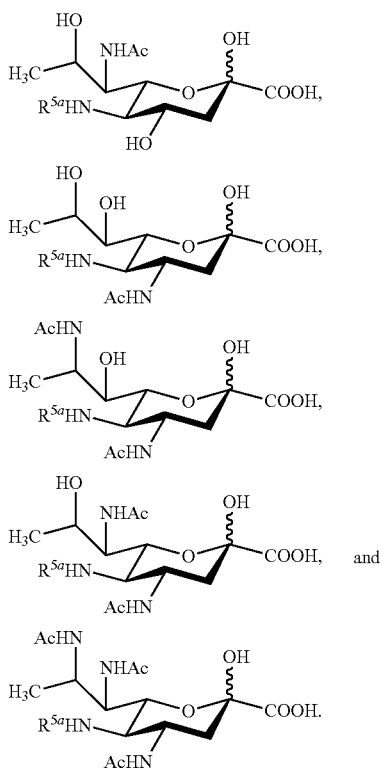

In some embodiments, $R^{5a}$ is Ac in compounds of Group C. In some embodiments, $R^{5a}$ is Gc in compounds of Group C.

In some embodiments, the compound is selected from Group D consisting of:

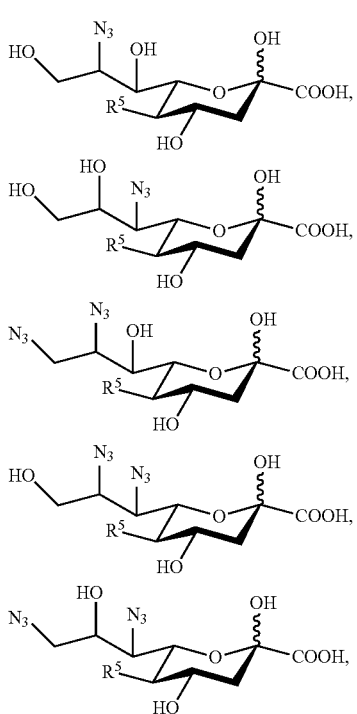

-continued

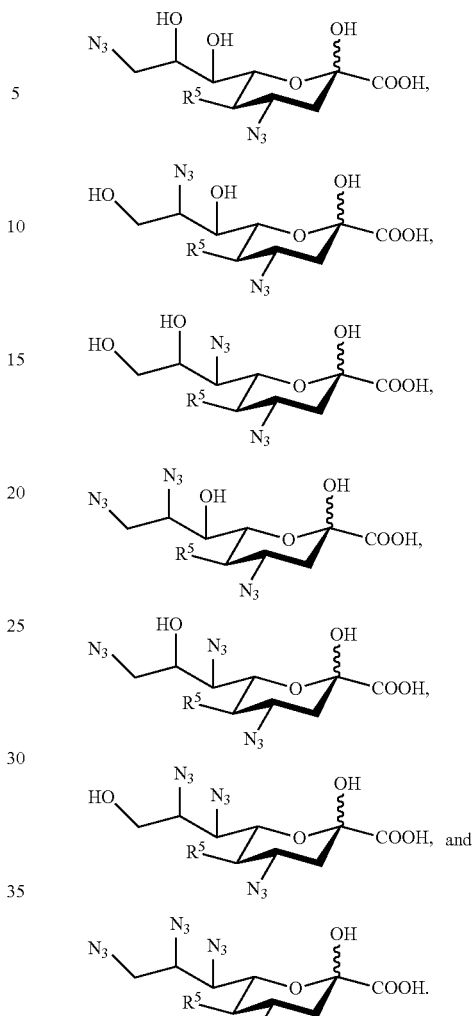

In some embodiments, $R^5$ is —OH in compounds of Group D. In some embodiments, $R^5$ is —OAc in compounds of Group D. In some embodiments, $R^5$ is —N$_3$ or —NH$_2$ in compounds of Group D. In some embodiments, $R^5$ is —N$_3$ in compounds of Group D. In some embodiments, $R^5$ is —NHAc in compounds of Group D. In some embodiments, $R^5$ is —NHGc in compounds of Group D.

In some embodiments, the compound is selected from Group E consisting of:

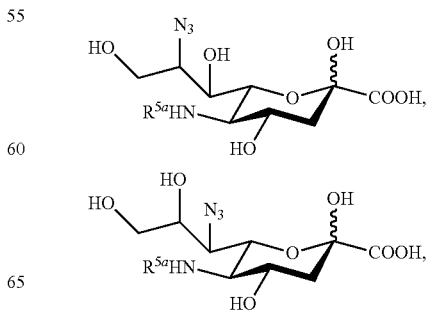

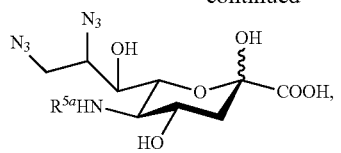
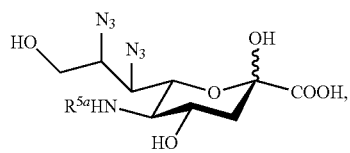
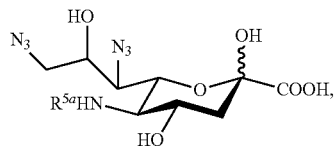
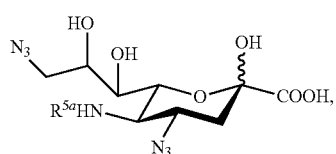
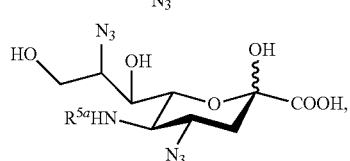
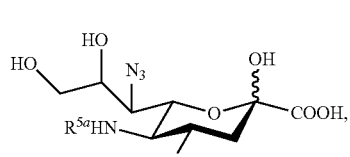
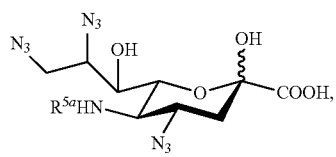
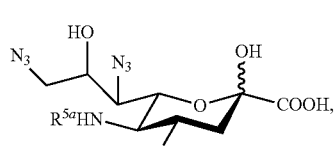
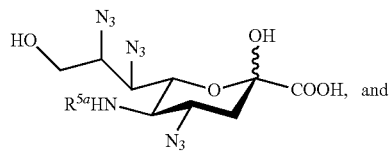
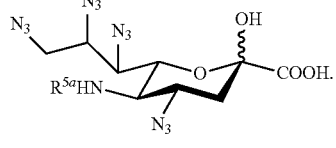
In some embodiments, the compound is selected from Group F consisting of:
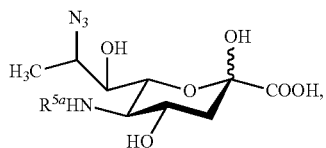
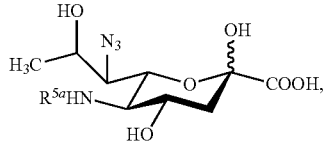
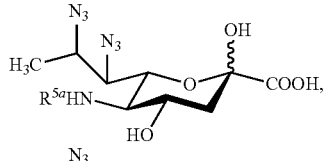
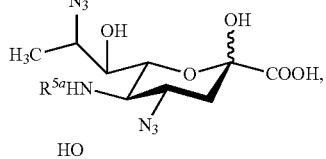
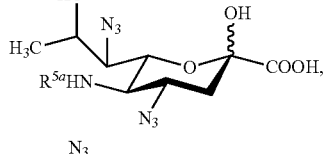
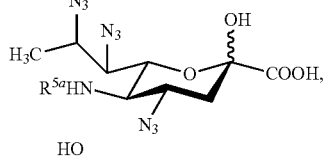
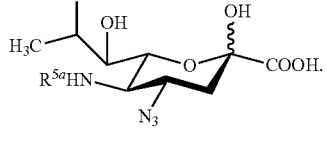
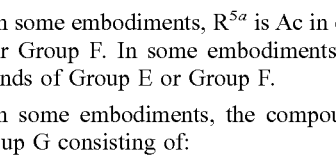
In some embodiments, $R^{5a}$ is Ac in compounds of Group E or Group F. In some embodiments, $R^{5a}$ is Gc in compounds of Group E or Group F.
In some embodiments, the compound is selected from Group G consisting of:
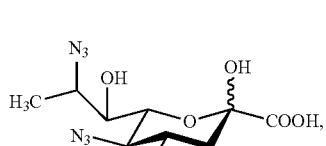
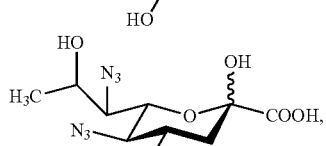
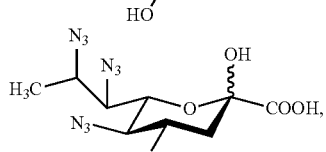

-continued

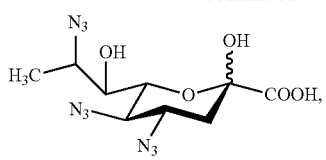

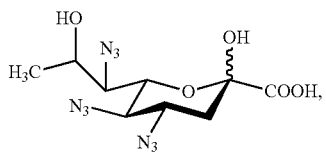

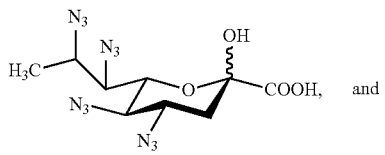 and

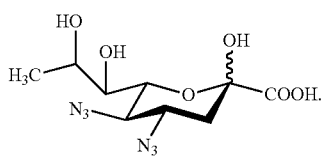

In some embodiments, the compound is selected from Group H consisting of:

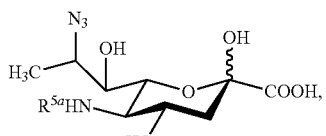

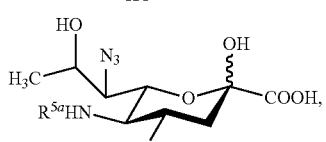

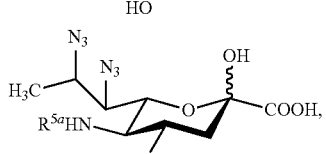

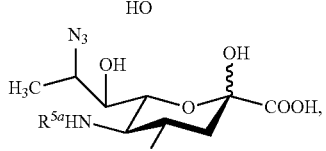

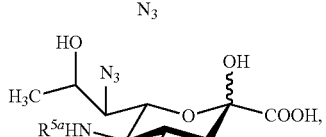

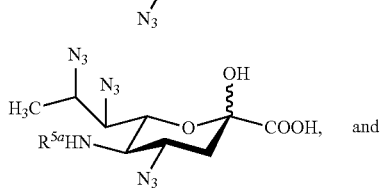 and

-continued

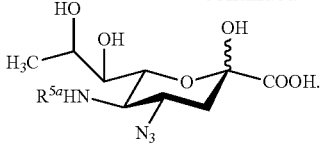

In some embodiments, $R^{5a}$ is Ac in compounds of Group H. In some embodiments, $R^{5a}$ is Gc in compounds of Group H.

In some embodiments, the compound is selected from Group J consisting of:

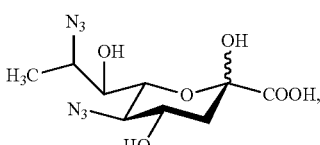

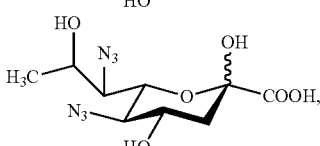

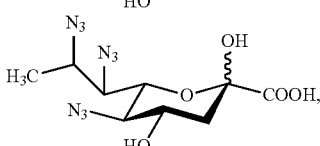

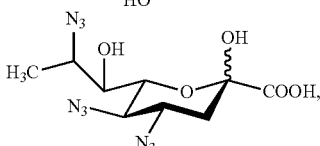

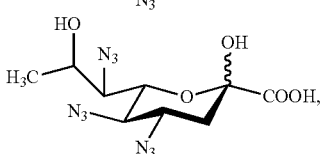

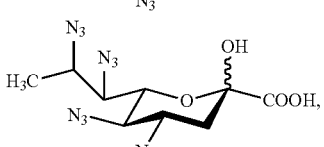

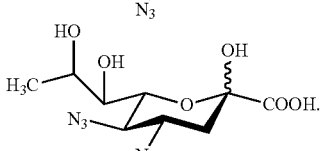

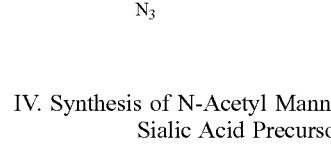 and

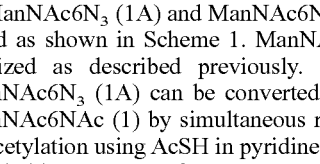

IV. Synthesis of N-Acetyl Mannosamine-Based Sialic Acid Precursors

ManNAc6N$_3$ (1A) and ManNAc6NAc (1) can be synthesized as shown in Scheme 1. ManNAc6N$_3$ (1A) was synthesized as described previously. The azido group in ManNAc6N$_3$ (1A) can be converted to N-acetyl group in ManNAc6NAc (1) by simultaneous reduction of azide and N-acetylation using AcSH in pyridine. ManNAc6NAc (1) is a suitable precursor for Neu5Ac9NAc and for one-pot three-enzyme synthesis of a library of α2-3- and α2-6- linked Neu5Ac9NAc-containing sialosides using a *Pasteurella multocida* sialic acid aldolase (PmAldolase), *Neisseria meningitidis* CMP-sialic acid synthetase (NmCSS), and *Pasteurella multocida* α2-3-sialyltransferase 1 M144D mutant (PmST1 M144D) or *Photobacterium* species α2-6-sialyltransferase (Psp2,6ST).

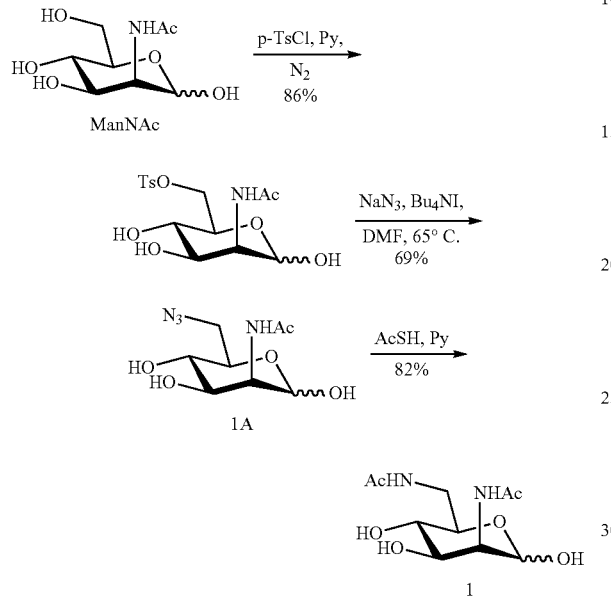

ManNAc4N$_3$ (2A) and ManNAc4NAc (2) can be prepared as shown in Scheme 2. ManNAc4N$_3$ (2A) can be synthesized using the method of Thomson (Carbohydrate Research 1995; 274:29-44). The azido group in ManNAc4N$_3$ (2A) can be converted to an N-acetyl group in ManNAc4NAc (2) in one step using AcSH in pyridine as described above for the conversion of ManNAc6N$_3$ (1A) to ManNAc6NAc (1). ManNAc4NAc (2) is a suitable substrate for synthesizing Neu5Ac7NAc and α2-3- and α2-6-linked Neu5Ac7NAc-containing sialosides using a one-pot three-enzyme sialylation strategy.

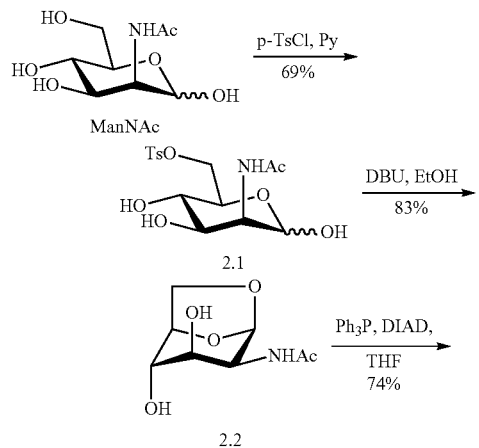

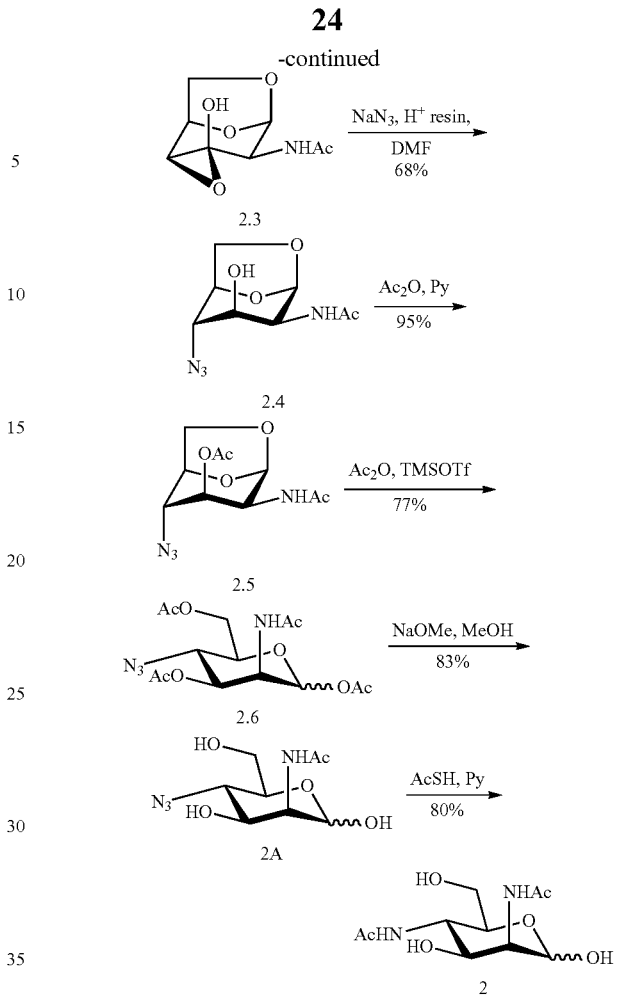

5-azido-ManNAc (ManNAc5N$_3$, 3A) can be synthesized from commercially available 1,2:5,6-di-O-isopropylidene-α-D-glucopyranose as shown in Scheme 3. After benzylation, the 5,6-isopropylidene protecting group in 3.1 can be selectively removed by mild acid hydrolysis and the resulting intermediate diol 3.2 is treated with methyl chloroformate to produce carbonate 3.3. Treatment of 3.3 with benzyl alcohol in the presence of acid ion exchange resin affords benzyl furanoside 3.4 as a mixture of α- and β-anomers, which can be separated by flash chromatography. The C-3 OH of the α-anomer 3.4 can be converted to the corresponding triflate ester by the treatment with Tf$_2$O followed by the reaction with NaN$_3$ in DMF to produce 2-azido-2-deoxy-manopyranoside 3.5. The carbonate protecting group can be removed by treatment of 3.5 with sodium methoxide in methanol, selective 6-O-benzylation of the azido diol can be achieved by forming a dibutylstannylene derivative followed by alkylation with this intermediate with benzyl bromide to produce 3.6. The 2-azido group of 3.6 can be converted to acetamido group to produce 3.7 by treating with AcSH in pyridine. Epimerization of 1,6-di-O-benzoyl-2,3-O-isopropylidene-β-D-mannofuranose (3.7) to the corresponding epi-hydroxyl stereoisomer (3.8) can be achieved by activation of the hydroxyl group by triflic anhydride in a mixture of pyridine and DCM followed by an S$_N^2$ reaction using a nucleophilic reagent (NaNO$_2$). The product 3.8 can be converted to triflate ester by the treatment with Tf$_2$O and then reacted with NaN$_3$ in DMF to yield 3.9. The azide group in 3.9 can be converted to an acetamido group to produce 3.10 by treating with AcSH in pyridine. After hydrogenation in the presence of $H_2$ and Pd/C, ManNAc5NAc (3) can be obtained. ManNAc5N$_3$ (3A) can be readily accessible from 3.9 by amino-azido conversion using trifluoromethanesulfonyl azide via intermediates 3.11 and 3.12.
Scheme 3. Preparation of Neu5Ac8NAc precursors.
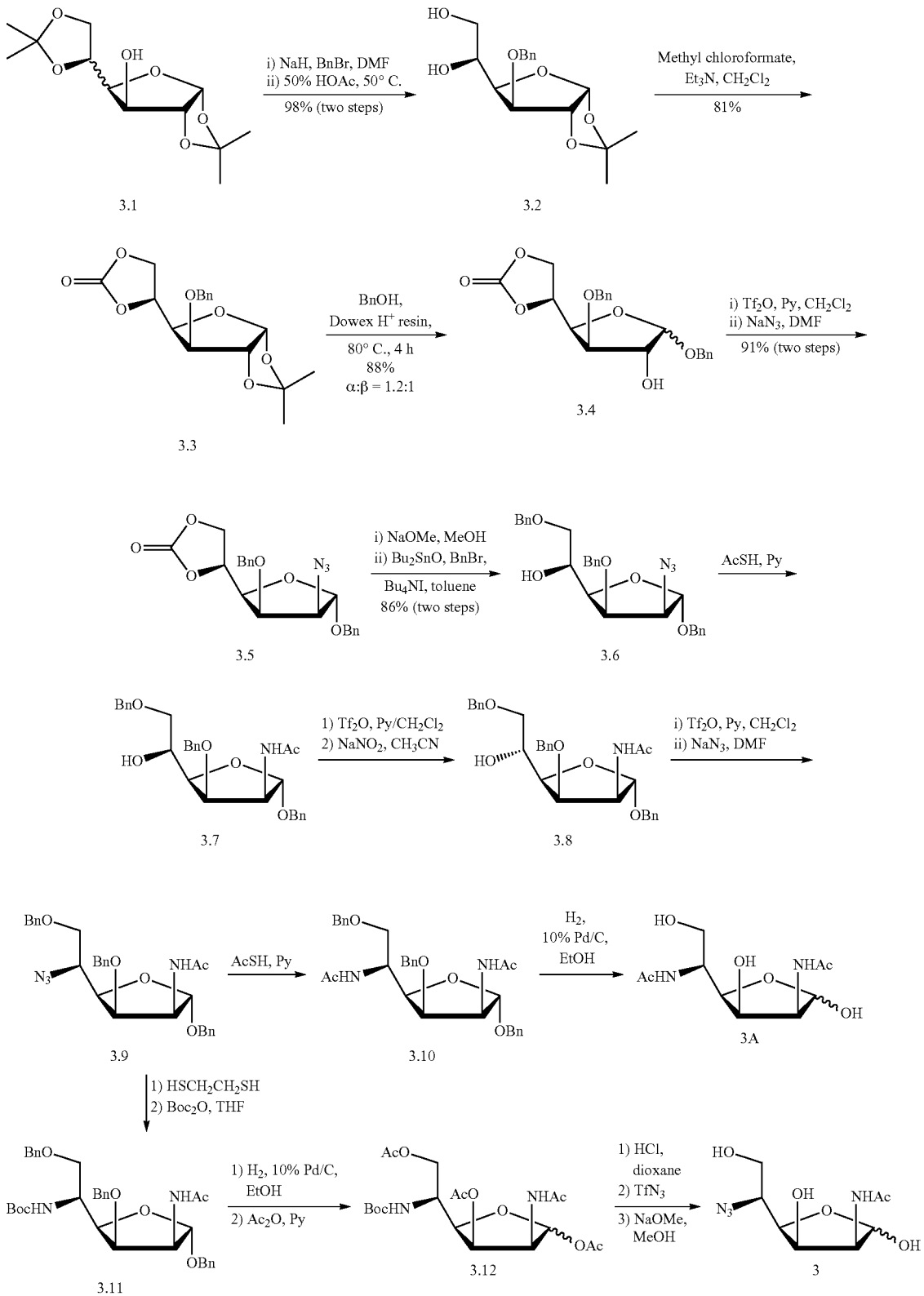

ManNAc4N$_3$6N$_3$ (4A) and ManNAc4,6NAc$_2$ (4) (Scheme 4) can be synthesized from ManNAc4N$_3$ (2A). The 6-OH in 3 can be converted into O-tosylate (4.1), which can be subsequently displaced by sodium azide in DMF to produce 4,6-diazido-ManNAc (ManNAc4N$_3$6N$_3$, 4A). Treating 4A with AcSH in pyridine affords ManNAc4,6NAc$_2$ (4) smoothly.

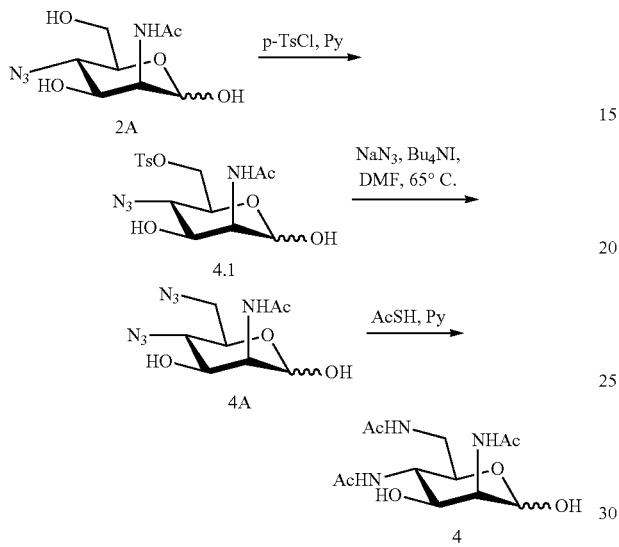

ManNAc5N$_3$6N$_3$ (SA), and ManNAc5,6NAc$_2$ (5) can be synthesized as shown in Scheme 5. Selective p-toluenesulfonylation of ManNAc5N$_3$ (3A) forms tosylate (5.1), which can be converted to ManNAc5N$_3$6N$_3$ (SA). Treating 5A with AcSH in pyridine provides ManNAc5,6NAc$_2$ (5).

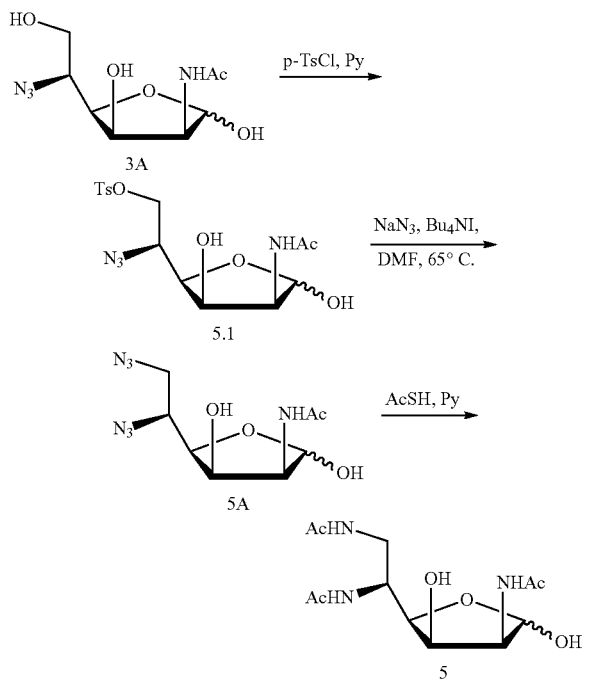

V. Synthesis of N-Acetyl Sialic Acids from ManNAc Precursors

N-acyl sialic acids can be prepared enzymatically from the precursors described above. For example, Neu5Ac9NAc can be obtained in good yield from ManNAc6NAc (1, Scheme 1) using an enzymatic reaction catalyzed by *Pasteurella multocida* sialic acid aldolase (PmAldolase). Neu5Ac9NAc can be used together with its 9-O-acetyl counterpart Neu5,9Ac$_2$ for metabolic incorporation studies as described below. Additional N-acetyl Neu5Ac derivatives including Neu5Ac7NAc, Neu5Ac8NAc, Neu5Ac7,9NAc$_2$, and Neu5Ac8,9NAc$_2$ can be synthesized from the corresponding precursors ManNAc4NAc (2), ManNAc5NAc (3), ManNAc4,6NAc$_2$ (4), and ManNAc5,6NAc$_2$ (5), respectively.

Accordingly another aspect of the invention provides method for preparing a compound according to Formula II:

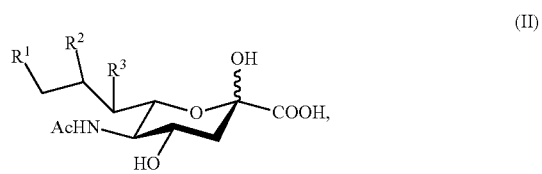

the method comprising forming a reaction mixture comprising a sialic acid aldolase, pyruvic acid, and a compound according to Formula III:
or an isomer thereof,

under conditions sufficient to form the compound of Formula II;
wherein:
$R^1$, $R^2$, $R^3$, and $R^4$ are independently selected from the group consisting of —NHAc, —N$_3$, —NH$_2$, —OAc, —OH, and hydrogen;
$R^5$ is selected from the group consisting of —NHR$^{5a}$, —N$_3$, —NH$_2$, —OAc, —OH, and hydrogen;
$R^{5a}$ is selected from the group consisting of Ac, Gc, GcAc, GcN$_3$, GcNH$_2$, GcNAc, and hydrogen;
Ac is —C(O)CH$_3$; Gc is —C(O)CH$_2$OH; GcAc is —C(O)CH$_2$OC(O)CH$_3$;
GcN$_3$ is —C(O)CH$_2$N$_3$; GcNH$_2$ is —C(O)CH$_2$NH$_2$; and
GcNAc is —C(O)CH$_2$NHC(O)CH$_3$.

In some embodiments, methods for preparing compounds according to Formula II are provided as described above wherein:
$R^1$, $R^2$, $R^3$, and $R^4$ are independently selected from the group consisting of —NHAc, —N$_3$, —OAc, —OH, and hydrogen;

$R^5$ is selected from the group consisting of —NHR$^{5a}$, —N$_3$, —OAc, —OH, and hydrogen; and $R^{5a}$ is selected from the group consisting of Ac and Gc.

In some embodiments, $R^1$, $R^2$, and $R^3$ are independently selected from the group consisting of —NHAc and —OH; at least one of $R^1$, $R^2$, and $R^3$ is —NHAc; and $R^5$ is —NHAc.

Any suitable sialic acid aldolase (i.e., N-Acetylneuraminate pyruvate lyase, EC 4.1.3.3) can be used in the methods of the invention. For example, sialic acid aldolases from *E. coli, L. plantarum, P. multocida,* or *N. meningitidis* can be used.

In some embodiments, the sialic acid aldolase is PmAldolase (NCBI Accession No. WP_005723432.1) or a catalytically active variant thereof. In some embodiments, the sialic acid aldolase comprises the polypeptide sequence: TNIAIIPARAGSKGIPDKNLQPVGGHSLIGRAILAAKNADVFDMIVVTSDGDNILREAE KYGALALKRPAELAQDNSRTIDAILHALESLNIREGTCTLLQPTSPLRDHLDIKNAMD MYVNGGVHSVV SACECEHHPYKAFALSKDHEVLPVREIADFEAVRQTLPKMYRAN GAIYINDIAQLLKEKYFFIPPLKFYLMPTYHSVDIDVKQDLELAEILSNK, or a catalytically active variant thereof.

In some embodiments, the sialic acid aldolase *E. coli* sialic acid aldolase.

VI. Synthesis of N-Acetyl Sialic Acids from Neu5Ac

Neu5Ac4NAc (6) can be synthesized from Neu5Ac as shown in Scheme 6. Target Neu5Ac4N$_3$ (6A) and Neu5Ac4NAc (6) can be synthesized by following the method of Zbiral (Carbohydrate Research. 1989; 194:c15-8). As shown in Scheme 6, sialic acid derivative 6.1 can be obtained from Neu5Ac. It is transformed via the 4-oxo-derivative 6.2 into the 4-epi-sialic acid derivative 6.3. Reacting 6.3 with PPh$_3$-diethylazodicarboxylate (DEAD)-3M ammonia (toluene) in THF produces compound 6.4 as the main product. Compound 6.4 can be treated with 80% HOAc and then go through saponification to produce Neu5Ac4N$_3$ (6A). The 4-azido group in 6.4 can be converted to an acetamido group to produce 6.5 by treating with AcSH in pyridine. Neu5Ac4NAc (6) can be produced from compound 6.5 after deprotection steps.

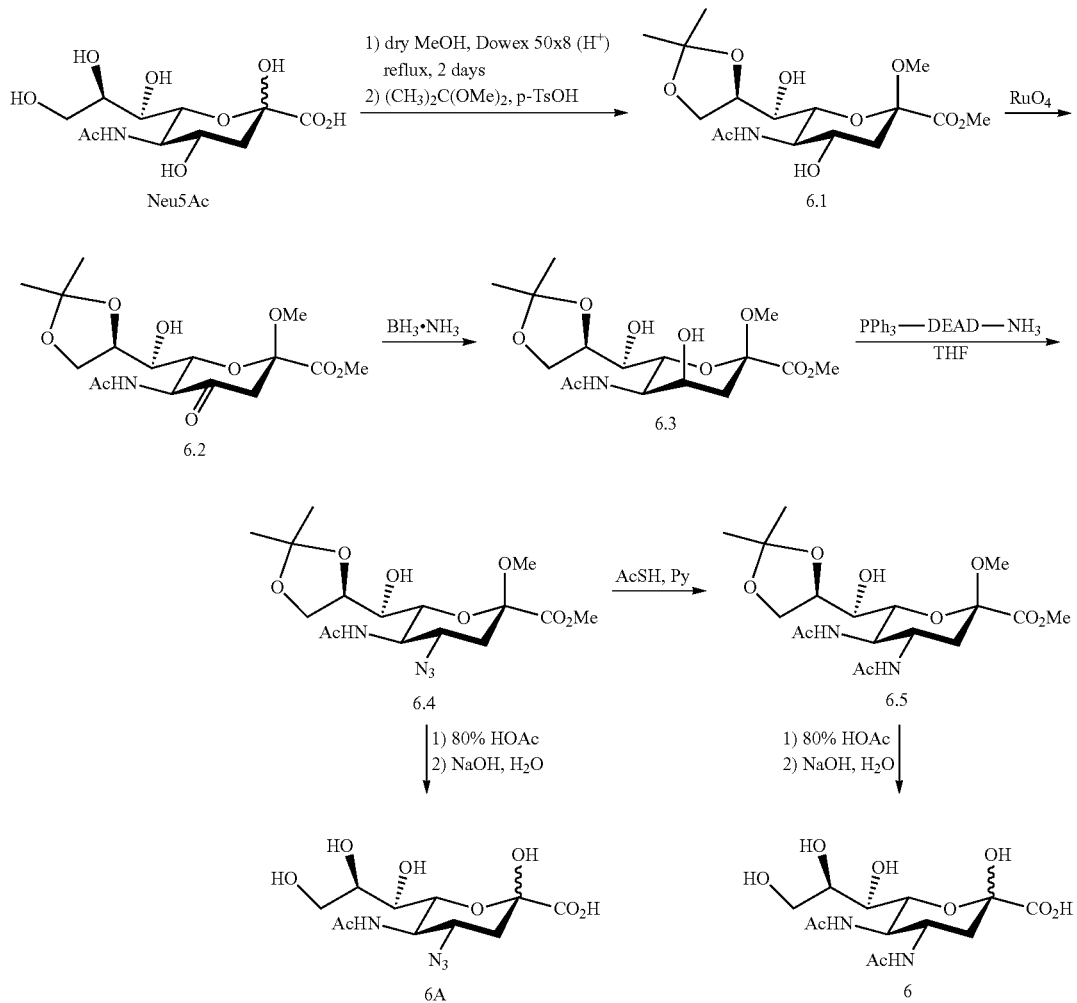

Scheme 6. Preparation of Neu5Ac4NAc and Neu5Ac4NAc precursors.

The preparation of Neu5Ac8NAc precursors is described above and depicted in Scheme 3. Alternatively, 8-azido-8-deoxy-N-acetylneuraminic acid (Neu5Ac8N$_3$) and 8-acetamido-8-deoxy-N-acetylneuraminic acid (Neu5Ac8NAc) can be prepared using 2,7-anhydro-N-acetylneuraminic acid (2,7-anhydro-Neu5Ac, 7.1) as a synthon. Using 2,7-anhydro-Neu5Ac as a starting material has several advantages. It can be readily obtained from Neu5Ac by a one-pot multienzyme (OPME) system containing cytidine 5'-triphosphate (CTP), a CMP-sialic acid synthetase, (e.g., *Neisseria meningitidis* CMP-sialic acid synthetase, "NmCSS"), an α2-3-sialyltransferase (e.g., *Pasteurella multocida* α2-3-sialyltransferase 1, "PmST1," or its mutant PmST1 M144D), a sialyltransferase acceptor (e.g., a galactoside such as lactose), and *Streptococcus pneumoniae* sialidase SpNanB as shown in Scheme 7A. The Neu5Ac can be obtained from N-acetylmannosamine using a sialic acid aldolase (e.g., from *P. multocida*), as shown in Scheme 7A. Also advantageously, the C-2 and C-7 positions of 2,7-anhydro-Neu5Ac (7.1) are already protected and less complicated protection scheme can be used.

As shown in Scheme 7B, treatment of 2,7-anhydro-Neu5Ac (7.1) with H$^+$ ion exchange resin in methanol can be used to produce ester 7.2. A benzylidene acetal can be used to protect hydroxyl groups at C-8 and C-9 simultaneously to produce 7.3. Acetylation of the C-4 hydroxyl group in 7.3 provides fully protected 2,7-anhydro-Neu5Ac 7.4. The C-8 hydroxyl group can be selectively deprotected using borane trimethylamine with aluminum chloride to provide 7.5. Double inversion of the stereocenter at the C-8 position of 7.5 can be achieved using trifluoromethanesulfonic anhydride (Tf$_2$O) and sodium nitrite, followed by trifluoromethanesulfonic anhydride (Tf$_2$O) and sodium azide, to produce 8-azido-8-deoxy compound 7.6. Thioacetic acid (AcSH) in pyridine can be used to covert the azido group to an acetamido group to produce compound 7.7. Finally, deprotection of compounds 7.6 and 7.7 (e.g., by sequential treatment with sodium methoxide in methanol; hydrochloric acid; and catalytic hydrogenation) provides target compounds 2,7-anhydro-Neu5Ac8N$_3$ (7A) and 2,7-anhydro-Neu5Ac8NAc (7). An analogous approach for the preparation of Neu5Ac4N$_3$ and Neu5Ac4NAc is described below in Example 17.

Scheme 7A. One-pot multi-enzyme preparation of 2,7-anhydro-Neu5Ac from ManNAc via Neu5Ac.

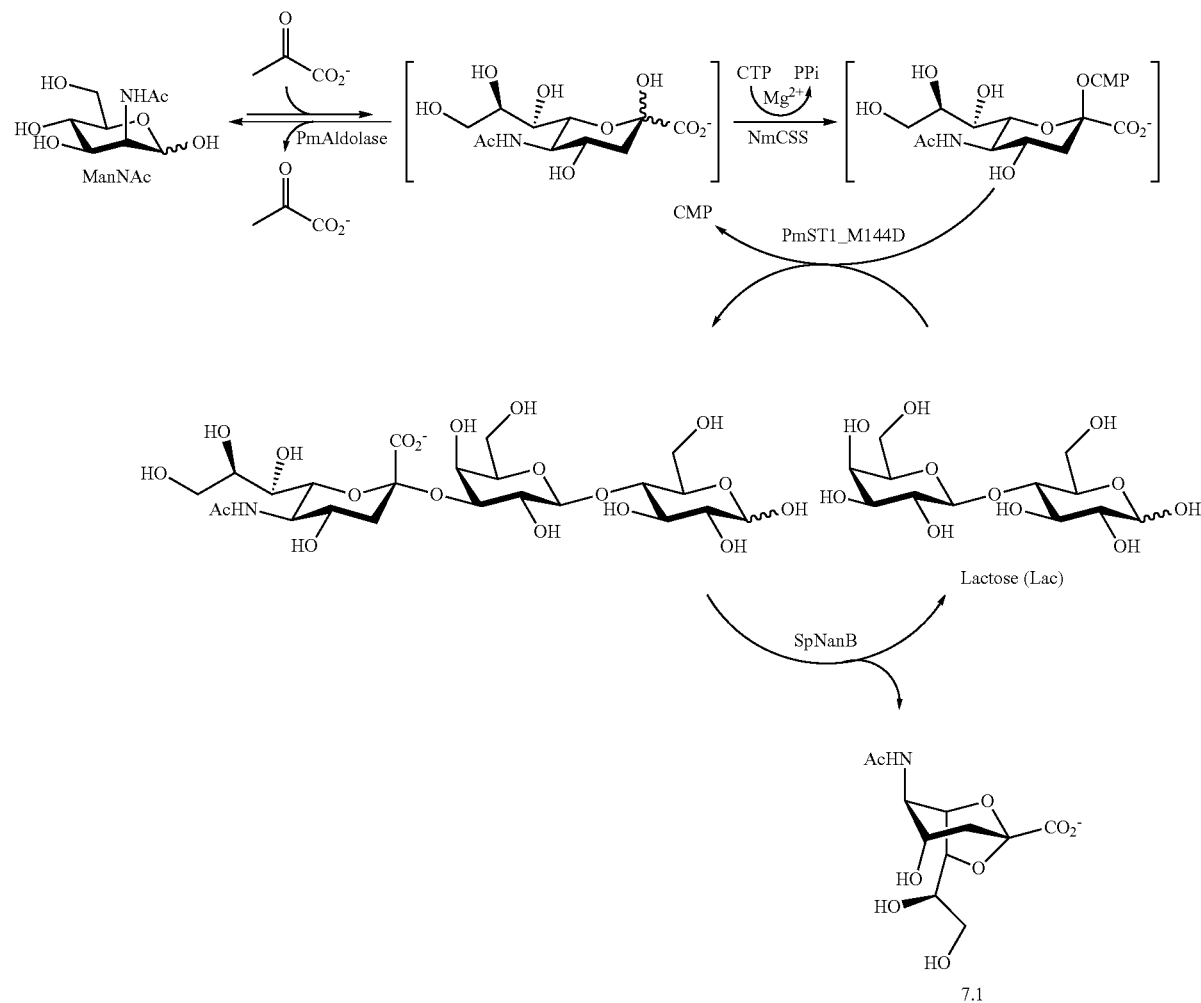

Scheme 7B. Preparation of 2,7-anhydro-Neu5Ac8N₃ and 2,7-anhydro-Neu5Ac8NAc.

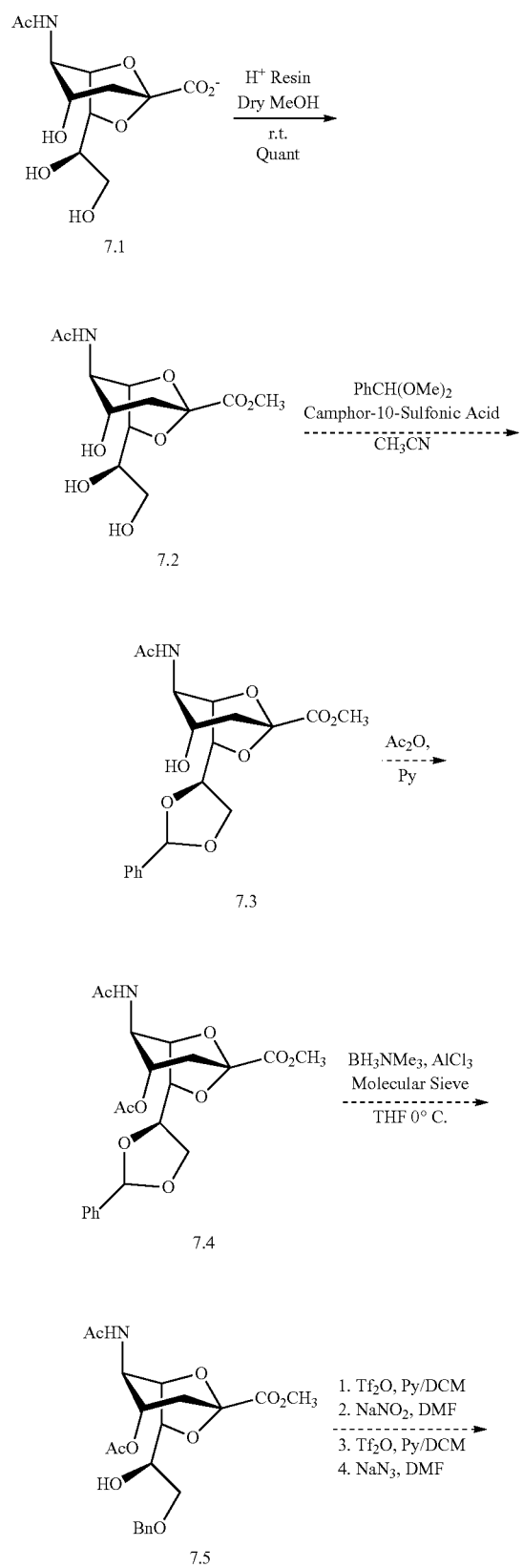

VII. Chemoenzymatic Synthesis of Sialosides

α2-3- and/or α2-6-linked sialosides containing Neu5Ac4NAc, Neu5Ac7NAc, and Neu5Ac8NAc, Neu5Ac7,9NAc₂, or Neu5Ac8,9NAc₂ can be synthesized using one-pot two enzyme (OP2E) and one-pot three enzyme (OP3E) systems, such as the systems depicted in Scheme 8.

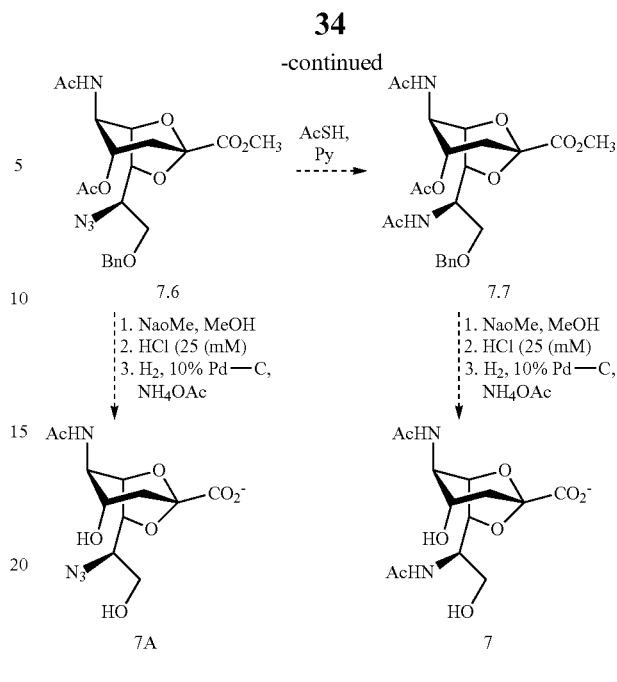

Scheme 8. One-pot multienzyme synthesis of sialosides.

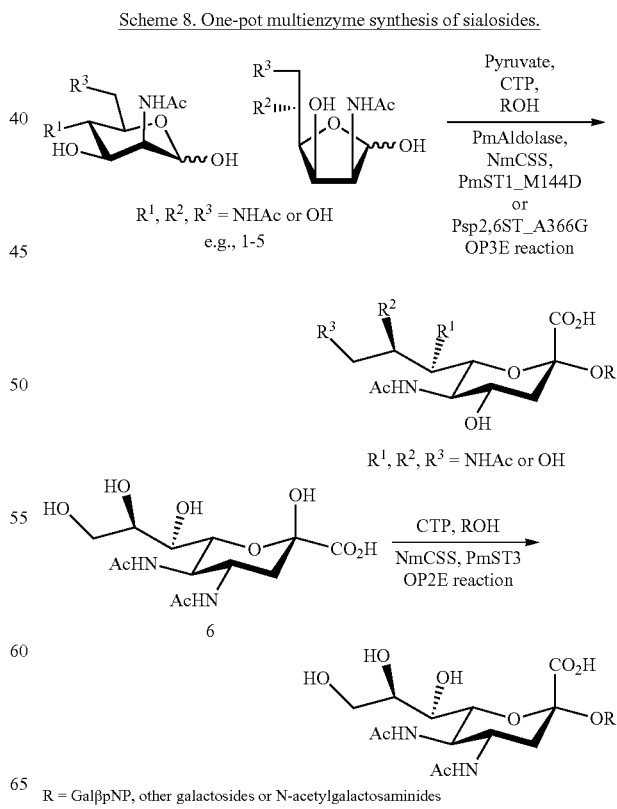

R = GalβpNP, other galactosides or N-acetylgalactosaminides

Similarly, 2,7-anhydro-Neu5Ac8N$_3$ and 2,7-anhydro-Neu5Ac8NAc (prepared according to Scheme 7B) can be utilized in one-pot multienzyme (OPME) sialylation systems containing SpNanB, NmCSS, and a sialyltransferase (PmST1, PmST1 M144D, Pd2,6ST, Psp2,6ST, or Psp2,6ST A366G) to synthesize Neu5Ac8N$_3$-containing glycosides and Neu5Ac8NAc-containing glycosides as shown below. The azido group in Neu5Ac8N$_3$-glycosides can be converted to Neu5Ac8NAc-glycosides using thioacetic acid (AcSH) in saturated sodium bicarbonate (NaHCO$_3$) in water.

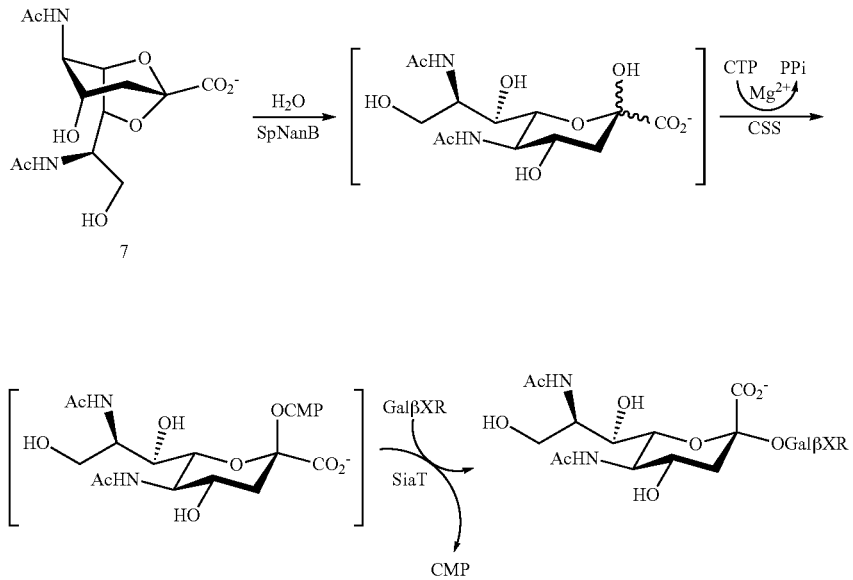

Scheme 9A. Chemoenzymatic synthesis of Neu5Ac8NAc-glycosides from 2,7-anhydro-Neu5Ac8NAc (7).

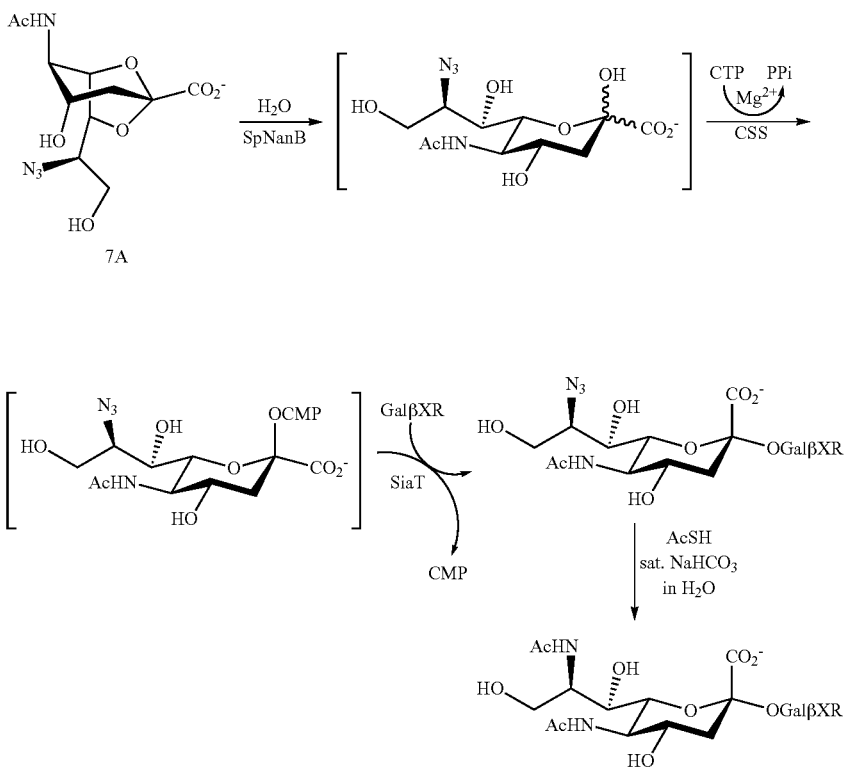

Scheme 9B. Chemoenzymatic synthesis of Neu5Ac8NAc-glycosides from 2,7-anhydro-Neu5Ac8N$_3$ (7A) via Neu5Ac8N$_3$-glycosides While a number of exemplary protecting groups are set forth herein, one of skill in the art will appreciate that still other protecting strategies can be employed in the methods for the synthesis of particular sugars and/or glycosides. Such protecting groups are described, for example, in *Protective Groups in Organic Synthesis*, 4th edition, T. W. Greene and P. G. M. Wuts, John Wiley & Sons, New York, 2006.

Accordingly, also provided are compounds according to Formula IV:

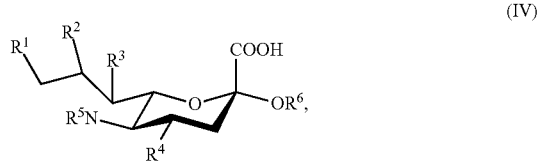

(IV)

wherein:
$R^1$, $R^2$, $R^3$, and $R^4$ are independently selected from the group consisting of —NHAc, —$N_3$, —$NH_2$, —OAc, —OH, and hydrogen;
$R^5$ is selected from the group consisting of —$NHR^{5a}$, —$N_3$, —$NH_2$, —OAc, —OH, and hydrogen;
$R^{5a}$ is selected from the group consisting of Ac, Gc, GcAc, $GcN_3$, $GcNH_2$, GcNAc, and hydrogen;
Ac is —$C(O)CH_3$; Gc is —$C(O)CH_2OH$; GcAc is —$C(O)CH_2OC(O)CH_3$;
$GcN_3$ is —$C(O)CH_2N_3$; $GcNH_2$ is —$C(O)CH_2NH_2$; GcNAc is —$C(O)CH_2NHC(O)CH_3$; and
$R^6$ is selected from the group consisting of a galactoside, an N-acetylgalactosaminide, a glucoside, an N-acetylglucosaminide, and a sialoside.

In some embodiments, compounds according to Formula IV are provided as described above wherein:
$R^1$, $R^2$, $R^3$, and $R^4$ are independently selected from the group consisting of —NHAc, —$N_3$, —OAc, —OH, and hydrogen;
$R^5$ is selected from the group consisting of —$NHR^{5a}$, —$N_3$, —OAc, —OH, and hydrogen; and
$R^{5a}$ is selected from the group consisting of Ac and Gc.

A variety of sialic acids and sialic derivatives can be used in the methods for forming sialosides according to Formula IV, including the sialic acid compounds described above. Sialosides according to Formula IV can include any combination of $R^1$, $R^2$, $R^3$, $R^4$, and $R^5$ set forth above, but are not limited to such combinations. In some embodiments, the methods provide sialosides where: i) when $R^5$ is —OH or —OAc, at least one of $R^1$, $R^2$, $R^3$, and $R^4$ are independently —NHAc or —$N_3$; ii) when $R^5$ is —$NHR^{5a}$, at least one of $R^1$, $R^2$, $R^3$, and $R^4$ is —NHAc or —$N_3$; iii) when $R^5$ and $R^1$ are —NHAc, at least one of $R^2$, $R^3$, and $R^4$ is —NHAc; and iv) when $R^5$ and $R^4$ are —NHAc, at least one of $R^1$, $R^2$, and $R^3$ is —NHAc.

In some embodiments, compounds according to Formula IV are provided wherein $R^5$ is —OH or —OAc, and at least two of $R^1$, $R^2$, $R^3$, and $R^4$ are independently —NHAc or —$N_3$. In some embodiments, $R^1$, $R^2$, $R^3$, and $R^4$ are independently selected from the group consisting of —$N_3$ and —OH. In some embodiments, $R^1$, $R^2$, $R^3$, and $R^4$ are independently selected from the group consisting of —NHAc and —OH.

In some embodiments, compounds according to Formula IV are provided wherein $R^5$ is selected from the group consisting of —$NHR^{5a}$, —OH, and —OAc. In some embodiments, $R^5$ is —NHAc. In some embodiments, $R^5$ is —NHGc.

In some embodiments, a galactoside $R^6$ is bonded to the compound via a 2-3 linkage or a 2-6 linkage; an N-acetylglucosaminide $R^6$ is bonded to the compound via a 2-6 linkage; a glucoside $R^6$ is bonded to the compound via a 2-6 linkage; or an N-acetylglucosaminide $R^6$ is bonded to the compound via a 2-6 linkage.

In some embodiments, $R^6$ is a sialoside comprising a Sia-α2,3-Gal moiety, a Sia-α2,8-Sia moiety, or a Sia-α2,9-Sia moiety, wherein each Sia is independently selected from Neu5Ac, Kdn, and Neu5Gc.

In some embodiments, $R^6$ is present as a member of an oligosaccharide, a polysaccharide, a glycosylated natural product, a glycopeptide, a glycoprotein, or a glycolipid. Suitable natural products include non-ribosomal glycopeptides (such as bleomycin), glycoalkaloids (such as solanine), ginsenosides (such as sanchinoside C1), aminoglycosides (such as gentamicin, kanamycin, neomycin, and streptomycin), avermectins, and anthracyclines (such as daunorubicin). Suitable glycolipids include glycoglycerolipids (such as monogalactosyldiacylglycerols, digalactosylmonoacylglycerols, and sulfoquinovosyl diacylglycerols), glycosphingolipids (such as lacto-, neolacto-, ganglio-, globo-, and iso-globo-series glycosphingolipids), and glycophosphatidylinositols (e.g., 1-phosphatidyl-L-myo-inositol 2,6-di-O-α-D-mannopyranoside). Suitable glycoproteins include mucins, immunoglobulins, lectins, and collagens.

In some embodiments, compounds according to Formula IVa are provided:

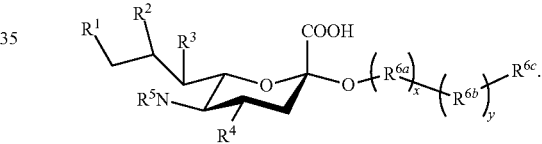

In compound according to Formula IVa, $R^{6a}$ is a monosaccharide, disaccharide or oligosaccharide, and subscript x is 0 or 1. $R^{6b}$ is a linker, and subscript y is 0 or 1. In some embodiments, the linker is selected from $C_{1-6}$ alkylene; $C_{1-6}$ alkylene-NH—C(O)—$C_{1-6}$ alkylene; and $C_{1-6}$ alkylene-NH—C(O)—$(CH_2—(CH_2CH_2O)_p—NH—C(O))_m$—$C_{1-6}$ alkylene, where subscript m is 0 or 1, and subscript p is an integer from 1 to 6. In some embodiments, subscript y is 1 and $R^{6c}$ is $C_{1-6}$ alkylene (e.g., n-propylene, denoted as "Pro" in Table 1 below).

In some embodiments, $R^{6c}$ in compounds of Formula IVa is a glycosylated natural product, a glycopeptide, a glycoprotein, or a glycolipid, as described above. In some embodiments, $R^{6c}$ is a functional group that can be used for further synthetic manipulations. For example, compounds wherein $R^{6c}$=—$N_3$, halo, or thiotolyl can be used for the synthesis of more complex glycosides. Alternatively, compounds wherein $R^{6c}$ is —$NH_2$, —SH, —$ONH_2$, or —$NHNH_2$, can be used for reaction with a suitably functionalized surface as described more detail below. In some embodiments, $R^{6c}$ is a chromophore or a chromogenic moiety (e.g., p-nitrophenyl) which can be used to assay the activity of enzymes such as glycosidases.

$R^{6a}$ can be any suitable monosaccharide, disaccharide, or oligosaccharide. Examples of monosaccharides include, but are not limited to, dioses such as glycoaldehyde; trioses such as D and L-glyceraldehyde; tetroses such as D and L-erythrose, threose, and erythrulose; pentoses such as D and L-arabinose, lyxose, ribose, xylose, ribulose, and xylulose; hexoses such as D and L-allose, altrose, glucose, mannose, gulose, idose, galactose, fructose, and talose; aminosugars such as N-acetylglucosamine, galactosamine, glucosamine, sialic acid, and D and L-duanosamine; and sulfosugars such as sulfoquinovose. Deuterated, oxidized, and N-acetyl derivatives of the foregoing are also suitable sugars. Oxidized derivatives can be carboxylic acid derivatives of the respective sugar at any carbon in the sugar capable of being oxidized to a carboxylic acid in the sugar.

Disaccharides are two monosaccharides linked together by glycosidic bonds. The glycosidic bonds can be O—, N—, or S-glycosidic bonds, and can be either α- or β-glycosidic bonds. Exemplary disaccharides include sucrose, lactose, maltose, and lactulose. However, any hydrolytically stable combination of two monosaccharides can be a suitable disaccharide. Oligosaccharides contain three or more monosaccharides linked by glycosidic bonds in the same manner as the aforementioned disaccharides.

Sialosides that can be synthesized via the methods disclosed herein also include, but are not limited to, those listed in Table 1.

TABLE 1

| N-acetyl Neu5Ac | Link | Symbol | Underlying Glycan |
|---|---|---|---|
| Neu5Ac4NAc | α2-3 | Galβ | GalβProN$_3$ |
|  | α2-3 | Lac/GM3 | LacβProN$_3$ (Galβ1-4GlcβProN$_3$) |
|  | α2-3 | Type 1 | Galβ1-3GlcNAcβProN$_3$ |
|  | α2-3 | Type 1α | Galβ1-3GlcNAcαProN$_3$ |
|  | α2-3 | Type 2 | LacNAcβProN$_3$ (Galβ1-4GlcNAcβProN$_3$) |
|  | α2-3 | Core 1 | Galβ1-3GalNAcαProN$_3$ |
|  | α2-3 | LNnT | Galβ1-4GlcNAcβ1-3Galβ1-4GlcβProN$_3$ |
|  | α2-3 | LNT | Galβ1-3GlcNAcβ1-3Galβ1-4GlcβProN$_3$ |
|  | α2-3 | GM2 | (GalNAcβ1-4)Galβ1-4GlcβProN$_3$ |
|  | α2-3 | GM1 | (Galβ1-3GalNAcβ1-4)Galβ1-4GlcβProN$_3$ |
|  | α2-3 | Core 1β | Galβ1-3GalNAcβProN$_3$ |
|  | α2-3 | iGb5 | Galβ1-3GalNAcβ1-3Galα1-3Galβ1-4GlcβProN$_3$ |
|  | α2-3 | iGb5NAc | Galβ1-3GalNAcβ1-3Galα1-3Galβ1-4GlcNAcβProN$_3$ |
|  | α2-3 | Gb5 | Galβ1-3GalNAcβ1-3Galα1-4Galβ1-4GlcβProN$_3$ |
|  | α2-3 | Gb5NAc | Galβ1-3GalNAcβ1-3Galα1-4Galβ1-4GlcNAcβProN$_3$ |
| Neu5Ac9NAc, Neu5Ac7NAc, Neu5Ac8NAc, Neu5Ac7, 9NAc$_2$, or Neu5Ac8, 9NAc$_2$ | α2-3 | Galβ | GalβProN$_3$ |
|  | α2-6 | Galβ | GalβProN$_3$ |
|  | α2-6 | GalNAcβ | GalNAcβProN$_3$ |
|  | α2-6 | Tn | GalNAcαProN$_3$ |
|  | α2-3 | Lac/GM3 | LacβProN$_3$ (Galβ1-4GlcβProN$_3$) |
|  | α2-6 | Lac/GM3 | LacβProN$_3$ (Galβ1-4GlcβProN$_3$) |
|  | α2-3 | Type 1 | Galβ1-3GlcNAcβProN$_3$ |
|  | α2-3 | Type 1α | Galβ1-3GlcNAcαProN$_3$ |
|  | α2-3 | Type 2 | LacNAcβProN$_3$ (Galβ1-4GlcNAcβProN$_3$) |
|  | α2-6 | Type 2 | LacNAcβProN$_3$ (Galβ1-4GlcNAcβProN$_3$) |
|  | α2-3 | Type 2-6S | 6S-LacNAcβProN$_3$ (Galβ1-4GlcNAc6SO$_3$βProN$_3$) |
|  | α2-6 | Type 2-6S | 6S-LacNAcβProN$_3$ (Galβ1-4GlcNAc6SO$_3$βProN$_3$) |
|  | α2-3 | Type 2-6'S | 6S'-LacNAcβProN$_3$ (Gal6SO$_3$β1-4GlcNAcβProN$_3$) |
|  | α2-3 | Core 1 | Galβ1-3GalNAcαProN$_3$ |
|  | α2-3 | Lewis$^x$ | Galβ1-4(Fucα1-3)GlcNAcβProN$_3$ |
| Neu5Ac9NAc, Neu5Ac7NAc, Neu5Ac8NAc, Neu5Ac7, 9NAc$_2$ or Neu5Ac8, 9NAc$_2$ | α2-3 | 6S-Lewis$^x$ | Galβ1-4(Fucα1-3) GlcNAc6SO$_3$βProN$_3$ |
|  | α2-3 | LNnT | Galβ1-4GlcNAcβ1-3Galβ1-4GlcβProN$_3$ |
|  | α2-6 | LNnT | Galβ1-4GlcNAcβ1-3Galβ1-4GlcβProN$_3$ |
|  | α2-3 | LNT | Galβ1-3GlcNAcβ1-3Galβ1-4GlcβProN$_3$ |
|  | α2-3 | GM2 | (GalNAcβ1-4)Galβ1-4GlcβProN$_3$ |
|  | α2-3 | GM1 | (Galβ1-3GalNAcβ1-4)Galβ1-4GlcβProN$_3$ |
|  | α2-8 | GD3 | Neu5Acα2-3Galβ1-4GlcβProN$_3$ |
|  | α2-8 | GD2 | Neu5Acα2-3(GalNAcβ1-4)Galβ1-4GlcβProN$_3$ |
|  | α2-8 | GD1a | Neu5Acα2-3(Galβ1-3GalNAcβ1-4)Galβ1-4GlcβProN$_3$ |
|  | α2-3 | Core 1β | Galβ1-3GalNAcβProN$_3$ |
|  | α2-3 | iGb5 | Galβ1-3GalNAcβ1-3Galα1-3Galβ1-4GlcβProN$_3$ |
|  | α2-3 | iGb5NAc | Galβ1-3GalNAcβ1-3Galα1-4Galβ1-4GlcNAcβProN$_3$ |
|  | α2-3 | Gb5 | Galβ1-3GalNAcβ1-3Galα1-4Galβ1-4GlcβProN$_3$ |
|  | α2-3 | Gb5NAc | Galβ1-3GalNAcβ1-3Galα1-4Galβ1-4GlcNAcβProN$_3$ |

In some embodiments, sialosides according to Formula IV are selected from:

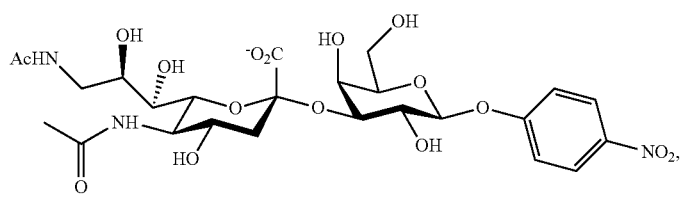

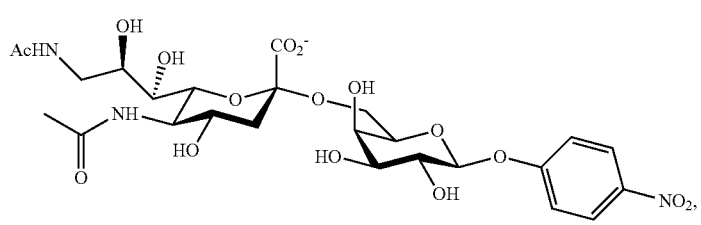

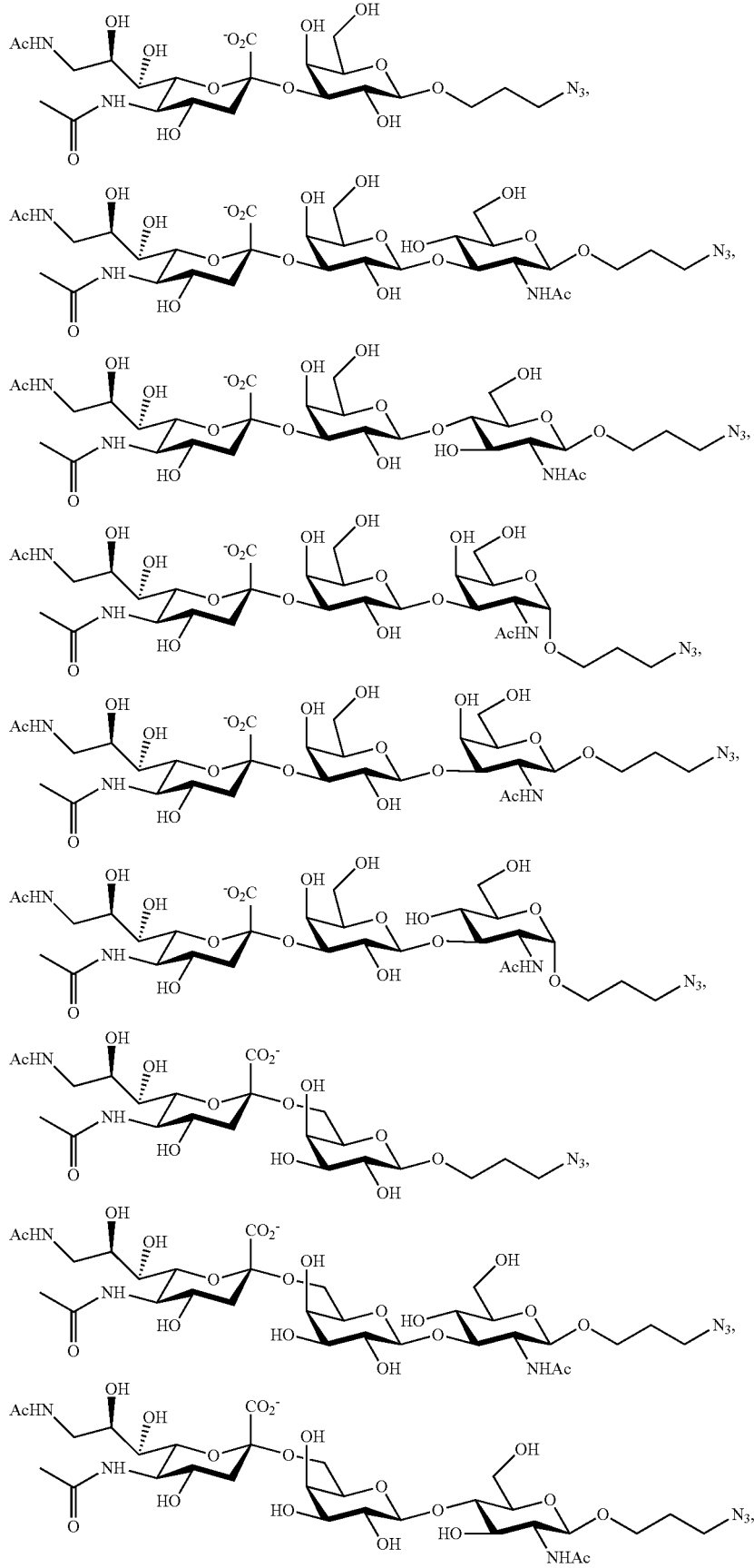

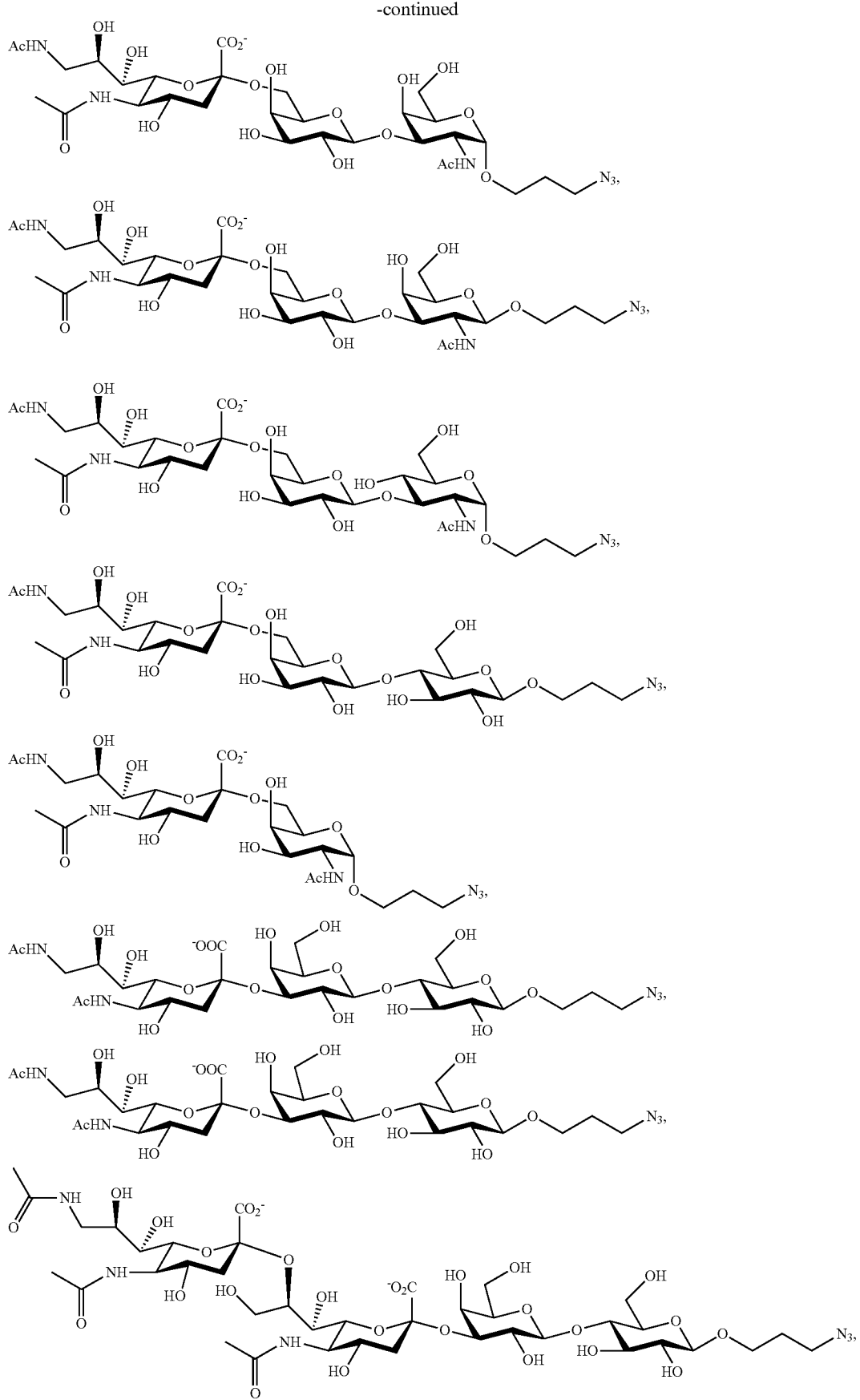

In some embodiments, sialosides according to Formula IV are selected from:
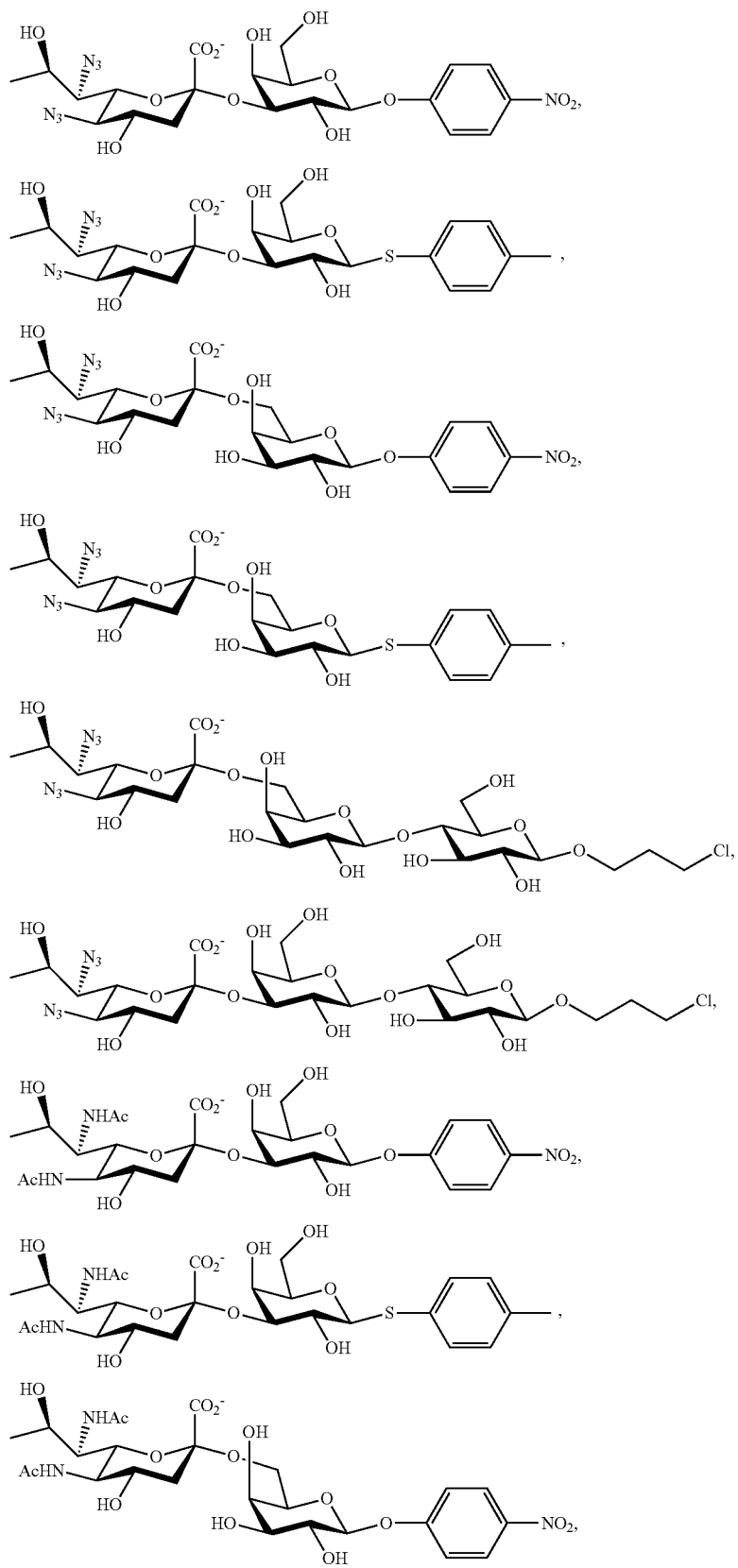

-continued

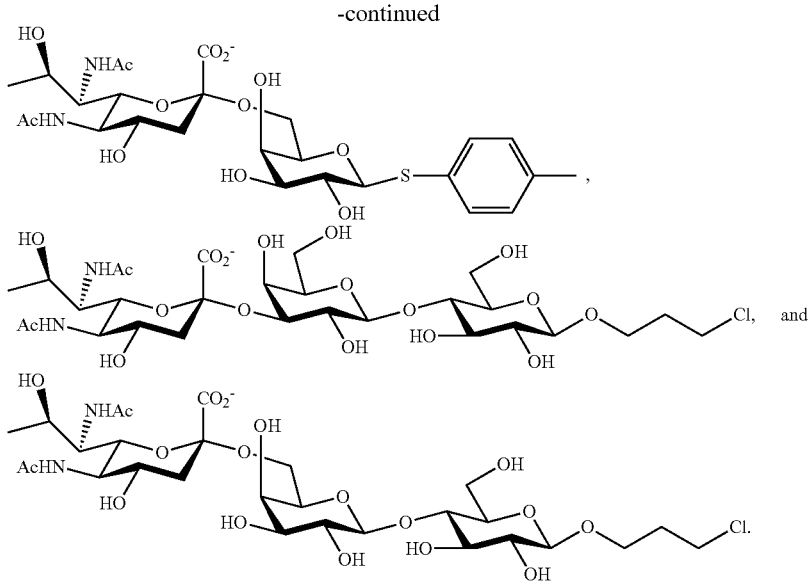

In a related aspect, methods are provided for preparing a compound according to Formula IV:

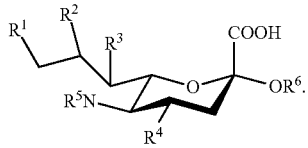

The methods include:
forming a reaction mixture comprising cytidine triphosphate, a CMP sialic acid synthetase, a sialyltransferase, a compound according to Formula V

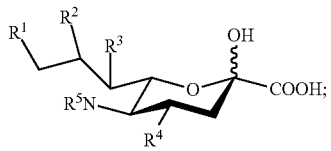

and
an acceptor according to Formula VI

under conditions sufficient to form the compound according to Formula IV.
wherein:
$R^1$, $R^2$, $R^3$, and $R^4$ are independently selected from the group consisting of —NHAc, —$N_3$, —$NH_2$, —OAc, —OH, and hydrogen;
$R^5$ is selected from the group consisting of —$NHR^{5a}$, —$N_3$, —$NH_2$, —OAc, —OH, and hydrogen;
$R^{5a}$ is selected from the group consisting of Ac, Gc, GcAc, Gc$N_3$, GcN$H_2$, GcNAc, and hydrogen;
Ac is —C(O)CH$_3$; Gc is —C(O)CH$_2$OH; GcAc is —C(O)CH$_2$OC(O)CH$_3$;
GcN$_3$ is —C(O)CH$_2$N$_3$; GcNH$_2$ is —C(O)CH$_2$NH$_2$; GcNAc is —C(O)CH$_2$NHC(O)CH$_3$; and $R^6$ is a glycoside selected from the group consisting of a galactoside, N-acetylgalactosaminide, a glucoside, an N-acetylglucosaminide, and a sialoside.

In some embodiments, methods for preparing compounds according to Formula IV are provided as described above wherein:
$R^1$, $R^2$, $R^3$, and $R^4$ are independently selected from the group consisting of —NHAc, —$N_3$, —OAc, —OH, and hydrogen;
$R^5$ is selected from the group consisting of —$NHR^{5a}$, —$N_3$, —OAc, —OH, and hydrogen; and
$R^{5a}$ is selected from the group consisting of Ac and Gc.

A described above, sialic acid compounds according to Formula VI can contain any combination of $R^1$, $R^2$, $R^3$, $R^4$, and $R^5$ set forth above, but are not limited to such combinations. In some embodiments, $R^1$, $R^2$, $R^3$, and $R^4$ are independently selected from the group consisting of —NHAc and —OH. In some embodiments, $R^5$ is selected from the group consisting of —$NHR^{5a}$, —OH, and —OAc. In some embodiments, $R^5$ is —NHAc.

Any suitable CMP-sialic acid synthetase (i.e., N-acylneuraminate cytidylyltransferase, EC 2.7.7.43, also referred to as "CSS") can be used in the methods for forming the sialosides disclosed herein. For example, CMP-sialic acid synthetases from *E. coli*, *C. thermocellum*, *S. agalactiae*, or *N. meningitidis* can be used. In some embodiments, the CMP sialic acid synthetase is *Neisseria meningitidis* CMP-sialic acid synthetase (NmCSS).

In some embodiments, the CMP-sialic acid synthetase is NmCSS (NCBI Accession No. WP_025459740.1) or a catalytically active variant thereof. In some embodiments, the CMP-sialic acid synthetase comprises the polypeptide sequence: EKQNIAVILARQNSKGLPLKNLRKMNGIS-LLGHTINAAISSKCFDRIIVSTDGGLIAEE AKNFGVEVVLRPAELASDTASSISGVIHALETIG-SNSGTVTLLQPTSPLRTGAHIREAF SLFDEKIKGSVVSACPMEHHPLKTLLQINNGEY-APMRHLSDLEQPRQQLPQAFRPNG AIYINDTASLI-ANNCFFIAPTKLYIMSHQDSIDIDTELDLQQAE-NILHHKES, or a catalytically active variant thereof.

Any suitable sialyltransferase (also referred to as "ST") can be used in the methods for forming the sialosides disclosed herein. In some embodiments, the sialyltransferase is a beta-galactoside alpha-2,3-sialyltransferases belonging to Glycosyltransferase family 80 (GT80 using CAZy nomenclature), which catalyzes the following conversion: CMP-sialic acid+β-D-galactosyl-R=CMP+α-sialic acid-(2-3)-β-D-galactosyl-R, where the acceptor is GalβOR, where R is H, a monosaccharide, an oligosaccharide, a polysaccharide, a glycopeptide, a glycoprotein, a glycolipid, or a hydroxyl-containing compound. GT80 family sialyltransferases also include galactoside or N-acetylgalactosaminide alpha-2,6-sialyltransferases that catalyze the following conversion: CMP-sialic acid+galactosyl/GalNAc-R=CMP+α-sialic acid-(2→6)-β-D-galactosyl/GalNAc-R, where the acceptor is GalOR or GalNAcOR, where R is H, serine or threonine on a peptide or protein, a monosaccharide, an oligosaccharide, a polysaccharide, a glycopeptide, a glycoprotein, a glycolipid, or a hydroxyl-containing compound.

Sialyltransferases in family EC 2.4.99, such as beta-galactosaminide alpha-2,6-sialyltransferase (EC 2.4.99.1), alpha-N-acetylgalactosaminide alpha-2,6-sialyltransferase (EC 2.4.99.3), beta-galactoside alpha-2,3-sialyltransferase (EC 2.4.99.4), N-acetyllactosaminide alpha-2,3-sialyltransferase (EC 2.4.99.6), alpha-N-acetyl-neuraminide alpha-2,8-sialyltransferase (EC 2.4.99.8), and lactosylceramide alpha-2,3-sialyltransferase (EC 2.4.99.9), can also be used in the methods for preparing sialosides.

In some embodiments, the sialyltransferase is selected from the group consisting of PmST1, a PmST1 variant, PmST2, a PmST2 variant, PmST3, a PmST3 variant, Pd2,6ST, Psp2,6ST, CstII, and a polysialyltransferase.

In some embodiments, the sialyltransferase is PmST1 (NCBI Accession No. WP_005753497.1) or a catalytically active variant thereof. In some embodiments, the sialyltransferase is PmST1_M144D or a catalytically active variant thereof. In some embodiments, the sialyltransferase comprises the polypeptide sequence: KTITLYLDPASLPAL-NQLMDFTQNNEDKTHPRIFGLSRFKIPD-NIITQYQNIHFVELKD NRPTEALFTILDQYPGNIELNIHLNIAHSVQLIRPILAY-RFKHLDRVSIQQLNLYDDGSD EYVDLEKEENKDIS-AEIKQAEKQLSHYLLTGKIKFDNP-TIARYVWQSAFPVKYHFLST DYFEKAEFLQPLKEYLAENYQKMDWTAYQQLT-PEQQAFYLTLVGFNDEVKQSLEV QQAK-FIFTGTTTWEGNTDVREYYAQQQLNLLNHFTQAE-GDLFIGDHYKIYFKGHPR GGEINDYILNNAKNITNIPANISFE-VLMMTGLLPDKVGGVASSLYFSLPKEKISHIIFTS NKQVKSKEDALNNPYVKVMRRLGIIDESQVIFWD-SLKQL, or a catalytically active variant thereof.

In some embodiments, the sialyltransferase is PmST2 (UniProtKB Accession No. Q9CNC4) or a catalytically active variant thereof. PmST2 are variants thereof are described in U.S. Pat. No. 9,102,967, which is incorporated herein by reference in its entirety. In some embodiments, the sialyltransferase comprises the polypeptide sequence: NLIICCTPLQVLIAEKIIAKFPHTPFYGVML-STVSNKKFDFYAKRLAQQCQGFFSMVQ HKDRFNLLKEILYLKRTFSGKHFDQVFVAN-INDLQIQFLLSAIDFNLLNTFDDGTINIV PNSLFYQDD-PATLQRKLINVLLGNKYSIQSL-RALSHTHYTIYKGFKNIIERVEPIELVA ADNSEKVTSAVINVLLGQPVFAEDERNIALAER-VIKQFNIHYYLPHPREKYRLAQVN YIDTE-LIFEDYILQQCQTHKYCVYTYFSSAIINIMNKSD-NIEVVALKIDTENPAYDACY DLFDELGVNVIDIRE, or a catalytically active variant thereof.

In some embodiments, the sialyltransferase is PmST3 or a catalytically active variant thereof, as described in U.S. Pat. No. 9,783,838, which is incorporated herein by reference in its entirety. In some embodiments, the sialyltransferase is PmST3A35 or a catalytically active variant thereof. In some embodiments, the sialyltransferase comprises the polypeptide sequence: DKFAEHEIPKAVIVAG-NGESLSQIDYRLLPKNYDVFRCNQFY-FEERYFLGNKIKAVFF TPGVFLEQYYTLYHL-KRNNEYFVDNVILSSFNHPTVDLEKSQKIQALFIDV-INGYEKY LSKLTAFDVYLRYKELY-ENQRITSGVYMCAVAIAMGYTDIYLTGIDFYQASEE-NYAF DNKKPNIIRLLPDFRKEKTLFSYHSKDIDL-EALSFLQQHYHVNFYSISPMSPLSKHFPIP TVEDDC-ETTFVAPLKENYINDILLVDKLAAALE, or a catalytically active variant thereof.

In some embodiments, the sialyltransferase is Psp2,6ST or a catalytically active variant thereof, as described in U.S. Pat. Appl. Pub. No. 2016/0177275, which is incorporated herein by reference in its entirety. In some embodiments, the sialyltransferase is Psp26ST(15-501) A366G or a catalytically active variant thereof. In some embodiments, the sialyltransferase comprises the polypeptide sequence: CNN-SEENTQSIIKNDINKTIIDEEYVNLEPINQSNIS-FTKHSWVQTCGTQQLLTEQNKES ISLSVVAPRLDD-DEKYCFDFNGVSNKGEKYITKVTLNVVAPSLEVYVD-HASLPTLQQ LMDIIKSEEENPTAQRYIAWGRIVPTDEQMKELNITS-FALINNHTPADLVQEIVKQAQ TKHRLNVKLSSN-TAHSFDNLVPILKELNSFNNVTVTNIDLYDDG-SAEYVNLYNWRDT LNKT-DNLKIGKDYLEDVINGINEDTSNTGTSSVYNWQK-LYPANYHFLRKDYLTLEP S LHELRDYIGD-SLKQMQWDGFKKFNSKQQELFL-SIVNFDKQKLQNEYNSSNLPNFVFT GTTVWAGNHEREYYAKQQINVINNAINESSPHYLGN-SYDLFFKGHPGGGIINTLIMQ NYPSMVDIPSKISFE-VLMMTDMLPDAVAGIASSLYFTIPAEKIK-FIVFTSTETITDRETA LRSPLVQVMIKLGIVKEENVLFWA, or a catalytically active variant thereof.

In some embodiments, the sialyltransferase is Pd2,6ST (GenBank Accession No. BAA25316) or a catalytically active variant thereof. Pd2,6ST are variants thereof are described, for example by Sun and Chen, et al. (Biotechnol Lett (2008) 30:671-676), which is incorporated herein by reference in its entirety. In some embodiments, the sialyltransferase is A15Pd2,6ST(N) or a catalytically active variant thereof. In some embodiments, the sialyltransferase comprises the polypeptide sequence: CNSDNT-SLKETVSSNSADVVETETYQLTPI-DAPSSFLSHSWEQTCGTPILNESDKQAIS FDFVAPELKQDEKYCFTFKGITGDHRYITNT-TLTVVAPTLEVYIDHASLPSLQQLIHIIQ AKDEY-PSNQRFVSWKRVTVDADNANKLNIHTYPLKGNNT-SPEMVAAIDEYAQSKN RLNIEFYTNTAHVFNNLPPIIQPLYNNEKVKISHIS-LYDDGSSEYVSLYQWKDTPNKIE TLEGEVSLLA-NYLAGTSPDAPKGMGNRYNWHKLYDTDYYFL-REDYLDVEANLHDL RDYLGSSAKQMPWDEFAKLSDSQQTLFLDIVGFD-KEQLQQQYSQSPLPNFIFTGTTT WAG-GETKEYYAQQQVNVINNAINET-SPYYLGKDYLFFKGHPAGGVINDIILGSFPD MINIPAKISFEVLMMTDMLPDTVAGIASSLYFTIPAD- KVNFIVFTSSDTITDREEALKSP LVQVMLTL-GIVKEKDVLFWA, or a catalytically active variant thereof.

In some embodiments, the sialyltransferase is CstII (GenBank Accession No. CS299360) or a catalytically active variant thereof. CstII are variants thereof are described by Cheng and Chen, et al. (Glycobiology, 18(9): 686-697, 2008), which is incorporated herein by reference in its entirety. In some embodiments, the sialyltransferase is C-His6-tagged CstII-$\Delta 32^{I53S}$ or a catalytically active variant thereof. In some embodiments, the sialyltransferase comprises the polypeptide sequence: KKVIIAG-NGPSLKEIDYSRLPNDFDVFRC-NQFYFEDKYYLGKKCKAVFYNPSLFFEQY YTLKHLIQNEYETELIMCSNYNQAHL-ENENFVKTFYDYFPDAHLGYDFFKQLKDFNA YFKFHEIYFNQRITSGVYMCAVAIAL-GYKEIYLSGIDFYQNGSSYAFDTKQKNLLKLA PNFKNDNSHYIGHSKNTDIKALEFLEKTYKIKLY-CLCPNSLLANFIELAPNLMSNFIIQ EKNNYTKDILIPS-SEAYGKFSKNIN, or a catalytically active variant thereof.

Sialidases can also be use in methods for forming sialic acids, as described above. In some embodiments, the sialidase is SpNanB (NCBI Accession No. NP_359124.1) or a catalytically active variant thereof. In some embodiments, the sialidase comprises the polypeptide sequence: NELNYGQLSISPIFQGGSYQLNNKSIDISPLLL-DKLSGDSQTVVMKFKADKPNSLQAL FGLSNSK-AGFKNNYFSIFMRDSGEIGVEIRDAQKGINYLFSR-PASLWGKHKGQAVEN TLVFVSDSKDKTYTMYVNGIEVFSETVDTFLPISNIN-GIDKATLGAVNREGKEHYLAK GSIDEISLFNKAI-SDQEVSTIPLSNPFQLIFQSGDSTQANYFRIPT-LYTLSSGRVLSSIDAR YGGTHDSKSKINIATSYSDDNGKTWSEPIFAMKFN-DYEEQLVYWPRDNKLKNSQISG SASFIDS-SIVEDKKSGKTILLADVMPAGIGNNNANKADSGFKE-INGHYYLKLKKNGD NDFRYTVRENGVVYDETTNKPTNYTINDKYEV-LEGGKSLTVEQYSVDFDSGSLRER HNGKQVPMNVFYKD-SLFKVTPTNYIAMTTSQNRGESWEQFKLLPP-FLGEKHNGTYL CPGQGLALKSSNRLIFATYTSG-ELTYLISDDSGQTWKKSSASIPFENATAEAQMVELR DGVIRTFFRTTTGKIAYMTSRDSGETWSEVSYIDG-IQQTSYGTQVSAIKYSQLIDGKE AVILSTPNSRS-GRKGGQLVVGLVNKEDDSIDWKYHYDIDLPSYG-YAYSAITELPNHHI GVLFEKYDSWSRNELHLSNVVQYIDLEINDLTK, or a catalytically active variant thereof.

In some embodiments, the sialidase is SpNanC (NCBI Accession No. WP_024478413.1) or a catalytically active variant thereof. In some embodiments, the sialidase comprises the polypeptide sequence: KKNIKQYVTLGTVVVLSAFVANSVAAQETETSEVST-PELVQPVAPTTSISEVQHKSGN SSEV-TVQPRTVETTVKDPSSTAEETLVLEKNNVTLTGG-GENVTKELKDKFTSGDFTV VIKYNQSSEKGLQALFGISNSKPGQQN-SYVDVFLRDNGELGMEARDTSSNKNNLVSR PASVWGKYKQEAVTNTVAVVADSVKKTYSLY-ANGTKVVEKKVDNFLNIKDIKGID YYMLGGVKRAGKTAFGFNGTLENIKFFN-SALDEETVKKMTTNAVTGHLIYTANDTT GSNY-FRIPVLYTFSNGRVFSSIDARYGGTHDFLNKINIAT-SYSDDNGKTWTKPKLTLA FDDFAPVPLEWPREVGGRDLQISGGATYIDSVIVEK-KNKQVLMFADVMPAGVSFRE ATRKDSGYKQIDGNYYLKLRKQGDT-DYNYTIRENGTVYDDRTNRPTEFSVDKNFGI KQNG-NYLTVEQYSVSFENNKKTEYRNGTKVHMNIFYK-DALFKVVPTNYIAYISSND HGESWSAPTLLPPIMGLNRNAPYLGPGRGIIESST-GRILIPSYTGKESAFIYSDDNGAS WKVKVVPLPSSW-SAEAQFVELSPGVIQAYMRTNNGKIAYLTSK-DAGTTWSAPEYLK FVSNPSYGTQLSIINYSQLIDGKKAVILSTPNSTN-GRKHGQIWIGLINDDNTIDWRYHH DVDYSNYGY-SYSTLTELPNHEIGLMFEKFDSWSR-NELHMKNVVPYITFKIEDLKKN, or a catalytically active variant thereof.

In some embodiments, the sialidase is *S. pneumoniae* TIGR4 SpNanC (NCBI Accession No. AAK75424.1) or a catalytically active variant thereof. In some embodiments, the sialidase comprises the polypeptide sequence:

KKNIKQYVTLGTVVVLSAFVANSVAAQETETSEVSTPKLVQPVAPTTPIS

EVQPTSDNSSEVTVQPRTVETTVKDPSSTAEETPVLEKNNVTLTGGGENV

TKELKDKFTSGDFTVVIKYNQSSEKGLQALFGISNSKPGQQNSYVDVFLR

DNGELGMEARDTSSNKNNLVSRPASVWGKYKQEAVTNTVAVVADSVKKTY

SLYANGTKVVEKKVDNFLNIKDIKGIDYYMLGGVKRAGKTAFGFNGTLEN

IKFFNSALDEETVKKMTTNAVTGHLIYTANDTTGSNYFRIPVLYTFSNGR

VFSSIDARYGGTHDFLNKINIATSYSDDNGKTWTKPKLTLAFDDFAPVPL

EWPREVGGRDLQISGGATYIDSVIVEKKNKQVLMFADVMPAGVSFREATR

KDSGYKQIDGNYYLKLRKQGDTDYNYTIRENGTVYDDRTNRPTEFSVDKN

FGIKQNGNYLTVEQYSVSFENNKKTEYRNGTKVHMNIFYKDALFKVVPTN

YIAYISSNDHGESWSAPTLLPPIMGLNRNAPYLGPGRGIIESSTGRILIP

SYTGKESAFIYSDDNGASWKVKVVPLPSSWSAEAQFVELSPGVIQAYMRT

NNGKIAYLTSKDAGTTWSAPEYLKFVSNPSYGTQLSIINYSQLIDGKKAV

ILSTPNSTNGRKHGQIWIGLINDDNTIDWRYHHDVDYSNYGYSYSTLTEL

PNHEIGLMFEKFDSWSRNELHMKNVVPYITFKIEDLKKN.

In some embodiments, galactoside $R^6$ is bonded to the compound via a 2-3 linkage or a 2-6 linkage; or wherein N-acetylglucosaminide $R^6$ is bonded to the compound via a 2-6 linkage; or wherein glucoside $R^6$ is bonded to the compound via a 2-6 linkage; or wherein N-acetylglucosaminide $R^6$ is bonded to the compound via a 2-6 linkage.

In some embodiments, $R^6$ is a sialoside comprising a Sia-α2,3-Gal moiety, a Sia-α2,8-Sia moiety, or a Sia-α2,9-Sia moiety, wherein each Sia is independently selected from Neu5Ac, Kdn, and Neu5Gc.

In some embodiments, $R^6$ is present as a member of an oligosaccharide, a polysaccharide, a glycopeptide, a glycoprotein, or a glycolipid.

Methods for preparing N-acetyl sialic acids sialosides generally include providing reaction mixtures that contain the one or more enzymes as described herein, e.g., a sialic acid aldolase (SAA), a CMP-sialic acid synthetase (CSS) or a sialyltransferase (ST). An SAA, a CSS, or an ST can be, for example, isolated or otherwise purified prior to addition to the reaction mixture. As used herein, a "purified" enzyme refers to an enzyme which is provided as a purified protein composition wherein the enzyme constitutes at least about 50% of the total protein in the purified protein composition. For example, the enzyme can constitute about 50%, 60%, 70%, 75%, 80%, 85%, 90%, 95%, or 99% of the total protein in the purified protein composition. In some embodiments, the enzymes in the reaction mixture are provided as purified protein compositions wherein the enzyme constitutes at least about 95% of the total protein in purified protein composition (prior to addition to the reaction mixture). The amount of the enzyme in a purified protein composition can be determined by any number of known methods including, for example, by polyacrylamide gel electrophoresis (e.g., SDS-PAGE) followed by detection with a staining reagent (e.g., Coomassie Brilliant Blue G-250, a silver nitrate stain, and/or a reagent containing a Psp26ST antibody). The enzymes used in the methods for forming sialosides can also be secreted by a cell present in the reaction mixture. Alternatively, the enzymes can catalyze the reaction within a cell expressing the variant.

Reaction mixtures can contain additional reagents for use in glycosylation techniques. For example, in certain embodiments, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, tetrahydrofuran, acetone, and acetic acid), salts (e.g., NaCl, KCl, $CaCl_2$, and salts of $Mn^{2+}$ and $Mg^{2+}$), detergents/surfactants (e.g., a non-ionic surfactant such as N,N-bis[3-(D-gluconamido)propyl]cholamide, polyoxyethylene (20) cetyl ether, dimethyldecylphosphine oxide, branched octylphenoxy poly(ethyleneoxy)ethanol, a polyoxyethylene-polyoxypropylene block copolymer, t-octylphenoxypolyethoxyethanol, polyoxyethylene (20) sorbitan monooleate, and the like; an anionic surfactant such as sodium cholate, N-lauroylsarcosine, sodium dodecyl sulfate, and the like; a cationic surfactant such as hexdecyltrimethyl ammonium bromide, trimethyl(tetradecyl) ammonium bromide, and the like; or a zwitterionic surfactant such as an amidosulfobetaine, 3-[(3-cholamidopropyl)dimethyl-ammonio]-1-propanesulfonate, and the like), chelators (e.g., ethylene glycol-bis(2-aminoethylether)-N,N,N',N'-tetraacetic acid (EGTA), 2-({2-[bis(carboxymethyl)amino]ethyl} (carboxymethyl) amino)acetic acid (EDTA), and 1,2-bis(o-aminophenoxy) ethane-N,N,N',N'-tetraacetic acid (BAPTA), reducing agents (e.g., dithiothreitol (DTT), β-mercaptoethanol (BME), and tris(2-carboxyethyl)phosphine (TCEP)), and labels (e.g., fluorophores, radiolabels, and spin labels). Buffers, cosolvents, salts, detergents/surfactants, chelators, reducing agents, and labels can be used at any suitable concentration, which can be readily determined by one of skill in the art. In general, buffers, cosolvents, salts, detergents/surfactants, chelators, reducing agents, and labels are included in reaction mixtures at concentrations ranging from about 1 µM to about 1 M. For example, a buffer, a cosolvent, a salt, a detergent/surfactant, a chelator, a reducing agent, or a label can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M. In some embodiments, the reaction mixture can contain CTP, a CSS, an ST, a compound according to Formula V, and an acceptor according to Formula VI as described herein, and one or more components selected from a buffer, a cosolvent, a salt, a detergent/surfactant, a chelator, a reducing agent, and a label. In some embodiments, the reaction mixture can contain CTP, a CSS, an ST, a compound according to Formula V, and an acceptor according to Formula VI as described herein, and one or more components selected from a buffer, a cosolvent, a salt, a detergent/surfactant, a chelator, and a reducing agent. In some embodiments, the reaction mixture consists essentially of CTP, a CSS, an ST, a compound according to Formula V, and an acceptor according to Formula VI as described herein, and one or more components selected from a buffer, a cosolvent, a salt, a detergent/surfactant, a chelator, and a reducing agent.

The enzymatic reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 4.5 to about 10. The reactions can be conducted, for example, at a pH of from about 5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Other reaction conditions may be employed in the methods of the invention, depending on the identity of a particular enzymes, sialic acids, or acceptor molecules employed.

VIII. Cellular Metabolic Incorporation of Free N-Acetyl and O-Acetyl Sialic Acids Free sialic acids added to culture media are taken up by cells via macropinocytosis and transported into the cytosol by the lysosomal transporter sialin. The cytosolic sialic acids can then be activated into CMP-Sias and utilized for biosynthesis, as if they were endogenously produced. Incorporation and cell surface expression of the sialic acids can then be detected by flow cytometry using specific probes (informed by glycan array studies as described herein), and also by biochemical analysis via derivatization with DMB and HPLC analysis of the fluorescent adducts. Free and CMP bound Sias can be differentiated by borohydride reduction without prior acid hydrolysis (CMP-Sias are resistant). Sias incorporated into glycans can be detected after being released by acid hydrolysis and/or use of specific sialidases.

BJA-B human lymphoma cells, Chinese Hamster Ovary (CHO) cells, or their counterparts incapable of endogenous sialic acid production (due to UDP-N-acetylglucosamine 2-epimerase/N-acetylmannosamine kinase deficiency can be cultured in presence of chemoenzymatically synthesized Neu5Ac4NAc, Neu5Ac7NAc, Neu5Ac8NAc, Neu5Ac9NAc, Neu5Ac7,9NAc$_2$ or Neu5Ac8,9NAc$_2$ for monitoring of metabolic incorporation, followed by pulse-chase analysis. Corresponding O-acetylated Neu5Ac counterparts can also be studied in this manner.

Accordingly, another aspect of the invention provides a method for sialylating the surface of a cell. The method includes culturing the cell in the presence of a sialic acid compound as described herein (e.g., a compound of Formula I, Formula Ia, or Formula II) under conditions sufficient to covalently link the compound to the surface of the cell A method for sialylating a glycoprotein is also provided. The method includes forming a mixture comprising the glycoprotein, a sialic acid compound as described herein (e.g., a compound of Formula I, Formula Ia, or Formula II), and a sialyltransferase under conditions sufficient to covalently bond the compound to the glycoprotein.

In a related aspect, a method for sialylating a glycolipid is provided. The method includes forming a mixture comprising the glycolipid, a sialic acid compound as described herein (e.g., a compound of Formula I, Formula Ia, or Formula II), and a sialyltransferase under conditions sufficient to covalently bond the compound to the glycolipid.

IX. Glycan Microarrays p-Nitrophenol-tagged sialosides (e.g., Neu5Ac9NAcα3GalβpNP and Neu5Ac9NAcα6GalβpNP) can be used for substrate specificity studies of various sialidases using a microtiter-plate-based colorimetric high-throughput screening method. In this method, pNP-tagged sialosides obtained by the chemical and/or enzymatic routes described above are incubated with a sialidase and an excess amount of exogalactosidase. When the sialoside is a substrate for the sialidase, the terminal sialic acid residue is cleaved by the sialidase to produce GalβpNP, which is quickly hydrolyzed by the excess amount of galactosidase in the reaction mixture to produce para-nitrophenol (pNP) and Gal. Upon adjustment of the reaction mixture pH to higher than 9.6, the assay is stopped and the amount of the para-nitrophenolate formed is determined spectrophotometrically at $A_{405\ nm}$. The amount of the para-nitrophenolate formed is equivalent to that of the sialic acid released from the sialoside by the sialidase. A comparison of the color developed for different sialosides by different sialidases reveals the effect of the structural diversity of the sialoside substrate on the hydrolytic activity of different sialidases. Siaα3GalβpNP and Siaα6GalβpNP containing different N-acetylated derivatives of O-acetylneuraminic acid mimetics can be used to test the substrate specificities of various sialidases including those from humans, bacteria, and viruses.

Propyl azide aglycones in sialosides of the invention can be reduced to an amino group by catalytic hydrogenation and printed on epoxide-derivatized slides using an appropriate printer (e.g., a SpotBot® Extreme Microarray Spotter) with micron and sub-micron feature sizes. Glycans at a suitable concentration (e.g., 100 μM) in a printing buffer (e.g., 300 mM phosphate buffer, pH 8.4) can be distributed into a 384-well source plate. Humidity level can be maintained at a desired level (e.g., ~60-65% RH) during printing. Slides are then blocked by 0.1 M Tris-HCl, 0.05 M ethanolamine, pH 9.0 (50° C., 1 h), washed twice with 50° C. water, dried, packed, vacuum-sealed, and stored at RT until use.

X. Examples

Materials.

Cy3 and PE affinipure goat anti-human IgG (H+L) antibodies were obtained from Jackson ImmunoResearch Laboratories. *Arthrobacter ureafaciens* sialidase (AUS) and *Vibrio cholerae* neuraminidase were purchased from EY Labs and Roche, respectfully. Chemical and biological material were purchased from commercial sources and used as received. Nuclear Magnetic Resonance (NMR) spectra were recorded in the NMR facility of the University of California, Davis on a Bruker Avance-400 NMR spectrometer (400 MHz for $^1$H, 100 MHz for $^{13}$C). Chemical shifts are reported in parts per million (ppm) on the δ scale. High resolution electrospray ionization (ESI) mass spectra were obtained using a Thermo Electron LTQ-Orbitrap Hybrid MS at the Mass Spectrometry Facility at the University of California, Davis. Column chromatography was performed using RediSep Rf silica columns or an ODS-SM column (51 g, 50 μm, 120 Å, Yamazen) on the CombiFlash® Rf 200i system. Thin layer chromatography (TLC) was performed on silica gel plates (Sorbent Technologies) using anisaldehyde sugar stain for detection. Gel filtration chromatography was performed with a column (100 cm×2.5 cm) packed with Bio-Gel P-2 Fine resins (Bio-Rad). *Pasteurella multocida* sialic acid aldolase (PmNanA), *Neisseria meningitidis* CMP-sialic acid synthetase (NmCSS), and *Pasteurella multocida* sialyltransferase 1 M144D mutant (PmST1 M144D) were expressed and purified as described previously.

Example 1. Chemical Synthesis of Neu5Ac9NAc Precursor 6-Acetamido-6-Deoxy-N-Acetylmannosamine (ManNAc6NAc) and Enzymatic Synthesis of Neu5Ac9NAc A new efficient chemoenzymatic synthetic strategy was developed for the synthesis of Neu5Ac9NAc. The design was to chemically synthesize ManNAc6NAc, a precursor of Neu5Ac9NAc, followed by a sialic acid aldolase-catalyzed reaction for the synthesis of desired Neu5Ac9NAc. ManNAc6NAc was synthesized in a 82% yield from previously obtained 6-azido-6-deoxy-N-acetylmannosamine (ManNAc6N$_3$) using a simple one step reduction and simultaneous acetylation process achieved by adding thioacetic acid to a pyridine solution containing ManNAc6N$_3$. Neu5Ac9NAc was readily obtained from ManNAc6NAc and pyruvate with a 78% yield using a reaction catalyzed by a sialic acid aldolase from *Pasteurella multocida* (PmAldolase).

Synthesis of 2,6-Diacetamido-2,6-dideoxy-D-mannopyranose (ManNAc6NAc) from 2-Acetamido-6-azido-2,6-dideoxy-D-mannopyranose (ManNAc6N$_3$)

To a solution of ManNAc6N$_3$ (300 mg, 1.14 mmol) in pyridine (8 mL), thioacetic acid (2 mL) was added and the mixture was stirred at room temperature for 24 h. The solvent was concentrated in vacuo. The crude product was purified by column chromatography (ethyl acetate/methanol=3:1) to produce ManNAc6NAc (262 mg, 82%) as a colorless amorphous solid. $^1$H NMR (400 MHz, D$_2$O) α-isomer: δ 5.10 (d, J=1.5 Hz, 1H), 4.31 (dd, J=4.7, 1.5 Hz, 1H), 4.04 (dd, J=9.8, 4.7 Hz, 1H), 3.96-3.86 (m, 1H), 3.68-3.33 (m, 3H), 2.07 (s, 3H), 2.03 (s, 3H); β-isomer: δ 5.00 (d, J=1.7 Hz, 1H), 4.46 (dd, J=4.5, 1.7 Hz, 1H), 3.82 (dd, J=9.0, 4.5 Hz, 1H), 3.68-3.33 (m, 4H), 2.11 (s, 3H), 2.04 (s, 3H); $^{13}$C NMR (100 MHz, D$_2$O) δ 175.70, 174.77, 174.54, 174.53, 93.01, 74.43, 71.73, 70.24, 68.58, 68.49, 68.20, 53.98, 53.21, 40.27, 40.16, 22.04, 21.90, 21.77; HRMS (ESI) Anal. Calcd for C$_{10}$H$_{19}$N$_2$O$_2$ [M+H]$^+$: 263.1243, Found: 263.1241.

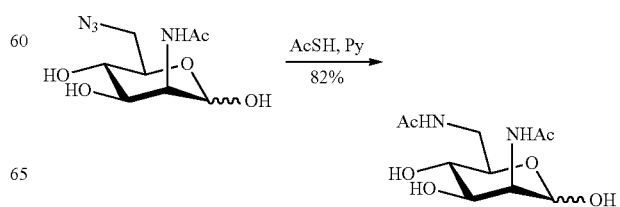

Synthesis of 5,9-Diacetamido-3,5,9-Trideoxy-D-glycero-D-galacto-2-nonulopyranosylonic Acid (Neu5Ac9NAc)

To a solution (10 mL) containing ManNAc6NAc (50 mg, 0.19 mmol), sodium pyruvate (210 mg, 1.9 mmol), and Tris-HCl buffer (100 mM, pH 7.5), PmAldolase (3.0 mg) was added and the reaction was incubated in an isotherm incubator for 48 h at 37° C. with agitation at 100 rpm. The reaction was quenched by adding the same volume of ice-cold ethanol and incubating at 4° C. for 1 h. The solvent was removed and the crude product was purified by column chromatography (ethyl acetate/methanol/water=4:2:1) and followed by a short BioGel P-2 gel filtration column to give Neu5Ac9NAc (55.4 mg, 78%) as a colorless amorphous solid. $^1$H NMR (400 MHz, D$_2$O) δ 4.06-3.92 (m, 3H, H-4, H-6, H-5), 3.80 (ddd, J=9.0, 7.7, 3.1 Hz, 1H, H-8), 3.59 (dd, J=14.1, 3.1 Hz, 1H, H-9), 3.44 (dd, J=9.0, 1.1 Hz, 1H, H-7), 3.24 (dd, J=14.1, 7.6 Hz, 1H, H-9), 2.22 (dd, J=12.9, 4.8 Hz, 1H, H-3e), 2.06 (s, 3H, COCH$_3$), 2.02 (s, 3H, COCH$_3$), 1.83 (dd, J=12.9, 11.4 Hz, 1H, H-3a); $^{13}$C NMR (100 MHz, D$_2$O) δ 176.64, 174.68, 174.56, 96.36, 70.09, 69.77, 68.77, 67.25, 52.26, 42.76, 39.35, 22.08, 21.82; HRMS (ESI) Anal. Calcd for C$_{13}$H$_{21}$N$_2$O$_9$ [M−H]$^-$: 349.1247, Found: 349.1255.

Example 2. One-Pot Multienzyme (OPME) Synthetic Approach for Facile Production of Neu5Ac9NAcα3Galβ4GlcβProNH$_2$ for Glycan Microarray Studies ManNAc6NAc was also used directly for synthesizing a sialoside analog Neu5Ac9NAcα3Galβ4GlcβProN$_3$ via an efficient one-pot multienzyme (OPME) sialylation system containing PmAldolase, a CMP-sialic acid synthetase from *Neisseria meningitidis* (NmCSS), and *Pasteurella multocida* sialyltransferase 1 M144D mutant (PmST1 M144D). Neu5Ac9NAcα3Galβ4GlcβProN$_3$ was obtained in 84% yield and was readily converted in a quantitative yield to Neu5Ac9NAcα3Galβ4GlcβProNH$_2$ by catalytic hydrogenation using H$_2$ in the presence of Pd/C.

solved in Tris-HCl buffer (100 mM, pH 8.5, 10 mL) containing 20 mM of MgCl$_2$. The pH of the solution was further adjusted to 8.5 with 4 M NaOH. PmAldolase (1.5 mg), NmCSS (2.5 mg) and PmST1 M144D (2.5 mg) were added. The reaction was incubated in an isotherm incubator for 24 h at 37° C. with agitation at 100 rpm. The reaction was quenched by adding the same volume of ice-cold ethanol and incubating at 4° C. for 1 h. The formed precipitates were removed by centrifugation and the supernatant was concentrated. The residue was purified by passing through a BioGel P-2 gel filtration column followed by a C18 column (H$_2$O/CH$_3$CN=10:1) (70.9 mg, Yield 84%). $^1$H NMR (400 MHz, D$_2$O) δ 4.52 (dd, J=12.8, 7.9 Hz, 2H), 4.10 (dd, J=9.9, 3.2 Hz, 1H), 4.06-3.86 (m, 4H), 3.88-3.53 (m, 13H), 3.54-3.43 (m, 3H), 3.37-3.23 (m, 2H), 2.76 (dd, J=12.4, 4.6 Hz, 1H), 2.04 (s, 3H), 2.04 (s, 3H), 1.92 (p, J=6.6 Hz, 2H), 1.81 (t, J=12.1 Hz, 1H); $^{13}$C NMR (100 MHz, D$_2$O) δ 174.92, 174.39, 173.81, 102.60, 102.11, 99.87, 78.17, 75.53, 75.14, 74.78, 74.33, 72.79, 72.73, 69.96, 69.58, 69.36, 68.30, 67.46, 67.34, 61.01, 60.01, 51.66, 47.86, 42.11, 39.61, 28.22, 22.02, 21.81; HRMS (ESI) Anal. Calcd for C$_{28}$H$_{46}$N$_5$O$_{19}$ [M−H]$^-$: 756.2787, Found: 756.2792.

Synthesis of 3-Aminopropyl O-(5,9-Diacetamido-3,5,9-trideoxy-D-glycero-α-D-galacto-2-nonulopyranosylonic acid)-(2→3)—O-β-D-galactopyranosyl-(1→4)-β-D-glucopyranoside (Neu5Ac9NAcα3Galβ4GlcβProNH$_2$)

A catalytic amount of 10% palladium on charcoal (Pd/C) was added to the solution of Neu5Ac9NAcα3Galβ4GlcβProN$_3$ (5.6 mg) in H$_2$O (1 mL). The mixture was stirred under hydrogen atmosphere for 3 h. The solution was diluted with MeOH (2 mL) and passed through a filter to remove the catalyst. The solvent was concentrated in vacuo to give Neu5Ac9NAcα3Galβ4GlcβProNH$_2$ (5.4 mg, quant.) as a colorless amorphous solid. HRMS (ESI) Anal. Calcd for C$_{28}$H$_{48}$N$_3$O$_{19}$ [M−H]$^-$: 730.2882, Found: 730.2914.

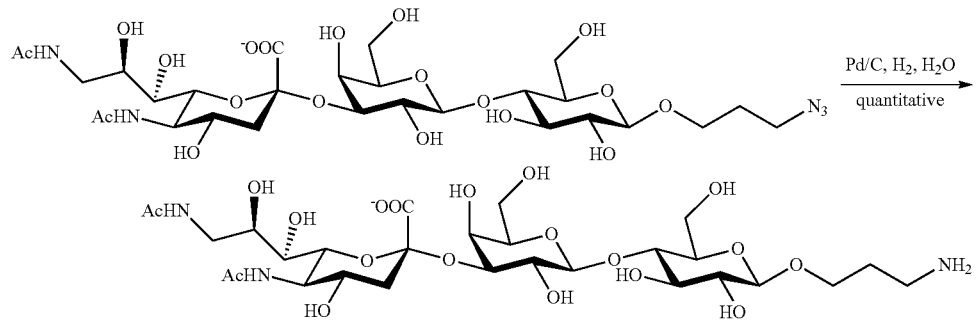

Synthesis of 3-Azidopropyl O-(5,9-Diacetamido-3,5,9-trideoxy-D-glycero-α-D-galacto-2-nonulopyranosylonic acid)-(2→3)—O-β-D-galactopyranosyl-(1→4)-β-D-glucopyranoside (Neu5Ac9NAcα3Galβ4GlcβProN$_3$)

Neu5Ac9NAcα3Galβ4GlcβProN$_3$ was synthesized following the general procedure for enzymatic synthesis of sialosides. Galβ4GlcβProN$_3$ (46 mg, 0.11 mmol), ManNAc6NAc (43 mg, 0.16 mmol), sodium pyruvate (91 mg, 0.83 mmol) and CTP (87 mg, 0.16 mmol) were dis- Reduction of Neu5,9Ac$_2$α3Galβ4GlcβProN$_3$ to Neu5,9Ac$_2$α3Galβ4GlcβProNH$_2$.

Neu5,9Ac$_2$α3Galβ4GlcβProN$_3$ (20 mg) was dissolved in H$_2$O/MeOH (3 mL, 2:1 by volume) and a drop of glacial acetic acid was added. The mixture was stirred under hydrogen atmosphere in the presence of 10% palladium on charcoal for 1 h. The reaction mixture was then passed through a HyperSep C18 cartridge (1 g, 40-60 μm, Thermo) and eluted with water. The collection fraction containing the desired product was collected and lyophilized. The obtained white power was stored at −20° C. for long-term storage.

HPLC Analysis of Neu5,9Ac$_2$α3Galβ4GlcβProNH$_2$.

Neu5,9Ac$_2$α3Galβ4Glc(ProNH$_2$ was first hydrolyzed in glacial acetic acid (2 M) for 3 h at 80° C. AUS hydrolysis was performed based on the company protocol. DMB derivatization was performed as reported previously. The DMB-derivatized samples were analyzed on a Dionex Ultra3000 HPLC System using a Phenomenex Gemini 5 μm C18 250×4.6 mm HPLC column at room temperature. The fluorescence was detected at 448 nm using excitation at 373 nm.

Example 3. Preparation of Hemagglutinin-Esterase Probes for 9-OAc Sia

The sequences for expressing the ectodomains of the hemagglutinin-esterase (HE) of two nidoviruses (PToV-P4 and BCoV-Mebus) were synthesized by GenScript (Piscataway, N.J.), with varied degrees of insect codon optimization. To generate the probe molecules, the esterase domains were inactivated by changing the active site of the Ser residue to Ala by site-directed mutagenesis using Q5 mutagenesis (New England Biolabs). The HE proteins were linked to the baculovirus gp64 signal sequence peptide at their N-termini, and the C-terminus fused to a linker containing a thrombin cleavage sequence, the Fc domain of Human IgG1, and a 6-His sequence. Constructs were cloned into pFastBac-1 (Life Technologies) to generate recombinant bacmids following the manufacturer's protocol. Recombinant baculoviruses were recovered by transfection of the bacmids into Sf9 insect cells using Cellfectin II (Life Technologies). Viruses were used to infect suspension High Five cells and the supernatant harvested 2-3 days post-infection. The proteins were purified by binding to a HiTrap ProteinG HP 5 ml column (GE Healthcare Life Sciences, Piscataway, N.J.) and eluted with 0.1M citrate, pH 3.0 (pH neutralization to 7.8 with 1 M of Tris-HCl, pH 9.0) using AKTA FPLC system (GE Healthcare Life Sciences). The HE-Fc containing fractions were dialyzed in PBS and concentrated using 30 kD Amicon Ultra-15 filters (EMD Millipore). Purified proteins were stored at −80° C. in aliquots.

Example 4. Glycan Microarray Studies of Viral Proteins and Human Siglec-9 Binding to Sialosides Containing Neu5,9Ac$_2$ and Neu5Ac9NAc The synthesized glycan Neu5Ac9NAcα3Galβ4GlcβProNH$_2$ was used in a glycan library for glycan microarray studies. Glycan microarrays were fabricated using epoxide-derivatized slides (Corning by Thermo Fisher Scientific) and Arrayit SpotBot® Extreme Microarray Spotter. The arrays were printed with Stealth SMP3 microarray spotting pins from ArrayIt (Sunnyvale, Calif., USA) generating 100 m diameter spots. 4 pins were used; with each pin printing 4 replicate spots/well. The glycoconjugates were prepared at 100 μM concentration in an optimized printing buffer (300 mM phosphate buffer, pH 8.4). They were then distributed into a 384-well source plate in 20 μL per well. To monitor printing quality, 4 replicate-wells of human IgG (Jackson ImmunoResearch) was used at 100 μg/ml (in PBS) for each printing-pin. One complete array was printed on each slide (within approx 12 hour/~28 slides). The humidity level in the arraying chamber was maintained at about 60-65% during printing. Printed slides were left on spotter deck overnight, allowing humidity to drop to ambient levels. Printed glycan microarray slides were blocked by 50° C. pre-warmed blocking solution (0.1 M Tris-HCl, 0.05 M ethanolamine, pH 9.0, 1 h). They were then washed twice with 50° C. pre-warmed water and dried. Slides were packed, vacuum-sealed and stored at RT until used.

To assure the quality of the printed slides, one or two slides were used for quality control using antibodies, lectins and serum samples with known glycan binding specificity. For glycan array binding, slides were fitted in a multi-well microarray hybridization cassette (AHC4X8S, ArrayIt, Sunnyvale, Calif., USA) to divide into 8 subarrays. The subarrays were blocked with Ovalbumin (1% w/v) in PBS (pH 7.4) for 1 h at RT, with gentle shaking. For the esterase activity studies on the array, after removing the blocking solution, slides were first treated with 20 μg/mL PToV-P4-Fc (esterase active) in blocking buffer for 2 h at RT and then washed with PBS in 0.1% Tween 20 and then PBS (10 min/wash with shaking). Subsequently, diluted protein samples in blocking solution with various concentrations were added to each subarray (both esterase treated and non-treated slides). After incubating the protein samples for 2 h at RT with gentle shaking, the slides were washed with PBS in 0.1% Tween 20 and then PBS (10 min/wash with shaking). Cy3 affinipure goat anti-human IgG (H+L) antibody (Jackson ImmunoResearch) was used for the detection of BCoV-Mebus-Fc, PToV-P4-Fc and human Siglec-9-Fc. Diluted antibody in PBS was added to the subarrays and incubated for 1 h at RT. They were washed with PBS in 0.1% Tween 20, PBS and water (10 min/wash with shaking) and dried. The microarray slides were scanned using a Genepix 4000B microarray scanner (Molecular Devices Corp., Union City, Calif., USA) at 100% laser power, PMT Gain 450 and 10 μM pixels. Data analysis was performed using Genepix Pro 7.0 analysis software (Molecular Devices Corp., Union City, Calif.) and the outputs were saved as gpr and jpg files. The gpr files then were saved as xls. The data were further analyzed with Excel. Local background subtraction was performed and data were plotted separately for each subarray. The binding specificity to glycoconjugates for each protein was plotted based on the RFU (Relative Fluorescence Units), average fluorescence value for 4 replicates, versus glycan IDs. The standard deviations were calculated and the error bars were found for each glycan binding. The final graphs (FIG. 3) were plotted based on the tested proteins versus RFU for each glycan in GraphPad Prism 5.

Investigating and Minimizing 9-O-Acetyl Group Loss at Various Steps in Sample Preparation, Preparing and Using of Glycan Microarrays.

The extent of de-O-acetylation at the final steps of the synthesis and entire glycan microarray process was investigated, for the model 9-OAc-glycan Neu5,9Ac$_2$α3Galβ4GlcβProN$_3$ and its reduced form Neu5,9Ac$_2$α3Galβ4GlcβProNH$_2$. The azide-containing glycan was analyzed using nuclear magnetic resonance (NMR) spectrometry and mass spectrometry (MS). It was found to be pure, without any loss of OAc group. The compound was then subjected to hydrogenolysis using H$_2$ and Pd—C in water with a drop of glacial acetic acid. The reaction was completed in one hour as detected using MS. To minimize de-O-acetylation during the celite filtration step which uses Na$_2$CO$_3$ as a mild base, filtration after catalytic hydrogenation was replaced by passing the reaction solution through a nylon syringe filter (0.2 μm). The product was then purified using a short C-18 cartridge (water as an eluant) instead of the commonly and previously used Bio-Gel purification, as it is faster. The fractions containing the pure product were collected and lyophilized. No noticeable loss of the O-acetyl group was observed using the improved procedures described above.

Figure 2A:
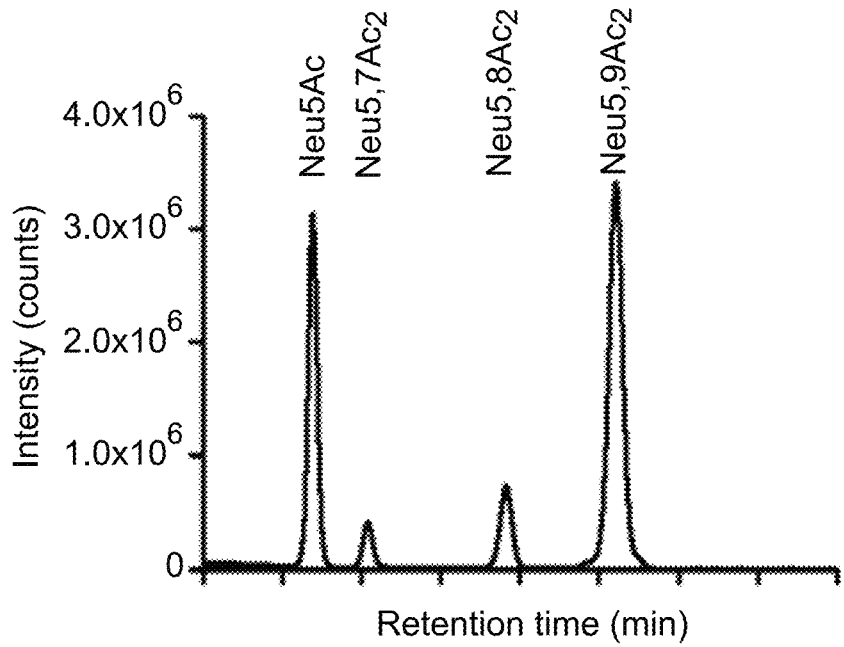
FIG. 2A shows the 1,2-diamino-4,5-methylenedioxybenzene (DMB) derivatization and HPLC analysis of sialic acids released from Neu5,9Ac$_2$α3Galβ4GlcβProNH$_2$ using acetic acid.
Figure 2B:
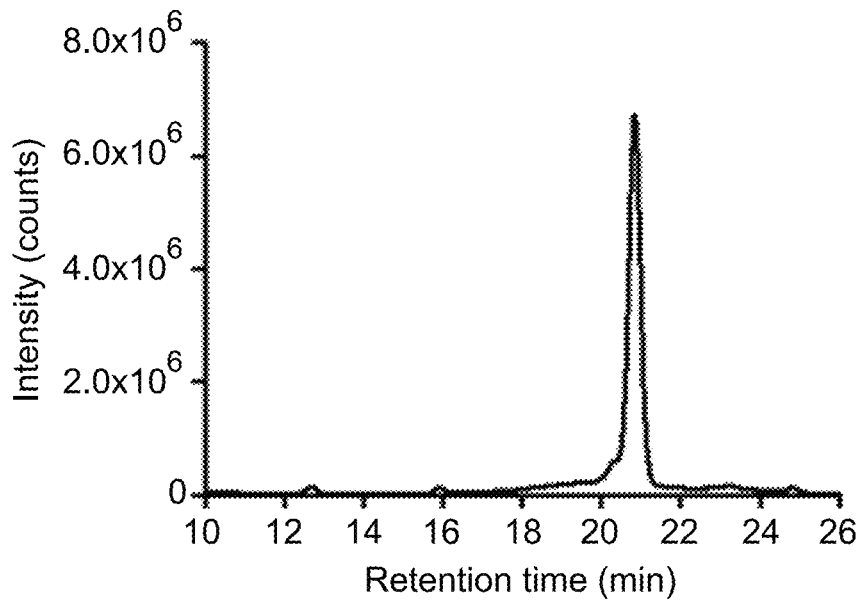
FIG. 2B shows the DMB derivatization and HPLC analysis of sialic acids released from Neu5,9Ac$_2$α3Galβ4GlcβProNH$_2$ using *Arthrobacter ureafaciens* sialidase (AUS).

Then, the reduced glycan was quantified for the OAc loss at each step of glycan microarray process. The results revealed that ~45% of the OAc group was either lost from the 9-position of Neu5Ac or migrated to 7- and 8-positions of the sialic acid upon conventional analysis procedures including release of sialic acids with acetic acid, derivatization with 1,2-diamino-4,5-methylenedioxybenzene (DMB), followed by high performance liquid chromatography (HPLC) analysis of fluorescent adducts (FIG. 2A). In comparison, *Arthrobacter ureafaciens* sialidase (AUS) treatment followed by DMB derivatization at low temperature showed only 1.5% loss of the OAc group (FIG. 2B). This means there is no significant de-O-acetylation during initial preparation of stock solution in water (it should be noted that the final synthetic product is a neutral sodium salt—earlier studies in which the acid form was prepared was associated with some de-O-acetylation, data not shown) and AUS treatment with low temperature DMB derivatization. However, about 3% loss of OAc was observed during storage in phosphate buffer (pH 8.4) at room temperature, a condition popular for current microarray printing. Furthermore, about 5% of the sialic acid is de-O-acetylated under the standard blocking condition used for glycan arrays (ethanolamine in Tris-HCl buffer, pH 9.0). The glycan stock solution was also analyzed again after three months of storage at −20° C. and a few freeze-thaw cycles. It was noticed that another 4% of the OAc group was released over three months. Therefore, a small amount of de-O-acetylation occurs under the storage conditions and under conditions used for microarray printing and slide blocking. Any further loss of O-acetylation after printing during the binding and analysis, however, cannot be directly monitored.

Overall, definitive conclusions about binding of probes can therefore only be made where binding is exclusively to the O-acetylated sialoglycan spots and not to the corresponding non-O-acetylated ones, as discussed later. A more general conclusion is that, even under the most carefully managed handling by skilled experimentalists, some loss of 9-O-acetylation appears inevitable. Taken together with the knowledge that esterases of bacterial and vertebrate origin are very common in biological systems, there is an intractable problem facing the systematic study of the chemistry and biology of sialic acid 9-O-acetylation.

Results.

Figure 3A:
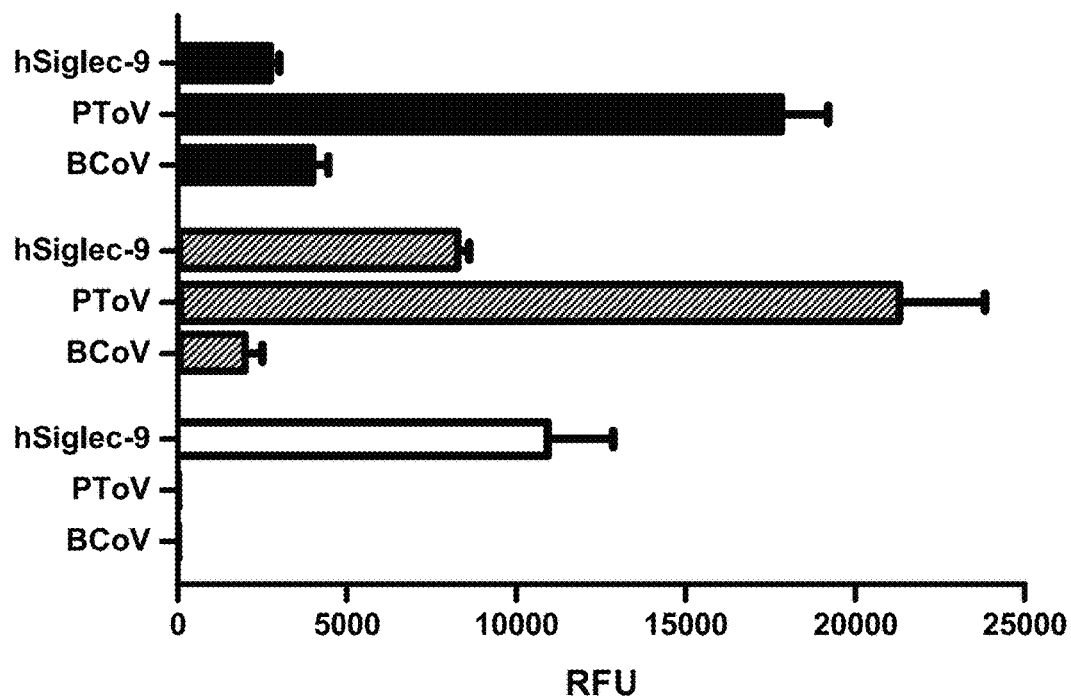
FIG. 3A shows sialoglycan microarray binding specificity studies of human Siglec-9 (hSiglec-9-Fc, hSiglec-9), porcine torovirus hemagglutinin-esterase (PToV), and bovine coronavirus hemagglutinin-esterase (BCoV) (both PToV and BCoV were mutated to ablate their esterase activity) towards Neu5Ac9NAcα3Galβ4GlcβProNH$_2$ (black columns), Neu5,9Ac$_2$α3Galβ4GlcβProNH$_2$ (gray columns), and Neu5Acα3Galβ4GlcβProNH$_2$ (white columns) without esterase treatment.
Figure 3B:
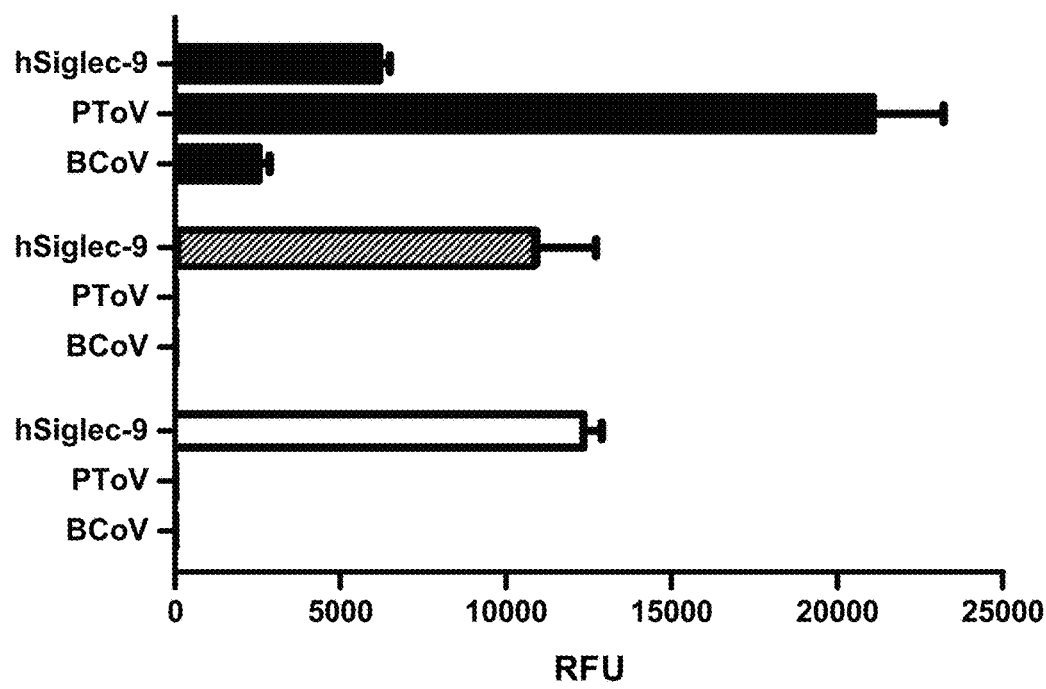
FIG. 3B shows sialoglycan microarray binding specificity studies of human Siglec-9 (hSiglec-9-Fc, hSiglec-9), porcine torovirus hemagglutinin-esterase (PToV), and bovine coronavirus hemagglutinin-esterase (BCoV) (both PToV and BCoV were mutated to ablate their esterase activity) towards Neu5Ac9NAcα3Galβ4GlcβProNH$_2$ (black columns), Neu5,9Ac$_2$α3Galβ4GlcβProNH$_2$ (gray columns), and Neu5Acα3Galβ4GlcβProNH$_2$ (white columns) treated with esterase active PToV.

Proteins known to recognize Neu5,9Ac$_2$ were tested including immunoglobulin Fc-fused human Siglec-9-Fc (hSiglec-9), as well as viral proteins (hemagglutinins in an esterase inactivated form) of porcine torovirus (PToV-P4-Fc, PToV) and bovine coronavirus (BCoV-Mebus-Fc, BCoV). The results were compared to those obtained using Neu5,9Ac$_2$α3Galβ4GlcβProNH$_2$, and Neu5Acα3Galβ4GlcβProNH$_2$ lacking 9-modification at sialic acid as probes in the same slides (FIG. 3). Results from glycan microarray studies (FIG. 3A) showed that hSiglec-9 prefers binding to Neu5Ac-glycan without 9-modification at sialic acid (white column), but with observable binding to both Neu5Ac9NAc (black column) and Neu5,9Ac$_2$ (grey column)-containing glycans. In comparison, both PToV and BCoV prefer binding to both sialoglycans with 9-modifications such as Neu5Ac9NAc and Neu5,9Ac$_2$. BCoV is a known viral protein probe for 9OAc sialic acids (both Neu5,9Ac$_2$ and Neu5Gc9Ac) and especially 7,9-di-OAc sialic acids. The more specific 9OAc-sialic acid viral probe PToV (prefers Neu5,9Ac$_2$ over Neu5Gc9Ac) binds to both 9OAc and 9NAc glycans although it shows slightly stronger binding to the 9OAc derivative. The specific recognition of 9-modified sialic acid by esterase-inactive PToV and BCoV, the stability of 9NAc, and the esterase lability of 9OAc were evident by comparing the binding study results of esterase active PToV-treated samples (FIG. 3B) with those non-treated ones (FIG. 3A).

Example 5. Incorporation of Neu5Ac9NAc and Neu5,9Ac$_2$ in Cell-Surface Glycans

Cell Culture and Sugar Supplementation.

BJA-B K20 cells were propagated as suspension with RPMI 1640 medium, supplemented with 10% heat-inactivated fetal calf serum, 2 mM glutamine, 100 U of penicillin per mL, 100 µg of streptomycin per mL in a humidified 5% CO$_2$, 37° C. atmosphere as described previously. For medium supplementation, Neu5Ac9NAc and Neu5,9Ac$_2$ were dissolved in PBS, titrated to a neutral pH and filter sterilized. The sugars were added at the indicated concentrations. For the sugar turnover experiments, the cells were fed as mentioned above and on day 0, the cell culture media was switched to RPMI 1640 medium, supplemented with 1% Nutridoma (Roche), 100 U of penicillin per mL and 100 µg of streptomycin without Neu5Ac9NAc and Neu5,9Ac$_2$.

Flow Cytometry.

Cells were washed with PBS and incubated with 10 rig/mL of PToV probes in PBS with 1% BSA and 10 mM EDTA for 30 minutes on ice. Subsequently, cells were washed with PBS and incubated with PE goat anti-human IgG antibody for 30 minutes on ice. After an additional washing step, the cells were analyzed by FACSCalibur (BD).

Feeding of Free Neu5Ac9NAc and Neu5,9Ac$_2$ to Human Cells Followed by Measuring Cell Surface Incorporation with PToV Probes.

Figure 4:
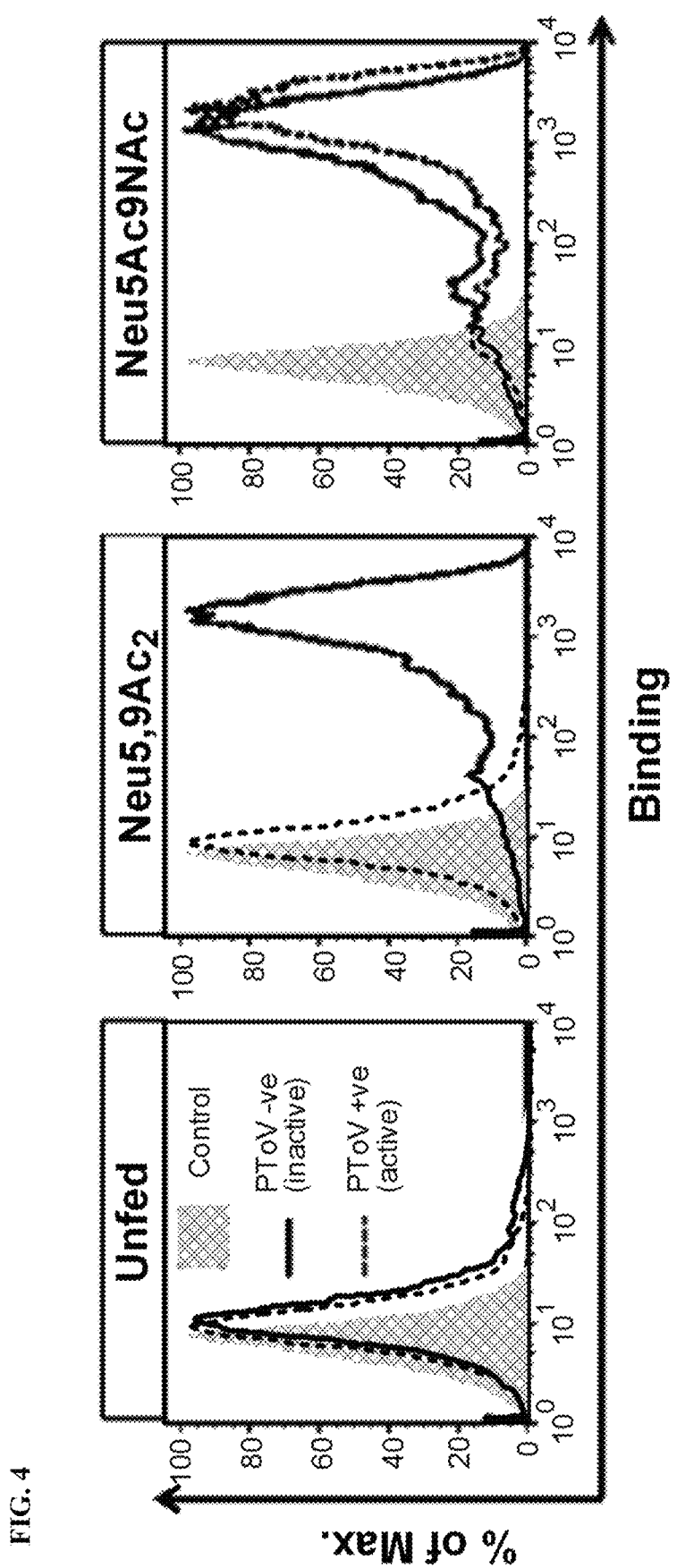
FIG. 4 shows the detection of incorporation of Neu5,9Ac$_2$ or Neu5Ac9NAc into hypo-sialylated human lymphoma BJA-B K20 cells. Cells were fed (or not) for 3 days with free Sias (1 mM) and then stained with PToV in inactive (mutated, solid black line) or active (dashed black line)O-acetylesterase forms. The binding was analyzed by flow cytometry.

Human Burkitt lymphoma B cells (BJA-B K20) cells are hypo-sialylated due to the lack of UDP-N-acetylglucosamine 2-epimerase/N-acetylmannosamine kinase, therefore maximizing exogenous sialic acid incorporation. After three days of feeding with either 1 mM of free Neu5Ac9NAc or Neu5,9Ac$_2$, cells were probed with PToV-P4-Fc (PToV) with or without active esterase to measure cell surface incorporation of the sugars. Both Neu5Ac9NAc and Neu5,9Ac$_2$ were detected on the cell surface, but only Neu5Ac9NAc-fed ones were resistant to virus-hemagglutinin-esterase activity (FIG. 4).

Feeding of Free Neu5Ac, Neu5,9Ac$_2$, Neu5Ac9NAc to Human BJA-B K20 Cells Followed by Measuring Cell Surface Incorporation of Sialic Acids with DMB Derivatization and HPLC Analysis.

Figure 5A:
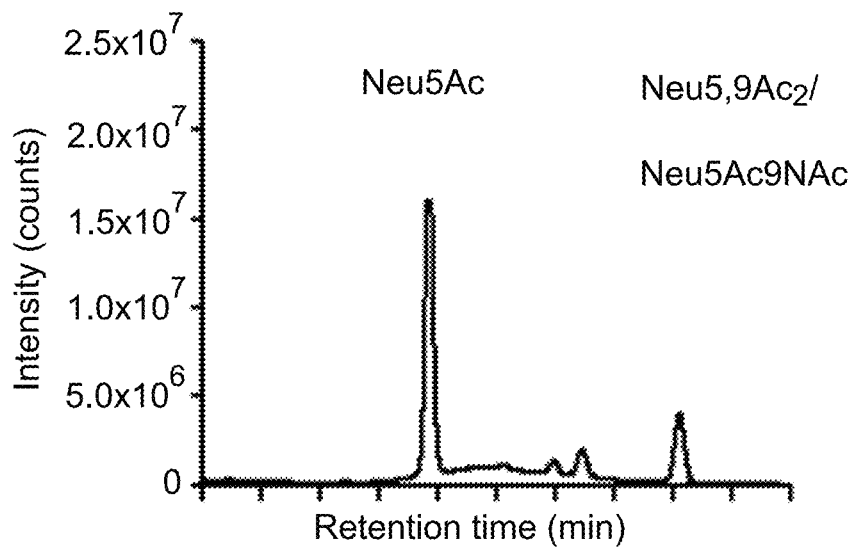
FIG. 5A shows DMB derivatization and high performance liquid chromatography (HPLC) analysis of sialic acids released from cell membranes of BJA-B K20 fed for 3 days with 1 mM of Neu5Ac.
Figure 5B:
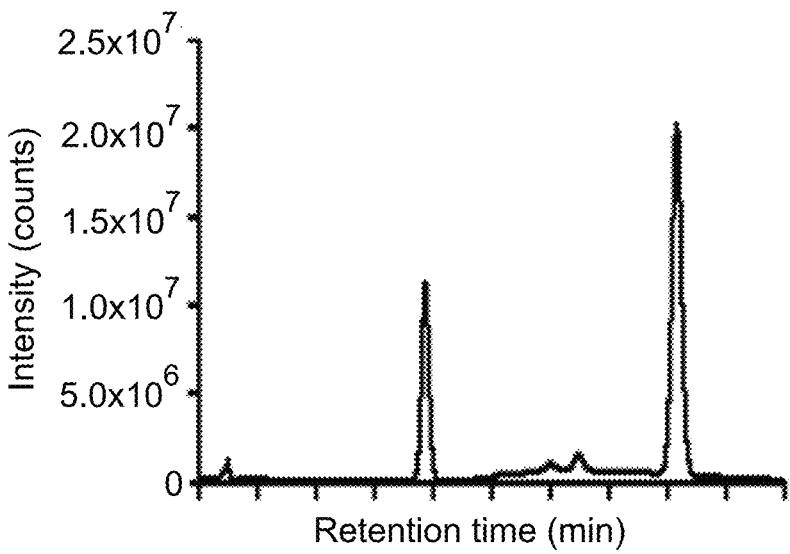
FIG. 5B shows DMB derivatization and HPLC analysis of sialic acids released from cell membranes of BJA-B K20 fed for 3 days with 1 mM of Neu5,9Ac$_2$.
Figure 5C:
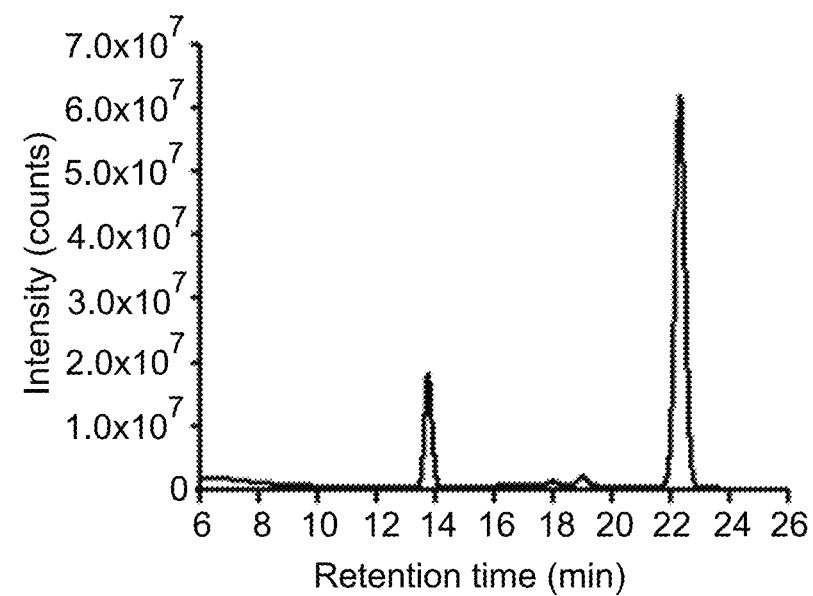
FIG. 5C shows DMB derivatization and HPLC analysis of sialic acids released from cell membranes of BJA-B K20 fed for 3 days with 1 mM of Neu5Ac9NAc.

BJA-B K20 cells were fed with 1 mM of Neu5Ac (FIG. 5A), Neu5,9Ac$_2$ (FIG. 5B), or Neu5Ac9NAc (FIG. 5C) for 3 days. The cell membranes were recovered and sialic acids were released with *Vibrio cholerae* neuraminidase. The released sialic acids were derivatized with DMB and subjected to HPLC analysis which showed incorporation of each sugar on the cell membrane. Although BJA-B K20 cells are hypo-sialylated, they still express some Neu5Ac as can be observed on the cell membrane of Neu5,9Ac$_2$ or Neu5Ac9NAc-fed cells (FIGS. 5B and 5C).

Monitoring Turnover of Neu5Ac9NAc and Neu5,9Ac$_2$ on the Cell Surface.

Figure 6A:
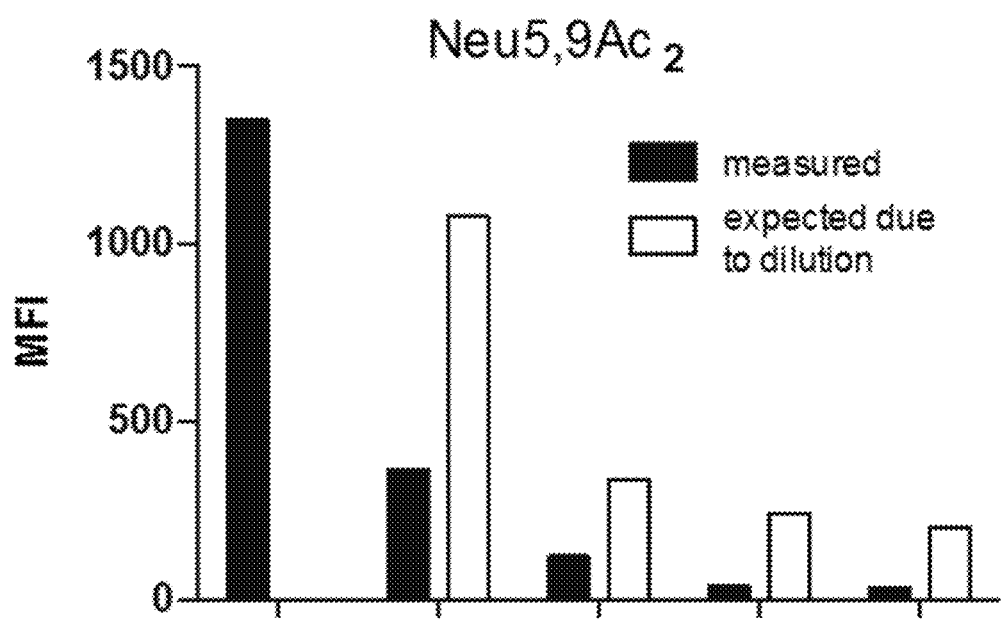
FIG. 6A shows the turnover of incorporated Neu5,9Ac$_2$ in BJA-B K20 cells. Cells were fed for two days with 1 mM of Neu5,9Ac$_2$ or Neu5Ac9NAc. After two days, the feeding with Neu5,9Ac$_2$ or Neu5Ac9NAc was stopped and the turnover of these sugars was measured with PToV (esterase inactive) probe by flow cytometry in the course of 4 days. The expected amount of sugar was calculated based on the initial MFI (Mean Fluorescence Intensity) at day 0 and the following cell doubling.
Figure 6B:
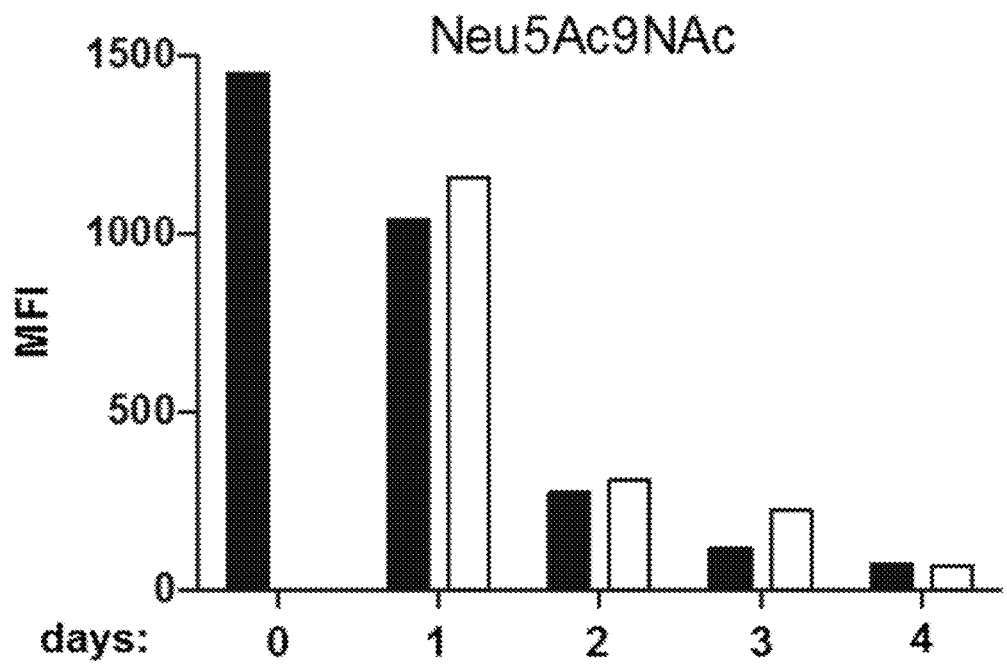
FIG. 6B shows the turnover of incorporated Neu5Ac9NAc in BJA-B K20 cells. Cells were fed for two days with 1 mM of Neu5,9Ac$_2$ or Neu5Ac9NAc. After two days, the feeding with Neu5,9Ac$_2$ or Neu5Ac9NAc was stopped and the turnover of these sugars was measured with PToV (esterase inactive) probe by flow cytometry in the course of 4 days. The expected amount of sugar was calculated based on the initial MFI (Mean Fluorescence Intensity) at day 0 and the following cell doubling.

After feeding BJA-B K20 cells for two days with either 1 mM of free Neu5Ac9NAc or Neu5,9Ac$_2$, the sugars were removed from the cell culture medium (day 0) and the presence of the sialic acids on the cell surface was monitored for 4 days with the PToV (esterase inactive) probe (FIG. 6). The turnover of Neu5,9Ac$_2$ on cell surface was shown to be faster than that of Neu5Ac9NAc.

Figure 7:
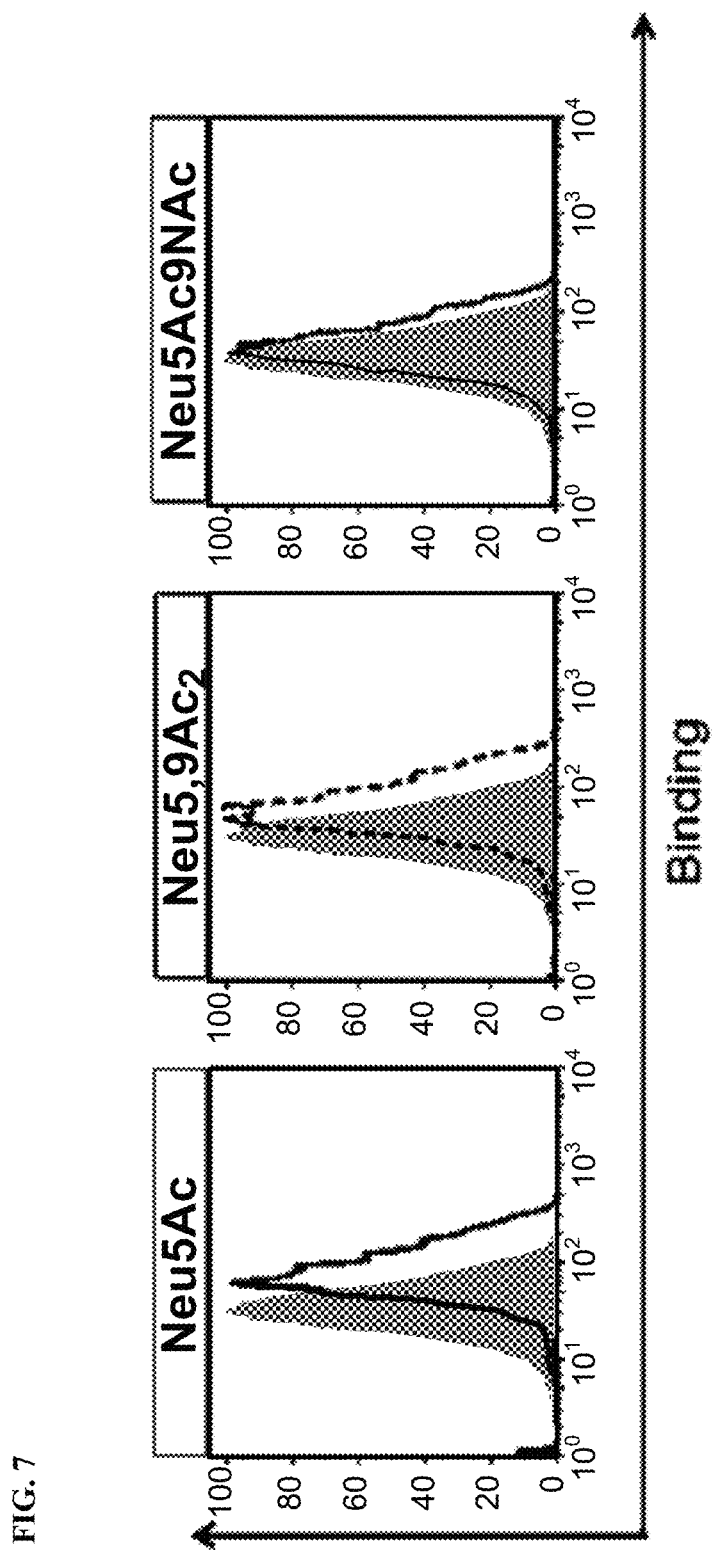
FIG. 7 shows the probing of Neu5Ac, Neu5,9Ac$_2$ or Neu5Ac9NAc-fed human lymphoma BJA-B K20 cells with CD22-Fc to detect ligands. Cells were fed for 3 days with 3 mM of Neu5Ac (solid black line), Neu5,9Ac$_2$ (dashed black line) or Neu5Ac9NAc (dotted line) and then stained with human CD22-Fc to detect ligands (and compared with non-fed cells, gray). The binding was analyzed by flow cytometry.

Feeding of Neu5Ac, Neu5,9Ac$_2$, and Neu5Ac9NAc to Human BJA-B K20 Cells Followed by Measuring Cell Surface Incorporation with Human CD22-Fc. P BJA-B K20 cells were fed with 3 mM of Neu5Ac, Neu5Ac9NAc, or Neu5,9Ac$_2$. After 3 days of feeding, BJA-B K20 cells were probed with human CD22-Fc/Siglec-2 to detect ligands (FIG. 7). It was found that there was a high expression of CD22 ligand when the cells were fed with Neu5Ac (FIG. 7A). However, when the cells were grown in the presence of Neu5Ac9NAc, the expression of the CD22 ligand was minimal (FIG. 7C). The level of CD22 ligand expressed on the cells fed with Neu5,9Ac$_2$ (FIG. 7B) was between the two which could be explained by possible partial de-O-acetylation of Neu5,9Ac$_2$. This supports previous observations that human CD22-Fc recognizes α2-6-linked sialosides with Neu5Ac or N-glycolylneuraminic acid (Neu5Gc) as the preferred naturally existing sialic acid form and 9-O-acetyl modification on sialic acid blocks the binding. Furthermore, it demonstrates further that Neu5Ac9NAc can be a suitable substituent for natural Neu5,9Ac$_2$ while has improved stability.

Example 6. Comparison of N-Acetylated and O-Acetylated Sialosides Using Molecular Dynamics The molecular dynamics simulations were carried out using the AMBER15 software suite, principally using tleap for setup and pmemd.cuda for dynamics. The simulations employed the GLYCAM force field and TIP3P water model; the sialoside was solvated in a rectangular water box with roughly 1000 water molecules. The simulations used a 2.0 fs time step and a Langevin thermostat set to 298.15 K and a collision frequency of 1.0 ps$^{-1}$. The equilibration simulations used a Berendsen barostat set to 1.0 atm, a compressibility of 44.6×10$^{-6}$ bar$^{-1}$ and a time constant of 1.0 ps$^{-1}$; the production simulations were carried out at constant volume. The particle mesh Ewald method was used to treat long range electrostatics with a real-space cutoff of 8.0 Å.

The parameters for the N-acetyl functional group were developed following the procedure outlined by Kirschner (*J. Comput. Chem.* 29, 622-655). The initial guess force field for Neu5Ac9NAc was constructed by replacing the 9-O-acetyl group with a copy of the 5-N-acetyl group and the corresponding force field parameters. After 100 ps of equilibration in the NPT ensemble, 50 ns of NVT dynamics were generated, and 50 snapshots at 1 ns intervals were saved. These snapshots were energy-minimized in the TeraChem software package with the dihedral angles constrained, employing the restricted Hartree-Fock method and 6-31G* basis set. The energy-minimized geometries were used as input to a restrained electrostatic potential calculation carried out using the R. E. D. server using the RESP-C2 charge model as appropriate for the GLYCAM force field. In the charge optimization, the charges for the terminal hydroxyl group were kept at the initial values and all hydrogen charges set to zero. The resulting final set of charges on the N-acetyl group has a slightly different total charge from the original O-acetyl group; the charge on the carbon atom that the N-acetyl group is bonded to is increased by +0.0014, instead of the +0.008 value used for 0-acetyl. An analogous calculation was carried out for the ProN$_3$ functional group to obtain a complete set of charges for Neu5, 9Ac$_2$α3Galβ4GlcβProN$_3$. The valence force field parameters for ProN$_3$ were copied over from the general AMBER force field (GAFF) by comparing GLYCAM atom types to GAFF atom types.

After the parameterization was finished, the production simulations of Neu5,9Ac$_2$α3Galβ4GlcβProN$_3$ and Neu5Ac9NAcα3Galβ4GlcβProN$_3$ were carried out to collect data for the free energy plots. The simulations were unbiased and each simulation ran for 2.5 μs, and configurations were saved every 10 ps. The free energy plot was constructed by projecting the ensemble of configurations onto the selected dihedral degrees of freedom.

Classical molecular dynamics (MD) simulations of Neu5, 9Ac$_2$α3Galβ4GlcβProN$_3$ and Neu5Ac9NAcα3Galβ4GlcβProN$_3$ were carried out to investigate any differences that the chemical modification would introduce into the conformational ensemble in aqueous solution. The simulations were based on the GLYCAM carbohydrate force field and TIP3P water model, with added electrostatic parameters for describing the N-acetylation. The total length of the simulation exceeded 2 μs for each of the two sialosides studied, which has previously been noted to provide good sampling of oligosaccharide conformational degrees of freedom.

Figure 8:
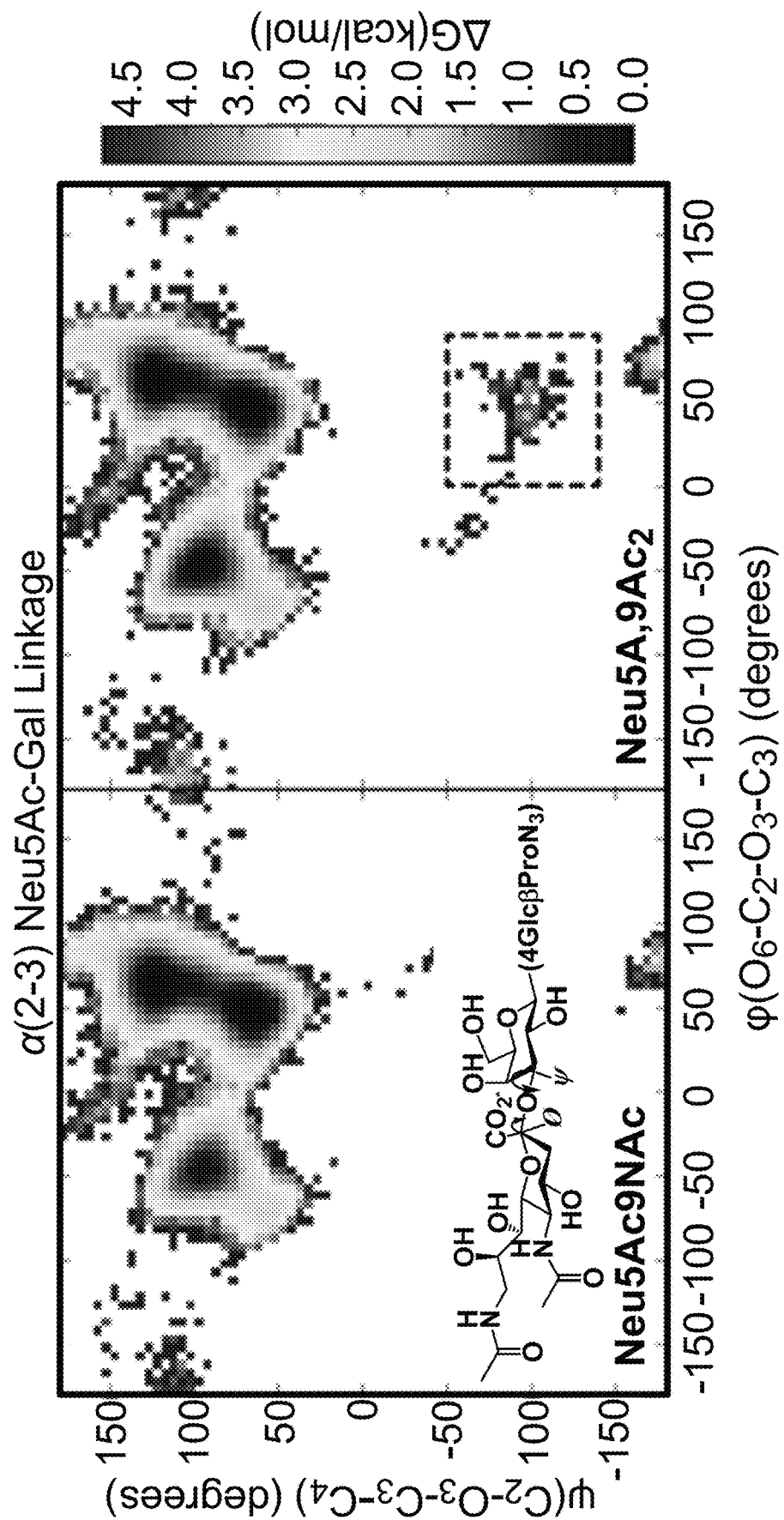
FIG. 8 shows free energy diagrams of glycosidic linkages in solution for Neu5Ac9NAcα3Galβ4GlcβProN$_3$ and the corresponding Neu5,9Ac$_2$α3Galβ4GlcβProN$_3$. The 9NAc and 9OAc analogs are compared in the left and right panels. The predominant states are almost identical for the two molecules, indicating that the 9NAc and 9OAc sialosides have similar structures in solution. The 9OAc sialoside has a sparsely populated state not seen in 9NAc (dotted box).

FIG. 8 shows the results of the simulations projected onto the ($\phi$, $\psi$) dihedral angles of the glycosidic linkage between Sia and Gal. The main observation is that the conformational ensembles of the N-acetylated and O-acetylated sialosides are highly equivalent. There are three free energy basins on the positive $\psi$ half of the plot with the same shape and the relative free energies between the basins are similar to within 1 kcal/mol.

Figure 9:
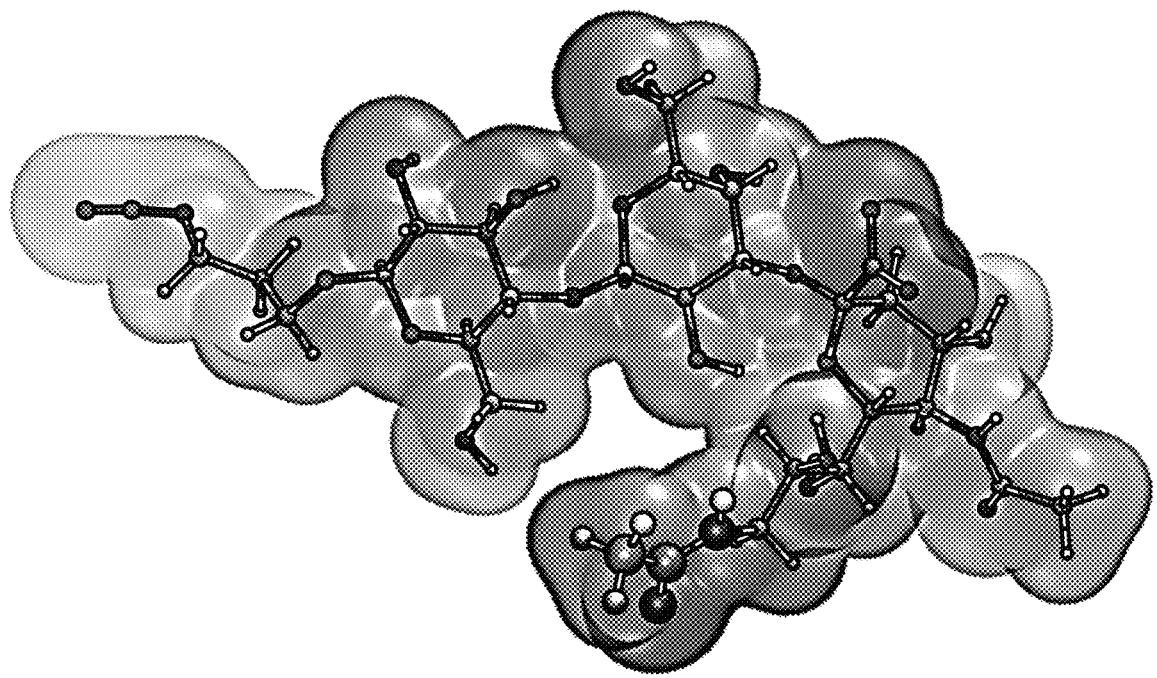
FIG. 9. Top: Calculated electrostatic potential for a representative sialoside structure extracted from simulations of Neu5Ac9NAcα3Galβ4GlcβProN$_3$ using the B3LYP/6-31G* level of theory and plotted on the ρ=0.002 density isosurface. Bottom: Electrostatic potential difference computed between Neu5Ac9NAcα3Galβ4GlcβProN$_3$ and Neu5,9Ac$_2$α3Galβ4GlcβProN$_3$ plotted on the same isosurface; the O-acetylated potential was calculated by replacing NH with O in the N-acetylated structure. The difference between the potentials is very small, although NH group has a slightly positive potential relative to O.
Figure 9:
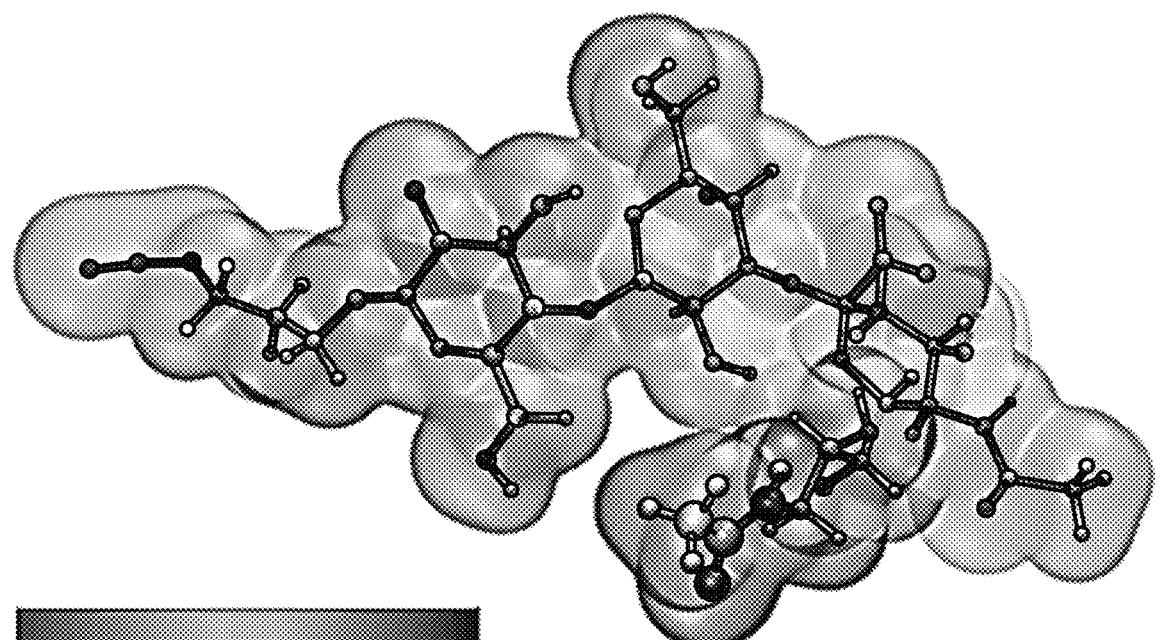
Figure 9:
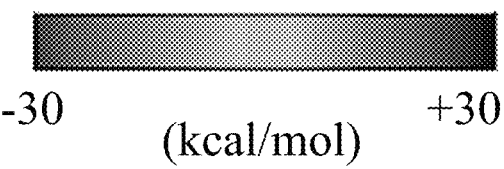

The classical MD simulation approximates the effect of the chemical modification as changing the force field parameters at the acetylation site. In particular, only the partial charges on the N-acetyl functional group are modified. To test this assumption, density functional theory was used to calculate the difference in electrostatic potential as a result of changing O-acetylation to N-acetylation. The results are shown in FIG. 9 which confirm that the change in electrostatic potential is entirely localized to the acetylation site, which lends credence to the results of the classical simulations.

Figure 10:
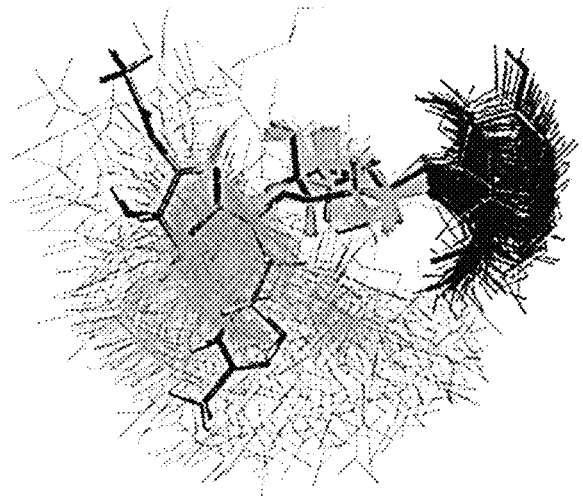
FIG. 10 shows superimposed conformations of the 9-O—Ac sialoside simulations, showing only carbohydrate residues and aligned using galactose heavy atoms. One representative conformation is shown in licorice representation (C, gray; 0, red; N, blue; H, white. Top: The full conformational ensemble of Neu5,9Ac$_2$α3Galβ4GlcβProN$_3$ with snapshots taken 10 ns apart (Neu5,9Ac$_2$, yellow; Gal, green; Glc, blue). Bottom: The conformations corresponding to the dotted box in FIG. 8 with snapshots taken 10 ps apart. These rarely seen conformations were only visited in the O-acetylated simulations but are only a small part of the ensemble, being higher in free energy.
Figure 10:
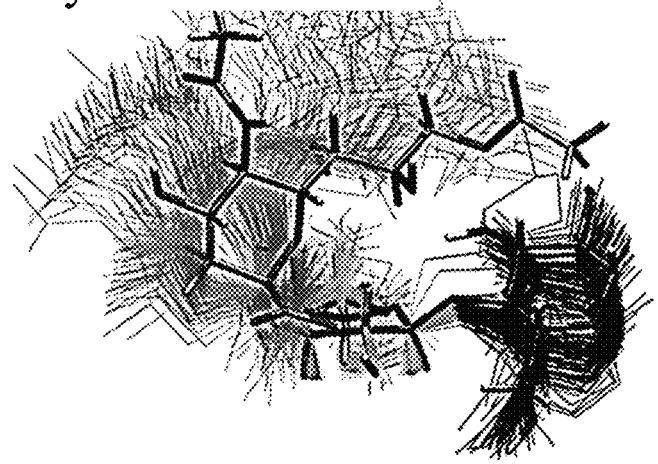

The O-acetylated sialoside appears to display a slightly higher amount of flexibility, as there exists a cluster of conformations at 3-4 kcal/mol higher in energy than the minimum (dotted box in FIG. 8) where $\psi$ adopts negative values. These conformations represent far less than 1% of the whole ensemble, but are nonetheless interesting to investigate for understanding the effects of chemical modification. The overall conformational ensemble is shown in the top panel of FIG. 10, and the negative-$\psi$ conformations are shown in the bottom panel, indicating that the position and orientation of Sia differ significantly between the full set vs. subset of conformations. The sialoside spends most of its time in an extended conformation, but occasionally it adopts a hairpin-like structure where the C7-C9 part of Sia bends back towards Glc. These hairpin conformations were not observed in the N-acetylated ensemble. The sialosides formed few intramolecular hydrogen bonds, which suggests that the chemical modification alters the conformational ensemble via the local hydrogen bonding network of the solvent; a more detailed analysis of solvent degrees of freedom is needed to test this hypothesis.

Example 7. One-Pot Three-Enzyme Synthesis of α2-3/6-Linked Sialosides

To synthesize a library of Neu5Ac9NAc-containing α2-3- and α2-6-linked sialosides, chemically synthesized ManNAc6NAc was used directly in an efficient one-pot multienzyme (OPME) sialylation system containing *Pasteurella multocida* sialic acid aldolase (PmAldolase), *Neisseria meningitidis* CMP-sialic acid synthetase (NmCSS), and a sialyltransferase (Scheme 10).

Scheme 10. One-pot three-enzyme chemoenzymatic synthesis of Neu5Ac9NAc-containing α2-3- and α2-6-linked sialosides.

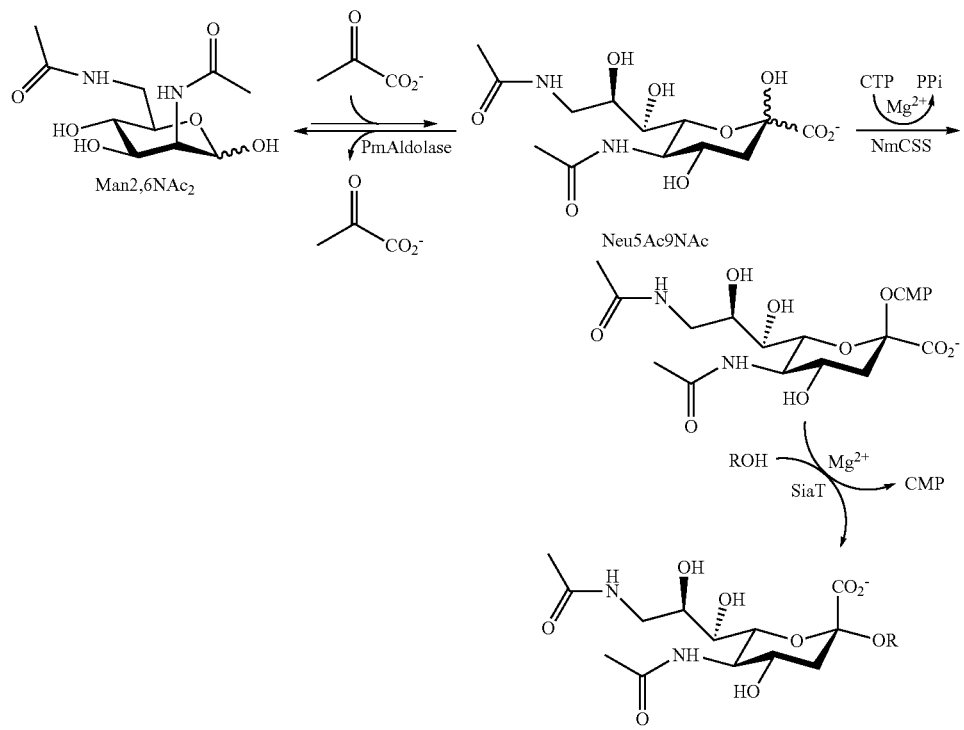

In this system, PmAldolase was used to catalyze the aldol addition reaction of ManNAc6NAc and sodium pyruvate (used in an excess to drive the reaction towards sialic acid formation) to obtain Neu5Ac9NAc. NmCSS was used for catalyzing the formation of the activated sugar nucleotide donor, cytidine 5′-monophosphate-Neu5Ac9NAc (CMP-Neu5Ac9NAc), for the subsequent sialyltransferase-catalyzed glycosylation reaction. *Pasteurella multocida* sialyltransferase 1 M144D mutant (PmST1 M144D) with decreased sialidase and donor hydrolysis activities was used for synthesizing α2-3-linked sialosides. *Photobacterium damselae* α2-6-sialyltransferase (Pd2,6ST) or *Photobacterium* sp. α2-6-sialyltransferase A366G mutant (Psp2,6ST A366G) with an improved expression level was used for synthesizing α2-6-linked sialosides. The reactions were carried out in Tris-HCl buffer (100 mM) with a pH of 8.5 to optimize the activity of NmCSS while retain high activity of PmAldolase and sialyltransferases used. The products were obtained in good to excellent (61-98%) yields after purification using a gel filtration column and a $C_{18}$ reverse phase column. The structures and the purities of the products were confirmed by high resolution mass spectrometry (HRMS) and nuclear magnetic resonance (NMR) spectroscopy.

An acceptor (30-50 mg, 10 mM) and ManNAc6NAc (1.2-1.5 equiv.) were incubated at 37° C. in Tris-HCl buffer (100 mM) (pH 8.5 for synthesizing α2-3-sialosides or α2-6-sialosides using Psp2,6STA366G, pH 7.5 for synthesizing α2-6-sialosides using Pd2,6ST) containing sodium pyruvate (6.0-7.5 equiv.), CTP (1.5 equiv.), $MgCl_2$ (20 mM), an appropriate amount of PmAldolase (1.5 mg), NmCSS (2.5 mg), and Pd2,6ST (2.5 mg), Psp2,6ST A366G mutant (2.5 mg), or PmST1 M144D mutant (2.5 mg). The reaction was monitored by thin-layer chromatography (TLC) using a developing solvent consisting of $EtOAc:MeOH:H_2O=5:2:1$ (by volume) and the TLC plates were stained with a p-anisaldehyde sugar stain. After 1-24 h, the reaction was quenched by adding the same volume of pre-chilled ethanol and the reaction mixture was centrifuged to remove precipitates. The supernatant was concentrated and passed through a BioGel P-2 gel filtration column eluting with water followed by a C18 column ($H_2O:CH_3CN=1:0-4:1$) to obtain the target products.

As shown in Table 2, using PmST1 M144D as the sialyltransferase, α2-3-linked sialosides (2.1-2.7) were obtained in 61-86% yields. These are comparable to the synthesis of α2-3-sialyllactoside, Neu5AcNAcα2-3Galβ1-4GlcβProN$_3$, which was obtained in 84% yield. Two α2-6-sialyltransferases were used for synthesizing α2-6-linked sialosides (2.8-2.16). Psp2,6ST A366G mutant with an increased expression level and improved activities in sialylating Tn antigens was used for synthesizing Neu5Ac9NAcα2-6GalNAcαProN$_3$ (2.16) with 71% yield. For other α2-6-linked Neu5Ac9NAc-containing sialosides (2.8-2.15) synthesized, both Pd2,6ST and Psp2,6ST A366G could provide similar yields in small scale reactions. Pd2,6ST was used for the synthesis of Neu5Ac9NAcα2-6GalβProN$_3$ (2.9) and Neu5Ac9NAcα2-6Galβ1-3GalNAcαProN$_3$ (2.12) with excellent 92% and 98% yields, respectively. Due to the higher expression level of Psp2,6ST A366G, it was used for the synthesis of the rest of the α2-6-linked sialoside targets (2.8, 2.10-2.11, 2.13-2.15). Good to excellent yields (64-96%) were obtained.

TABLE 2
Neu5Ac9NAc-containing sialosides synthesized via the OP3E sialylation system.
| | Yield (No.) |
|---|---|
| α2-3/6-Sialosides | |
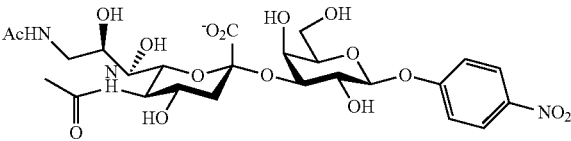
Neu5Ac9NAcα2-3GalβpNP
80% (2.1)
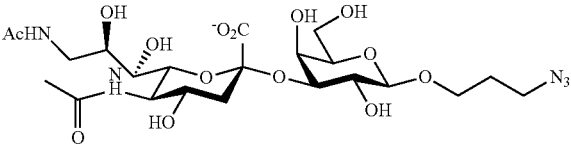
Neu5Ac9NAcα2-3GalβProN₃
72% (2.2)
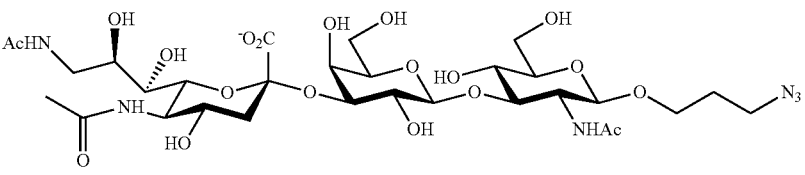
Neu5Ac9NAcα2-3Galβ1-3GlcNAcβProN₃
61% (2.3)
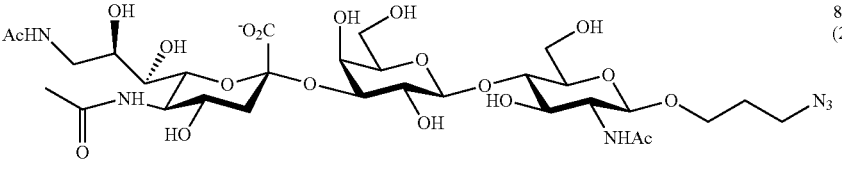
Neu5Ac9NAcα2-3Galβ1-4GlcNAcβProN₃
86% (2.4)
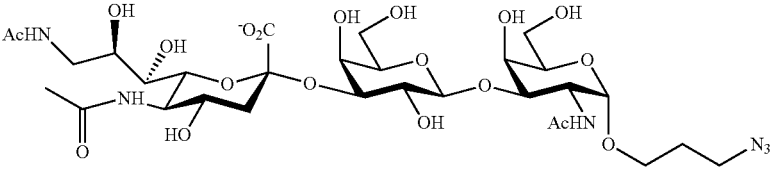
Neu5Ac9NAcα2-3Galβ1-3GalNAcαProN₃
64% (2.5)
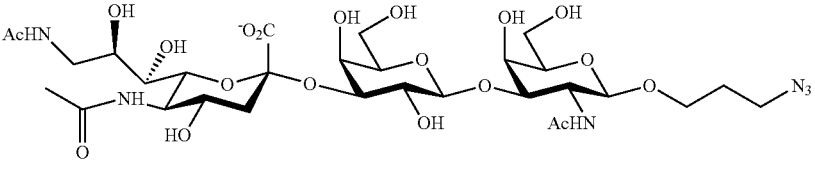
Neu5Ac9NAcα2-3Galβ1-3GalNAcβProN₃
84% (2.6)
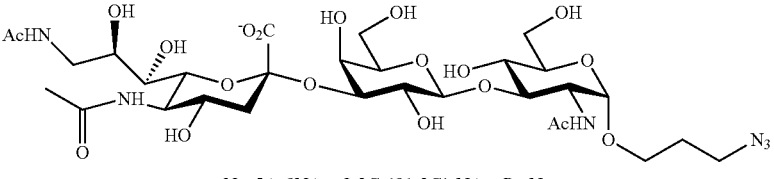
Neu5Ac9NAcα2-3Galβ1-3GlcNAcαProN₃
63% (2.7)

TABLE 2-continued
Neu5Ac9NAc-containing sialosides synthesized via the OP3E sialylation system.
| Structure | Yield (No.) |
|---|---|
| 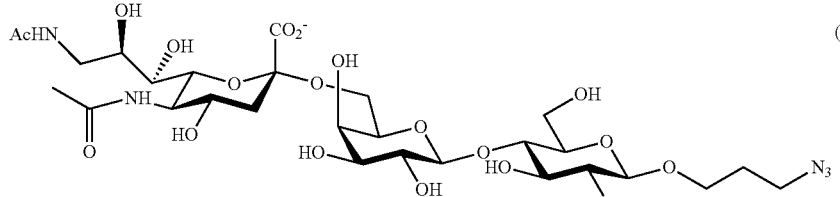 Neu5Ac9NAcα2-6Galβ1-4GlcβProN$_3$ | 94% (2.15) |
α2-6-Sialosides
| Structure | Yield (No.) |
|---|---|
| 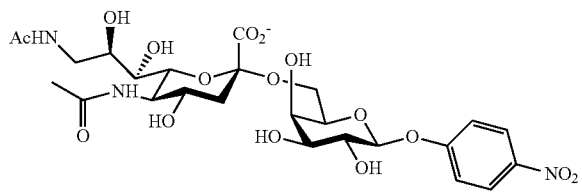 Neu5Ac9NAcα2-6GalβpNP | 64% (2.8) |
| 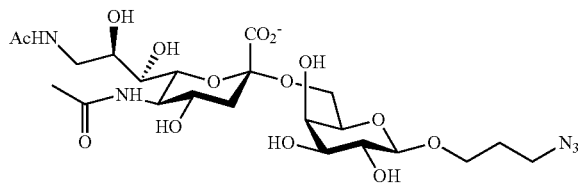 Neu5Ac9NAcα2-6GalβProN$_3$ | 92% (2.9) |
| 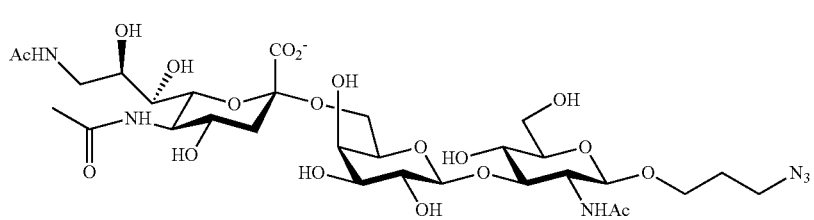 Neu5Ac9NAcα2-6Galβ1-3GlcNAcβProN$_3$ | 68% (2.10) |
| 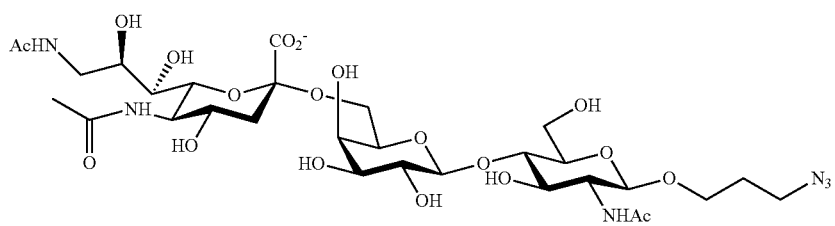 Neu5Ac9NAcα2-6Galβ1-4GlcNAcβProN$_3$ | 91% (2.11) |

TABLE 2-continued

Neu5Ac9NAc-containing sialosides synthesized via the OP3E sialylation system.

| Structure | Yield (No.) |
|---|---|
| Neu5Ac9NAcα2-6Galβ1-3GalNAcαProN₃ | 98% (2.12) |
| Neu5Ac9NAcα2-6Galβ1-3GalNAcβProN₃ | 96% (2.13) |
| Neu5Ac9NAcα2-6Galβ1-3GlcNAcαProN₃ | 76% (2.14) |
| Neu5Ac9NAcα2-6GalNAcαProN₃ | 71% (2.16) |

The α2-3/6-sialosides obtained include Neu5Ac9NAcα2-3/6GalβpNP (2.1 and 2.8) and propyl azide (ProN₃)-containing ones (2.2-2.7 and 2.9-2.16) such as disaccharides Neu5Ac9NAcα2-3/6GalβProN₃ (2.2 and 2.9), sialyl type I glycans Neu5Ac9NAcα2-3/6Galβ1-3GlcNAcβProN₃ (2.3 and 2.10), sialyl type II glycans Neu5Ac9NAcα2-3/6Galβ1-4GlcNAcβProN₃ (2.4 and 2.11), sialyl type III glycans Neu5Ac9NAcα2-3/6Galβ1-3GalNAcαProN₃ (2.5 and 2.12), sialyl type IV glycans Neu5Ac9NAcα2-3/6Galβ1-3GalNAcβProN₃ (2.6 and 2.13), Neu5Ac9NAcα2-3/6Galβ1-3GlcNAcαProN₃ (2.7 and 2.14), α2-6-sialyl type VI glycan Neu5Ac9NAcα2-6Galβ1-4GlcβProN₃ (2.15), and sialyl Tn antigen Neu5Ac9NAcα2-6GalNAcαProN₃ (2.16). These represent common terminal sialyl glycan structures in vertebrates.

4-Nitrophenyl O-(5,9-diacetamido-3,5,9-trideoxy-D-glycero-α-D-galacto-2-nonulopyranosylonic acid)-(2→3)—O-β-D-galactopyranoside (Neu5Ac9NAcα2-3GalβpNP, 2.1)

Yield 80%; 87 mg, White foam. $^1$H NMR (400 MHz, D$_2$O) δ 8.32-8.15 (m, 2H), 7.32-7.17 (m, 2H), 5.29 (d, J=7.8 Hz, 1H), 4.25 (dd, J=3.2 and 9.8 Hz, 1H), 4.06 (d, J=3.2 Hz, 1H), 3.98-3.84 (m, 4H), 3.81-3.64 (m, 4H), 3.61-3.46 (m, 2H), 3.29 (dd, J=7.6 and 14.2 Hz, 1H), 2.80 (dd, J=4.6 and 12.4 Hz, 1H), 2.04 (s, 3H), 1.95 (s, 3H), 1.84 (t, J=12.1 Hz, 1H); $^{13}$C NMR (100 MHz, D$_2$O) δ 174.95, 174.32, 173.75, 161.70, 142.47, 126.07 (2C), 116.41 (2C), 99.94, 99.70, 75.50, 75.45, 72.76, 70.00, 69.60, 68.77, 68.29, 67.29, 60.67, 51.67, 42.10, 39.67, 22.03, 21.75; HRMS (ESI) Anal. Calcd for $C_{25}H_{34}N_3O_{16}$ [M−H]⁻: 632.1945, Found: 632.1957.

3-Azidopropyl O-(5,9-diacetamido-3,5,9-trideoxy-D-glycero-α-D-galacto-2-nonulopyrano-sylonic acid)-(2→3)—O-β-D-galactopyranoside (Neu5Ac9NAc(α2-3GalβProN₃, 2.2)

Yield 72%; 73 mg, White foam. ¹H NMR (400 MHz, D₂O) δ 4.47 (d, J=7.8 Hz, 1H), 4.08 (dd, J=3.2 and 9.8 Hz, 1H), 4.05-3.63 (m, 10H), 3.59-3.45 (m, 5H), 3.32 (dd, J=7.8 and 14.2 Hz, 1H), 2.76 (dd, J=4.6 and 12.4 Hz, 1H), 2.04-2.03 (m, 6H), 1.96-1.89 (m, 2H), 1.81 (t, J=12.2 Hz, 1H); ¹³C NMR (100 MHz, D₂O) δ 174.93, 174.40, 173.80, 102.54, 99.93, 75.85, 74.88, 72.70, 69.95, 69.54, 69.13, 68.31, 67.52, 67.14, 60.93, 51.66, 47.90, 42.09, 39.61, 28.25, 22.02, 21.82; HRMS (ESI) m/z calcd for $C_{22}H_{36}N_5O_{14}$ [M−H]⁻: 594.2264, found 594.2282.

3-Azidopropyl O-(5,9-diacetamido-3,5,9-trideoxy-D-glycero-α-D-galacto-2-nonulopyranosylonic acid)-(2→3)—O-β-D-galactopyranosyl-(1→3)-2-acetamido-2-deoxy-β-D-glucopyranoside (Neu5Ac9NAcα2-3Galβ1-3GlcNAcβProN₃, 2.3)

Yield 61%; 38 mg, White foam. ¹H NMR (400 MHz, D₂O) δ 4.58 (d, J=7.8 Hz, 1H), 4.50 (d, J=7.8 Hz, 1H), 4.07 (dd, J=3.2 and 9.8 Hz, 1H), 4.03-3.47 (m, 19H), 3.39 (t, J=6.4 Hz, 2H), 3.27 (dd, J=7.6 and 14.2 Hz, 1H), 2.76 (dd, J=4.8 and 12.8 Hz, 1H), 2.13-2.03 (m, 9H), 1.89-1.77 (m, 3H); ¹³C NMR (100 MHz, D₂O) δ 174.79, 174.35, 174.25, 173.79, 103.25, 100.76, 99.70, 82.41, 75.52, 75.25, 74.95, 72.54, 69.82, 69.40, 69.03, 68.64, 68.24, 67.17, 67.02, 60.89, 60.62, 54.33, 51.55, 47.67, 41.93, 39.56, 27.98, 22.14, 21.92, 21.69; HRMS (ESI) m/z calcd for $C_{30}H_{49}N_6O_{19}$ [M−H]⁻: 797.3058, found 797.3064.

3-Azidopropyl O-(5,9-diacetamido-3,5,9-trideoxy-D-glycero-α-D-galacto-2-nonulopyranosylonic acid)-(2→3)—O-β-D-galactopyranosyl-(1→4)-2-acetamido-2-deoxy-β-D-glucopyranoside (Neu5Ac9NAcα2-3Galβ1-4GlcNAcβProN₃, 2.4)

Yield 86%; 48 mg, White foam. ¹H NMR (400 MHz, D₂O) δ 4.56-4.52 (m, 2H), 4.11 (dd, J=3.2 and 10.0 Hz, 1H), 4.04-3.82 (m, 6H), 3.80-3.54 (m, 12H), 3.50 (dd, J=1.8 and 9.0 Hz, 1H), 3.39 (td, J=1.8 and 6.6 Hz, 2H), 3.28 (dd, J=7.8 and 14.0 Hz, 1H), 2.76 (dd, J=4.6 and 12.4 Hz, 1H), 2.12-1.98 (m, 9H), 1.92-1.74 (m, 3H); ¹³C NMR (100 MHz, D₂O) δ 174.93, 174.46, 174.39, 173.79, 102.54, 101.13, 99.87, 78.23, 75.53, 75.14, 74.76, 72.74, 72.33, 69.95, 69.58, 69.37, 68.30, 67.46, 67.11, 61.01, 59.99, 55.06, 51.65, 47.76, 42.12, 39.61, 28.08, 22.14, 22.02, 21.81; HRMS (ESI) m/z calcd for $C_{30}H_{49}N_6O_{19}$ [M−H]⁻: 797.3058, found 797.3079.

3-Azidopropyl O-(5,9-diacetamido-3,5,9-trideoxy-D-glycero-α-D-galacto-2-nonulopyranosylonic acid)-(2→3)—O-β-D-galactopyranosyl-(1→3)-2-acetamido-2-deoxy-α-D-galactopyranoside (Neu5Ac9NAcα2-3Galβ1-3GalNAcαProN₃, 2.5)

Yield 64%; 57 mg, White foam. ¹H NMR (400 MHz, D₂O) δ 4.92 (d, J=3.8 Hz, 1H), 4.55 (d, J=7.8 Hz, 1H), 4.32 (dd, J=3.8 and 11.2 Hz, 1H), 4.28-4.23 (m, 1H), 4.16-3.39 (m, 20H), 3.28 (dd, J=7.6 and 14.2 Hz, 1H), 2.75 (dd, J=4.6 and 12.4 Hz, 1H), 2.13-2.03 (m, 9H), 1.95-1.88 (m, 2H), 1.80 (t, J=12.2 Hz, 1H); ¹³C NMR (100 MHz, D₂O) δ 174.92, 174.51, 174.37, 173.90, 104.35, 99.88, 97.15, 77.44, 75.64, 74.72, 72.65, 70.60, 69.93, 69.49, 69.14, 68.51, 68.34, 67.43, 64.92, 61.20, 60.97, 51.66, 48.84, 48.66, 48.17, 42.03, 39.62, 27.94, 22.01, 21.82; HRMS (ESI) m/z calcd for $C_{30}H_{49}N_6O_{19}$ [M−H]⁻: 797.3058, found 797.3072.

3-Azidopropyl O-(5,9-diacetamido-3,5,9-trideoxy-D-glycero-α-D-galacto-2-nonulopyranosylonic acid)-(2→3)—O-β-D-galactopyranosyl-(1→3)-2-acetamido-2-deoxy-β-D-galactopyranoside (Neu5Ac9NAcα2-3Galβ1-3GalNAcβProN₃, 2.6)

Yield 84%; 14.8 mg, White foam. ¹H NMR (600 MHz, D₂O) δ 4.51-4.46 (m, 2H), 4.16 (d, J=3.2 Hz, 1H), 4.03-3.93 (m, 3H), 3.97-3.50 (m, 15H), 3.47-3.45 (m, 1H), 3.36 (td, J=1.5 and 6.8 Hz, 2H), 3.23 (dd, J=7.6 and 14.1 Hz, 1H), 2.71 (dd, J=4.6 and 12.3 Hz, 1H) 2.03-1.96 (m, 9H), 1.87-1.80 (m, 2H), 1.75 (t, J=12.1 Hz, 1H); ¹³C NMR (151 MHz, D₂O) δ 174.80, 174.56, 174.27, 173.85, 104.39, 101.28, 99.72, 79.95, 75.45, 74.63 (2C), 72.53, 69.82, 69.42, 68.95, 68.26, 67.71, 67.29, 66.88, 60.88, 60.83, 51.55, 51.04, 48.74, 41.94, 39.53, 28.00, 22.16, 21.92, 21.71. HRMS (ESI) m/z calcd for $C_{30}H_{49}N_6O_{19}$ [M−H]⁻: 797.3058, found 797.3064

3-Azidopropyl O-(5,9-diacetamido-3,5,9-trideoxy-D-glycero-α-D-galacto-2-nonulopyranosylonic acid)-(2→3)—O-β-D-galactopyranosyl-(1→3)-2-acetamido-2-deoxy-α-D-glucopyranoside (Neu5Ac9NAcα2-3Galβ1-3GlcNAcαProN₃, 2.7)

Yield 63%; 85 mg, White foam. ¹H NMR (400 MHz, D₂O) δ 4.88 (d, J=3.6 Hz, 1H), 4.53 (d, J=7.8 Hz, 1H), 4.09 (ddd, J=3.4, 7.4 and 10.0 Hz, 2H), 4.01-3.42 (m, 20H), 3.28 (dd, J=7.6 and 14.2 Hz, 1H), 2.76 (dd, J=4.6 and 12.4 Hz, 1H), 2.04-2.03 (m, 9H), 1.95-1.89 (m, 2H), 1.80 (t, J=12.2 Hz, 1H); ¹³C NMR (100 MHz, D₂O) δ 174.91, 174.35 (2C), 173.88, 103.26, 99.87, 97.04, 80.47, 75.67, 75.01, 72.66, 71.57, 69.94, 69.47, 69.22, 68.71, 68.34, 67.32, 64.96, 60.97, 60.51, 52.43, 51.66, 48.17, 42.01, 39.64, 27.93, 22.02, 21.99, 21.81; HRMS (ESI) m/z calcd for $C_{30}H_{49}N_6O_{19}$ [M−H]⁻: 797.3058, found 797.3071.

4-Nitrophenyl O-(5,9-diacetamido-3,5,9-trideoxy-D-glycero-α-D-galacto-2-nonulopyranosylonic acid)-(2→6)—O-β-D-galactopyranoside (Neu5Ac9NAcα2-6GalβpNP, 2.8)

Yield 64%; 69 mg, White foam. ¹H NMR (400 MHz, D₂O) δ 8.26-8.15 (m, 2H), 7.26-7.12 (m, 2H), 5.09 (d, J=7.6 Hz, 1H), 3.95 (dd, J=4.0 and 7.6 Hz, 2H), 3.91-3.56 (m, 8H), 3.47 (dd, J=2.8 and 14.2 Hz, 1H), 3.36 (dd, J=1.6 and 8.8 Hz, 1H), 3.14 (dd, J=8.0 and 14.2 Hz, 1H), 2.67 (dd, J=4.4 and 12.4 Hz, 1H), 1.94 (s, 3H), 1.86 (s, 3H), 1.67-1.49 (m, 1H); ¹³C NMR (100 MHz, D₂O) δ 174.94, 174.30, 173.48, 161.84, 142.51, 126.12 (2C), 116.39 (2C), 100.42, 99.88, 74.04, 72.47, 72.33, 70.25, 69.96, 69.69, 68.36, 68.15, 63.02, 51.80, 42.15, 40.14, 21.98, 21.72; HRMS (ESI) Anal. Calcd for $C_{25}H_{34}N_3O_{16}$ [M−H]⁻: 632.1945, Found: 632.1955.

3-Azidopropyl O-(5,9-diacetamido-3,5,9-trideoxy-D-glycero-α-D-galacto-2-nonulopyranosylonic acid)-(2-6)-O-β-D-galactopyranoside (Neu5Ac9NAcα2-6GalβProN₃, 2.9)

Yield 92%; 107 mg, White foam. ¹H NMR (400 MHz, D₂O) δ 4.39 (d, J=7.8 Hz, 1H), 4.05-3.88 (m, 4H), 3.87-3.57

(m, 8H), 3.54-3.44 (m, 4H), 3.28 (dd, J=7.8 and 14.0 Hz, 1H), 2.73 (dd, J=4.8 and 12.4 Hz, 1H), 2.04-2.02 (m, 6H), 1.95-1.89 (m, 2H), 1.70 (t, J=12.2 Hz, 1H); $^{13}$C NMR (100 MHz, D$_2$O) δ 174.98, 174.37, 173.41, 102.90, 100.47, 73.39, 72.57, 72.48, 70.65, 69.94, 69.69, 68.54, 68.17, 67.45, 63.29, 51.83, 47.87, 42.13, 40.17, 28.30, 22.01, 21.82; HRMS (ESI) m/z calcd for C$_{22}$H$_{36}$N$_5$O$_{14}$ [M−H]$^-$: 594.2264, found 594.2285.

3-Azidopropyl O-(5,9-diacetamido-3,5,9-trideoxy-D-glycero-α-D-galacto-2-nonulopyranosylonic acid)-(2→6)—O-β-D-galactopyranosyl-(1→3)-2-acetamido-2-deoxy-β-D-glucopyranoside (Neu5Ac9NAcα2-6Galβ1-3GlcNAcβProN$_3$, 2.10)

Yield 68%; 34 mg, White foam. $^1$H NMR (400 MHz, D$_2$O) δ 4.58 (d, J=8.4 Hz, 1H), 4.39 (d, J=7.8 Hz, 1H), 4.05-3.45 (m, 20H), 3.39 (td, J=1.2 and 6.6 Hz, 2H), 3.30 (dd, J=7.6 and 14.2 Hz, 1H), 2.70 (dd, J=4.8 and 12.4 Hz, 1H), 2.10-1.89 (m, 9H), 1.89-1.83 (m, 2H), 1.70 (t, J=12.2 Hz, 1H); $^{13}$C NMR (100 MHz, D$_2$O) δ 174.84, 174.59, 174.38, 173.46, 103.89, 100.88, 100.11, 84.01, 75.46, 73.61, 72.37, 72.28, 70.48, 69.93, 68.91 (2C), 68.48, 68.25, 67.14, 63.56, 60.87, 54.30, 51.78, 47.78, 42.15, 40.12, 28.08, 22.19, 22.03, 21.83; HRMS (ESI) m/z calcd for C$_{30}$H$_{49}$N$_6$O$_{19}$ [M−H]$^-$: 797.3058, found 797.3065.

3-Azidopropyl O-(5,9-diacetamido-3,5,9-trideoxy-D-glycero-α-D-galacto-2-nonulopyranosylonic acid)-(2→6)—O-β-D-galactopyranosyl-(1→4)-2-acetamido-2-deoxy-β-D-glucopyranoside (Neu5Ac9NAcα2-6Galβ1-4GlcNAcβProN$_3$, 2.11)

Yield 91%; 56 mg, White foam. $^1$H NMR (400 MHz, D$_2$O) δ 4.62-4.52 (m, 1H), 4.45 (d, J=7.8 Hz, 1H), 4.04-3.89 (m, 5H), 3.88-3.51 (m, 14H), 3.45 (dd, J=1.8 and 9.0 Hz, 1H), 3.39 (td, J=1.4 and 6.6 Hz, 2H), 3.30 (dd, J=7.8 and 14.0 Hz, 1H), 2.76 (dd, J=4.6 and 12.4 Hz, 1H), 2.16-1.98 (m, 9H), 1.89-1.83 (m, 2H), 1.71 (t, J=12.2 Hz, 1H); $^{13}$C NMR (100 MHz, D$_2$O) δ 174.83, 174.51, 174.39, 173.49, 103.46, 100.95, 100.18, 80.74, 74.45, 73.68, 72.39 (2C), 70.70, 69.87 (2C), 68.39, 68.17, 67.09, 63.44, 61.75, 60.34, 54.83, 51.85, 47.77, 42.14, 40.06, 28.09, 22.27, 22.01, 21.83; HRMS (ESI) m/z calcd for C$_{30}$H$_{49}$N$_6$O$_{19}$ [M−H]$^-$: 797.3058, found 797.3063.

3-Azidopropyl O-(5,9-diacetamido-3,5,9-trideoxy-D-glycero-α-D-galacto-2-nonulopyranosylonic acid)-(2→6)—O-β-D-galactopyranosyl-(1→3)-2-acetamido-2-deoxy-α-D-galactopyranoside (Neu5Ac9NAcα2-6Galβ1-3GalNAcαProN$_3$, 2.12)

Yield 98%; 86 mg, White foam. $^1$H NMR (400 MHz, D$_2$O) δ 4.91 (d, J=3.6 Hz, 1H), 4.46 (d, J=7.8 Hz, 1H), 4.33 (dd, J=3.8 and 11.2 Hz, 1H), 4.29-4.24 (m, 1H), 4.10-3.41 (m, 20H), 3.31 (dd, J=7.6 and 14.0 Hz, 1H), 2.74 (dd, J=4.8 and 12.4 Hz, 1H), 2.13-1.99 (m, 9H), 1.95-1.89 (m, 2H), 1.66 (t, J=12.2 Hz, 1H); $^{13}$C NMR (100 MHz, D$_2$O) δ 174.98, 174.51, 174.40, 173.40, 104.52, 100.39, 97.16, 77.27, 73.20, 72.43, 72.37, 70.73, 70.48, 69.81, 69.65, 68.67, 68.56, 68.20, 64.90, 63.48, 61.42, 51.86, 48.72, 48.19, 42.08, 40.19, 27.96, 22.00, 21.98, 21.82; HRMS (ESI) m/z calcd for C$_{30}$H$_{49}$N$_6$O$_{19}$ [M−H]$^-$: 797.3058, found 797.3079.

3-Azidopropyl O-(5,9-diacetamido-3,5,9-trideoxy-D-glycero-α-D-galacto-2-nonulopyranosylonic acid)-(2→6)—O-β-D-galactopyranosyl-(1→3)-2-acetamido-2-deoxy-β-D-galactopyranoside (Neu5Ac9NAcα2-6Galβ1-3GalNAcβProN$_3$, 2.13)

Yield 96%; 16.8 mg, White foam. $^1$H NMR (600 MHz, D$_2$O) δ 4.47-4.38 (m, 2H), 4.17 (dd, J=3.2 Hz, 1H), 3.98-3.55 (m, 17H), 3.51-3.42 (m, 2H), 3.35 (td, J=4.5 and 6.5 Hz, 2H), 3.26-3.21 (m, 1H), 2.68 (dd, J=4.6 and 12.4 Hz, 1H), 2.11-1.89 (m, 9H), 1.84-1.77 (m, 2H), 1.64 (t, J=12.2 Hz, 1H); $^{13}$C NMR (151 MHz, D$_2$O) δ 174.85, 174.58, 174.28, 173.31, 104.79, 101.38, 100.35, 79.80, 74.85, 73.00, 72.40, 72.38, 70.43, 69.81, 69.60, 68.48, 68.08, 67.72, 67.11, 63.26, 60.85, 52.24, 51.70, 51.07, 42.07, 40.11, 28.06, 22.11, 21.90, 21.72; HRMS (ESI) m/z calcd for C$_{30}$H$_{49}$N$_6$O$_{19}$ [M−H]$^-$: 797.3058, found 797.3067.

3-Azidopropyl O-(5,9-diacetamido-3,5,9-trideoxy-D-glycero-α-D-galacto-2-nonulopyranosylonic acid)-(2→6)—O-β-D-galactopyranosyl-(1→3)-2-acetamido-2-deoxy-α-D-glucopyranoside (Neu5Ac9NAcα2-6Galβ1-3GlcNAcαProN$_3$, 2.14)

Yield 76%; 51 mg, White foam. $^1$H NMR (400 MHz, D$_2$O) δ 4.87 (d, J=3.6 Hz, 1H), 4.39 (d, J=7.8 Hz, 1H), 4.10 (dd, J=3.6 and 10.6 Hz, 1H), 4.03-3.37 (m, 21H), 3.30 (dd, J=7.7 and 14.1 Hz, 1H), 2.70 (dd, J=4.7 and 12.4 Hz, 1H), 2.09-1.94 (m, 9H), 1.94-1.90 (m, 2H), 1.71 (t, J=12.2 Hz, 1H); $^{13}$C NMR (101 MHz, D$_2$O) δ 174.83, 174.42, 174.38, 173.48, 103.71, 100.12, 96.91, 81.81, 73.60, 72.42, 72.29, 71.58, 70.53, 69.93, 69.91, 68.79, 68.50, 68.26, 64.91, 63.51, 60.64, 52.27, 51.78, 48.14, 42.15, 40.14, 27.96, 22.03, 21.93, 21.82; HRMS (ESI) m/z calcd for C$_{30}$H$_{49}$N$_6$O$_{19}$ [M−H]$^-$: 797.3058, found 797.3078.

3-Azidopropyl O-(5,9-diacetamido-3,5,9-trideoxy-D-glycero-α-D-galacto-2-nonulopyranosylonic acid)-(2→6)—O-β-D-galactopyranosyl-(1-4)-β-D-glucopyranoside (Neu5Ac9NAcα2-6Galβ1-4GlcβProN$_3$, 2.15)

Yield 94%; 73 mg, White foam. $^1$H NMR (400 MHz, D$_2$O) δ 4.50 (d, J=8.0 Hz, 1H), 4.44 (d, J=7.8 Hz, 1H), 4.04-3.24 (m, 23H), 2.71 (dd, J=4.8 and 12.4 Hz, 1H), 2.14-2.03 (m, 6H), 1.96-1.89 (m, 2H), 1.74 (t, J=12.2 Hz, 1H); $^{13}$C NMR (100 MHz, D$_2$O) δ 174.82, 174.39, 173.43, 103.18, 101.98, 100.30, 79.62, 74.62, 74.59, 73.68, 72.71, 72.33, 70.75, 69.93, 69.89, 68.52, 68.33, 67.31, 63.62, 60.24, 51.75, 48.85, 47.86, 42.16, 40.06, 28.22, 22.04, 21.84; HRMS (ESI) m/z calcd for C$_{28}$H$_{46}$N$_5$O$_{19}$ [M−H]$^-$: 756.2792, found 756.2812.

3-Azidopropyl O-(5,9-diacetamido-3,5,9-trideoxy-D-glycero-α-D-galacto-2-nonulopyranosylonic acid)-(2→6)-2-acetamido-2-deoxy-α-D-galactopyranoside (Neu5Ac9NAcα2-6GalNAcαProN$_3$, 2.16)

Yield 71%; 78 mg, White foam. $^1$H NMR (400 MHz, D$_2$O) δ 4.89 (d, J=3.6 Hz, 1H), 4.15 (dd, J=3.8 and 11.2 Hz, 1H), 4.06-4.00 (m, 2H), 3.96-3.89 (m, 3H), 3.84-3.78 (m, 2H), 3.74-3.41 (m, 8H), 3.29 (dd, J=7.8 and 14.0 Hz, 1H), 2.73 (dd, J=4.8 and 12.4 Hz, 1H), 2.13-2.03 (m, 9H), 1.94-1.88 (m, 2H), 1.69 (t, J=12.2 Hz, 1H); $^{13}$C NMR (100 MHz, D$_2$O) δ 174.94, 174.51, 174.37, 173.37, 100.37, 97.04, 72.40, 69.96, 69.74, 69.49, 68.49, 68.21, 67.46, 65.15, 63.79, 51.82, 49.92, 48.14, 42.14, 40.23, 27.91, 22.01, 21.92, 21.82; HRMS (ESI) m/z calcd for $C_{24}H_{39}N_6O_{14}$ [M–H]$^-$: 635.2530, found 635.2554.

3-azidopropyl O-(5,9-diacetamido-3,5,9-trideoxy-D-glycero-α-D-galacto-2-nonulopyranosylonic acid)-(2→8)—O-(5-acetamido-3,5-dideoxy-D-glycero-α-D-galacto-2-nonulopyrano-sylonic acid)-(2→3)—O-β-D-galactopyranosyl-(1-4)-β-D-glucopyranoside (Neu5Ac9NAcα2-8Neu5Acα2-3LacβProN$_3$, 2.21). Sialoside 2.21 was synthesized according to Scheme 11.

C18 reverse phase column. Yield: 73%; 52 mg, White foam. $^1$H NMR (800 MHz, D$_2$O) δ 4.52 (d, J=7.9 Hz, 1H), 4.48 (d, J=8.0 Hz, 1H), 4.18-4.12 (m, 2H), 4.09 (dd, J=9.9, 3.1 Hz, 1H), 4.02-3.93 (m, 4H), 3.89-3.49 (m, 18H), 3.49-3.42 (m, 3H), 3.31 (m, 2H), 2.77 (dd, J=12.4, 4.6 Hz, 1H), 2.67 (dd, J=12.3, 4.4 Hz, 1H), 2.16-1.98 (m, 9H), 1.91 (p, J=6.7 Hz, 2H), 1.74 (td, J=12.1, 8.9 Hz, 2H); $^{13}$C NMR (200 MHz, D$_2$O) δ 174.84, 174.80, 174.42, 173.34, 173.26, 102.56, 102.02, 100.28, 100.23, 78.13, 77.92, 75.32, 75.08, 74.69, Scheme 11. One-pot multienzyme (OPME) chemoenzymatic synthesis of Neu5Ac9NAcα2-8Neu5Acα2-3Galβ1-4GlcβProN$_3$.

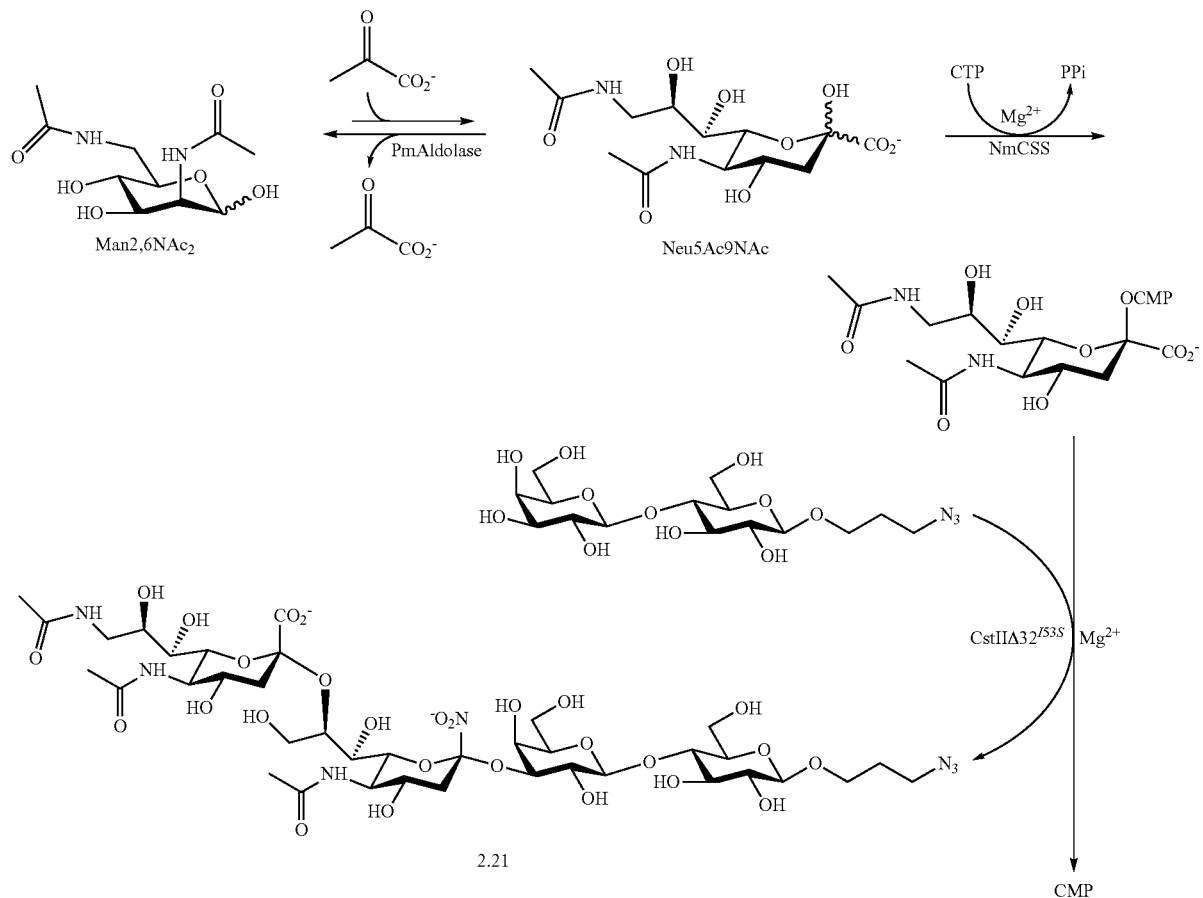

Neu5Acα2-3LacβProN$_3$ (50 mg, 0.067 mmol), Man2,6NAc$_2$ (22 mg, 0.084 mmol), sodium pyruvate (45 mg, 0.41 mmol) and CTP (50 mg, 0.089 mmol) were dissolved in Tris-HCl buffer (100 mM, pH=8.5, 10 mL) containing MgCl$_2$ (20 mM). *Pasteurella multocida* sialic acid aldolase (PmAldolase) (1.5 mg), *Neisseria meningitidis* CMP-sialic acid synthetase (NmCSS) (2.5 mg), and *Campylobacter jejuni* sialyltransferase CstII mutant (CstIIΔ32$^{I53S}$) (2.5-3.0 mg) were added. The reaction was incubated in an incubator shaker at 37° C. for 1 h with agitation at 140 rpm and then at room temperature for 48 h. Product formation was monitored by thin layer chromatography (EtOAc:MeOH:H$_2$O=5:3:1, by volume) and stained with p-anisaldehyde sugar stain. With the achievement of optimal yield, the reaction was quenched by adding the same volume (10 mL) of ice-cold MeOH and incubated at 4° C. for 30 min. The mixture was centrifuged and supernatant was concentrated, followed by passing through a BioGel P-2 gel filtration column and a 74.17, 74.06, 72.72, 72.33, 69.69, 69.57, 69.25, 69.19, 68.39, 67.87, 67.44, 67.23, 61.49, 60.96, 59.87, 52.15, 51.59, 47.76, 42.19, 40.35, 39.45, 28.12, 22.17, 21.91, 21.70.

Figure 11:
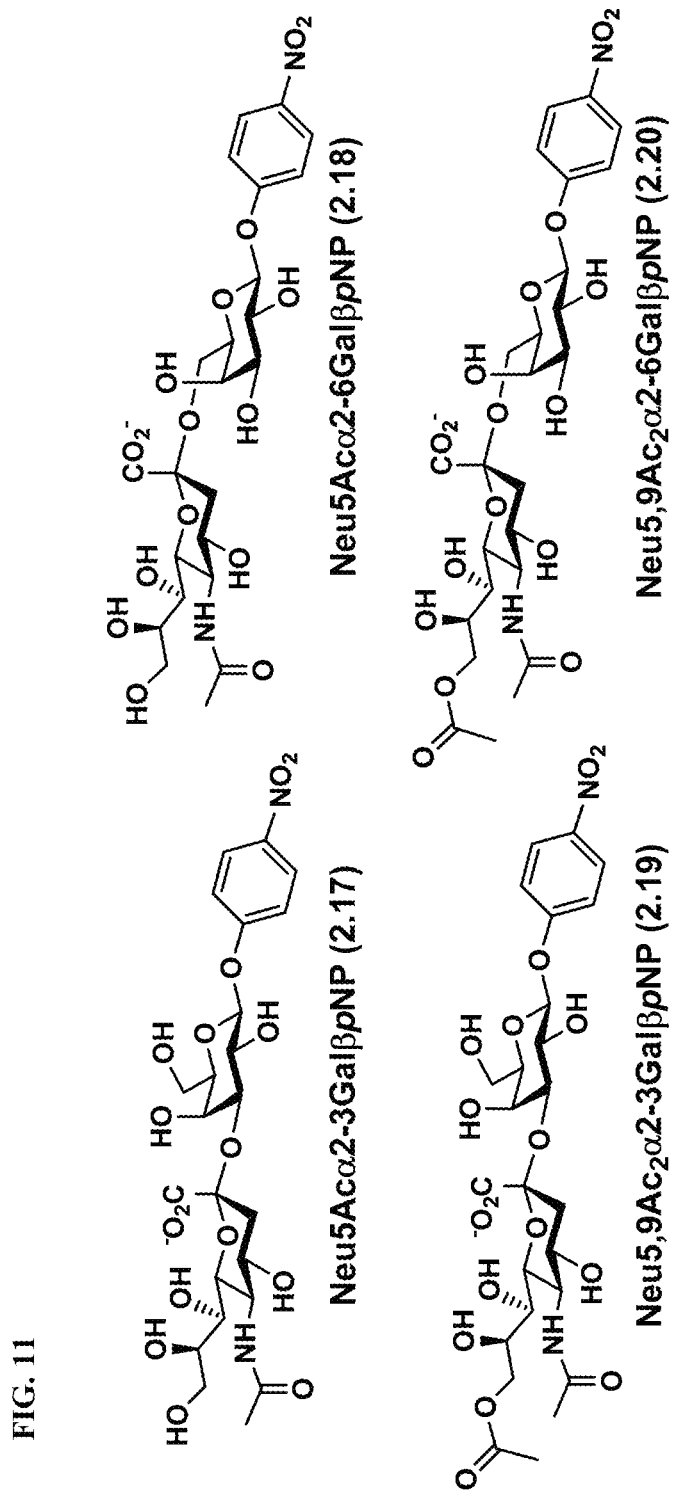
FIG. 11 shows the structures of Neu5Ac-sialosides Neu5Acα2-3GalβpNP (2.17) and Neu5Acα2-6GalβpNP (2.18) as well as Neu5,9Ac$_2$-sialosides Neu5,9Ac$_2$α2-3GalβpNP (2.19) and Neu5,9Ac$_2$α2-6GalβpNP (2.20), which were used as substrates for microtiter plate-based high-throughput sialidase assays.

Example 8. Sialidase Substrate Specificity Study Using Neu5Ac9NAc-Containing Sialosides Among the compounds synthesized in Example 7, two pNP-tagged Neu5Ac9NAc-containing sialosides Neu5Ac9NAcα2-3GalβpNP (2.1) and Neu5Ac9NAcα2-6GalβpNP (2.8) were used conveniently in a 384-well plate-based high-throughput colorimetric assay for substrate specificity studies of nine sialidases. Four additional pNP-tagged sialosides including Neu5Ac-containing ones such as Neu5Acα2-3GalβpNP (2.17) and Neu5Acα2-6GalβpNP (2.18) as well as Neu5,9Ac$_2$-containing ones such as Neu5,9Ac$_2$α2-3GalβpNP (2.19) and Neu5,9Ac$_2$α2-6GalβpNP (2.20) (FIG. 11) were also used as sialidase substrates for comparison purpose. Sialidases used include six recombinant sialidases and three commercially available sialidases. The recombinant sialidases used were human cytosolic sialidase hNEU2, bacterial sialidases PmST1 (a multifunctional sialyltransferase which also has sialidase activity), *Bifidobacterium infantis* sialidase NanH2, and three *Streptococcus pneumoniae* sialidases SpNanA, SpNanB, and SpNanC. Three commercial bacterial sialidases used were those from *Arthrobacter ureafaciens*, *Vibrio cholerae*, and *Clostridium perfringens*.

In this assay method, individual sialosides were incubated in duplicates at 37° C. for 30 min with an appropriate amount of a sialidase as well as an excess amount of β-galactosidase. The reactions were stopped by adding N-cyclohexyl-3-aminopropanesulfonic acid (CAPS) buffer (0.5 M, pH 10.5) to adjust the pH value of the solution to higher than 9.5 to convert the para-nitrophenol formed in the enzymatic reactions to para-nitrophenolate which was quantified by a microplate reader at $A_{405\ nm}$.

Assays were carried out in duplicates. For each reaction in a final volume of 20 μL, a sialoside was incubated with an appropriate amount of a sialidase and an excess amount of β-galactosidase (12 μg) in a buffer solution in a 384-well plate at 37° C. for 30 min. The sialidase amounts and buffers used were: *A. ureafciens* sialidase (0.5 mU), NaOAc buffer (100 mM, pH 5.5); *C. perfringens* sialidase (0.75 mU), MES buffer (100 nM, pH 5.0); *V. cholerae* sialidase (1.5 mU), NaCl (150 mM), $CaCl_2$ (10 mM), NaOAc buffer (100 mM, pH 5.5); SpNanA (1.5 ng), NaOAc buffer (100 mM, pH 6.0); SpNanB (3 ng), NaOAc buffer (100 mM, pH 6.0); SpNanC (20 ng), MES buffer (100 mM, pH 6.5); PmST1 (0.4 g), NaOAc buffer (100 mM, pH 5.5), CMP (0.4 mM); hNEU2 (1.3 μg), MES buffer (100 mM, pH 5.0); BiNanH2 (4 ng), NaOAc buffer (100 mM, pH 5.0). The reactions were stopped by adding 40 μL of N-cyclohexyl-3-aminopropanesulfonic acid (CAPS) buffer (0.5 M, pH 10.5) to adjust pH to higher than 9.5 and $A_{405\ nm}$ values of samples were read by a microplate reader.

Figure 12:
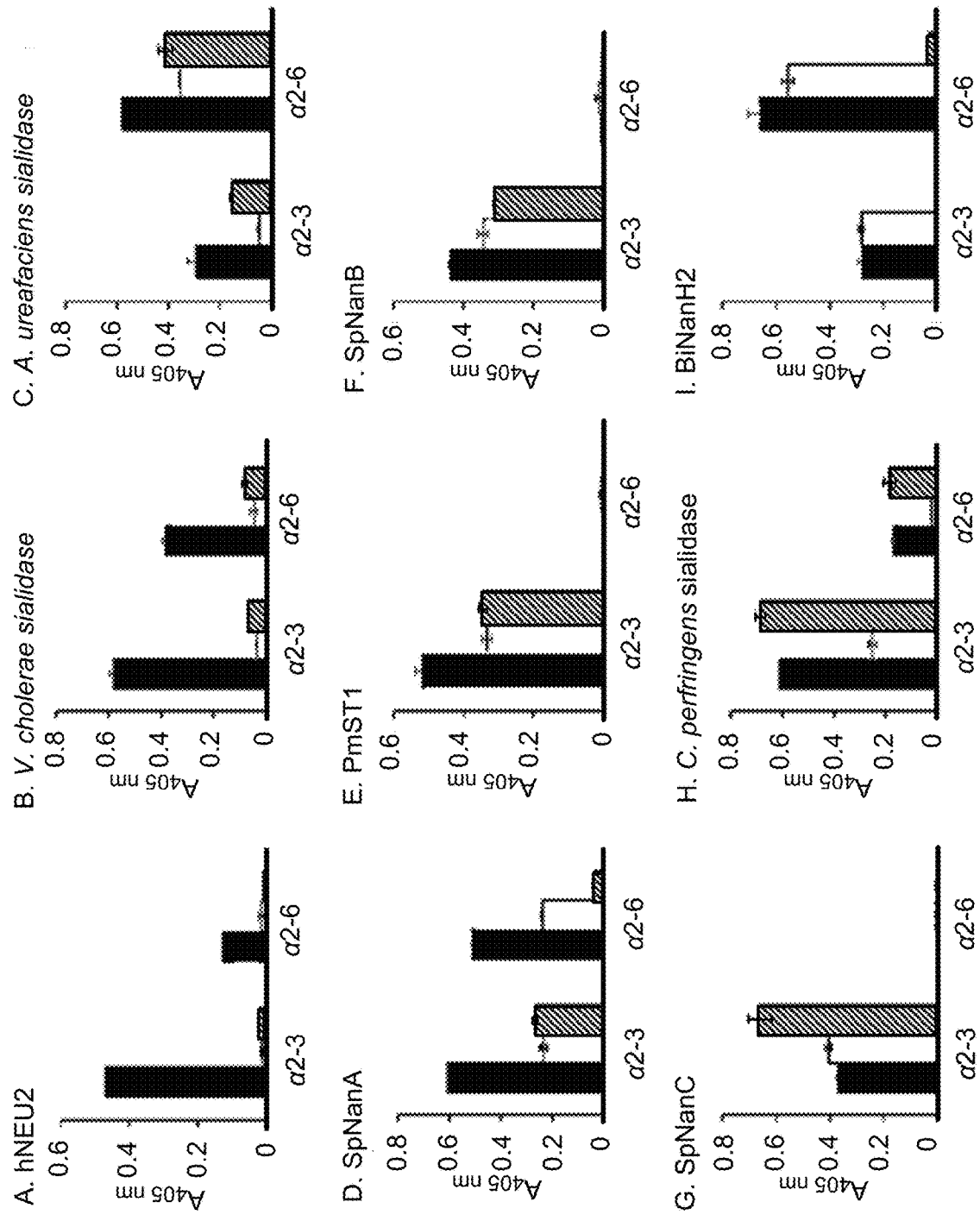
FIG. 12 shows the results of sialidase substrate specificity studies using Neu5Ac-sialosides (black bars) Neu5Acα2-3GalβpNP (2.17) and Neu5Acα2-6GalβpNP (2.18), Neu5Ac9NAc-sialosides (white bars) Neu5Ac9NAcα2-3GalβpNP (2.1) and Neu5Ac9NAcα2-6GalβpNP (2.8), as well as Neu5,9Ac$_2$-sialosides (grey bars) Neu5,9Ac$_2$α2-3GalβpNP (2.19) and Neu5,9Ac$_2$α2-6GalβpNP (2.20) as substrates.

As shown in FIG. 12, substituting the 9-hydroxy group of the Neu5Ac in sialosides by an acetamido group led to significant reduction of the activities of hNEU2 (FIG. 12A) and *V. cholerae* sialidase (FIG. 12B), in which the 9-N-acetyl modification protected sialosides against sialidase cleavage. The effect was similar to that observed for Neu5Ac 9-O-acetyl modification (FIGS. 12A and 12B). In comparison, both 9-N— and 9-O-acetyl modifications decreased the sialoside cleavage efficiencies of *A. ureafaciens* sialidase (FIG. 12C), SpNanA (FIG. 12D), PmST1 (FIG. 12E), and SpNanB (FIG. 12F) only moderately or slightly. Overall, these examples (FIG. 12A-12G) showed that Neu5Ac9NAc-sialosides are good mimics of Neu5,9Ac2-sialosides in probing the activities of these sialidases. Nevertheless, there were exceptions. Different effects were observed for 9-N— and 9-O-acetylation of Neu5Ac in affecting sialoside cleavage by SpNanC (FIG. 12G), *C. perfringens* sialidase (FIG. 12H), and BiNanH2 (FIG. 12I). While 9-N-acetylation of Neu5Ac did not alter the sialidase activity of SpNanC significantly, 9-O-acetylation of Neu5Ac improved the efficiency of sialoside cleavage by SpNanC (FIG. 12G). In comparison, 9-N-acetylation of Neu5Ac decreased the efficiency of sialoside cleavage by *C. perfringens* sialidase while 9-O-acetylation of Neu5Ac did not alter its activity significantly (FIG. 12H). On the other hand, Neu5Ac 9-N-acetylation did not have significant effect on the sialic acid cleavage efficiency of BiNanH2, but Neu5Ac 9-O-acetylation completely blocked its activity (FIG. 12I). A possible factor to consider for the differences is that "NH" in the amide in Neu5Ac9NAc can serve as both a hydrogen bond donor and a hydrogen bond acceptor while the oxygen atom in the ester in Neu5,9Ac2 can only serve as a hydrogen bond acceptor. The mechanism for these differences, however, needs further investigation.

Example 9. Kinetic Study of Sialidase Activity Using Neu5Ac9NAc-Containing Sialosides The results obtained by the microtiter plate-based assays for PmST1, SpNanC, *C. perfringens* sialidase, and BiNanH2 were further confirmed by high-performance liquid chromatography (HPLC)-based assays. In addition, time course studies for BiNanH2 and more detailed kinetics studies for SpNanC and BiNanH2 (Table 3) were carried out.

HPLC-based assays were carried out as described above for microtiter plate-based assays. The reactions were stopped by adding 40 μL of pre-chilled ethanol. The mixtures were then centrifuged and the supernatants were analyzed by Agilent 1290 Infinity HPLC system at 315 nm. A C14 reverse phase Rapid Resolution High Definition column (BONUS RP RRHD 1.8 μm, 2.1×150 mm, Agilent) was used for analyzing samples with Neu5Acα2-3GalβpNP (2.17), Neu5,9Ac2α2-3GalβpNP (2.19), Neu5Ac9NAcα2-6GalβpNP (2.8), or Neu5Acα2-6GalβpNP (2.18). A C18 reverse phase Rapid Resolution High Definition column (EclipsePlusC18 RRHD 1.8 μm, 2.1×50 mm, Agilent) was used for analyzing samples with Neu5Ac9NAcα2-3GalβpNP (2.1) or Neu5,9Ac2α2-6GalβpNP (2.20). The mobile phases used were acetonitrile (ACN) in $H_2O$ mixed solvent with varied percentages of acetonitrile: 4.5% for Neu5Acα2-6GalβpNP (2.18); 6.5% for Neu5Ac9NAcα2-3GalβpNP (2.1) or Neu5,9Ac2α2-6GalβpNP (2.20); 9% for Neu5Ac9NAcα2-6GalβpNP (2.8); and 12% for Neu5Acα2-3GalβpNP (2.17) or Neu5,9Ac2α2-3GalβpNP (2.19).

Time course studies for BiNanH2 were carried out in duplicate at 37° C. in reaction mixtures (200 μL each) containing NaOAc buffer (100 mM, pH 5.0), BiNanH2 (220 ng/mL), and a sialidase substrate (0.3 mM) selected from Neu5Acα2-3GalβpNP (2.17), Neu5Acα2-6GalβpNP (2.18), Neu5Ac9NAcα2-3GalβpNP (1), and Neu5Ac9NAcα2-6GalβpNP (2.8). Aliquots (20 μL each) were taken at 5, 10, 15, 20, 30, 45, or 60 min intervals and added to microcentrifuge tubes (500 μL) containing 40 μL of pre-chilled ethanol. The mixtures were centrifuged on a bench-top centrifuge (13,000 rpm×3 min). The supernatants (45 μL) were analyzed by Agilent 1290 Infinity HPLC system at 315 nm as described above.

The kinetic studies for BiNanH2 were performed in duplicates at 37° C. for 10 min in a total volume of 20 μL each containing NaOAc buffer (100 mM, pH 5.0), a sialidase substrate [selected from Neu5Ac9NAcα2-3GalβpNP (2.1), Neu5Ac9NAcα2-6GalβpNP (8), Neu5Acα2-3GalβpNP (2.17), and Neu5Acα2-6GalβpNP (2.18)], and BiNanH2 (5.8 ng when compound 2.1 or 2.17 was used as the substrate and 1.5 ng when compound 2.8 or 2.18 was used as the substrate). The reactions were stopped by adding 40 μL of pre-chilled ethanol. The mixtures were then centrifuged and the supernatants were analyzed by the HPLC system described above for HPLC-based assays. Apparent kinetic parameters were obtained by varying substrate concentrations from 0.1-40 mM (0.1, 0.2, 0.4, 1, 2, 4, 10, 20, and 40 mM) and fitting the data (the average values of duplicate assay results) into the Michaelis-Menten equation using Grafit 5.0.

The kinetic studies for SpNanC were performed in duplicates at 37° C. for 10 min in a total volume of 20 μL each containing MES buffer (100 mM, pH 6.5), a sialidase substrate [selected from Neu5Ac9NAcα2-3GalβpNP (2.1), Neu5Acα2-3GalβpNP (2.17), and Neu5,9Ac$_2$α2-3GalβpNP (2.19)], and SpNanC (2.5 ng when compound 2.1 or 2.17 was used as the substrate and 1.5 ng when compound 2.19 was used as the substrate). After stopping the reactions by adding 40 μL of pre-chilled ethanol, the mixtures were centrifuged and the supernatants were analyzed by the HPLC system as described above. Apparent kinetic parameters were obtained by varying substrate concentrations from 0.1-40 mM (0.1, 0.2, 0.4, 1, 2, 4, 10, 20, and 40 mM) and fitting the data (the average values of duplicate assay results) into the Michaelis-Menten equation using Grafit 5.0.

As shown in Table 3, SpNanC catalyzes the cleavage of Neu5Ac9NAcα2-3GalβpNP (2.1) and Neu5Acα2-3GalβpNP (2.17) with similar efficiencies ($k_{cat}/K_M$=137 s$^{-1}$ mM$^{-1}$ and 130 s$^{-1}$ mM$^{-1}$, respectively). The catalytic efficiency of SpNanC for Neu5,9Ac$_2$α2-3GalβpNP (2.19) ($k_{cat}/K_M$=302 s$^{-1}$ mM$^{-1}$) is much (2.2-2.3 fold) higher. For BiNanH2, it has similar catalytic efficiencies towards Neu5Ac9NAcα2-3GalβpNP (2.1) and Neu5Acα2-3GalβpNP (2.17) ($k_{cat}/K_M$=59.3 s$^{-1}$ mM$^{-1}$ and 66.7 s$^{-1}$ mM$^{-1}$, respectively). Its catalytic efficient towards Neu5Ac9NAcα2-6GalβpNP (2.8) ($k_{cat}/K_M$=179 s$^{-1}$ mM$^{-1}$) is slightly lower than that of Neu5Acα2-6GalβpNP (2.18) ($k_{cat}/K_M$=242 s$^{-1}$ mM$^{-1}$). In comparison, its activity towards Neu5,9Ac$_2$α2-3GalβpNP (2.19) and Neu5,9Ac$_2$α2-6GalβpNP (2.20) are not high enough for obtaining apparent kinetics parameters. These results validated those shown in FIG. 12.

TABLE 3

Apparent kinetics parameters for SpNanC and BiNanH2.

| Sialidases | Substrate | $k_{cat}$ (s$^{-1}$) | $K_M$ (mM) | $k_{cat}/K_M$ (s$^{-1}$ mM$^{-1}$) |
|---|---|---|---|---|
| SpNanC | Neu5Acα2-3GalβpNP (2.17) | (3.65 ± 0.10) × 10$^2$ | 2.66 ± 0.3 | 137 |
| | Neu5Ac9NAcα2-3GalβpNP (2.1) | (3.38 ± 0.15) × 10$^2$ | 2.60 ± 0.4 | 130 |
| | Neu5,9Ac$_2$α2-3GalβpNP (2.19) | (3.78 ± 0.12) × 10$^2$ | 1.25 ± 0.2 | 302 |
| BiNanH2 | Neu5Acα2-3GalβpNP (2.17) | (1.66 ± 0.02) × 10$^2$ | 2.8 ± 0.1 | 59.3 |
| | Neu5Ac9NAcα2-3GalβpNP (2.1) | (1.08 ± 0.02) × 10$^2$ | 1.61 ± 0.2 | 66.7 |
| | Neu5Acα2-6GalβpNP (2.18) | (3.31 ± 0.06) × 10$^2$ | 1.37 ± 0.1 | 242 |
| | Neu5Ac9NAcα2-6GalβpNP (2.8) | (8.07 ± 0.08) × 10$^2$ | 4.51 ± 0.2 | 179 |

In summary, a library of sixteen new α2-3/6-linked Neu5Ac9NAc-containing sialosides have been successfully synthesized in good to excellent (61-98%) yields using highly efficient one-pot three-enzyme sialylation systems. Among the sialosides synthesized, para-nitrophenylated α2-3- and α2-6-linked Neu5Ac9NAc-containing sialyl galactosides have been used together with their Neu5Ac—, and Neu5,9Ac$_2$-sialoside analogs in microtiter plate-based high-throughput substrate specificity studies of various sialidases. In general, Neu5Ac9NAc-sialosides are good mimics of Neu5,9Ac$_2$-sialosides in probing the activities of most sialidases. Nevertheless, exceptions do exist and different effects were observed for Neu5Ac 9-N— and 9-O-acetylation in affecting sialoside cleavage by SpNanC, *C. per-* *fringens* sialidase, and BiNanH2. Further investigation will be needed to elucidate the mechanism for these differences.

Example 10. Chemical Synthesis of 6deoxyMan2,4diN$_3$ (3-9) and 6Deoxy ManNAc4NAc (3-4)

An efficient method was developed for the production of 6deoxyManNAc4NAc (3-4), the six-carbon precursor of Leg5,7Ac$_2$ (3-1). Commercially available D-fucose (3-5) was chosen as the starting material to allow simultaneous inversion of its stereochemistry at C-2 and C-4 for the formation of mannose derivative. See, Sanapala et al. *J. Am. Chem. Soc.* 2016, 138, 4938-4947. As shown in Scheme 12, per-O-acetylation of D-fucose (3-5) followed by BF$_3$·Et$_2$O-catalyzed nucleophilic displacement of the anomeric acetate with p-methoxyphenol in CH$_2$Cl$_2$ produced intermediate 3-6 in 84% yield. De-O-acetylation with sodium methoxide in methanol produced triol. Dimethyltin chloride (Me$_2$SnCl$_2$)-catalyzed regio-selective benzoyl protection of 3-OH formed D-fucosyl-2,4-diol (3-7) in two steps in 94% yield.

Scheme 12. Chemical synthesis of 6deoxyManNac4NAc from commercially available D-fucose via a diazido intermediate 2,4-diazido-2,4,6-trideoxy mannose (6deoxyMan2,4diN$_3$).

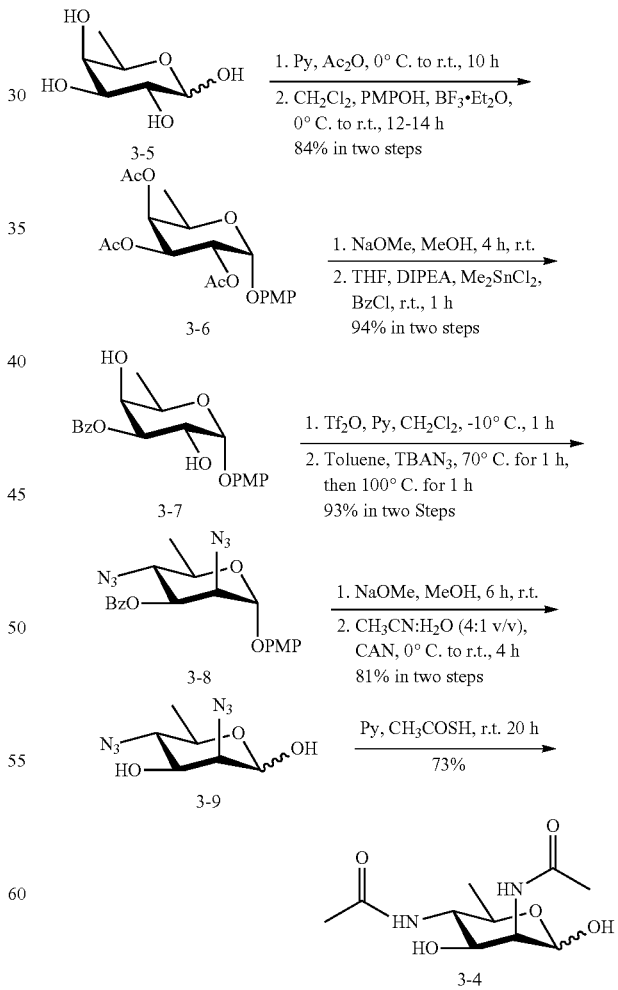

Compound 3-7 was then treated with trifluoromethanesulfonic anhydride (Tf$_2$O) and pyridine to form the corresponding 2,4-bistriflate which upon treating with 2.5 equivalent of tetrabutylammonium azide (TBAN3) in anhydrous toluene at 70° C. to reflux, 6-deoxy-D-mannose derivative 3-8 was formed in 2 hour in 93% yield. Debenzoylation and ceric ammonium nitrate-catalyzed removal of the p-methoxyphenyl group produced 2,4-diazido-2,4,6-trideoxy mannose (6deoxyMan2,4diN$_3$, 3-9) in 81% yield. Overall, the production of 6deoxyMan2,4diN$_3$(3-9) from D-fucose (3-5) was achieved in eight steps with an overall yield of 60%. ManNAc derivative 6deoxyManNAc4NAc (3-4) was obtained readily from compound 9 in 73% yield by treating with thioacetic acid in pyridine at room temperature for 20 hours.

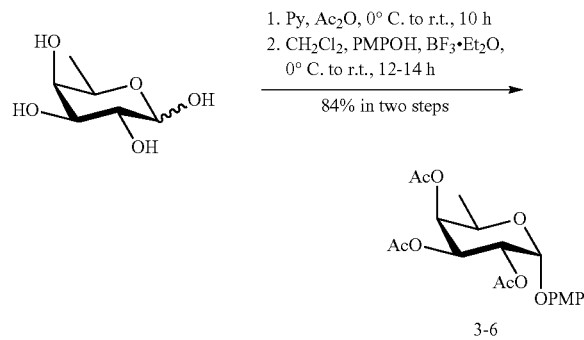

p-Methoxy Phenyl-2,3,4-Tri-O-Acetyl-α-D-Fucopyranoside (3-6).

To a solution of D-fucose (5 g, 30.48 mmol) in 30 mL pyridine at 0° C., 25 mL acetic anhydride was added dropwise. After stirring at 0° C. for 1 h, the mixture was allowed to warm to room temperature and stirred for total 10 h. The solvent was removed in vacuo and co-evaporated with 30 mL of toluene 4 times. The peracetylated D-fucose was dried in vacuo for 5-6 h and directly used for next step without further purification.

To a solution of peracetate (9.34 g, 28.10 mmol) and p-methoxyphenol (5.23 g, 42.15 mmol) in anhydrous CH$_2$Cl$_2$ (75 mL) under nitrogen at 0° C., BF$_3$·OEt$_2$ (6.9 mL, 56.2 mmol) was added drop-wisely. After stirring at 0° C. for 2 h, the mixture was allowed to warm to room temperature, stirred for 12 h and diluted with another 50 mL of CH$_2$Cl$_2$. The organic layer was washed with water, saturated NaHCO$_3$ and brine, dried over Na$_2$SO$_4$. After filtration, the solvent was removed under reduced pressure and the product was purified by silica gel chromatography using hexane:EtOAc=8:1 (by volume) as an eluent to produce the compound 3-6 (9.3 g, 84% in 2 steps) as a white solid. $^1$H NMR (400 MHz, CDCl$_3$) δ 6.97 (d, J=9.1 Hz, 2H), 6.82 (d, J=9.1 Hz, 2H), 5.62 (d, J=3.7 Hz, 1H), 5.59 (dd, J=10.8, 3.6 Hz, 1H), 5.36 (dd, J=3.4, 1.3 Hz, 1H), 5.28 (dd, J=10.8, 3.6 Hz, 1H), 4.31 (dd, J=13.2, 7.0 Hz, 1H), 3.77 (s, 3H), 2.18 (s, 3H), 2.07 (s, 3H), 2.02 (s, 3H), 1.13 (d, J=6.6 Hz, 3H). $^{13}$C NMR (100 MHz, CDCl$_3$) δ 170.70, 170.59, 170.24, 155.33, 150.76, 117.90, 114.81, 95.80, 71.17, 68.11, 68.07, 65.34, 55.78, 20.91, 20.86, 20.78, 16.01. $^1$H NMR (400 MHz, Chloroform-d) δ 5.59 (dd, J=10.8, 3.6 Hz, 1H), 5.28 (dd, J=10.8, 3.6 Hz, 1H).

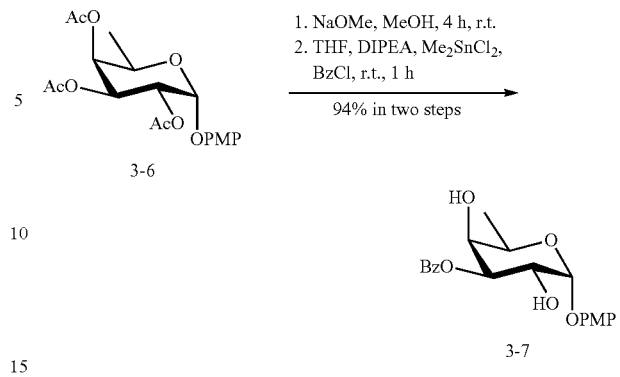

p-Methoxy Phenyl-3-O-Benzoyl-α-D-Fucopyranoside (3-7).

To a solution of 4-methoxy phenyl-2,3,4-tri-O-acetyl-α-D-fucopyranoside 3-6 (9 g, 22.7 mmol) in methanol (50 mL) was added sodium methoxide (0.5 g) at room temperature. After 4 h, the reaction mixture was neutralized with Dowex 50W (H$^+$), filtered and concentrated under reduced pressure. This intermediate was dried in vacuo for 5-6 h used in the next step without further purification.

To a stirred solution of intermediate (6.1 g, 22.7 mmol) in a mixture of THF (30 mL) and water (6 mL) and Me$_2$SnCl$_2$ (273 mg, 1.13 mmol) and DIPEA (15.8 mL, 2.37 mmol) were added and stirred for 15 min. To this BzCl (2.7 mL, 23.4 mmol) was added dropwise, after 1 h the reaction mixture was quenched with 1N HCl (50 mL) and extracted with EtOAc, dried over Na$_2$SO$_4$. After filtration, the solvent was removed under reduced pressure and the product was purified by silica gel chromatography using hexane:EtOAc=4:1 (by volume) as an eluent to produce compound 3-7 (7.9 g, 94% in 2 steps) as a white solid. $^1$H NMR (400 MHz, CDCl$_3$) δ 8.12 (d, J=8.2 Hz, 2H), 7.59 (t, J=7.4 Hz, 1H), 7.46 (t, J=7.7 Hz, 2H), 7.05 (d, J=9.0 Hz, 2H), 6.85 (d, J=9.1 Hz, 2H), 5.54-5.46 (m, 2H), 4.34-4.20 (m, 2H), 4.05 (s, 1H), 3.78 (s, 3H), 2.35-2.11 (m, 2H), 1.29 (d, J=6.6 Hz, 3H). $^{13}$C NMR (100 MHz, CDCl$_3$) δ 166.68, 155.41, 150.76, 133.58, 130.02, 129.75, 128.63, 118.13, 114.85, 98.77, 74.51, 70.95, 67.25, 66.86, 55.80, 16.17. HRMS (ESI) m/z calculated for C$_{20}$H$_{22}$O$_7$ (M+Na) 397.1258 found 397.1243.

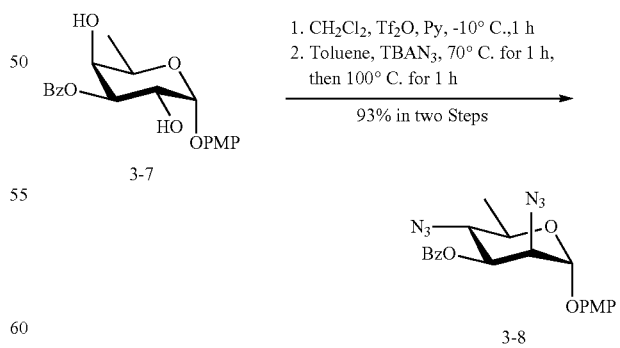

p-Methoxy Phenyl-2,4-Di-Azido-3-O-Benzoyl-6-Deoxy-α-D-Mannopyranoside (3-8).

To a solution of compound 3-7 (3 g, 8.01 mmol) in anhydrous CH$_2$Cl$_2$ (30 mL) and anhydrous pyridine (6.48 mL) at −10° C. triflouromethanesulfonic anhydride (10.8 mL, 64.08 mmol) was added. Temperature was slowly increased to 0° C. over a period of 1 h. The reaction was diluted with addition of 70 mL of $CH_2Cl_2$. The organic layer was washed with 1 N HCl, saturated $NaHCO_3$, and brine solution, dried over anhydrous $Na_2SO_4$. After filtration, the solvent was removed under reduced pressure at room temperature, was dried in vacuo for 2 h and directly used for next step without further purification.

To a solution of the 2,4-bistriflate in anhydrous toluene (50 mL) at 70° C., tetrabutylammonium azide (6.8 g, 24.03 mmol) was added and the mixture was stirred for 1 h. The temperature was then increased to 100° C. and the mixture was stirred for another 1 h. Then the solvent was removed and the condensed mixture was diluted with 75 mL of $CH_2Cl_2$. The organic layer was washed with brine solution, dried over anhydrous $Na_2SO_4$. After filtration, the solvent was removed under reduced pressure and the product was purified by silica gel chromatography using toluene:hexane=25:1 (by volume) as an eluent to produce compound 3-8 (3.1 g, 93% over 2 steps) as a white solid. $^1$H NMR (400 MHz, $CDCl_3$ δ 8.15 (d, J=8.0 Hz, 2H), 7.64 (t, J=8.0 Hz, 1H), 7.51 (t, J=8.0 Hz, 2H), 7.02 (d, J=8.8 Hz, 2H), 6.85 (d, J=8.8 Hz, 2H), 5.72 (dd, J=10.0, 4.4 Hz, 1H), 5.40 (s, 1H), 4.50-4.27 (m, 1H), 3.85 (dq, J=11.9, 5.9, 5.4 Hz, 1H), 3.78 (s, 3H), 3.75 (d, J=10.0 Hz, 1H), 1.38 (d, J=6.0 Hz, 3H). $^{13}$C NMR (100 MHz, $CDCl_3$) δ 165.71, 155.54, 149.98, 134.04, 130.25, 128.88, 117.77, 114.94, 97.20, 72.67, 68.01, 63.22, 61.48, 55.87, 18.62. HRMS (ESI) m/z calculated for $C_{20}H_{20}N_6O_5$ (M−H) 423.1422 found 423.1434.

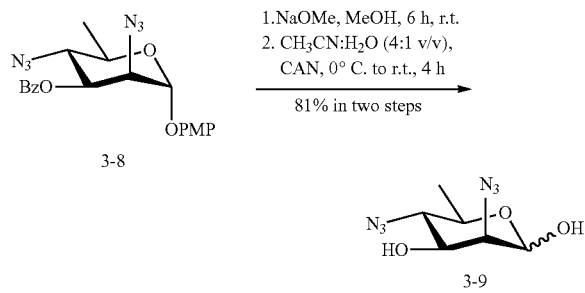

2,4-Diazido-2,4,6-trideox-D-mannose (3-9).

To a solution of compound 3-8 (3 g, 7.06 mmol) in anhydrous methanol (30 mL) was added sodium methoxide (0.3 g) at room temperature. After 6 h, the reaction mixture was neutralized with Dowex 50W ($H^+$), filtered and concentrated under reduced pressure. This intermediate was dried in vacuo and used in the next step without further purification.

To a solution of the 2,4-diazido intermediate in 40 mL of acetonitrile:water=4:1 (by volume) at 0° C., ceric ammonium nitrate (12.32 g, 21.09 mmol) was added and the reaction mixture was stirred for 1 h. The reaction was warmed up to room temperature and was stirred for another 3 h. The acetonitrile was then removed under reduced pressure at room temperature and diluted with 100 mL of ethylacetate. The organic layer was washed with water saturated $NaHCO_3$, and brine solution, dried over anhydrous $Na_2SO_4$. After filtration, the solvent was removed under reduced pressure and the product was purified by silica gel chromatography using hexane:EtOAc=1:2 (by volume) as an eluent to produce compound 3-9 (1.2 g, 81% over 2 steps) as a reddish solid. $^1$H NMR (400 MHz, $D_2O$) δ 5.24 (d, J=1.3 Hz, 1H), 4.98 (d, J=1.2 Hz, 1H), 4.14 (dd, J=10.0, 3.8 Hz, 1H), 4.07 (dd, J=3.7, 1.4 Hz, 1H), 4.02 (dd, J=3.8, 1.8 Hz, 1H), 3.94 (dd, J=9.7, 3.7 Hz, 1H), 3.89-3.79 (m, 1H), 3.44-3.26 (m, 3H), 1.33 (dd, J=7.8, 6.1 Hz, 6H). $^{13}$C NMR (100 MHz, $D_2O$) δ 92.79, 92.09, 71.80, 70.99, 69.21, 66.94, 65.66, 64.99, 64.47, 64.02, 17.40, 17.36. HRMS (ESI) m/z calculated for $C_6H_{10}N_6O_3$ (M+Na) 269.1108 found 269.1098.

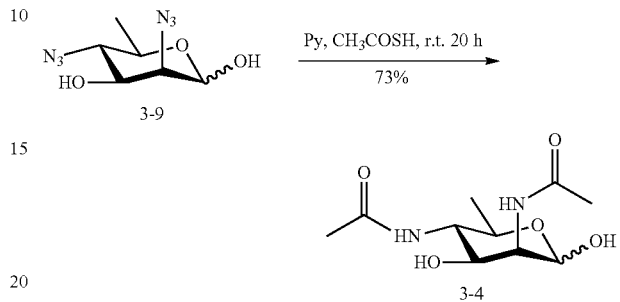

6DeoxyManNAc4NAc (3-4).

To a solution of compound 9 (200 mg, 0.93 mmol) in pyridine (10 mL) was added thioacetic acid (0.530 mL, 7.44 mmol) under argon at room temperature and stir for 20 h and the product was purified by silica gel chromatography using a mixed solvent (EtOAc:methanol=10:1, by volume) as an eluent to produce compound 4 (167 mg, 73%) as a reddish solid. $^1$H NMR (400 MHz, $D_2O$) δ 5.03 (d, J=1.6 Hz, 1H), 4.88 (d, J=1.7 Hz, 1H), 4.39 (dd, J=4.4, 1.7 Hz, 1H), 4.22 (dd, J=4.6, 1.7 Hz, 1H), 3.99 (dd, J=10.7, 4.6 Hz, 2H), 3.94-3.84 (m, J=10.2, 6.3 Hz, 1H), 3.80-3.65 (m, 2H), 3.59 (t, J=10.4 Hz, 1H), 3.43 (m, 1H), 2.04 (s, 3H), 2.00 (s, 3H), 1.96 (s, 3H), 1.95 (s, 3H), 1.13 (dd, J=10.8, 6.2 Hz, 6H). $^{13}$C NMR (100 MHz, $D_2O$) δ 175.85, 174.92, 174.75, 174.68, 92.77, 92.74, 71.58, 69.97, 67.00, 66.53, 53.57, 53.54, 53.18, 52.72, 22.12, 22.10, 22.08, 21.92, 16.81, 16.77. HRMS (ESI) m/z calculated for $C_{10}H_{18}N_2O_5$ (M+$Cl^+$) 281.0910, found 281.0917.

Example 11. Enzymatic Synthesis of 5,7-Di-N-Acetyllegionaminic Acid (Leg5,7$Ac_2$) (3-1)

To our delight, 6deoxyManNAc4NAc (3-4) was a suitable substrate for both recombinant *Escherichia coli* (EcAldolase) and *Pasteurella multocida* (PmAldolase) sialic acid aldolases. PmAldolase was found to be more efficient and was used for preparative-scale synthesis of Leg5,7$Ac_2$ (3-1) with a 71% yield (Scheme 13). Nevertheless, the resulting Leg5,7$Ac_2$ (3-1) was not a suitable substrate for *Neisseria meningitidis* CMP-sialic acid synthetase (NmCSS) for the synthesis of the corresponding CMP-Leg5,7$Ac_2$.

Scheme 13. PmAldolase-catalyzed synthesis of Leg5,7$Ac_2$ from 6deoxyManNaAc4NAc and sodium pyruvate.

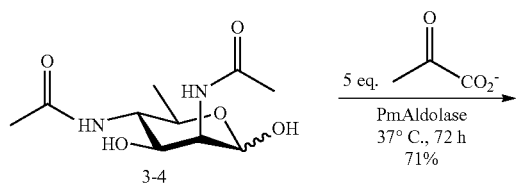

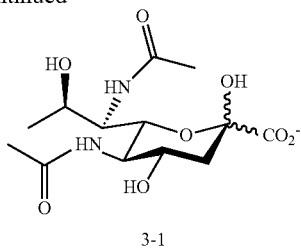

3-1

The 6deoxyManNAc4NAc (3-4, 150 mg, 0.69 mmol) and sodium pyruvate (385 mg, 3.5 mmol) were dissolved in water in a 50 mL centrifuge tube containing Tris-HCl buffer (100 mM, pH 7.5) and MgCl$_2$ (20 mM). After the addition of appropriate amount of PmAldolase (7 mg), water was added to bring the final volume of the reaction mixture to 30 mL. The reaction was carried out by incubating the solution at 37° C. with agitation at 125 rpm in an incubator for 72 h. The product formation was monitored by thin layer chromatography (TLC) developed with EtOAc:MeOH:H$_2$O:HOAc=4:2:1:0.1 (by volume) and stained with p-anisaldehyde sugar stain. The mixture was then centrifuged. The supernatant was concentrated and passed through a BioGel P-2 gel filtration (water was used as an eluent). Then the product was further purified by silica gel chromatograph to produce 3-1 (144 mg, 71%)$^1$H NMR (800 MHz, D$_2$O) δ 4.28 (dd, J=10.5, 1.6 Hz, 1H), 3.97-3.92 (m, 1H), 3.89-3.85 (m, 1H), 3.85-3.80 (m, 1H), 3.70 (t, J=10.3 Hz each, 1H), 2.29 (dd, J=13.1, 4.8 Hz, 1H), 1.85 (t, J=12.3 Hz, 1H), 1.13 (d, J=6.4 Hz, 1H). $^{13}$C NMR (200 MHz, D$_2$O) δ 173.44, 173.27, 172.80, 94.87, 69.14, 66.66, 65.70, 52.68, 52.13, 38.60, 21.62, 21.30, 18.65. HRMS (ESI) m/z calculated for C$_{13}$H$_{22}$N$_2$O$_8$ (M–H) 333.1303, found 333.1289.

Example 12. One-Pot Three-Enzyme (OP3E) Preparative Scale Synthesis of α2-3-Linked Leg5,7diN$_3$-Glycosides and α2-6-Linked Leg5,7diN$_3$-Glycosides Azido derivatives of N-acetylmannosamine (ManNAc) and mannose have been shown to be suitable starting materials for OPME sialylation systems for the synthesis of various α2-3/6-linked sialosides including those containing 7-azido- or 9-deoxy-derivative of NeuSAc. Here, the diazido-compound 3-9 was tested for the synthesis of glycosides. Advantageously, compound 3-9 was well tolerated by the OPME α2-3/6-sialylation systems as demonstrated with three different acceptors including para-nitrophenyl β-galactoside (GalβpNP, 3-10), thiotolyl β-galactoside (GalβSTol, 3-11), and lactosyl β-propylchloride (LacβProCl, 3-12). In these systems, compound 3-9 was coupled with pyruvate to formation the diazido-derivative of Leg (Leg5,7diN$_3$) by a PmAldolase-catalyzed reaction. The Leg5,7diN$_3$ was activated by cytidine 5'-triphosphate (CTP) using an NmCSS-catalyzed reaction to form CMP-Leg5,7diN$_3$ which was used by a sialyltransferase (e.g., PmST1_M144D or Psp2,6ST) to produce α2-3/6-linked Leg5,7diN$_3$-containing glycosides (3-13-3-18) (Table 4).

TABLE 4

One-pot multienzyme (OPME) synthesis of Leg5,7diN$_3$-containing glycosides.

| Acceptor | Product | Yield (%) |
|---|---|---|
| GalβpNP (3-10) | Leg5,7diN$_3$α2-3GalβpNP (3-13) | 71 |

TABLE 4-continued

One-pot multienzyme (OPME) synthesis of Leg5,7diN$_3$-containing glycosides.

| Acceptor | Product | Yield (%) |
|---|---|---|
|  | Leg5,7diN$_3$α2-6Galβp NP (3-14) | 73 |
| GalβSTol (3-11) | Leg5,7diN$_3$α2-3GalβSTol (3-15) | 98 |
|  | Leg5,7diN$_3$α2-6GalβSTol (3-16) | 93 |
| LacβProCl (3-12) | Leg5,7diN$_3$α2-3LacβProCl (3-17) | 91 |
|  | Leg5,7diN$_3$α2-6LacβProCl (3-18) | 97 |

Leg5,7diN$_3$α2-3GalβNP (3-13).

GalβpNP (15 mg, 0.050 mmol), 2,4-di-azido-6-deoxy-mannose (16 mg, 0.075 mmol), sodium pyruvate (38 mg, 0.35 mmol), CTP (39 mg, 0.075 mmol) were dissolved in water in a 15 mL centrifuge tube containing Tris-HCl buffer (100 mM, pH 8.5) and MgCl$_2$ (20 mM). After adding sialic acid aldolase (0.5 mg), NmCSS (0.5 mg), and a sialyltransferase PmST1_M144D (1.5 mg) water was added to bring the final volume to 5 mL. The reaction mixture was incubated at 30° C. for 48 h. The reaction progress was monitored using TLC (EtOAc:MeOH:H$_2$O=6:1:1, by volume) and mass spectrometry. The reaction mixture was diluted with the same volume of ethanol and incubated at 4° C. for 30 min. The mixture was then centrifuged and concentrated, which was purified by automated flash chromatograph using C18 column (CH$_3$CN in H$_2$O gradient was used as running solvents) to produce 3-13 (22 mg, 73%). $^1$H NMR (800 MHz, D$_2$O) δ 8.28 (d, J=9.2 Hz, 2H), 7.25 (d, J=9.2 Hz, 2H), 5.28 (d, J=7.8 Hz, 1H), 4.18-4.13 (m, 2H), 4.05-3.99 (m, 1H), 3.89 (q, J=8.4, 6.9 Hz, 2H), 3.79-3.72 (m, 3H), 3.70 (d, J=10.3 Hz, 1H), 3.61-3.55 (m, 1H), 3.42 (d, J=8.7 Hz, 1H), 2.75 (dd, J=12.7, 4.6 Hz, 1H), 1.91 (t, J=12.3 Hz, 1H), 1.37 (d, J=6.4 Hz, 3H). $^{13}$C NMR (200 MHz, D$_2$O) δ 172.87, 161.19, 142.04, 125.60, 115.93, 100.08, 99.08, 75.07, 74.91, 71.76, 68.94, 68.20, 67.12, 66.05, 64.80, 62.86, 60.14, 38.46, 18.33. HRMS (ESI) m/z calculated for C$_{21}$H$_{27}$N$_7$O$_{13}$ (M−H) 585.1594, found 585.1583.

Leg5,7diN$_3$α2-3GalSTol (3-15).

GalβالسTol (20 mg, 0.070 mmol), 2,4-di-azido-6-deoxy-mannose (22 mg, 0.10 mmol), sodium pyruvate (58 mg, 0.52 mmol), CTP (54 mg, 0.10 mmol) were dissolved in water in a 15 mL centrifuge tube containing Tris-HCl buffer (100 mM, pH 8.5) and MgCl$_2$ (20 mM). After adding sialic acid aldolase (0.5 mg), NmCSS (0.5 mg), and a sialyltransferase PmST1_M144D (1.5 mg) water was added to bring the final volume to 5 mL. The reaction mixture was incubated at 30° C. for 48 h. The reaction progress was monitored using TLC (EtOAc:MeOH:H$_2$O=6:1:1, by volume) and mass spectrometry. The reaction mixture was diluted with the same volume of ethanol and incubated at 4° C. for 30 min. The mixture was then centrifuged and concentrated, which was purified by automated flash chromatograph using C18 column (CH$_3$CN in H$_2$O gradient was used as running solvents) to produce 3-15 (39 mg, 98%). $^1$H NMR (800 MHz, D$_2$O) δ 7.48 (d, J=8.0 Hz, 2H), 7.25 (d, J=8.0 Hz, 2H), 4.71 (d, J=9.9 Hz, 1H), 4.18-4.10 (m, 1H), 4.05 (dd, J=9.4, 3.2 Hz, 1H), 3.97-3.94 (m, 1H), 3.79-3.73 (m, 1H), 3.73-3.67 (m, 2H), 3.67-3.61 (m, 2H), 3.60-3.48 (m, 2H), 3.43 (dd, J=8.5, 2.2 Hz, 1H), 2.70 (dd, J=12.8, 4.7 Hz, 1H), 2.33 (s, 3H), 1.92 (t, J=12.4 Hz, 1H), 1.37 (d, J=6.4 Hz, 3H). $^{13}$C NMR (200 MHz, D$_2$O) δ 172.07, 138.37, 131.85, 129.41, 127.59, 99.74, 87.03, 78.20, 76.57, 71.91, 68.70, 67.68, 66.75, 66.04, 64.72, 62.83, 60.36, 38.11, 19.66, 18.51. HRMS (ESI) m/z calculated for C$_{22}$H$_{30}$N$_6$O$_{10}$S (M−H) 569.1671, found 569.1666.

Leg5,7diN$_3$α2-3LacβProCl (3-17).

LacβProCl (20 mg, 0.048 mmol), 2,4-di-azido-6-deoxy-mannose (15 mg, 0.070 mmol), sodium pyruvate (37 mg, 0.34 mmol), CTP (38 mg, 0.073 mmol) were dissolved in water in a 15 mL centrifuge tube containing Tris-HCl buffer (100 mM, pH 8.5) and MgCl$_2$ (20 mM). After adding sialic acid aldolase (0.5 mg), NmCSS (0.5 mg), and a sialyltransferase PmST1_M144D (1.5 mg) water was added to bring the final volume to 5 mL. The reaction mixture was incubated at 30° C. for 48 h. The reaction progress was monitored using TLC (EtOAc:MeOH:H$_2$O=5:2:1, by volume) and mass spectrometry. The reaction mixture was diluted with the same volume of ethanol and incubated at 4° C. for 30 min. The mixture was then centrifuged and concentrated, which was purified by automated flash chromatograph using C18 column (CH$_3$CN in H$_2$O gradient was used as running solvents) to produce 3-17 (32 mg, 91%). $^1$H NMR (800 MHz, D$_2$O) δ 4.51 (d, J=7.9 Hz, 1H), 4.50 (d, J=8.0 Hz, 1H), 4.17 (p, J=6.4 Hz, 1H), 4.08-4.01 (m, 2H), 3.99 (d, J=12.2 Hz, 1H), 3.92 (d, J=2.7 Hz, 1H), 3.83 (dq, J=11.3, 5.5, 4.9 Hz, 2H), 3.78-3.62 (m, 9H), 3.61-3.57 (m, 1H), 3.55 (t, J=9.6 Hz, 1H), 3.46-3.40 (m, 1H), 3.31 (t, J=8.2 Hz, 1H), 2.71 (dd, J=12.6, 4.6 Hz, 1H), 2.09 (p, J=6.2 Hz, 2H), 1.88 (t, J=12.3 Hz, 1H), 1.39 (d, J=6.3 Hz, 3H). $^{13}$C NMR (200 MHz, D$_2$O) δ 172.92, 102.13, 101.70, 100.13, 77.85, 75.18, 74.63, 74.26, 73.88, 72.30, 71.74, 68.96, 68.85, 67.37, 66.65, 66.08, 64.80, 62.85, 60.49, 59.55, 41.26, 38.35, 31.29, 18.32. HRMS (ESI) m/z calculated for C$_{24}$H$_{39}$C$_1$N$_6$O$_{16}$ (M−H) 701.2038, found 701.2028.

Leg5,7diN$_3$α2-6Gal1pNP (3-14).

GalβpNP (15 mg, 0.050 mmol), 2,4-di-azido-6-deoxy-mannose (16 mg, 0.075 mmol), sodium pyruvate (38 mg, 0.35 mmol), CTP (39 mg, 0.075 mmol) were dissolved in water in a 15 mL centrifuge tube containing Tris-HCl buffer (100 mM, pH 8.5) and MgCl$_2$ (20 mM). After adding sialic acid aldolase (0.5 mg), NmCSS (0.5 mg), and Psp2,6ST (1.5 mg) water was added to bring the final volume to 5 mL. The reaction mixture was incubated at 30° C. for 48 h. The reaction progress was monitored using TLC (EtOAc:MeOH: H$_2$O=6:1:1, by volume) and mass spectrometry. The reaction mixture was diluted with the same volume of ethanol and incubated at 4° C. for 30 min. The mixture was then centrifuged and concentrated, which was purified by automated flash chromatograph using C18 column (CH$_3$CN in H$_2$O gradient was used as running solvents) to produce 3-14 (21 mg, 70%). $^1$H NMR (800 MHz, D$_2$O) δ 8.29 (d, J=8.8 Hz, 2H), 7.26 (d, J=9.6 Hz, 2H), 5.18 (d, J=7.2 Hz, 1H), 4.09-4.04 (m, 1H), 4.01 (d, J=3.3 Hz, 1H), 3.97 (dd, J=7.6, 4.5 Hz, 1H), 3.88 (dd, J=10.5, 7.8 Hz, 1H), 3.86-3.83 (m, 1H), 3.78 (dd, J=10.0, 3.4 Hz, 1H), 3.75-3.69 (m, 2H), 3.67 (dd, J=10.6, 4.4 Hz, 1H), 3.48 (dd, J=8.6, 2.2 Hz, 1H), 3.43 (t, J=9.8 Hz, 1H), 2.74-2.71 (m, 1H), 1.71 (t, J=12.3 Hz, 1H), 1.34 (d, J=6.4 Hz, 3H). $^{13}$C NMR (200 MHz, D$_2$O) δ 172.62, 161.33, 142.01, 125.58, 116.04, 100.08, 99.26, 73.56, 71.85, 71.37, 69.78, 68.82, 67.89, 66.25, 65.35, 63.13, 62.77, 39.50, 18.29. HRMS (ESI) m/z calculated for C$_{21}$H$_{27}$N$_7$O$_{13}$ (M−H) 585.1594, found 585.1589.

Leg5,7diN$_3$α2-6GalSTol (3-16).

GalβSTol (15 mg, 0.052 mmol), 2,4-diazido-6-deoxy-mannose (16 mg, 0.075 mmol), sodium pyruvate (41 mg, 0.37 mmol), CTP (42 mg, 0.080 mmol) were dissolved in water in a 15 mL centrifuge tube containing Tris-HCl buffer (100 mM, pH 8.5) and MgCl$_2$ (20 mM). After adding sialic acid aldolase (0.5 mg), NmCSS (0.5 mg), and Psp2,6ST (1.5 mg) water was added to bring the final volume to 5 mL. The reaction mixture was incubated at 30° C. for 48 h. The reaction progress was monitored using TLC (EtOAc:MeOH: H$_2$O=6:1:1, by volume) and mass spectrometry. The reaction mixture was diluted with the same volume of ethanol and incubated at 4° C. for 30 min. The mixture was then centrifuged and concentrated, which was purified by automated flash chromatograph using C18 column (CH$_3$CN in H$_2$O gradient was used as running solvents) to produce 3-16 (29 mg, 93%). $^1$H NMR (800 MHz, D$_2$O) δ 7.48 (d, J=8.0 Hz, 2H), 7.26 (d, J=8.0 Hz, 2H), 4.63 (d, J=9.8 Hz, 1H), 4.10 (p, J=6.4 Hz, 1H), 3.96 (d, J=3.3 Hz, 1H), 3.86 (dd, J=10.1, 7.6 Hz, 1H), 3.80-3.77 (m, 1H), 3.75-3.69 (m, 2H), 3.64 (dd, J=9.4, 3.2 Hz, 1H), 3.59-3.53 (m, 2H), 3.51-3.47 (m, 2H), 2.69 (dd, J=12.8, 4.8 Hz, 1H), 2.34 (s, 3H), 1.70 (t, J=12.3 Hz, 1H), 1.36 (d, J=6.4 Hz, 3H). $^{13}$C NMR (200 MHz, D$_2$O) δ 172.30, 138.22, 131.51, 129.43, 128.14, 99.99, 87.65, 76.79, 73.33, 71.54, 68.76, 68.61, 68.14, 66.21, 65.29, 63.09, 62.99, 58.81, 39.41, 19.67, 18.40. HRMS (ESI) m/z calculated for C$_{22}$H$_{30}$N$_6$O$_{10}$S (M−H) 569.1671, found 569.1662.

Leg5,7diN$_3$α2-6LacβProCl (3-18).

LacβProCl (25 mg, 0.060 mmol), 2,4-di-azido-6-deoxy-mannose (20 mg, 0.093 mmol), sodium pyruvate (51 mg, 0.47 mmol), CTP (49 mg, 0.093 mmol) were dissolved in water in a 15 mL centrifuge tube containing Tris-HCl buffer (100 mM, pH 8.5) and $MgCl_2$ (20 mM). After adding sialic acid aldolase (0.5 mg), NmCSS (0.5 mg), and Psp2,6ST (1.5 mg) water was added to bring the final volume to 5 mL. The reaction mixture was incubated at 30° C. for 48 h. The reaction progress was monitored using TLC (EtOAc:MeOH:$H_2O$=5:2:1, by volume) and mass spectrometry. The reaction mixture was diluted with the same volume of ethanol and incubated at 4° C. for 30 min. The mixture was then centrifuged and concentrated, which was purified by automated flash chromatograph using C18 column ($CH_3CN$ in $H_2O$ gradient was used as running solvents) to produce 3-18 (42 mg, 97%). $^1H$ NMR (800 MHz, $D_2O$) δ 4.50 (d, J=8.0 Hz, 1H), 4.41 (d, J=7.9 Hz, 1H), 4.18-4.13 (m, 1H), 4.06 (dt, J=11.0, 6.1 Hz, 1H), 3.97 (d, J=12.3 Hz, 1H), 3.93-3.88 (m, 2H), 3.84 (dt, J=11.0, 6.2 Hz, 1H), 3.82-3.75 (m, 3H), 3.71 (ddd, J=24.5, 10.4, 4.2 Hz, 4H), 3.64 (dd, J=10.0, 3.3 Hz, 1H), 3.61-3.54 (m, 4H), 3.53-3.50 (m, 1H), 3.46 (dd, J=8.7, 2.1 Hz, 1H), 3.32 (t, J=8.7 Hz, 1H), 2.69 (dd, J=12.8, 4.8 Hz, 1H), 2.09 (p, J=6.4 Hz, 2H), 1.79 (t, J=12.3 Hz, 1H), 1.38 (d, J=6.4 Hz, 3H). $^{13}C$ NMR (200 MHz, $D_2O$) δ 172.71, 102.80, 101.60, 100.04, 79.41, 74.13, 74.11, 73.07, 72.13, 71.94, 71.53, 70.33, 68.93, 67.85, 66.62, 66.04, 65.27, 63.02, 62.86, 59.81, 41.29, 39.39, 31.30, 18.38. HRMS (ESI) m/z calculated for $C_{24}H_{39}C_1N_6O_{16}$ (M−H) 701.2038, found 701.2031.

Example 13. Conversion of Leg5,7diN$_3$-Glycosides to Leg5,7Ac$_2$-Glycosides

Different strategies were tested to convert the azido groups in the glycosides synthesized (3-13-3-18) to N-acetyl groups to form desired Leg5,7Ac$_2$-containing glycosides (3-19-3-24). A conventional Perlman catalyst-mediated reduction of azide to amine followed by selective acetylation of the amine worked for 3-13, 3-15, 3-16, and 3-18 with ~50% in two steps but hydrogenation also converted the aromatic nitro group of 3-13 and 3-14 to the corresponding amine which was undesirable. PMe3-mediated Staudinger reaction worked well for all compounds and quantitatively produced the corresponding di-amine derivatives. However, selective acetylation of amine by a combination of acetylchloride and trietyl amine in tetrahydrofuran and water (4:1 v/v) produced the di-N-acetyl derivative in poor yields (~40%). An alternative N-acetylation strategy using thioacetic acid and catalytic copper sulfate in methanol produced Leg5,7Ac$_2$-glycosides with very poor yields (<20%). Finally, thioacetic acid-mediated one-pot conversion of azido to acetamido group using saturated sodium bicarbonate in water was employed to afford Leg5,7Ac$_2$-containing glycosides (3-19-3-24) in 69-88% yields (Table 5). See, Shangguan et al. *J. Am. Chem. Soc.* 2003, 125, 7754-7755. In comparison, poorer yields (45-70%) were obtained when pyridine was used as the solvent in the same method (data not shown).

Notably, Leg5,7Ac$_2$α2-3Gal-containing structures have been found in O-antigens of *Cronobacter turicensis* HPB3287 and G3882, and *Enterobacter cloacae* $C_{6285}$. Leg5,7Ac$_2$α2-6Gal-containing structures have been found in an extracellular polysaccharide fraction of *Enterococcus faecium*. Therefore, the obtained thiotolyl β-glycosides (Leg5,7Ac$_2$α2-3GalβSTol 3-21 and Leg5,7Ac$_2$α2-6GalβSTol 3-22) can be used as building blocks for efficient chemical synthesis of more complex glycosides similar to those described before for Neu5Ac-containing sialosides.

To a stirred solution of azido glycoside (6-30 mg) in saturated sodium bicarbonate solution at 65° C. thioacetic acid (10 eq) was added drop-wisely under inert atmosphere after 12 h add another portion of thioacetic acid (15 eq) and stir the reaction for another 24 h. After completion of the reaction the reaction mixture passed through a BioGel P-2 gel filtration (water was used as an eluent). Then the product containing fractions concentrated was further purified by automated flash chromatograph using C18 column ($CH_3CN$ in $H_2O$ gradient was used as running solvents) to get pure compound.

TABLE 5

Production of Leg5,7Ac2-containing glycosides via azide reduction.

Leg5,7Ac$_2$α2-3GalβpNP (3-19) — Yield (%) 81

TABLE 5-continued
Production of Leg5,7Ac2-containing glycosides via azide reduction.
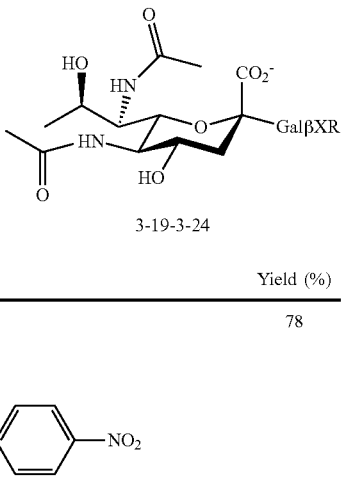
3-13-3-18 →(AcSH, sat. NaHCO₃ in H₂O, 69-88%)→ 3-19-3-24
| Product | Yield (%) |
|---|---|
| Leg5,7Ac₂α2-6GalβpNP (3-20) | 78 |
| Leg5,7Ac₂α2-3GalβSTol (3-21) | 88 |
| Leg5,7Ac₂α2-6GalβSTol (3-22) | 84 |
| Leg5,7Ac₂α2-3LacβProCl (3-23) | 72 |
| Leg5,7Ac₂α2-6LacβProCl (3-24) | 69 |

Leg5,7Ac$_2$α2-3GalβpNP (3-19).

8.5 mg, 81% was obtained as a white solid. $^1$H NMR (800 MHz, D$_2$O) δ 8.28 (d, J=9.6 Hz, 1H), 7.26 (d, J=9.6 Hz, 1H), 5.29 (d, J=7.8 Hz, 1H), 4.25-4.21 (m, 1H), 4.03 (d, J=2.8 Hz, 1H), 3.99-3.94 (m, 1H), 3.94-3.88 (m, 2H), 3.85-3.80 (m, 3H), 3.76 (d, J=6.1 Hz, 2H), 3.73 (s, OH), 3.58 (td, J=11.2, 5.0 Hz, 1H), 2.81 (dd, J=12.8, 4.8 Hz, 1H), 1.96 (s, 2H), 1.94 (s, 2H), 1.77 (t, J=12.0 Hz, 1H), 1.13 (d, J=6.4 Hz, 3H). $^{13}$C NMR (200 MHz, D$_2$O) δ 173.49, 173.35, 173.24, 161.18, 142.05, 125.61, 115.93, 99.14, 99.13, 74.97, 74.94, 71.29, 68.31, 68.22, 66.84, 66.29, 60.17, 53.39, 51.50, 39.62, 21.62, 21.45, 17.56. HRMS (ESI) m/z calculated for C$_{25}$H$_{35}$N$_3$O$_{15}$ (M–H) 616.1995, found 616. 1991.

Leg5,7Ac$_2$α2-6GalβpNP (3-20).

6.5 mg, 78% was obtained as a white solid. $^1$H NMR (800 MHz, D$_2$O) δ 8.31 (d, J=8.8 Hz, 2H), 7.29 (d, J=9.6 Hz, 2H), 5.19 (d, J=7.2 Hz, 1H), 4.04-3.97 (m, 3H), 3.96-3.91 (m, 1H), 3.89-3.83 (m, 2H), 3.81-3.74 (m, 2H), 3.64 (dd, J=10.0, 2.2 Hz, 1H), 3.60-3.54 (m, 2H), 2.80 (dd, J=12.8, 4.8 Hz, 1H), 1.92 (s, 3H), 1.85 (s, 3H), 1.62 (t, J=11.2 Hz, 1H), 1.12 (d, J=6.4 Hz, 3H). $^{13}$C NMR (200 MHz, D$_2$O) δ 173.43, 173.06, 173.02, 161.45, 142.06, 125.63, 115.96, 99.67, 99.44, 73.61, 71.88, 71.10, 69.79, 68.10, 68.04, 66.63, 62.89, 53.46, 51.65, 39.92, 21.60, 21.34, 17.57. HRMS (ESI) m/z calculated for C$_{25}$H$_{35}$N$_3$O$_{15}$ (M–H) 616.1995, found 616. 1984.

Leg5,7Ac$_2$α2-3GalβSTol (3-21). 27.8 mg, 88% was obtained as a white solid. $^1$H NMR (800 MHz, D$_2$O) δ 7.49 (d, J=8.0 Hz, 2H), 7.26 (d, J=8.0 Hz, 2H), 4.73 (d, J=9.8 Hz, 1H), 4.11 (dd, J=9.3, 3.1 Hz, 1H), 3.96 (dd, J=12.9, 6.5 Hz, 2H), 3.82 (ddd, J=20.2, 9.8, 3.1 Hz, 2H), 3.71 (dd, J=12.7, 3.8 Hz, 2H), 3.69-3.65 (m, 2H), 3.61 (t, J=9.6 Hz, 1H), 3.58-3.54 (m, 1H), 2.76 (dd, J=12.8, 4.8 Hz, 1H), 2.33 (s, 3H), 1.98 (s, 3H), 1.93 (s, 3H), 1.74 (t, J=12.0 Hz, 1H), 1.14 (d, J=6.4 Hz, 3H). $^{13}$C NMR (200 MHz, D$_2$O) δ 173.48, 173.38, 173.28, 138.37, 131.82, 129.42, 127.63, 99.25, 87.12, 78.28, 76.63, 71.29, 68.23, 66.91, 66.81, 66.78, 60.44, 53.40, 51.49, 39.56, 21.62, 21.48, 19.65, 17.58. HRMS (ESI) m/z calculated for C$_{26}$H$_{38}$N$_2$O$_{12}$S (M–H) 601.2072, found 601.2078.

Leg5,7Ac$_2$α2-6GalβSTol (3-22).

5.2 mg, 84% was obtained as a white solid. $^1$H NMR (800 MHz, D$_2$O) δ 7.53 (d, J=8.0 Hz, 2H), 7.28 (d, J=8.0 Hz, 2H), 4.68 (d, J=9.6 Hz, 1H), 4.01-3.94 (m, 3H), 3.89 (dd, J=10.3, 2.9 Hz, 1H), 3.84-3.80 (m, 1H), 3.78 (dd, J=8.3, 3.1 Hz, 1H), 3.71-3.64 (m, 2H), 3.61 (t, J=9.6 Hz, 1H), 3.59-3.53 (m, 2H), 2.75 (dd, J=12.8, 4.8 Hz, 1H), 2.34 (s, 3H), 1.93 (s, 3H), 1.87 (s, 3H), 1.64 (t, J=12.0 Hz, 2H), 1.13 (d, J=6.3 Hz, 3H). $^{13}$C NMR (200 MHz, D$_2$O) δ 173.43, 173.11, 173.00, 138.09, 130.87, 129.51, 128.64, 99.72, 87.52, 76.94, 73.36, 71.09, 68.66, 68.42, 68.15, 66.62, 63.53, 53.51, 51.64, 39.94, 21.63, 21.36, 19.62, 17.61. HRMS (ESI) m/z calculated for C$_{26}$H$_{38}$N$_2$O$_{12}$S (M–H) 601.2072, found 601.2063.

Leg5,7Ac$_2$α2-3LacβProCl (3-23).

5.6 mg, 72% was obtained as a white solid. $^1$H NMR (800 MHz, D$_2$O) δ 4.50 (t, J=8.0 Hz, 2H), 4.11 (dd, J=9.9, 2.9 Hz, 1H), 4.05 (dt, J=11.2, 6.0 Hz, 1H), 3.99 (dt, J=8.2, 4.7 Hz, 2H), 3.94 (d, J=2.8 Hz, 1H), 3.86-3.79 (m, 4H), 3.78-3.69 (m, 5H), 3.69-3.63 (m, 3H), 3.57 (ddt, J=20.3, 10.5, 5.8 Hz, 3H), 3.31 (t, J=8.2 Hz, 1H), 2.78 (dd, J=12.8, 4.8 Hz, 1H), 2.08 (p, J=6.2 Hz, 2H), 1.98 (s, 3H), 1.94 (s, 3H), 1.74 (t, J=12.0 Hz, 1H), 1.16 (d, J=6.4 Hz, 3H). $^{13}$C NMR (200 MHz, D$_2$O) δ 173.48, 173.47, 173.22, 102.15, 101.69, 99.00, 77.82, 74.88, 74.64, 74.26, 73.87, 72.30, 71.31, 68.90, 68.24, 66.74, 66.65, 66.39, 60.52, 59.59, 53.39, 51.53, 41.25, 39.62, 31.28, 21.63, 21.44, 17.58. HRMS (ESI) m/z calculated for C$_{28}$H$_{47}$C$_1$N$_2$O$_{18}$ (M–H) 733.2439, found 734.2425.

Leg5,7Ac$_2$α2-6LacβProCl (3-24). 7.1 mg, 69% was obtained as a white solid. $^1$H NMR (800 MHz, D$_2$O) δ 4.51 (d, J=8.0 Hz, 1H), 4.43 (d, J=7.2 Hz, 1H), 4.06 (dt, J=10.9, 6.0 Hz, 1H), 4.02-3.96 (m, 3H), 3.94-3.87 (m, 2H), 3.86-3.78 (m, 4H), 3.75-3.69 (m, 3H), 3.69-3.60 (m, 4H), 3.59-3.52 (m, 3H), 3.36 (t, J=8.4 Hz, 1H), 2.72 (dd, J=12.8, 4.8 Hz, 1H), 2.09 (p, J=6.2 Hz, 2H), 2.00 (s, 3H), 1.94 (s, 3H), 1.73 (t, J=12.0 Hz, 1H), 1.15 (d, J=6.4 Hz, 3H). $^{13}$C NMR (200 MHz, D$_2$O) δ 173.43, 173.27, 172.92, 102.70, 101.57, 99.83, 78.93, 74.17, 74.12, 73.13, 72.37, 71.91, 71.12, 70.21, 68.26, 67.93, 66.62, 62.91, 59.72, 53.51, 51.57, 41.28, 39.63, 31.31, 21.64, 21.62, 17.57. HRMS (ESI) m/z calculated for C$_{28}$H$_{47}$C$_1$N$_2$O$_{18}$ (M–H) 733.2439, found 734.2431.

Example 14. Production of Leg5,7Ac$_2$-Terminated Propylazido-β-Glycosides from Propyl Chloro-β-Glycosides The propyl chloride linker in compounds 3-23 and 3-24 was readily converted to propyl azide by treating them with sodium azide (NaN$_3$) and a catalytic amount of sodium iodide (NaI) in dimethylformamide (DMF) at 60° C. for a period of 12 hours to produce Leg5,7Ac$_2$α2-3LacβProN$_3$ (3-25, shown below) and Leg5,7Ac$_2$α2-6LacβProN$_3$ (3-26, shown below) in 85% and 92% yields, respectively. The azido group in the final products can be easily reduced to an amine group for microarray studies and for synthesizing glycoconjugates, as described above.

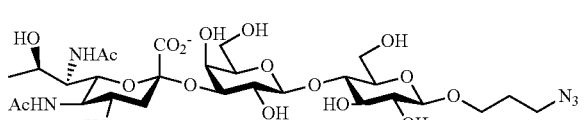

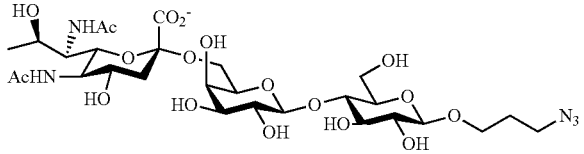

To a stirred solution of Leg5,7Ac$_2$α2-3LacβProCl (5.0 mg) or Leg5,7Ac$_2$α2-6LacβProCl (5.2 mg) in DMF, NaN$_3$ (10 eq) and NaI (1 eq) were added and the reaction was left under 60° C. for 12 h. After completion of the reaction the solvent was concentrated in vaccuo. The crude product was purified by automated flash chromatograph using C18 column (CH$_3$CN in H$_2$O gradient was used as running solvents) to give the pure compounds.

Leg5,7Ac$_2$α2-3LacβProN$_3$ (3-25).

4.3 mg, 85% was obtained as a white solid. $^1$H NMR (800 MHz, D$_2$O) δ 4.51 (d, J=7.8 Hz, 1H), 4.49 (d, J=8.0 Hz, 1H), 4.11 (dd, J=9.9, 3.0 Hz, 1H), 4.02-3.96 (m, 3H), 3.95 (d, J=2.9 Hz, 1H), 3.86-3.79 (m, 3H), 3.78-3.73 (m, 2H), 3.73-3.69 (m, 2H), 3.69-3.63 (m, 3H), 3.62-3.54 (m, 3H), 3.46 (t, J=6.7 Hz, 2H), 3.31 (t, J=8.4 Hz, 1H), 2.78 (dd, J=12.8, 4.8 Hz, 1H), 1.98 (s, 3H), 1.94 (s, 3H), 1.91 (q, J=6.6 Hz, 2H), 1.74 (t, J=12.0 Hz, 1H), 1.16 (d, J=6.4 Hz, 3H). $^{13}$C NMR (200 MHz, D$_2$O) δ 173.48, 173.47, 173.22, 102.15, 101.63, 99.00, 77.83, 74.88, 74.64, 74.26, 73.88, 72.29, 71.31, 68.90, 68.23, 66.87, 66.73, 66.39, 60.51, 59.59, 53.39, 51.53, 47.37, 39.61, 27.74, 21.63, 21.43, 17.57. HRMS (ESI) m/z calculated for $C_{28}H_{47}N_5O_{18}$ (M−H) 740.2843, found 740.2840.

Leg5,7Ac$_2$α2-6Lac ProN$_3$ (3-26).

4.8 mg, 92% was obtained as a white solid. $^1$H NMR (800 MHz, D$_2$O) δ 4.50 (d, J=8.0 Hz, 1H), 4.43 (d, J=8.0 Hz, 1H), 4.03-3.96 (m, 4H), 3.92-3.88 (m, 2H), 3.86-3.79 (m, 3H), 3.79-3.74 (m, 1H), 3.71 (t, J=10.0 Hz, 1H), 3.69-3.64 (m, 4H), 3.64-3.60 (m, 3H), 3.59-3.53 (m, 2H), 3.46 (t, J=6.4 Hz, 1H), 3.36 (t, J=8.8 Hz, 1H), 2.72 (dd, J=12.8, 4.8 Hz, 1H), 2.00 (s, 3H), 1.94 (s, 3H), 1.91 (q, J=6.3 Hz, 1H), 1.73 (t, J=12.0 Hz, 1H), 1.15 (d, J=6.4 Hz, 3H). $^{13}$C NMR (200 MHz, D$_2$O) δ 173.43, 173.27, 172.93, 102.71, 101.51, 99.83, 78.97, 74.17, 74.13, 73.13, 72.36, 71.91, 71.12, 70.22, 68.26, 67.93, 66.84, 66.62, 62.91, 59.73, 53.51, 51.57, 47.39, 39.63, 27.75, 21.64, 21.62, 17.57. HRMS (ESI) m/z calculated for $C_{28}H_{47}N_5O_{18}$ (M−H) 740.2843, found 740.2807.

Example 15. Sialidase Substrate Specificity Studies

Leg5,7diN$_3$α2-3/6GalβpNP (3-13 and 3-14) and Leg5,7Ac$_2$α2-3/6GalβpNP (3-19 and 3-20) were tested as potential substrates for recombinant human cytosolic sialidase hNEU2 and several bacterial sialidases (including three commercially available sialidases from *Arthrobacter ureafaciens*, *Vibrio cholerae*, and *Clostridium perfringens* (CpNanH), as well as five recombinant bacterial sialidases such as PmST1, *Bifidobacterium infantis* sialidase BiNanH2, *Streptococcus pneumoniae* sialidases SpNanA, SpNanB, and SpNanC). It was interesting to note that Leg5,7Ac$_2$α2-3GalβpNP (3-19), but not Leg5,7diN$_3$α2-3GalβpNP (3-13), was a substrate for the α2-3-sialidase activity of wild-type PmST1. Other sialidases tested did not show activity for any of the compounds (3-13, 3-14, 3-19, and 3-20).

Assays were carried out in duplicate. For each reaction in a final volume of 20 μL, a sialoside was incubated with an appropriate amount of a sialidase in a buffer solution in a 0.5 mL microcentrifuge tube at 37° C. for 16 hs. The sialidase amounts and buffers used were: *A. ureaficiens* sialidase (0.5 mU), NaOAc buffer (100 mM, pH 5.5); *C. perfringens* sialidase (0.75 mU), MES buffer (100 mM, pH 5.0); *V. cholerae* sialidase (1.5 mU), NaCl (150 mM), CaCl$_2$ (10 mM), NaOAc buffer (100 mM, pH 5.5); SpNanA (1.5 ng), NaOAc buffer (100 mM, pH 6.0); SpNanB (3 ng), NaOAc buffer (100 mM, pH 6.0); SpNanC (20 ng), MES buffer (100 mM, pH 6.5); PmST1 (0.4 μg), NaOAc buffer (100 mM, pH 5.5), CMP (0.4 mM); hNEU2 (1.3 μg), MES buffer (100 mM, pH 5.0); BiNanH2 (4 ng), NaOAc buffer (100 mM, pH 5.0). The reactions were stopped by adding 20 μL of pre-chilled ethanol. The mixtures were then centrifuged and the supernatants were analyzed by Agilent 1290 Infinity HPLC system at 315 nm or P/ACE™ MDQ Capillary Electrophoresis at 315 nm. A C14 reverse phase Rapid Resolution High Definition column (BONUS RP RRHD 1.8 μm, 2.1×150 mm, Agilent) was used for analyzing samples with Neu5Acα2-3GalβpNP and Neu5Acα2-6GalβpNP, which are used as control. A C$_{18}$ reverse phase Rapid Resolution High Definition column (EclipsePlusC18 RRHD 1.8 μm, 2.1×50 mm, Agilent) was used for analyzing samples with Leg5,7Ac$_2$α2-3GalβpNP (3-19) and Leg5,7Ac$_2$α2-6GalβpNP (3-20). The mobile phases used were acetonitrile in H$_2$O mixed solvent with varied percentages of acetonitrile: 12% for Neu5Acα2-3GalβpNP; 4.5% for Neu5Acα2-6GalβpNP; 6% for Leg5,7Ac$_2$α2-3GalβpNP (3-19) and Leg5,7Ac$_2$α2-6GalβpNP (3-20). P/ACE™ MDQ Capillary Electrophoresis was used for analyzing Leg5,7diN$_3$α2-3GalβpNP (3-13) and Leg5,7diN$_3$α2-6GalβpNP (3-14).

Example 16. Kinetic Studies for PmST1

Kinetic studies for PmST1 were performed in duplicates at 37° C. for 10 min. Each reaction in a total volume of 20 μL contained NaOAc buffer (100 mM, pH 5.5), CMP (0.4 mM), a sialidase substrate Neu5Acα2-3GalβpNP or Leg5,7Ac$_2$α2-3GalβpNP (3-19), and PmST1 (0.2 μg when Neu5Acα2-3GalβpNP was used as the substrate and 4 μg when Leg5,7Ac$_2$α2-3GalβpNP (3-19) was used as the substrate). The reactions were stopped by adding 20 μL of pre-chilled ethanol. The mixtures were then centrifuged and the supernatants were analyzed by the HPLC system described above for sialidase substrate specificity studies assays. Apparent kinetic parameters were obtained by varying substrate concentrations from 0.1-40 mM (0.1, 0.2, 0.4, 1, 2, 4, 10, 20, and 40 mM) and fitting the data (the average values of duplicate assay results) into the Michaelis-Menten equation using Grafit 5.0.

The kinetics studies showed that in the presence of 0.4 mM CMP, α2-3-sialidase activity of PmST1 for Leg5,7Ac$_2$α2-3GalβpNP (3-19) ($k_{cat}/K_M$=4 min$^{-1}$ mM$^{-1}$) was about 30-fold less efficient than for Neu5Acα2-3GalβpNP ($k_{cat}/K_M$=117 min$^{-1}$ mM$^{-1}$) which was contributed by both a lower $k_{cat}$ value and a higher $K_M$ value when Leg5,7Ac$_2$α2-3GalβpNP (3-19) was used as the substrate. (See Table 6) Therefore, the PmST1 α2-3-sialidase activity is not a concern for synthesizing α2-3-linked Leg5,7diN$_3$-glycosides described here but is a factor for consideration for the synthesis of α2-3-linked Leg5,7Ac$_2$-glycosides.

TABLE 6

Apparent kinetics parameters for PmST1.

| Sialidase | Substrate | $k_{cat}$ (min$^{-1}$) | $K_M$ (mM) | $k_{cat}/K_M$ (min$^{-1}$ mM$^{-1}$) |
|---|---|---|---|---|
| PmST1 | Neu5Acα2-3GalβpNP | 555.4 ± 11.1 | 4.73 ± 0.31 | 117 |
|  | Leg5,7Ac$_2$α2-3GalβpNP (3-19) | 69.3 ± 1.3 | 17.38 ± 0.70 | 4 |

Indeed, commercially available wild-type PmST1 was found to be as effective as its M144D mutant (with decreased sialidase activity) in synthesizing α2-3-linked Leg5,7Ac$_2$-glycosides 3-13, 3-15, and 3-17 (data not shown). Psp2,6ST A336G mutant with a higher expression level and commercially available *Photobacterium damselae* α2-6-sialyltransferase (Pd2,6ST) are also suitable sialyltransferases for OPME synthesis of α2-6-linked Leg5,7diN$_3$-glycosides 3-14, 3-16, and 3-18 (data not shown).

In conclusion, 2,4-diazido-2,4,6-trideoxy mannose (6deoxyMan2,4diN$_3$) has been designed as an easy-to-obtained and highly effective chemoenzymatic synthon. It was readily synthesized from commercially available D-fucose by chemical methods in eight steps with an overall yield of 60% and was successfully used for highly efficient chemoenzymatic synthesis of a library of α2-3- and α2-6-linked di-N-acetyllegionaminic acid (Leg5,7Ac$_2$)-containing glycosides in 57-86% yields. The chemoenzymatic method described here allows high-yield synthesis of a diverse array of biologically important Leg5,7Ac$_2$-containing glycosides using commercially available enzymes. The method of designing chemoenzymatic synthons for enzymatic formation of glycosides followed by chemical derivatization can be a general strategy for producing complex N-acetyl-containing glycosides.

Example 17. 4-Azido-2,3-Dehydro-2,4-Dideoxy-N-Acetylneuraminic Acid (Neu5Ac4N$_3$2En) as a Chemoenzymatic Synthon for Neu5Ac4N$_3$-Glycosides and Neu5Ac4NAc-Glycosides 4-Azido-4-deoxy-N-acetylneuraminic acid (Neu5Ac4N$_3$, 6A) and 4-acetamido-4-deoxy-N-acetylneuraminic acid (Neu5Ac4NAc, 6) were synthesized by chemoenzymatic methods via 4-azido-2,3-dehydro-2,4-dideoxy-N-acetylneuraminic acid (Neu5Ac4N$_3$2en, 4-5) as a key intermediate (Scheme 14). C-4 modified sialic acid cannot be achieved by sialic acid aldolase-catalyze reactions due to the mandatory installation of a hydroxyl group on C-4 during the aldolase reactions. Described herein is the first enzymatic method to obtain Neu5Ac4N$_3$ (7) by the hydration of Neu5Ac4N$_3$2en catalyzed by *Streptococcus pneumoniae* sialidase SpNanC,[1-2] a sialidase that catalyzed the formation and also hydration of Sia2ens.

The starting material N-acetylneuraminic acid (Neu5Ac) was fully protected to produce compound 4-2. Compound 4-2 was then converted to a 4,5-oxazoline intermediate (4-3), which was conveniently converted to the protected compound 4. Deprotection of compound 4-4 formed Neu5Ac4N$_3$2en (4-5). Hydration of Neu5Ac4N$_3$2en by SpNanC was slower compared to the hydration of Neu5Ac. However, the reaction could be driven to completion with a long reaction time. A yield of 60-80% was obtained for a 3-day reaction. Neu5Ac4N$_3$ (6A) was converted to the target product Neu5Ac4NAc (6) by treating with thioacetic acid (AcSH) in saturated sodium bicarbonate (NaHCO$_3$) in water. The new chemoenzymatic method for synthesizing 4-modified sialic acids has significant advantages compared to previously reported chemical methods (Carbohydrate Research. 1989; 194:c15-8).

Scheme 14. Chemoenzymatic synthesis of Neu5Ac4N$_3$ and Neu5Ac4NAc.

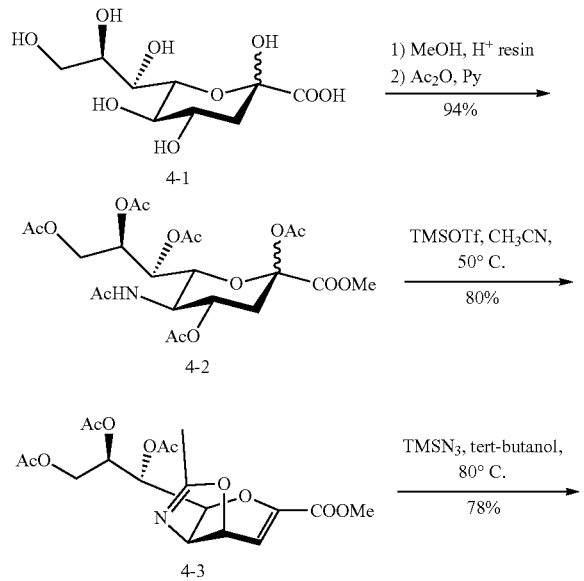

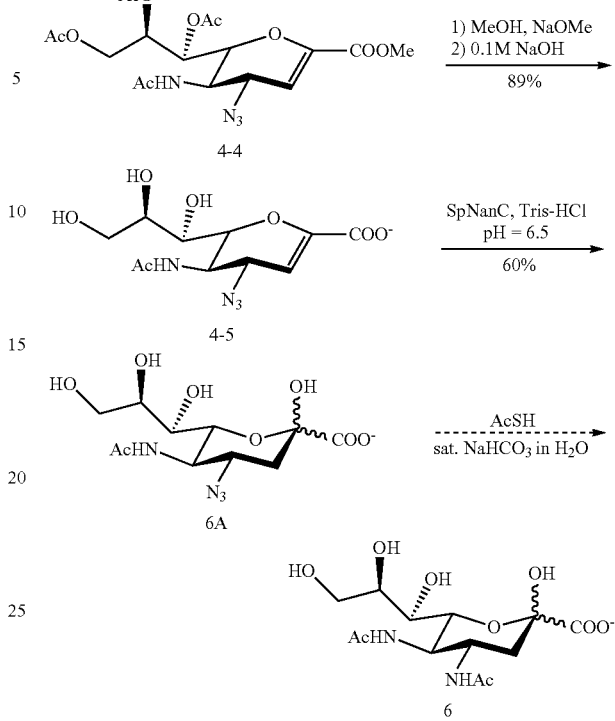

Example 18. Chemoenzymatic Synthesis of Neu5Ac7NAc-Glycosides

O-Acetylation at the C7 position of sialic acid is notoriously challenging to study. It can easily migrate to the C8 position and then to the C9 position and is commonly presented as a mixture of the multi-O-acetylated forms. It is also labile and can be lost easily, particularly when pH is above 6 or below 3. It is also subjected to esterase-catalyzed hydrolysis. To overcome the challenges in study of 7-O-acetyl Neu5Ac (Neu5,7Ac$_2$), its stable analog 7-acetamido-7-deoxy-N-acetylneuraminic acid (Neu5Ac7NAc) is described here. Neu5Ac7NAc-containing sialosides can be prepared as described above and used for functional studies.

Chemical syntheses of 2,4-diacetamido-2,4-dideoxymannose (Man2,4NAc$_2$, 2) have been successfully achieved by two methods: a route from N-acetylmannosamine (ManNAc, 4.0) via modified 1,6-anhydro sugar and 4-azido-4-deoxy-N-acetylmannoamine (ManNAc4N$_3$, 2A) (Scheme 15), and a route from commercially available D-galactose (4-10) via formation of mannose derivative 4-14 as an intermediate for the formation of Man2,4NAc$_2$ (2) (Scheme 16). The route shown in Scheme 15 is particularly advantageous for preparation of purified Man2,4NAc$_2$ in good yield.

Scheme 15: Synthesis of ManNAc4N$_3$ and Man2,4NAc2 from ManNAc.

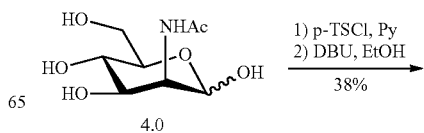

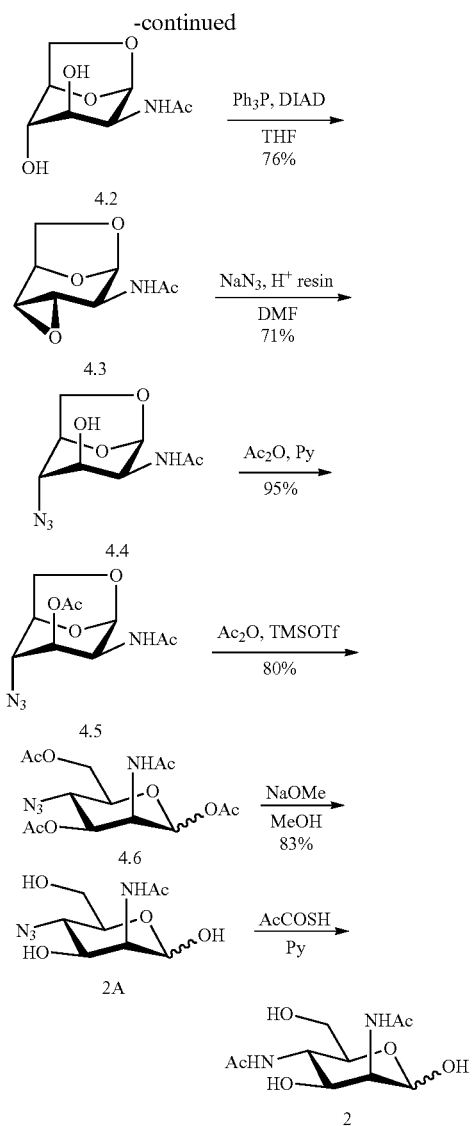

ManNAc4N₃ (2A) and Man2,4NAc₂ (2) were prepared via a modified 1,6-anhydro sugar as shown in Scheme 15. 2-Acetamido-2-deoxy-D-mannopyranose (4.0) (2.00 g, 9.04 mmol) was dissolved in anhydrous pyridine (20 mL), cooled in an ice-water bath, a solution of p-toluene sulfonylchloride (2.09 g, 5.42 mmol) in anhydrous pyridine (5.0 mL) was slowly added. The reaction was stirred for 5.0 h in an ice-water bath to produce 2-acetamido-2-deoxy-6-O-p-tolylsulfonyl-D-mannopyranose. The reaction was stopped and quenched by adding methanol and the solution was concentrated under reduced pressure. The compound was purified by silica gel column chromatography (dichloromethane:acetone=1:2, by volume).

2-Acetamido-2-deoxy-6-O-p-tolylsulfonyl-D-mannopyranose (1.3 g, 3.56 mmol) was dissolved in anhydrous ethanol (30 mL) at room temperature. 1,8-Diazabicyclo[5.4.0]undec-7-ene (1.1 mL, 7.19 mmol) was added slowly to the reaction mixture, and the reaction was stirred for 20 h under nitrogen. The solvent was removed under reduced pressure, and the compound was purified by silica gel column chromatography (ethyl acetate:methanol=15:1, by volume) to produce compound 4.2 (0.70 g, 38% over two step). $^1$H NMR (400 MHz, CD₃OD) δ 2.05 (s, 3H), 3.38 (s, 1H), 3.70 (t, 1H, J=6.8 Hz), 3.76 (bs, 1H), 3.83 (m, 1H), 4.13 (dd, 1H, J=2 Hz, 5.6H), 4.29 (dd, 1H, J=1.2 Hz, 6.8 Hz), 4.503 (1H, m), 5.27 (bs, 1H). $^{13}$C NMR (100 MHz, CD₃OD) δ 21.3, 48.5, 64.2, 69.4, 72.0, 75.9, 100.5, 171.7.

2-Acetamido-1,6-anhydro-2-deoxy-β-D-mannopyranose (4.2) (0.51 g, 2.52 mmol) and triphenylphosphine (0.79 g, 3.03 mmol) were added to a round bottom flask and dissolved in anhydrous tetrahydrofuran (23 mL) under nitrogen. The reaction mixture was cooled in an ice-water bath, and diisopropylazodicarboxylate (0.59 mL, 3.03 mmol) was added drop-wisely. The reaction mixture was stirred in an ice-water bath for 4 h before it was concentrated under reduced pressure. The compound was purified by silica gel column chromatography (acetone:dichloromethane=1:20, by volume) to produce 2-acetamido-1,6:3,4-dianhydro-2-deoxy-β-D-talopyranose (4.3) in 76% yield. $^1$H NMR (400 MHz, CD₃OD) δ 2.03 (s, 3H), 3.23 (bt, 1H, J=4 Hz), 3.47 (m, 1H), 3.73 (t, 1H, J=4 Hz), 3.93 (d, 1H, J=8 Hz), 4.22 (m, 1H), 4.85 (m, 1H), 5.23 (d, 4 Hz). $^{13}$C NMR (100 MHz, CD₃OD) δ 21.1, 48.3, 48.5, 55.3, 63.8, 71.9, 96.6, 171.9.

2-Acetamido-1,6:3,4-dianhydro-2-deoxy-β-D-talopyranose (4.3) (0.47 g, 2.52 mmol), anhydrous Dowex H⁺ resin (120 mg) and sodium azide (0.66 g, 10.15 mmol) were added to a round bottom flask and anhydrous N, N-dimethylformamide (15 mL) was added. The solution was stirred for 10 h at 100° C. in an oil bath. Resin was removed by filtration on celite and washed with ethyl acetate. The reaction mixture was concentrated under reduced pressure on high vacuum and the compound was purified by silica gel column chromatography (dichloromethane:acetone=3:1, by volume) to produce 2-acetamido-1,6-anhydro-4-azido-2,4-dideoxy-β-D-mannopyranose (4.4) in 71% yield. $^1$H NMR (400 MHz, CD₃OD) δ 2.04 (s, 3H), 3.62 (bs, 1H), 3.75 (dd, 1H, J=6 Hz, 8 Hz), 3.91 (m, 1H), 4.04 (m, 1H), 4.34 (dd, 1H, J=1.2 Hz, 7.2 Hz), 4.673 (m, 1H), 5.29 (s, 1H).

A mixture of 2-acetamido-1,6-anhydro-4-azido-2,4-dideoxy-β-D-mannopyranose (4.4) was acetylated in the presence of acetic anhydride and pyridine. The solution was stirred for 5 h at room temperature. The reaction was stopped by adding MeOH and the reaction mixture was subjected to silica gel column chromatography (hexane:ethyl acetate=1:2, by volume) to produce 2-acetamido-3-O-acetyl-1,6-anhydro-4-azido-2,4-dideoxy-β-D-mannopyranose (4.5). $^1$H NMR (400 MHz, CD₃Cl) δ 1.99 (s, 3H), 2.14 (s, 3H), 3.56 (s, 1H), 3.83 (dd, 1H, J=5.6 Hz, 8.4 Hz), 4.31 (dd, 1H, 7.6 Hz), 4.43 (m, 1H), 4.59 (m, 1H), 5.05 (dd, 1H, J=5.2 Hz), 5.53 (bs, 1H). $^{13}$C NMR (100 MHz, CD₃Cl) δ 20.9, 23.2, 466.7, 60.5, 65.9, 69.2, 73.8, 100.7, 169.7, 169.7.

2-Acetamido-3-O-acetyl-1,6-anhydro-4-azido-2,4-dideoxy-β-D-mannopyranose (4.5) (0.72 g, 2.65 mmol) was dissolved in acetic anhydride (10 mL) under nitrogen at 0° C. Trimethylsilyl triflate (0.48 mL, 2.65 mmol) was added slowly. The reaction was stirred under ice-cold water for 3 h. The reaction was stopped by adding sodium bicarbonate solution. The reaction mixture was extracted by ethyl acetate. Organic layer was washed using a sodium chloride solution and dried over Na₂SO₄. The reaction mixture was concentrated under reduced pressure on high vacuum and the compound was purified by silica gel column chromatography (dichloromethane:methanol=40:1, by volume) to produce 2-acetamido-1,3,6-tri-O-acetyl-4-azido-2,4-dideoxy-D-mannopyranose (6) in 80% yield. $^1$H NMR (400 MHz, CD₃Cl) δ 2.06 (s, 3H), 2.06 (s, 3H), 2.07 (s, 3H), 2.07 (s, 3H), 2.08 (s, 3H), 2.10 (s, 3H), 2.11 (s, 3H), 2.12 (s, 3H), 2.15 (s, 3H), 3.55-3.73 (m, 2H), 3.78-3.83 (m, 1H), 4.24-4.35 (m, 3H), 4.59-4.63 (m, 1H), 4.71-4.74 (m, 1H), 4.99 (dd, 1H, J=4.8 Hz, 9.6 Hz), 5.24 (dd, 1H, 4.4 Hz, 10.4 Hz), 5.79 (1H, bs), 5.97 (1H, bs), 6.05 (d, 1H, J=8.4 Hz), 6.23 (d, 1H, J=9.6 Hz). $^{13}$C NMR (400 MHz, CD$_3$Cl) δ 20.7, 20.7, 20.7, 20.7, 20.7, 20.8, 23.0, 23.2, 48.6, 49.5, 56.2, 56.5, 62.8, 63.0, 70.5, 70.6, 73.4, 73.6, 90.5, 91.7, 168.2, 168.2, 169.8, 169.9, 170.6, 170.6, 170.7, 171.1

2-Acetamido-1,3,6-tri-O-acetyl-4-azido-2,4-dideoxy-D-mannopyranose (4.6) (0.78 g, 2.09 mmol) was dissolved in dry MeOH and 0.2 mL of sodium methoxide solution (5.4 M) was added. After the reaction was completed, the reaction mixture was neutralized by H$^+$ resin. Product was purified by silica gel column chromatography (dichloromethane:methanol=25:1, by volume) to produce 0.43 g of 2-acetamido-4-azido-2,4-dideoxy-D-mannopyranose (2A). $^1$H NMR (400 MHz, CD$_3$OD) δ 2.02 (s, 3H), 2.04 (s, 3H), 3.41-3.49 (m, 2H), 3.61 (d, 1H, J=8 Hz), 3.66-3.78 (m, 4H), 3.79-3.87 (m, 2H), 3.93 (dd, 1H, J=3.6 Hz, 10.4 Hz), 4.10-4.15 (m, 1H), 4.26 (dd, 1H, J=1.2 Hz, 4.8 Hz), 5.03 (bs, 1H), 5.12 (d, 1H, J=3.6 Hz). $^{13}$C NMR (400 MHz, CD$_3$OD) δ 21.2, 21.3, 53.4, 54.6, 59.5, 61.1, 61.2, 63.0, 68.4, 70.1, 70.2, 70.6, 91.3, 93.6, 172.4, 172.7.

2-Acetamido-4-azido-2,4-dideoxy-D-mannopyranose (2A) was dissolved in pyridine (4 mL) and thioacetic acid (1.8 mL) was added. The reaction mixture was stirred for 24 h under argon at room temperature. The reaction was quenched by adding methanol and the solvent was removed under reduced pressure. The compound was purified by silica gel column chromatography (ethyl acetate:methanol=15:1, by volume) to produce 2,4-diacetamido-2,4-dideoxy-D-mannopyranose (2). $^1$H NMR (800 MHz, D$_2$O) δ 1.92 (s, 3H), 1.93 (s, 3H), 1.96 (s, 3H), 2.00 (s, 2H), 3.35 (m, 1H), 3.50 (s, 1H), 3.54-3.58 (m, 2H), 3.61 (dd, 1H, J=1.6 Hz, 12.8 Hz), 3.73 (t, 1H, J=10.4 Hz), 3.77-3.82 (m, 2H), 3.85 (t, 1H, J=11.2 Hz), 4.02 (dd, 1H, J=4 Hz, 10.4 Hz), 4.22 (bd, 1H, J=4 Hz), 4.37 (bd, 1H, J=4.8 Hz), 4.89 (s, 1H), 5.06 (s, 1H). $^{13}$C NMR (200 MHz, D$_2$O) δ 21.9, 22.0, 22.0, 22.0, 47.9, 48.2, 52.5, 53.5, 60.8, 66.6, 70.1, 70.8, 75.5, 93.0, 174.7, 174.8, 174.8 175.8.

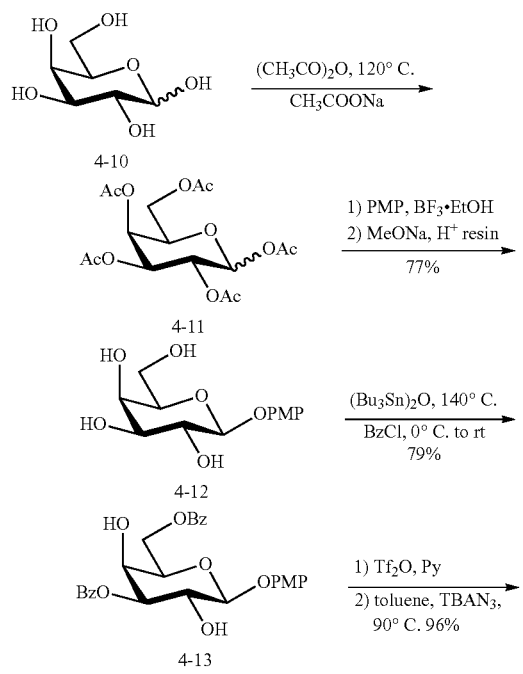

Scheme 16. Synthesis of Man2,4NAc$_2$ and Man2,4diN$_3$ from galactose.

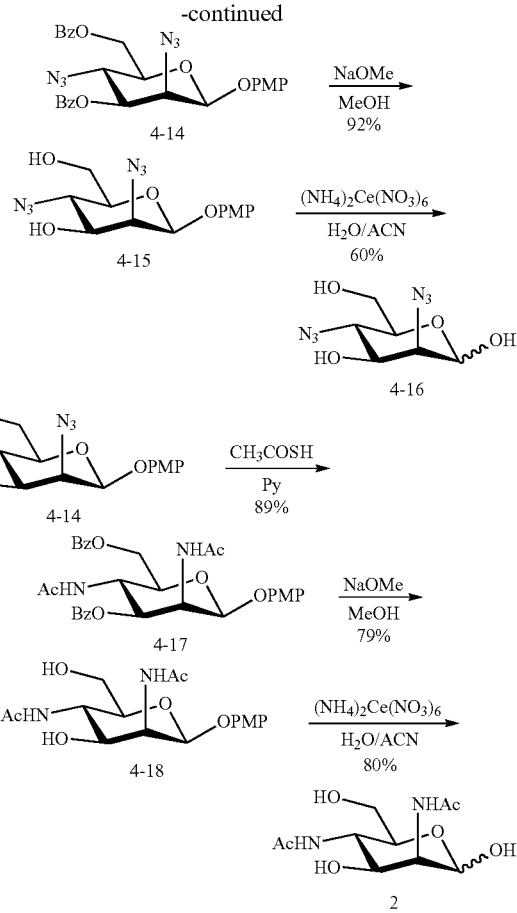

Man2,4diN$_3$ (4-16) and Man2,4NAc$_2$ (2) were prepared from galactose as shown in Scheme 16. D-Galactopyranose (4-10) (7.00 g, 38.8 mmol) and sodium acetate (3.7 g, 0.045 mole) were dissolved in acetic anhydride (50 mL). The reaction mixture was heated at 120° C. for 1 h and neutralized using sodium bicarbonate. The compound was extracted by washing with dichloromethane and the dichloromethane solution was washed with brine. Organic layer was dried on sodium sulfate and the solvent was removed under reduced pressure to produce 1,2,3,4,6-penta-O-acetyl-D-galactopyranose (4-11) in quantitative yield.

Compound 4-11 (21.67 g, 0.055 mmol) and 4-methoxyphenol (10.33 g, 0.083 mmol) were added to a round bottom flask and dissolved in dichloromethane (50 mL). The reaction mixture was cooled in ice-water bath. Boron trifluoride diethyl etherate (11.86 g, 0.0832 mmol) was added slowly in to the reaction mixture. The reaction was stirred for 6 h and quenched by MeOH. The solvent was removed under reduced pressure and the residue was subjected to silica gel column chromatography (hexane:ethyl acetate=3:1, by volume) to produce 1-(4-methoxybenzyl)-2,3,4,6-tetra-O-acetyl-D-galactopyranose in 81% yield.[11]

1-(4-Methoxybenzyl)-2,3,4,6-tetra-O-acetyl-D-galactopyranose was dissolved in dry MeOH and 0.2 mL of sodium methoxide solution (5.4 M) was added. After the reaction was completed, the reaction mixture was neutralized by H$^+$ resin. The product was purified by silica gel column chromatography (ethyl acetate:methanol=20:1, by volume) to produce 1-(4-methoxybenzyl)-D-galactopyranosides (4-12) in 95% yield. Oα-isomer $^1$H NMR (400 MHz, CD$_3$OD) δ 3.64 (d, 2H, J=6.4 Hz), 3.75 (s, 3H), 3.75-3.81 (m, 1H), 4.08-4.18 (m, 2H), 4.21-4.26 (m, 1H), 5.42 (d, 1H, J=1.6 Hz), 6.82-6.87 (m, 2H), 6.98-7.04 (m, 2H). $^{13}$C NMR (100 MHz, CD$_3$OD) δ 54.76, 63.0, 70.9, 76.9, 82.2, 83.4, 107.3, 114.2, 114.2, 117.9, 117.9, 151.1, 155.0. β-isomer $^1$H NMR (400 MHz, CD$_3$OD) δ 3.31-3.34 (m, 2H), 3.36 (s, 1H), 3.56 (dd, 1H, J=3.2 Hz, 9.6 Hz), 3.63-3.67 (m, 1H), 3.76 (s, 3H), 3.77-3.81 (m, 1H), 3.91 (bs, 1H, J=3.6 Hz), 6.81-6.86 (m, 2H), 7.06-7.09 (m, 2H). $^{13}$C NMR (100 MHz, CD$_3$OD) δ 54.6, 61.0, 68.8, 70.9, 73.5, 75.5, 102.7, 113.9, 113.9, 117.8, 117.8, 151.9, 155.2.

Compound 4-12 (0.60 g, 2.10 mmol) and bis(tri-n-butyltin) oxide (1.78 g, 3.15 mmol) were dissolved in toluene (70 mL). The reaction mixture was heated to 140° C. in oil bath for 15 minutes. Reaction mixture was cooled down to 0° C. in ice-water bath and benzoyl chloride (0.88 g, 6.30 mmol) was added. The reaction was stirred for 6 h at low temperature and quenched by adding methanol. The solvent was removed under reduced pressure. Compound was purified by silica gel column chromatography (toluene:ethyl acetate=7:1, by volume) to produce 3,6-dibenzoyl-1-(4-methoxybenzyl)-β-D-galactopyranose (4-13) in 79% yield. $^1$H NMR (400 MHz, CD$_3$OD) δ 3.76 (s, 3H), 4.09 (t, 1H, J=6.8 Hz), 4.30-4.37 (m, 2H), 4.59-4.73 (m, 2H), 4.90 (d, 1H, J=7.2 Hz), 5.24 (dd, 1H, J=3.2 Hz, 10.4 Hz), 6.71-6.79 (m, 2H), 7.02-7.12 (m, 2H), 7.42-7.53 (m, 4H), 7.57-7.66 (m, 2H), 8.03-8.17 (m, 4H). $^{13}$C NMR (100 MHz, CD$_3$OD) δ 55.7, 62.9, 67.3, 69.3, 72.6, 75.3, 102.8, 114.5, 118.8, 128.5, 128.6, 129.4, 129.6, 129.8, 129.9, 133.4, 133.6, 151.0, 155.6, 166.2, 166.4

3,6-Dibenzoyl-1-(4-methoxybenzyl)-β-D-galactopyranose (4-13) (0.40 g, 0.81 mmol) was dissolved in dichloromethane (25 mL) at 0° C. Pyridine (0.65 mL, 8.09 mmol) was added followed by slow addition of triflouromethanesulfonic anhydride (0.68 mL 4.04 mmol) at 0° C. After stirring at the same temperature for 30 min, the reaction was quenched by adding sodium bicarbonate. The organic layer was washed with hydrochloric acid (1 N) and brine. Organic layer was combined and concentrated under reduced pressure to produce a crude product, which was used for the next step without any purification. To a solution of 2,4-bistriflate in toluene (20 mL), tetrabutylammonium azide (0.76 g, 2.67 mmol) was added at room temperature. The reaction was stirred at 70° C. for 1 h and then at 90° C. for another 1 h. The solvent was removed under reduced pressure and the residue was purified by silica gel column chromatography (toluene) to produce 2,4-diazido-3,6-dibenzoyl-2,4-dideoxy-1-(4-methoxybenzyl)-β-D-mannopyranose (4-14) in 95.9% yield. $^1$H NMR (400 MHz, CD$_3$Cl) δ 3.71-3.74 (m, 1H), 3.75 (s, 3H), 4.11 (t, 1H, J=10.4 Hz), 4.53-4.65 (m, 2H), 4.80 (dd, 1H, J=2.4, 12.8 Hz) 5.24 (bs, 1H), 5.30 (dd, 1H, J=3.6 Hz, 10 Hz), 6.73-6.78 (m, 2H), 6.99-7.06 (m, 2H), 7.47-7.56 (m, 4H), 7.60-7.69 (m, 2H), 8.09-8.20 (m, 4H). $^{13}$C NMR (200 MHz, CD$_3$Cl) δ 55.5, 57.4, 61.5, 63.7, 73.0, 74.1, 98.8, 114.5, 118.5, 125.3, 128.2, 128.5, 128.8, 129.1, 129.7, 129.9, 130.1, 133.4, 134.1, 150.3, 155.8, 165.6, 166.1.

2,4-Diazido-3,6-dibenzoyl-2,4-dideoxy-1-(4-methoxybenzyl)-β-D-mannopyranose (4-14) (0.50 g, 0.92 mmol) was dissolved in dry MeOH and 0.2 mL of sodium methoxide solution (5.4 M) added. After the reaction was completed, the reaction mixture was neutralized using H$^+$ resin. The product was purified by silica gel column chromatography (toluene:ethyl acetate=7:1, by volume) to produce 0.28 g of 2,4-diazido-2,4-dideoxy-1-(4-methoxybenzyl)-β-D-mannopyranose (4-15). $^1$H NMR (400 MHz, CD$_3$Cl) δ 2.06-2.10 (m, 1H), 2.61 (d, 1H, J=4.8 Hz), 3.22-3.25 (m, 1H), 3.64 (t, 1H, J=5.2 Hz), 3.77 (s, 3H), 3.91-3.95 (m, 1H), 4.18 (d, 1H, J=1.6 Hz), 5.11 (bs, 1H), 6.82-6.85 (m, 2H), 6.93-6.96 (m, 2H). $^{13}$C NMR (100 MHz, CD$_3$Cl) δ 55.69, 59.4, 62.0, 63.8, 72.4, 75.11, 98.8, 114.7, 117.6, 150.1, 155.6.

2,4-Diazido-2,4-dideoxy-1-(4-methoxybenzyl)-β-D-mannopyranose (4-15) (0.28 g 0.84 mmol) was added to a round bottom flask and dissolved in acetonitrile (6 mL). Ammonium cerium nitrate (1.4 g) dissolved in water (1.5 mL) was added slowly while stirring. The reaction was run for 2.5 h at room temperature. The reaction mixture was concentrated, and the residue was purified by silica gel column chromatography (toluene:ethyl acetate=2:1, by volume) to produce 2,4-diazido-2,4-dideoxy-D-mannopyranose (4-16) in 60% yield. $^1$H NMR (800 MHz, D$_2$O) δ 3.30-3.33 (m, 1H), 3.54 (t, 1H, J=11.2 Hz), 3.66 (t, 1H, J=8.8 Hz), 3.64-3.68 (m, 2H), 3.77-3.80 (m, 1H), 3.83 (dd, 1H, J=1.6 Hz, 12.8 Hz), 3.87 (dd, 1H, J=2.4 Hz, 12.8 Hz), 3.99-7.03 (m, 2H), 4.07 (bd, 1H, J=3.2 Hz), 4.21 (dd, 1H, J=3.2 Hz, 9.6 Hz), 4.99 (bs, 1H), 5.29 (bs, 1H)$^{13}$C NMR (200 MHz, D$_2$O) δ 58.7, 59.1, 60.9, 61.0, 63.9, 65.6, 69.5, 70.7, 72.1, 74.7, 92.2, 92.9.

2,4-Diazido-3,6-dibenzoyl-2,4-dideoxy-1-(4-methoxybenzyl)-β-D-mannopyranose (4-14) (0.22 g, 0.41 mmol) was dissolved in pyridine 4 (mL) and thioacetic acid (1.0 mL) was added. The reaction mixture was stirred for 24 h under reduced pressure at room temperature. The reaction was quenched by adding methanol and the solvent was removed under reduced pressure. The compound was purified by silica gel column chromatography (toluene:ethyl acetate=2:1, by volume) to produce 2,4-diacetamido-3,6-dibenzoyl-2,4-dideoxy-1-(4-methoxybenzyl)-β-D-mannopyranose (4-17) in 88.9% yield. $^1$H NMR (800 MHz, CD$_3$Cl): 1.89 (s, 3H), 2.06 (s, 3H), 3.65 (s, 3H), 3.98 (bt, 1H, J=9.6 Hz), 4.47 (q, 1H, J=9.9), 4.55 (1H, dd, J=11.9, 8.6), 4.65 (bd, J=12 Hz), 5.10 (dd, 1H, J=9.7, 4.0), 5.19 (s, 1H), 5.42 (dd, 1H, J=10.6, 4.0), 6.56-6.52 (m, 2H), 6.90 (d, 2H, J=8.7), 7.36 (t, 2H, J=7.7), 7.43 (t, 2H, J=7.6), 7.51 (t, 1H, J=7.5), 7.59 (t, 1H, J=7.5), 7.95 (d, 2H, J=7.8), 8.00 (d, 2H, J=7.8). $^{13}$C NMR (200 MHz, D$_2$O) δ 23.1, 23.4, 47.6, 50.6, 55.5, 64.4, 72.0, 74.4, 97.9, 114.4, 118.2, 128.3, 128.4, 128.6, 129.1, 129.3, 129.7, 129.8, 129.8, 133.2, 133.5, 150.6, 155.3, 166.2, 166.8, 171.1, 171.3.

2,4-Diacetamido-3,6-dibenzoyl-2,4-dideoxy-1-(4-methoxybenzyl)-β-D-mannopyranose (4-17) (0.51 g, 0.88 mmol) was dissolved in dry MeOH and 0.2 mL of sodium methoxide solution (5.4 M) was added. After the reaction was completed, the reaction mixture was neutralized using H$^+$ resin. Compound was purified by silica gel column chromatography (ethyl acetate:methanol=9:1, by volume) to produce 2,4-diacetamido-2,4-dideoxy-1-(4-methoxybenzyl)-β-D-mannopyranose (4-18) in 79.5% yield. $^1$H NMR (800 MHz, CD$_3$OD) δ 2.02 (s, 3H), 2.12 (s, 3H), 3.38-3.41 (m, 1H), 3.67-3.71 (m, 2H), 3.74 (s, 3H), 3.87-3.93 (m, 2H), 4.69 (bd, 1H, J=2.4 Hz), 5.12 (bd, 1H, J=1.6 Hz), 6.82-6.84 (m, 2H), 6.95-6.98 (m, 2H). $^{13}$C NMR (200 MHz, CD$_3$OD) δ 22.7, 22.8, 49.7, 54.4, 56.0, 62.4, 71.7, 77.5, 99.6, 115.5, 119.1, 152.4, 156.7, 174.6, 174.9.

2,4-Diacetamido-2,4-dideoxy-1-(4-methoxybenzyl)-β-D-mannopyranose (4-18) (0.13 g, 0.34 mmol) was added to a round bottom flask and dissolved in acetonitrile (6 mL). Ammonium cerium nitrate (0.6 g) was dissolved in water (1.5 mL) and was added slowly while stirring. The reaction was run for 4.5 h at room temperature. The reaction mixture was concentrated, and the residue was purified by silica gel column chromatography (ethyl acetate:methanol:water=9:1: 0.5, by volume) to produce 2,4-diacetamido-2,4-dideoxy-D-mannopyranose (2) in 80% yield. $^1$H NMR (800 MHz, D$_2$O) δ 1.92 (s, 3H), 1.93 (s, 3H), 1.96 (s, 3H), 2.00 (s, 2H), 3.35 (m, 1H), 3.50 (s, 1H), 3.54-3.58 (m, 2H), 3.61 (dd, 1H, J=1.6 Hz, 12.8 Hz), 3.73 (t, 1H, J=10.4 Hz), 3.77-3.82 (m, 2H), 3.85 (t, 1H, J=11.2 Hz), 4.02 (dd, 1H, J=4 Hz, 10.4 Hz), 4.22 (bd, 1H, J=4 Hz), 4.37 (bd, 1H, J=4.8 Hz), 4.89 (s, 1H), 5.06 (s, 1H). $^{13}$C NMR (200 MHz, D$_2$O) δ 21.9, 22.0, 22.0, 22.0, 47.9, 48.2, 52.5, 53.5, 60.8, 66.8, 70.1, 70.8, 75.5, 93.0, 174.7, 174.8, 174.8 175.8.

Scheme 17. PmAldolase-catalyzed synthesis of Neu5Ac7NAc from Man2,4diNAc (4).

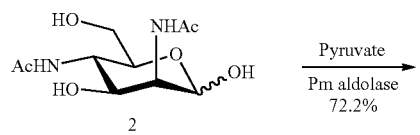

-continued

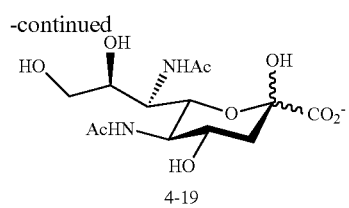

4-19

Neu5Ac7NAc (4-19) was synthesized from Man2,4diNAc (2) and sodium pyruvate by a *Pasteurella multocida* sialic acid aldolase (PmAldolase)-catalyzed reaction. Sodium pyruvate (0.94 g, 8.52 mmol) and 2,4-diacetamido-2,4-dideoxy-D-mannopyranose (2) (0.28 g, 20 mM, 1.07 mmol) were dissolved in water in 50 mL centrifuge tubes. An appropriate amount of PmNanA was added. The reaction mixture was incubated at 37° C. for 4-5 days. The reaction was quenched by adding an equal amount of cold methanol. Reaction mixture was centrifuged to remove precipitates. The supernatant was concentrated under reduced pressure and the residue was purified using a Biogel P-2 gel filtration column using water as the eluant, followed by silica gel column chromatography (ethyl acetate:methanol:water=6:2: 1, by volume) to produce 5,7-diacetamido-3,5,7-trideoxy-D-glycero-α-D-galacto-2-nonulopyranosylonic acid (4-19) in 72% yield. $^1$H NMR (400 MHz, D$_2$O) δ 1.83 (t, 1H, J=12.4 Hz), 1.98 (s, 3H), 2.00 (s, 3H), 2.22 (dd, 1H, J=4.8 Hz, 12.8 Hz), 3.43-3.50 (m, 1H), 3.62 (dd, 1H, J=2.8 Hz, 12.4 Hz), 3.69-3.78 (m, 2H), 3.90-4.00 (m, 2H), 4.23 (dd, 1H, J=2.4 Hz, 10.4 Hz). $^{13}$C NMR (100 MHz, D$_2$O) δ 21.7, 22.1, 39.2, 49.2, 52.4, 63.2, 67.2, 69.6, 70.1, 95.7, 173.9, 174.0, 174.2.

A library of α2-3 and α2-6-linked Neu5Ac7NAc-glycosides can be produced readily from chemically synthesized 2,4-diazido-2,4-dideoxy-D-mannopyranose (Man2,4diN$_3$) as a chemoenzymatic synthon using highly efficient one-pot multienzyme (OPME) sialylation systems containing a sialic acid aldolase, a CMP-sialic acid synthetase, and a sialyltransferase. As examples, para-nitrophenyl β-galactoside (GalβpNP) was used as a sialyltransferase acceptor for the synthesis of the corresponding α2-3 and α2-6-linked Neu5Ac7NAc-glycosides.

Scheme 18. One-pot three-enzyme (OPME) synthesis of Neu5,7diN$_3$α2-3/6GalβpNP.

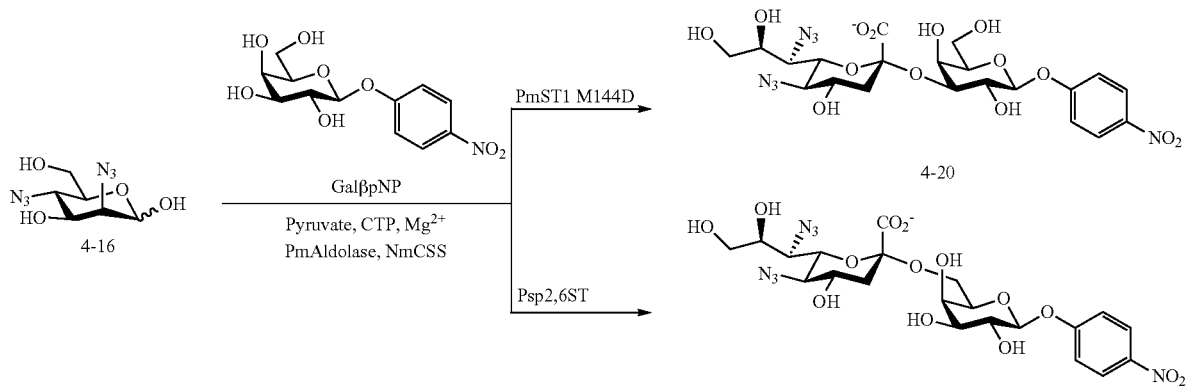

GalβpNP (1.0 equiv, 10 mM, 0.043 mmol), 2,4-diazido-2,4-dideoxy-D-mannopyranose (4-16) (1.5 equiv, 15 mM, 0.065 mmol), sodium pyruvate (7.5 equiv, 75 mM, 0.217 mmol), and CTP (2.0 equiv, 20 mM, 0.086 mmol) were dissolved in water in a 50 mL centrifuge tube. Tris-HCl buffer (1 M, pH 8.5, 0.43 mL) and MgCl$_2$ (200 mM, 0.43 mL) were added. Appropriate amounts of *Pasteurella multocida* sialic acid aldolase (PmNanA, 2 mg), *Neisseria meningitidis* CMP-sialic acid synthetase (NmCSS, 2.5 mg), and a sialyltransferase (PmST1 M144D, 5 mg) were added. Water was then added to bring the volume of the reaction mixture to 4.3 mL. The reaction was incubated at 37° C. for 24 h and quenched by adding 5 mL of ice-cold EtOH. The mixture was incubated on ice for 30 min and centrifuged to remove precipitates. The product 4-nitrophenyl-O-(5,7-diacetamido-3,5,7-trideoxy-D-glycero-β-D-galacto-2-nonulopyranosylonic acid)-(2-3)-O-β-D-galactopyranoside (4-20) was observed via HRMS; m/z 622.1243 observed for M+Na$^+$-2H.

GalβpNP (1.0 equiv, 10 mM, 0.043 mmol), 2,4-diazido-2,4-dideoxy-D-mannopyranose (4-16) (1.5 equiv, 15 mM, 0.065 mmol), sodium pyruvate (7.5 equiv, 75 mM, 0.217 mmol), and CTP (2.0 equiv, 20 mM, 0.086 mmol) were dissolved in water in a 50 mL centrifuge tube. Tris-HCl buffer (1 M, pH 8.5, 0.43 mL) and MgCl$_2$ (200 mM, 0.43 mL) were added. Appropriate amounts of *Pasteurella multocida* sialic acid aldolase (PmNanA, 2 mg), *Neisseria meningitides* CMP-sialic acid synthetase (NmCSS, 2.5 mg), and a sialyltransferase (Psp2,6ST, 3.5 mg) were added. Water was then added to bring the volume of the reaction mixture to 4.3 mL. The reaction was incubated at 37° C. for 24 h. The reaction was quenched by adding 5 mL of ice-cold EtOH. The mixture was incubated on ice for 30 min and centrifuged to remove precipitates. The product 4-nitrophenyl-O-(5,7-diacetamido-3,5,7-trideoxy-D-glycero-β-D-galacto-2-nonulopyranosylonic acid)-(2-6)-O-β-D-galactopyranoside (4-21) was observed via HRMS; m/z 622.1241 observed for M+Na$^+$-2H.

Although the foregoing has been described in some detail by way of illustration and example for purposes of clarity and understanding, one of skill in the art will appreciate that certain changes and modifications can be practiced within the scope of the appended claims. All publications, patents, patent applications, and sequence accession numbers cited herein are hereby incorporated by reference in their entirety for all purposes.

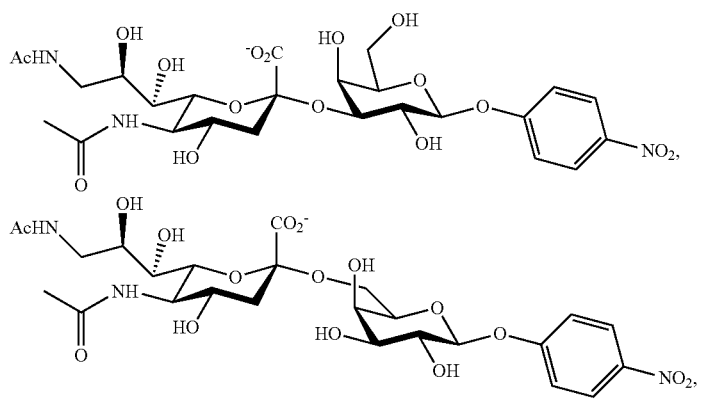

-continued
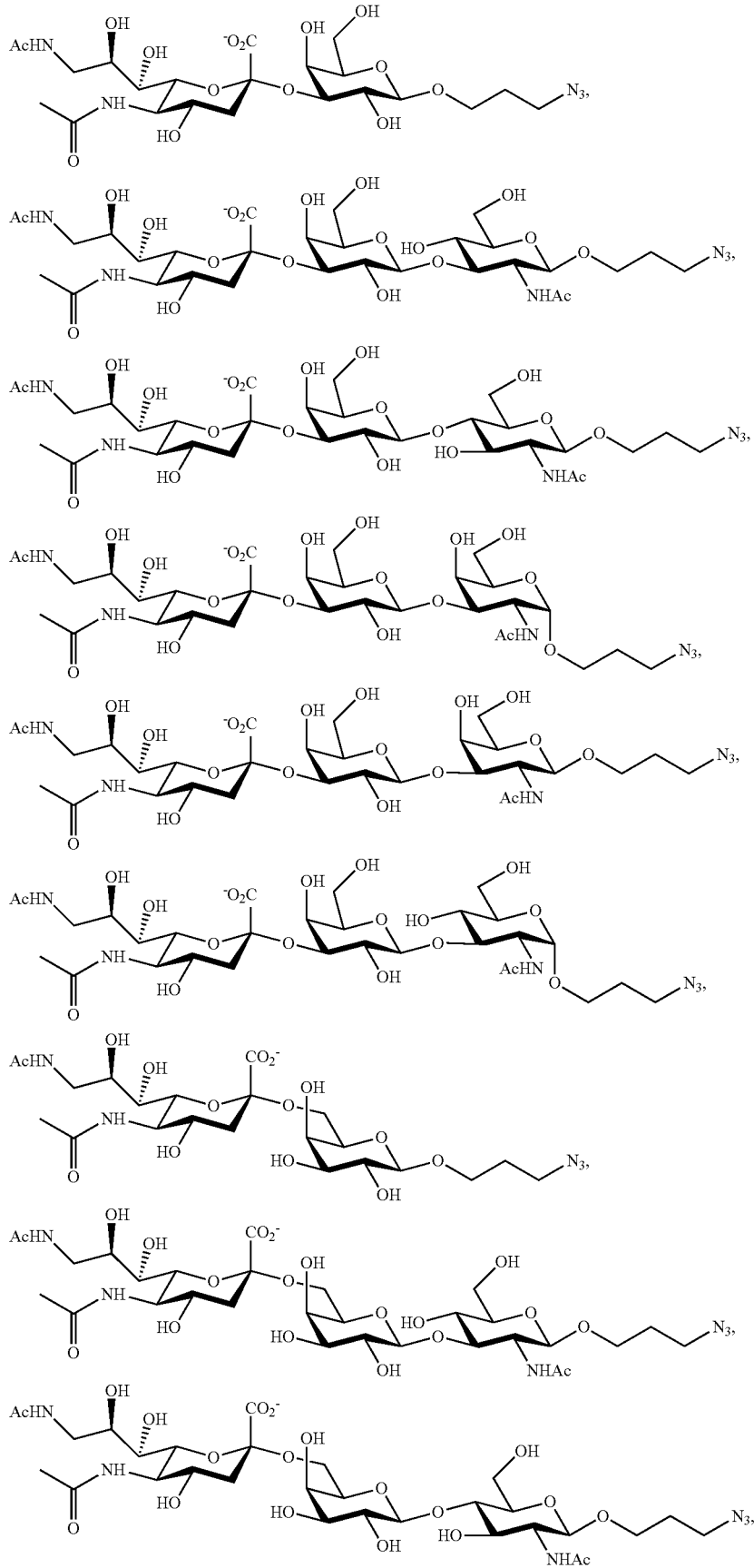

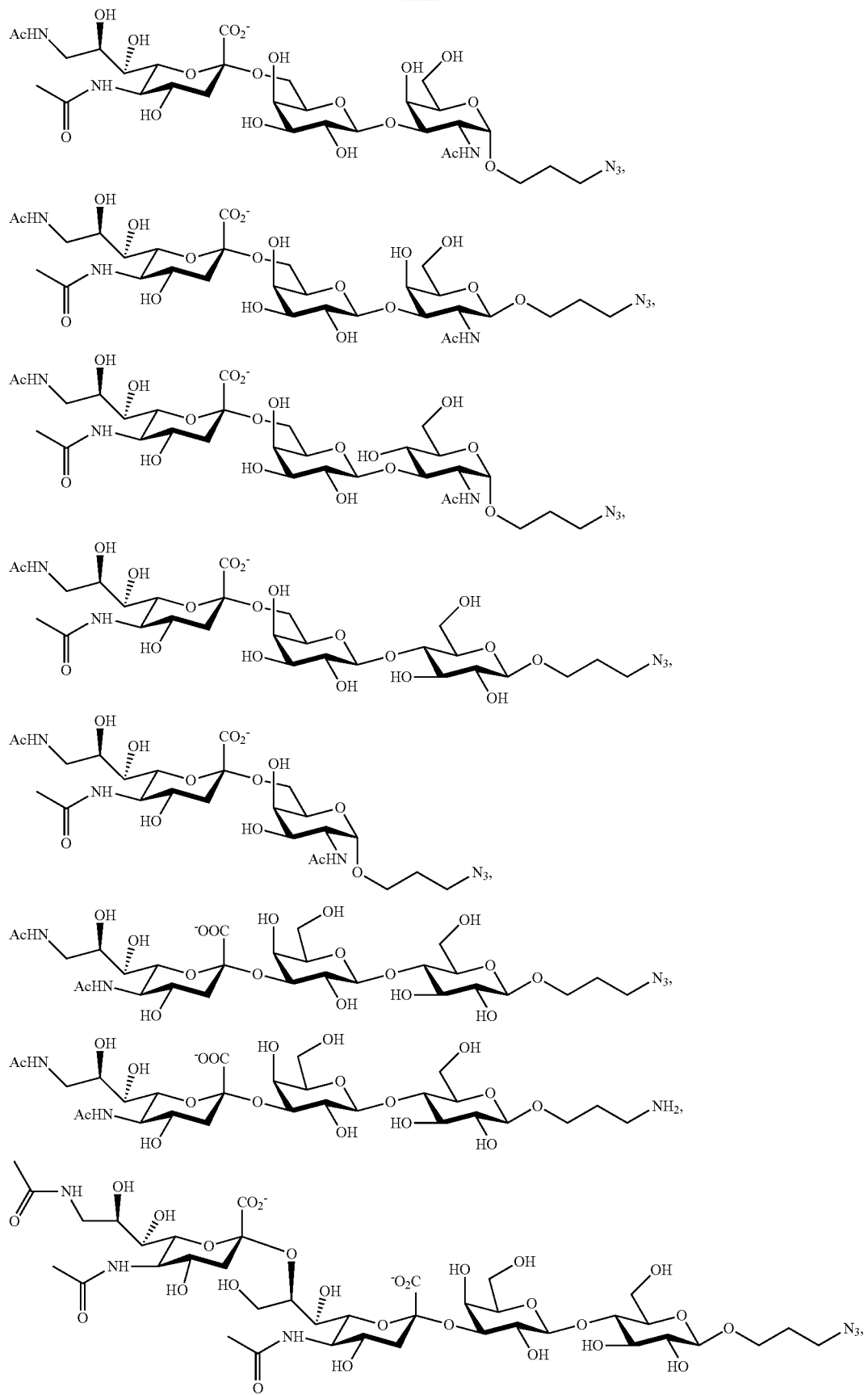

-continued
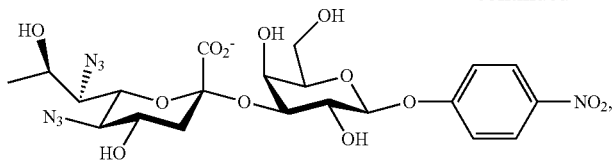
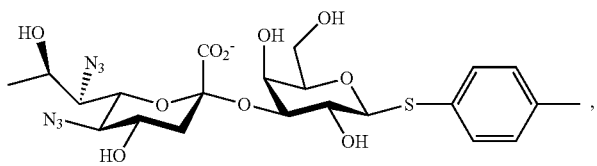
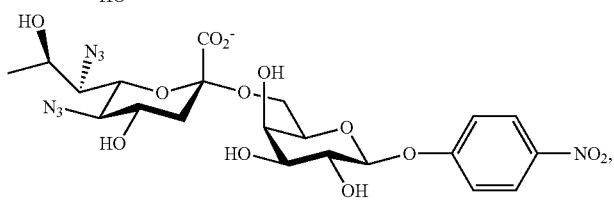
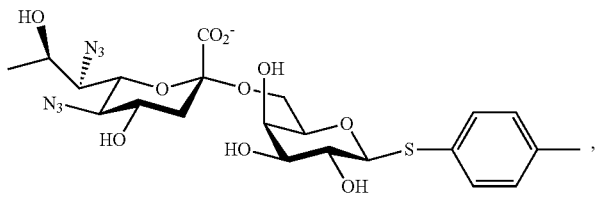
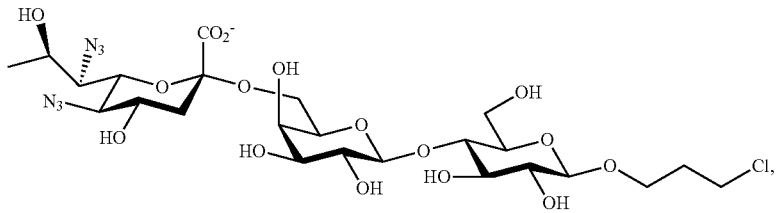
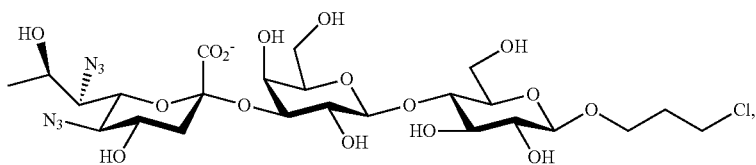
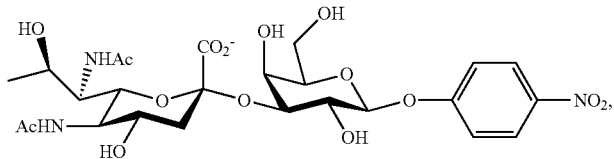
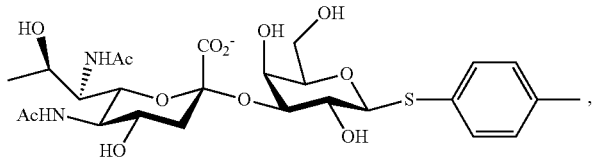
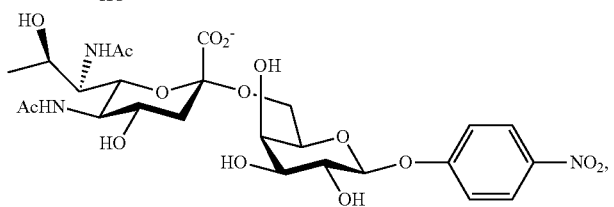

-continued
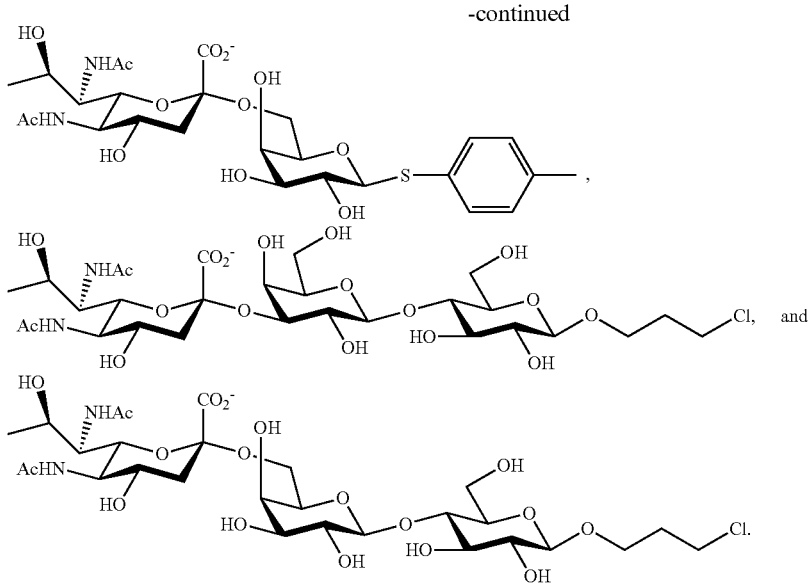

What is claimed is:

1. A compound according to Formula IVa:

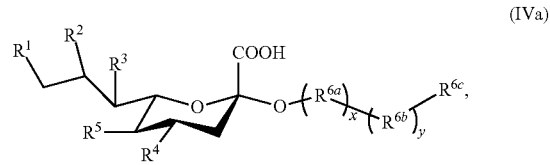

wherein:
$R^1$ is selected from the group consisting of hydrogen, —NH$_2$, —NHAc, and —OH;
$R^2$, $R^3$, and $R^4$ are independently selected from the group consisting of —NHAc and —OH;
$R^5$ is selected from the group consisting of —NHR$^{5a}$, —OH, and —OAc;
$R^{5a}$ is selected from the group consisting of Ac, Gc, GcAc, GcN$_3$, GcNH$_2$, GcNAc, and hydrogen;
Ac is —C(O)CH$_3$; Gc is —C(O)CH$_2$OH; GcAc is —C(O)CH$_2$OC(O)CH$_3$; GcN$_3$ is —C(O)CH$_2$N$_3$; GcNH$_2$ is —C(O)CH$_2$NH$_2$; GcNAc is —C(O)CH$_2$NHC(O)CH$_3$;
at least one of $R^1$, $R^2$, $R^3$, and $R^4$ is —NHAc;
when $R^5$ and $R^1$ are —NHAc, at least one of $R^2$, $R^3$, and $R^4$ is —NHAc; and
when $R^5$ and $R^4$ are —NHAc, at least one of $R^1$, $R^2$, and $R^3$ is —NHAc;
subscript x is 0 or 1;
$R^{6a}$ is selected from the group consisting of a monosaccharide, disaccharide, and an oligosaccharide;
subscript y is 0 or 1;
$R^{6b}$ is a linker selected from the group consisting of C$_{1-6}$ alkylene; C$_{1-6}$ alkylene-NH—C(O)—C$_{1-6}$ alkylene; and C$_{1-6}$ alkylene-NH—C(O)—(CH$_2$—(CH$_2$CH$_2$O)$_p$—NH—C(O))$_m$—C$_{1-6}$ alkylene, where subscript m is 0 or 1, and subscript p is an integer from 1 to 6; and
$R^{6c}$ is a selected from the group consisting of —N$_3$, halo, thiotolyl, —NH$_2$, —SH, —ONH$_2$, and —NHNH$_2$.

2. The compound of claim 1, wherein:
$R^1$ is selected from the group consisting of hydrogen, —NHAc, and —OH;
$R^5$ is selected from the group consisting of —NHR$^{5a}$, OAc, and —OH; and
$R^{5a}$ is selected from the group consisting of Ac and Gc.

3. A compound selected from the group consisting of: